United States Patent
Grant et al.

(10) Patent No.: US 11,598,329 B2
(45) Date of Patent: Mar. 7, 2023

(54) LIQUID PUMPING CASSETTES AND ASSOCIATED PRESSURE DISTRIBUTION MANIFOLD AND RELATED METHODS

(71) Applicant: DEKA Products Limited Partnership, Manchester, NH (US)

(72) Inventors: Kevin L. Grant, Litchfield, NH (US); Benjamin E. Colburn, Deerfield, NH (US); Joseph M. Rauseo, Manchester, NH (US); Benjamin J. Doucette, Nashua, NH (US); Marc J. Gorayeb, Hampton, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 17/751,342

(22) Filed: May 23, 2022

(65) Prior Publication Data

US 2022/0282721 A1    Sep. 8, 2022

Related U.S. Application Data

(62) Division of application No. 16/370,039, filed on Mar. 29, 2019, now Pat. No. 11,371,498.
(Continued)

(51) Int. Cl.
*F16K 11/20* (2006.01)
*F04B 43/02* (2006.01)
(Continued)

(52) U.S. Cl.
CPC .......... *F04B 43/026* (2013.01); *A61B 5/1405* (2013.01); *A61B 5/150221* (2013.01);
(Continued)

(58) Field of Classification Search
CPC .............. F04B 43/026; F04B 43/0736; A61M 2205/12; A61M 2205/128
See application file for complete search history.

(56) References Cited

U.S. PATENT DOCUMENTS

| 3,410,202 A | 11/1968 | Chrubasik |
| 3,656,873 A | 4/1972 | Schiff |
| (Continued) | | |

FOREIGN PATENT DOCUMENTS

| EP | 0 406 562 A2 | 1/1991 |
| EP | 1 195 171 A2 | 4/2002 |
| (Continued) | | |

OTHER PUBLICATIONS

International Search Report and Written Opinion for International Application No. PCT/US2019/024933 dated Aug. 27, 2019.
(Continued)

*Primary Examiner* — Reinaldo Sanchez-Medina
(74) *Attorney, Agent, or Firm* — Wolf, Greenfield & Sacks, P.C.

(57) ABSTRACT

A fluid-handling cassette comprising a plurality of diaphragm valves and pumps is configured to have its actuation ports located along a thin or narrow edge of the cassette. Actuation channels within the cassette lead from the actuation ports to actuation chambers of the valves and pumps in a space between plates that comprise the cassette. The individual plates have a nominal thickness that is sufficient to provide a rigid ceiling for the actuation channels, but sufficiently thin to minimize the overall thickness of the cassette. The cassette can be plugged into or unplugged from an actuation receptacle or a manifold by its narrow edge. A plurality of such cassettes can be stacked together or spaced apart from each other to form a cassette assembly, providing for a convenient way to install and remove the cassette assembly from its actuation receptacle. The arrangement
(Continued)

allows for an improved way of connecting a complex cassette assembly to its associated pressure distribution manifold without the use of a plurality of flexible connecting tubes between the two.

13 Claims, 63 Drawing Sheets

Related U.S. Application Data

(60) Provisional application No. 62/745,807, filed on Oct. 15, 2018, provisional application No. 62/650,820, filed on Mar. 30, 2018.

(51) Int. Cl.
*A61B 5/15* (2006.01)
*F04B 39/10* (2006.01)
*A61M 1/16* (2006.01)
*F04B 43/073* (2006.01)

(52) U.S. Cl.
CPC ........... *A61M 1/16* (2013.01); *F04B 39/1066* (2013.01); *F04B 43/073* (2013.01); *A61M 2205/128* (2013.01); *A61M 2205/3331* (2013.01)

(56) References Cited

U.S. PATENT DOCUMENTS

| | | | |
|---|---|---|---|
| 3,946,731 A | 3/1976 | Lichtenstein | |
| 4,468,223 A | 8/1984 | Minagawa et al. | |
| 4,479,762 A | 10/1984 | Bilstad et al. | |
| 4,583,920 A | 4/1986 | Lindner | |
| 4,623,450 A | 11/1986 | Vantard et al. | |
| 4,906,816 A | 3/1990 | van Leerdam | |
| 4,927,411 A | 5/1990 | Pastrone et al. | |
| 5,062,774 A | 11/1991 | Kramer et al. | |
| 5,088,515 A * | 2/1992 | Kamen | G05D 16/0636 137/315.04 |
| 5,098,262 A | 3/1992 | Wecker et al. | |
| 5,178,182 A | 1/1993 | Kamen | |
| 5,214,241 A | 5/1993 | Benwell | |
| 5,247,434 A | 9/1993 | Peterson et al. | |
| 5,267,956 A | 12/1993 | Beuchat | |
| 5,275,724 A | 1/1994 | Bucchianeri et al. | |
| 5,302,093 A | 4/1994 | Owens et al. | |
| 5,306,242 A | 4/1994 | Joyce et al. | |
| 5,324,422 A * | 6/1994 | Colleran | A61M 1/28 210/85 |
| D350,823 S | 9/1994 | Lanigan | |
| 5,350,357 A | 9/1994 | Kamen et al. | |
| 5,357,827 A | 10/1994 | Natwick et al. | |
| 5,378,126 A | 1/1995 | Abrahamson et al. | |
| 5,415,528 A | 5/1995 | Ogden et al. | |
| 5,421,823 A | 6/1995 | Kamen et al. | |
| 5,427,509 A | 6/1995 | Chapman et al. | |
| 5,431,627 A | 7/1995 | Pastrone et al. | |
| 5,438,510 A | 8/1995 | Bryant et al. | |
| 5,462,416 A | 10/1995 | Dennehey et al. | |
| 5,476,368 A * | 12/1995 | Rabenau | F04B 53/101 417/540 |
| 5,480,294 A | 1/1996 | Di Perna et al. | |
| 5,488,967 A | 2/1996 | Minami et al. | |
| 5,496,273 A | 3/1996 | Pastrone et al. | |
| 5,499,909 A | 3/1996 | Yamada et al. | |
| 5,591,344 A | 1/1997 | Kenley et al. | |
| 5,593,290 A | 1/1997 | Greisch et al. | |
| 5,609,572 A | 3/1997 | Lang | |
| 5,628,908 A * | 5/1997 | Kamen | A61M 1/281 210/252 |
| 5,640,995 A | 6/1997 | Packard et al. | |
| 5,704,520 A | 1/1998 | Gross | |
| 5,714,060 A | 2/1998 | Kenley et al. | |
| 5,722,947 A | 3/1998 | Jeppsson et al. | |
| 5,863,421 A | 1/1999 | Peter, Jr. et al. | |
| 5,938,634 A | 8/1999 | Packard | |
| 6,165,154 A | 12/2000 | Gray et al. | |
| 6,210,361 B1 | 4/2001 | Kamen et al. | |
| 6,223,130 B1 | 4/2001 | Gray et al. | |
| 6,234,989 B1 | 5/2001 | Brierton et al. | |
| 6,261,065 B1 | 7/2001 | Nayak et al. | |
| 6,261,262 B1 | 7/2001 | Briggs et al. | |
| 6,270,673 B1 | 8/2001 | Belt et al. | |
| 6,284,131 B1 | 9/2001 | Hogard et al. | |
| 6,416,293 B1 | 7/2002 | Bouchard et al. | |
| 6,419,462 B1 | 7/2002 | Horie et al. | |
| 6,481,980 B1 | 11/2002 | Vandlik et al. | |
| 6,491,656 B1 | 12/2002 | Morris | |
| 6,497,676 B1 | 12/2002 | Childers et al. | |
| 6,537,445 B2 | 3/2003 | Muller | |
| 6,579,074 B2 | 6/2003 | Chiba | |
| 6,579,253 B1 | 6/2003 | Burbank et al. | |
| RE38,203 E | 7/2003 | Kelly | |
| 6,638,478 B1 | 10/2003 | Treu et al. | |
| 6,692,457 B2 | 2/2004 | Flaherty | |
| 6,709,417 B1 * | 3/2004 | Houle | F16K 5/0478 604/153 |
| 6,723,062 B1 | 4/2004 | Westberg et al. | |
| 6,743,201 B1 | 6/2004 | Donig et al. | |
| 6,752,599 B2 | 6/2004 | Park | |
| 6,811,707 B2 | 11/2004 | Rovatti et al. | |
| 6,814,547 B2 | 11/2004 | Childers et al. | |
| 6,852,090 B2 | 2/2005 | Burbank et al. | |
| 6,860,846 B2 | 3/2005 | Odak et al. | |
| 6,905,314 B2 | 6/2005 | Danby | |
| 6,905,479 B1 | 6/2005 | Bouchard et al. | |
| 6,949,079 B1 | 9/2005 | Westberg et al. | |
| 6,953,323 B2 | 10/2005 | Childers et al. | |
| 7,029,245 B2 | 4/2006 | Maianti et al. | |
| 7,041,076 B1 | 5/2006 | Westberg et al. | |
| 7,044,432 B2 | 5/2006 | Beden et al. | |
| 7,083,719 B2 | 8/2006 | Bowman, Jr. et al. | |
| 7,153,286 B2 | 12/2006 | Busby et al. | |
| 7,175,606 B2 | 2/2007 | Bowman, Jr. et al. | |
| 7,214,210 B2 | 5/2007 | Kamen et al. | |
| 7,232,418 B2 | 6/2007 | Neri et al. | |
| 7,238,164 B2 | 7/2007 | Childers et al. | |
| 7,300,413 B2 | 11/2007 | Burbank et al. | |
| 7,465,285 B2 | 12/2008 | Hutchinson et al. | |
| 7,473,238 B2 | 1/2009 | Brugger et al. | |
| 7,500,962 B2 | 3/2009 | Childers et al. | |
| 7,559,524 B2 | 7/2009 | Gray et al. | |
| 7,563,248 B2 | 7/2009 | Smisson, III et al. | |
| 7,575,564 B2 | 8/2009 | Childers | |
| 7,632,078 B2 | 12/2009 | Demers et al. | |
| 7,632,080 B2 | 12/2009 | Tracey et al. | |
| 7,648,627 B2 | 1/2010 | Beden et al. | |
| 7,662,139 B2 | 2/2010 | Demers et al. | |
| 7,699,806 B2 | 4/2010 | Ware et al. | |
| 7,717,682 B2 | 5/2010 | Orr | |
| 7,727,176 B2 | 6/2010 | Tonelli et al. | |
| 7,736,328 B2 | 6/2010 | Childers et al. | |
| 7,776,006 B2 | 8/2010 | Childers et al. | |
| 7,780,619 B2 | 8/2010 | Brugger et al. | |
| 7,794,141 B2 | 9/2010 | Perry et al. | |
| 7,798,997 B2 | 9/2010 | Kamen et al. | |
| 7,867,214 B2 | 1/2011 | Childers et al. | |
| 7,892,331 B2 | 2/2011 | Childers et al. | |
| 7,909,795 B2 | 3/2011 | Childers et al. | |
| 7,935,074 B2 | 5/2011 | Plahey et al. | |
| 7,955,295 B2 | 6/2011 | Lee et al. | |
| 7,967,022 B2 | 6/2011 | Grant et al. | |
| 8,029,454 B2 | 10/2011 | Kelly et al. | |
| 8,038,639 B2 | 10/2011 | Lo et al. | |
| 8,038,640 B2 * | 10/2011 | Orr | A61M 60/109 417/477.2 |
| 8,042,563 B2 | 10/2011 | Wilt et al. | |
| 8,105,265 B2 | 1/2012 | Demers et al. | |
| 8,246,826 B2 | 8/2012 | Wilt et al. | |
| 8,251,953 B2 | 8/2012 | Kamen et al. | |
| 8,273,049 B2 | 9/2012 | Demers et al. | |
| 8,292,594 B2 | 10/2012 | Tracey et al. | |

(56) References Cited

U.S. PATENT DOCUMENTS

| | | |
|---|---|---|
| 8,317,492 B2 | 11/2012 | Demers et al. |
| 8,330,579 B2 | 12/2012 | Kneip et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,491,184 B2 | 7/2013 | Kamen et al. |
| 8,496,609 B2 | 7/2013 | Childers et al. |
| 8,499,780 B2 | 8/2013 | Wilt et al. |
| 8,512,553 B2 | 8/2013 | Cicchello et al. |
| 8,535,525 B2 | 9/2013 | Heyes et al. |
| 8,545,698 B2 | 10/2013 | Wilt et al. |
| 8,562,834 B2 | 10/2013 | Kamen et al. |
| 8,673,139 B2 | 3/2014 | Hedmann et al. |
| 8,721,879 B2 | 5/2014 | van der Merwe et al. |
| 8,721,884 B2 | 5/2014 | Wilt et al. |
| 8,764,702 B2 | 7/2014 | Childers et al. |
| 8,771,508 B2 | 7/2014 | Grant et al. |
| 8,803,044 B2 | 8/2014 | Kienman et al. |
| 8,840,581 B2 | 9/2014 | McGill et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,870,811 B2 | 10/2014 | Gavin et al. |
| 8,888,470 B2 | 11/2014 | Demers et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,078,971 B2 | 7/2015 | Scarpaci et al. |
| 9,115,708 B2 | 8/2015 | van der Merwe et al. |
| 9,115,709 B2 | 8/2015 | Gray et al. |
| 9,121,403 B2 | 9/2015 | Lanigan et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,358,332 B2 | 6/2016 | McGill et al. |
| 9,364,655 B2 | 6/2016 | Grant et al. |
| 9,514,283 B2 | 12/2016 | Childers et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,593,679 B2 | 3/2017 | Gray et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,717,834 B2 | 8/2017 | Wilt et al. |
| 9,724,458 B2 | 8/2017 | Grant et al. |
| 9,795,728 B2 | 10/2017 | Grant et al. |
| 9,839,775 B2 | 12/2017 | McGill et al. |
| 9,861,732 B2 | 1/2018 | Scarpaci et al. |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,060,867 B2 | 8/2018 | Kamen et al. |
| 10,077,766 B2 | 9/2018 | Demers et al. |
| 10,098,996 B2 | 10/2018 | Scarpaci et al. |
| 10,098,998 B2 | 10/2018 | Wilt |
| 10,172,988 B2 | 1/2019 | McGill et al. |
| 10,201,650 B2 | 2/2019 | Wilt et al. |
| 10,265,451 B2 | 4/2019 | McGill et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,485,914 B2 | 11/2019 | Scarpaci et al. |
| 10,500,327 B2 | 12/2019 | Grant et al. |
| 10,537,671 B2 | 1/2020 | Wilt et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 11,007,311 B2 | 5/2021 | Scarpaci et al. |
| 11,033,671 B2 | 6/2021 | van der Merwe et al. |
| 11,052,181 B2 | 7/2021 | Wilt et al. |
| 11,103,625 B2 | 8/2021 | Wilt |
| 11,110,212 B2 | 9/2021 | Grant et al. |
| 11,154,646 B2 | 10/2021 | Wilt et al. |
| 11,197,951 B2 | 12/2021 | Wilt et al. |
| 11,253,636 B2 | 2/2022 | McGill et al. |
| 11,311,656 B2 | 4/2022 | Kamen et al. |
| 11,364,329 B2 | 6/2022 | Demers et al. |
| 11,371,498 B2 | 6/2022 | Grant et al. |
| 11,400,272 B2 | 8/2022 | Norris et al. |
| 11,419,965 B2 | 8/2022 | Demers et al. |
| 2003/0138334 A1* | 7/2003 | Vandlik ............... A61M 1/3696 |
| | | 417/477.2 |
| 2003/0194332 A1 | 10/2003 | Jahn et al. |
| 2004/0136843 A1 | 7/2004 | Jahn et al. |
| 2004/0243049 A1 | 12/2004 | Brugger et al. |
| 2005/0095141 A1 | 5/2005 | Lanigan et al. |
| 2005/0209563 A1 | 9/2005 | Hopping et al. |
| 2005/0234385 A1 | 10/2005 | Vandlik et al. |
| 2006/0084906 A1 | 4/2006 | Burbank et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0278155 A1 | 12/2007 | Lo et al. |
| 2008/0015515 A1 | 1/2008 | Hopkins et al. |
| 2008/0033346 A1 | 2/2008 | Childers et al. |
| 2008/0058697 A1 | 3/2008 | Kamen et al. |
| 2008/0077068 A1 | 3/2008 | Orr |
| 2008/0132828 A1 | 6/2008 | Howard |
| 2008/0138223 A1 | 6/2008 | Lanigan et al. |
| 2008/0208111 A1* | 8/2008 | Kamen ................... F04B 43/00 |
| | | 604/29 |
| 2008/0216898 A1 | 9/2008 | Grant et al. |
| 2008/0240929 A1* | 10/2008 | Kamen ................... F04B 43/06 |
| | | 417/477.2 |
| 2008/0253911 A1 | 10/2008 | Demers et al. |
| 2009/0012450 A1 | 1/2009 | Shah et al. |
| 2009/0095679 A1 | 4/2009 | Demers et al. |
| 2009/0107335 A1 | 4/2009 | Wilt et al. |
| 2009/0107902 A1 | 4/2009 | Childers et al. |
| 2009/0124963 A1 | 5/2009 | Hogard et al. |
| 2009/0137940 A1 | 5/2009 | Orr |
| 2009/0294359 A1 | 12/2009 | Hopping et al. |
| 2010/0056975 A1 | 3/2010 | Dale et al. |
| 2010/0191181 A1 | 7/2010 | Childers et al. |
| 2011/0005992 A1 | 1/2011 | Kelly et al. |
| 2011/0092894 A1 | 4/2011 | McGill et al. |
| 2011/0105877 A1 | 5/2011 | Wilt et al. |
| 2012/0106289 A1 | 5/2012 | Wilt et al. |
| 2013/0074959 A1 | 3/2013 | Demers et al. |
| 2013/0126413 A1 | 5/2013 | van der Merwe et al. |
| 2013/0165847 A1 | 6/2013 | Scarpaci et al. |
| 2013/0184638 A1 | 7/2013 | Scarpaci et al. |
| 2013/0304020 A1 | 11/2013 | Wilt et al. |
| 2014/0112828 A1 | 4/2014 | Grant et al. |
| 2014/0194820 A1 | 7/2014 | Gray et al. |
| 2014/0199193 A1 | 7/2014 | Wilt et al. |
| 2014/0309611 A1 | 10/2014 | Wilt et al. |
| 2014/0322053 A1 | 10/2014 | van der Merwe et al. |
| 2014/0364800 A1 | 12/2014 | McGill et al. |
| 2015/0050166 A1 | 2/2015 | Tracey et al. |
| 2015/0196698 A1 | 7/2015 | Grant et al. |
| 2015/0196699 A9 | 7/2015 | Wilt et al. |
| 2015/0265760 A1 | 9/2015 | Wilt et al. |
| 2015/0359956 A1 | 12/2015 | Gray et al. |
| 2016/0030657 A1 | 2/2016 | Kelly et al. |

(56) References Cited

U.S. PATENT DOCUMENTS

| | | |
|---|---|---|
| 2016/0144093 A1 | 5/2016 | Demers et al. |
| 2016/0175505 A1 | 6/2016 | Demers et al. |
| 2016/0175506 A1 | 6/2016 | Wilt et al. |
| 2018/0368704 A1 | 12/2018 | Kawamura et al. |
| 2018/0372084 A1 | 12/2018 | Grant et al. |
| 2019/0314565 A1 | 10/2019 | McGill et al. |
| 2019/0344002 A1 | 11/2019 | McGill et al. |
| 2020/0139031 A1 | 5/2020 | Wilt et al. |
| 2020/0171226 A1 | 6/2020 | Wilt et al. |
| 2020/0222609 A1 | 7/2020 | Ballantyne et al. |
| 2020/0376185 A1 | 12/2020 | Wilt et al. |
| 2020/0376186 A1 | 12/2020 | Wilt et al. |
| 2020/0400595 A1 | 12/2020 | Kamen et al. |
| 2021/0060231 A1 | 3/2021 | Grant et al. |
| 2021/0285435 A1 | 9/2021 | Tracey et al. |
| 2021/0290928 A1 | 9/2021 | Grant et al. |
| 2021/0316058 A1 | 10/2021 | van der Merwe et al. |
| 2021/0332813 A1 | 10/2021 | Wilt et al. |
| 2021/0361841 A1 | 11/2021 | van der Merwe et al. |
| 2022/0096718 A1 | 3/2022 | Grant et al. |
| 2022/0133968 A1 | 5/2022 | Wilt et al. |
| 2022/0152286 A1 | 5/2022 | Wilt et al. |
| 2022/0233754 A1 | 7/2022 | McGill et al. |
| 2022/0241479 A1 | 8/2022 | Kamen et al. |
| 2022/0249755 A1 | 8/2022 | Helmore et al. |
| 2022/0280706 A1 | 9/2022 | Demers et al. |
| 2022/0282721 A1 | 9/2022 | Grant et al. |

FOREIGN PATENT DOCUMENTS

| | | |
|---|---|---|
| JP | S60-30489 A | 2/1985 |
| JP | H06-237988 A | 8/1994 |
| JP | H09-287441 A | 11/1997 |
| JP | H10-196814 A | 7/1998 |
| JP | 2002-113096 A | 4/2002 |
| JP | 2003-000706 A | 1/2003 |
| JP | 2003-180825 A | 7/2003 |
| JP | 2005-013502 A | 1/2005 |
| JP | 2007-097746 A | 4/2007 |
| WO | WO 84/02473 A1 | 7/1984 |
| WO | WO 96/25214 A1 | 8/1996 |
| WO | WO 99/10028 A1 | 3/1999 |
| WO | WO 01/17607 A1 | 3/2001 |
| WO | WO 01/18396 A1 | 3/2001 |
| WO | WO 01/19430 A1 | 3/2001 |
| WO | WO 01/037895 A2 | 5/2001 |
| WO | WO 03/008076 A1 | 1/2003 |
| WO | WO 03/099353 A2 | 12/2003 |
| WO | WO 03/101510 A1 | 12/2003 |
| WO | WO 2006/120415 A1 | 11/2006 |
| WO | WO 2007/120812 A2 | 10/2007 |
| WO | WO 2009/006498 A2 | 1/2009 |
| WO | WO 2009/051669 A1 | 4/2009 |
| WO | WO 2010/139918 A1 | 12/2010 |
| WO | WO 2015/183981 A2 | 12/2015 |

OTHER PUBLICATIONS

International Preliminary Report on Patentability for International Application No. PCT/US2019/024933 dated Oct. 6, 2020.
Examination Report and Notice of Eligibility for Grant for SG Application No. 11202009360W dated Nov. 17, 2021 and Allowed Claims.
[No Author Listed], Homechoice Patient At-Home Guide, Jun. 1998. 84 pages.
[No Author Listed], Patient At-Home Guide, HomeChoice Automated PD System. Version 2.0 (published May 1997); Baxter Healthcare Corporation. Copyright 1994. 61 pages.

* cited by examiner

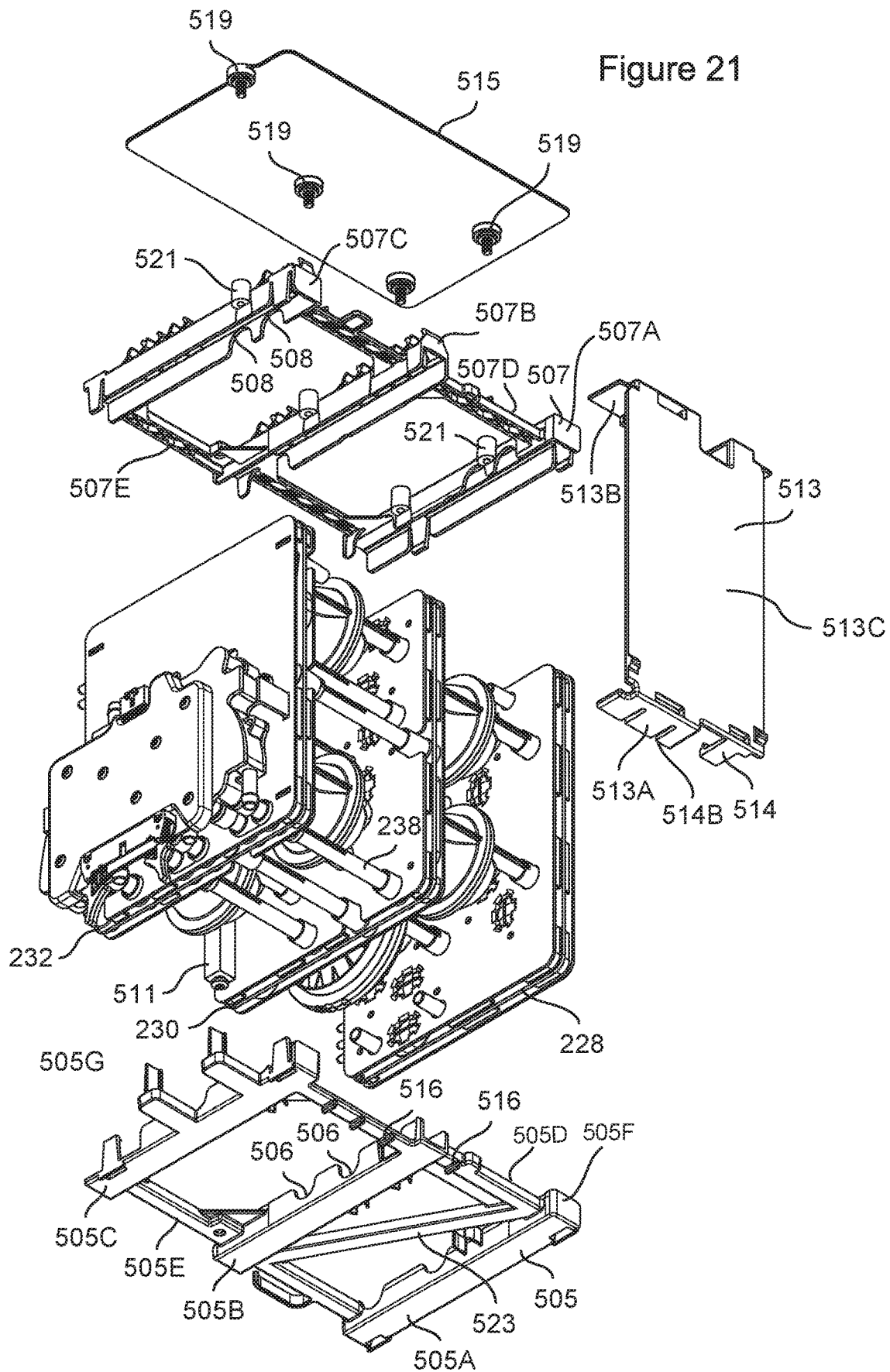

LIQUID PUMPING CASSETTES AND ASSOCIATED PRESSURE DISTRIBUTION MANIFOLD AND RELATED METHODS

CROSS-REFERENCE TO RELATED APPLICATION

The present application is a division of U.S. patent application Ser. No. 16/370,039, filed Mar. 29, 2019 and entitled LIQUID PUMPING CASSETTES AND ASSOCIATED PRESSURE DISTRIBUTION MANIFOLD AND RELATED METHODS, which claims the benefit of U.S. Provisional Patent Application Ser. No. 62/650,820, filed Mar. 30, 2018 and entitled LIQUID PUMPING CASSETTES AND ASSOCIATED COMPONENTS, and U.S. Provisional Patent Application Ser. No. 62/745,807, filed Oct. 15, 10 2018 and entitled LIQUID PUMPING CASSETTES AND ASSOCIATED PRESSURE DISTRIBUTION MANIFOLD, all of which are hereby incorporated herein by reference in their entireties.

FIELD OF THE INVENTION

This disclosure generally relates to improvements in the design and construction of fluid pumping or mixing cassettes, cassette assemblies, their constituent parts, and associated devices.

BACKGROUND

Liquid-handling cassettes comprising diaphragm pumps and/or valves can be actuated fluidically (either hydraulically or pneumatically). In some examples, a cassette is designed to be fluidically connected to a pneumatic actuation manifold having electromechanical valves that selectively distribute positively or negatively pressurized gas or air to the cassette. A programmable electronic controller can be used to control the electromechanical valves to selectively deliver positive or negative pneumatic pressure to various pumps or valves of the cassette in a pre-determined manner.

Some fluid-handling cassettes can be substantially planar in shape, having a broad side flanked by a thin or narrow side having a relatively smaller thickness that the overall broad side dimensions of the cassettes. Liquid inlet and outlet ports can be incorporated into the edge or thin side of the cassette. But in many of these devices, actuation ports for the cassette have been located on the face or broad side of the cassette directly over the actuation chambers of the pumps or valves being controlled. This generally provides the shortest route for an actuation channel in the cassette from an external cassette actuation port to the actuation chamber and diaphragm of a pump or valve in the cassette. Furthermore, in many cases the pumping or valve stations or regions of the cassette—comprising either the actuation chamber on one side or the liquid carrying chamber on the opposing side— may be defined by spheroid or hemi-spheroid chamber walls that extend above the plane of the cassette face, which makes the overall cassette thicker than desirable in some applications. In other cases, a pump module may comprise a set of blocks sandwiched or laminated together, with the pneumatic actuation channels or fluid channels embedded within one or more of the blocks. This arrangement may also result in an overall device thickness greater than desirable for certain applications. Some applications may require a plurality of fluid handling cassettes to be mounted next to each other in tight spaces. In these cases, it may be desirable to position a number of cassettes adjacent to one another, to stack them against each other, or at least to place their broad sides face-to-face in close proximity. Reducing or minimizing the thickness of the individual cassettes constituting these assemblies may be particularly desirable.

It may be advantageous to arrange for a pump cassette to plug directly into its associated pressure distribution manifold (for example, a manifold that selectively delivers pneumatic pressure to the pump cassette under control of an electronic controller). In previously disclosed embodiments of a hemodialysis system using pneumatically actuated self-contained pump cassettes, the pump cassettes were connected to a corresponding pneumatic manifold via flexible tubes, which has led to significant challenges during assembly and in their operation. If a pump cassette can be located close to its associated manifold, a direct plug-in connection between the two would have substantial advantages. Under these circumstances, it would be particularly advantageous to have a compact manifold that allows for a direct interface to a pump cassette, arranged in such a manner as to allow the cassette or cassette assembly to be plugged into and unplugged from the actuation ports of the manifold with minimal effort.

In the design and operation of a pneumatic distribution manifold, the ability to use binary pressure control valves rather than continuously variable orifice valves would also provide significant advantages in both cost and reliability. But in this case, the control of pressure delivery to individual cassette pumps or valves by binary pressure control valves poses additional challenges that must be overcome. A sufficiently robust electronic controller can be programmed to use control algorithms to control the frequency and duration of binary valve actuation to achieve precise control of associated pneumatically actuated pumps or valves.

SUMMARY

In an embodiment, a pump and/or valve cassette has a relatively planar shape, with a broad side flanked by a thinner narrow side or edge. It comprises a midplate positioned between two outer plates: a first outer plate facing a first side of the midplate, and a second outer plate facing an opposing second side of the midplate. The first outer plate is spaced apart from the midplate to form a first inter-plate space. The second outer plate is spaced apart from the midplate to form a second inter-plate space. The thickness of the first and second outer plates is limited to a thickness sufficient to impart rigidity to the plate and to provide a sealing surface against opposing channel walls of either side of the midplate. In some embodiments, the thickness of each outer plate, together with the thickness of the midplate between them, define the overall thickness of the cassette. In other embodiments, liquid inlet and outlet ports jut out from an outer face of the cassette, which adds to the overall thickness of the cassette. The cassette can include one or more pump stations or regions and two or more valve stations or regions. The number of pump or valve stations and their size may determine the overall broad-side dimensions of the cassette. The stroke volume of an on-board pump is a function of the diameter of a pump station and its associated diaphragm and the depth of excursion of the diaphragm defined by the depth of channel walls of the midplate, and this will in turn determine the thickness of the cassette as well as its broad-side dimension. For any given pump or valve station, the midplate comprises an actuation side and an opposing liquid side, with the actuation side holding a pump or valve diaphragm. Actuation channels in the cassette to the respective pump or valve stations can be contained within midplate channels of the first inter-plate space and run generally parallel to the broad side of the cassette. Liquid channels in the cassette can be contained within midplate channels of the second inter-plate space and also generally run parallel to the broad side of the cassette, except in some cases where the liquid channels connect to an inlet or outlet of the cassette. In this arrangement, the first and second outer plates function primarily to provide a roof or limit wall over the respective actuation and liquid carrying valve or pump regions.

In an embodiment, a fluid handling cassette can comprise a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate spaced apart from the mid-plate defining a width of a second inter-plate space. An edge of the cassette has a cassette thickness defined by the thickness of each plate plus the width of the first and second inter-plate spaces, and a face of the cassette being defined by the length and width of the first or second plate. The mid-plate can comprise a pump station defined by a pump diaphragm and the first side of the mid-plate, said pump diaphragm seated against the first side of the midplate and having an excursion range defined by the width of the first inter-plate space. A pump actuation channel runs parallel to the face of the cassette in the first inter-plate space connecting a pump actuation chamber bounded by the first plate and the pump diaphragm with a cassette pump actuation port located within the first inter-plate space at a first edge of the cassette. A first and a second pump fluid port in the pump station may fluidly connect a respective first and second fluid channel in the second inter-plate space to a pumping chamber defined by the pump diaphragm and the first side of the mid-plate. A pump fluid port in the pump station fluidly may connect a fluid channel in the second inter-plate space with a pumping chamber defined by the pump diaphragm and the first side of the mid-plate. Alternatively, there may be an aperture in the mid-plate at the pump station, the aperture allowing the pump diaphragm to move from the first plate to the second plate when actuated by positive or negative pressure delivered through the pump actuation channel. The plates (first, mid-plate and second) are generally insufficiently thick to allow fluid or actuation channels to travel within the plates in a direction parallel to the face of the cassette. A fluid channel may run in the second inter-plate space, and fluidly connect to a pumping chamber defined by the pump diaphragm and the first side of the mid-plate, the connection being made through one or more pump fluid ports in the mid-plate, so that the fluid channel runs parallel to the face of the cassette in the second inter-plate space connecting the pumping chamber with a cassette fluid port located within the second inter-plate space at the first edge or at a second edge of the cassette.

In an embodiment, a fluid handling cassette may comprise a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette is defined by the length and width of the first or second plate. The mid-plate may comprise a valve station defined by a valve diaphragm and the first side of the mid-plate, the valve diaphragm seated against the first side of the midplate and having an excursion range defined by the width of the first inter-plate space. And a valve actuation channel may run parallel to the face of the cassette in the first inter-plate space connecting a valve actuation chamber bounded by the first plate and the valve diaphragm with a cassette valve actuation port located within the first inter-plate space at a first edge of the cassette. A first and second valve fluid port in the valve station fluidly may fluidly connect a respective first and second fluid channel in the second inter-plate space to a valve fluid chamber defined by the valve diaphragm and the first side of the mid-plate. One or both valve fluid ports may comprise a raised valve seat to seal the valve diaphragm over the first or second valve fluid port when positive pressure is applied to the valve diaphragm via the valve actuation channel. The first fluid channel is fluidically isolated from the second fluid channel other than through the first and second valve fluid ports. A fluid channel may run in the second inter-plate space, and fluidly connect to a valve fluid chamber defined by the valve diaphragm and the first side of the mid-plate, the connection being made through two valve fluid ports in the mid-plate, so that the fluid channel runs parallel to the face of the cassette in the second inter-plate space connecting the valve fluid chamber with a cassette fluid port located within the second inter-plate space at the first edge or at a second edge of the cassette.

In another embodiment, a fluid handling cassette may comprise a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette being defined by the length and width of the first or second plate. The mid-plate may comprise a pump station defined by a pump diaphragm and the first side of the mid-plate, the pump diaphragm seated against the first side of the mid-plate and having an excursion ranged defined by the width of the first inter-plate space. The mid-plate may also comprise first and second valve stations, each defined by a valve diaphragm and the first side of the mid-plate, the valve diaphragm seated against the first side of the midplate and having an excursion range defined by the width of the first inter-plate space. There is a pump actuation channel for the pump station, and a valve actuation channel for each of the first and second valve stations. The pump actuation channel runs parallel to the face of the cassette in the first inter-plate space connecting a pump actuation chamber bounded by the first plate and the pump diaphragm with a cassette pump actuation port located within the first inter-plate space at a first edge of the cassette. And each of the valve actuation channels run parallel to the face of the cassette in the first inter-plate space connecting a valve actuation chamber bounded by the first plate and the valve diaphragm with a cassette valve actuation port located within the first inter-plate space at the first edge of the cassette. There may be an inlet and outlet valve fluid port in each of the two valve stations, and one or more pump fluid ports in the pump station, each of the valve and pump fluid ports fluidly connecting a fluid channel in the second inter-plate space with: a pumping chamber defined by the pump diaphragm and the first side of the mid-plate, and a valve fluid chamber in each of said valve stations defined by the corresponding valve diaphragm and the first side of the mid-plate. The fluid channel has a flowpath that passes through the inlet and outlet valve fluid ports and the one or more pump fluid ports, so that selective actuation of the pump actuation chamber and the valve actuation chambers allows for uni-directional flow of a fluid through the fluid channel. A fluid channel may run in the second inter-plate space, and fluidly connect to: a pumping chamber defined by the pump diaphragm and the first side of the mid-plate, the connection being made through a pump fluid port in the mid-plate, and a valve fluid chamber of each valve station, each of the valve fluid chambers being defined by the corresponding valve diaphragm and the first side of the mid-plate, each of the connections being made through two valve fluid ports in the mid-plate, so that the fluid channel runs parallel to the face of the cassette in the second inter-plate space connecting the pumping chamber and each of the valve fluid chambers with a cassette fluid inlet port and a cassette fluid outlet port located within the second inter-plate space at the first edge or at a second edge of the cassette. The cassette fluid inlet port and cassette fluid outlet port may be located at a second edge of the cassette, so that the cassette pump actuation port and the cassette valve actuation port are configured to be plugged directly into a mating actuation receptacle external to the cassette, and so that the fluid inlet port and fluid outlet port are arranged to be connected via flexible or malleable tubing to a fluid source or destination external to the cassette. A fluid channel may run in the second inter-plate space, and fluidly connect to: a pumping chamber defined by the pump diaphragm and the first side of the mid-plate, the connection being made through a pump fluid port in the mid-plate, and a valve fluid chamber of each valve station, each of the valve fluid chambers being defined by the corresponding valve diaphragm and the first side of the mid-plate, each of the connections being made through two valve fluid ports in the mid-plate. The fluid channel may then run parallel to the face of the cassette in the second inter-plate space and connect the pumping chamber and each of the valve fluid chambers with a cassette fluid inlet port and a cassette fluid outlet port, the cassette fluid inlet port and fluid outlet port exiting the cassette through rigid conduits originating on the mid-plate and penetrating the face of the cassette through the first or second outer plates.

In a further embodiment, a plurality of walls may be formed on the first and second sides of the mid-plate, said walls arranged to be fused with the first and second plates to form the actuation or fluid channels within the cassette. A first type of the walls may comprise parallel walls to define the actuation or fluid channels, a second type of the walls may comprise circumferential perimeter walls defining pump or valve actuation stations, and a third type of the walls may comprise adjacent end walls defining a channel termination at which a valve or pump fluid port penetrates the mid-plate. The first plate may comprise one or more circumferential valve or pump diaphragm retainers configured to fit within the circumferential perimeter walls of the opposing mid-plate that define pump or valve actuation stations, the retainers arranged to clamp a peripheral bead or rim of an associated diaphragm positioned in the pump or valve station of the mid-plate. The retainers may include holes, fenestrations or slots to permit transmission of actuation fluid or gas between the valve or pump actuation chamber surrounded by the retainer and an associated actuation channel. The first plate may comprise an elongate rib configured to be positioned within a mating actuation channel of the mid-plate, the cross-sectional size and length of the rib arranged to adjust the actuation channel volume to a pre-determined value between an actuation port of the cassette and an associated valve or pump actuation chamber.

In another embodiment, a fluid handling cassette may comprise a mid-plate positioned between a first plate and a second plate, said plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette being defined by the length and width of the first or second plate. The mid-plate may comprise first and second valve stations, the first valve station defined by a first valve diaphragm and the first side of the mid-plate, and the second valve station defined by a second valve diaphragm and the second side of the mid-plate, the first valve diaphragm seated against the first side of the midplate and having an excursion range defined by the width of the first inter-plate space, and the second valve diaphragm seated against the second side of the mid-plate and having an excursion range defined by the width of the second inter-plate space. A first valve actuation channel for the first valve station may run parallel to the face of the cassette in the first inter-plate space, and a second valve actuation channel for the second valve station may run parallel to the face of the cassette in the second inter-plate space. The first valve actuation channel connects a first valve actuation chamber bounded by the first plate and the first valve diaphragm with a first cassette valve actuation port located within the first inter-plate space at a first edge of the cassette, and the second valve actuation channel connects a second valve actuation chamber bounded by the second plate and the second valve diaphragm with a second cassette valve actuation port located within the second inter-plate space at the first edge of the cassette.

In another embodiment, a fluid handling cassette may comprise a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette being defined by the length and width of the first or second plate. The mid-plate may comprise first and second pump stations, the first pump station defined by a first pump diaphragm and the first side of the mid-plate, and the second pump station defined by a second pump diaphragm and the second side of the mid-plate, the first pump diaphragm seated against the first side of the midplate and having an excursion range defined by the width of the first inter-plate space, and the second pump diaphragm seated against the second side of the mid-plate and having an excursion range defined by the width of the second inter-plate space. A first pump actuation channel for the first pump station may run parallel to the face of the cassette in the first inter-plate space, and a second pump actuation channel for the second pump station may run parallel to the face of the cassette in the second inter-plate space, the first pump actuation channel connecting a first pump actuation chamber bounded by the first plate and the first pump diaphragm with a first cassette pump actuation port located within the first inter-plate space at a first edge of the cassette. The second pump actuation channel connects a second pump actuation chamber bounded by the second plate and the second pump diaphragm with a second cassette pump actuation port located within the second inter-plate space at the first edge of the cassette.

In another embodiment, a fluid-handling cassette assembly may comprise a middle cassette interposed between a first outer cassette and a second outer cassette, each cassette comprising: a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette is defined by the length and width of the first or second plate. A plurality of diaphragm valves or pumps comprising valve or pump actuation chambers may be connected to actuation channels running parallel to the face of the cassette within the first or second inter-plate space, and terminating in respective cassette valve or pump actuation ports at a first edge of the cassette between the first or second inter-plate space. A fluid-handling pod is positioned in an inter-cassette space between the middle cassette and the first or second cassette, the pod having a fluid connection to fluid channels in the middle, first or second cassette via a fluid conduit penetrating the face of the middle, first or second cassette. The first edge of the middle, first and second cassettes are located on a first side of the cassette assembly, so that the cassette valve or pump actuation ports are configured to plug into or unplug from an actuation port receptacle assembly opposite the first side of the cassette assembly. The fluid-handling pod may comprise a diaphragm pump pod having an actuation and a fluid connection to actuation and fluid channels in the middle, first or second cassette via an actuation conduit and a fluid conduit, each penetrating the face of the middle, first or second cassette. The actuation conduit of the diaphragm pump pod may connect to an actuation channel in a first or second inter-plate space of the middle, first or second cassette, and has an uninterrupted connection to a cassette actuation port for the diaphragm pump pod on the first edge of the middle, first or second cassette. The fluid conduit of the diaphragm pump pod may connect to a fluid channel in a first or second inter-plate space of the middle, first or second cassette, and may connect with a diaphragm valve in the cassette, and an actuation channel of the diaphragm valve may connect to a cassette actuation port for the diaphragm valve in the first edge of the middle, first or second cassette. The fluid conduit in any of these arrangements may be rigid. A plurality of fluid-handling pods may be positioned between the middle cassette and the first cassette, and between the middle cassette and the second cassette, and the associated fluid conduits of this plurality of fluid-handling pods may be rigid to provide structural support for the cassette assembly. A cassette assembly frame may be configured to enhance the structural stiffness of the cassette assembly, the cassette assembly frame comprising a rigid support plate on a second side of the cassette assembly opposite the first side of the cassette assembly, the support plate configured to engage a cassette loading apparatus opposite the actuation port receptacle.

In another embodiment, a fluid-handling cassette assembly may comprise: a middle cassette interposed between a first outer cassette and a second outer cassette, each cassette comprising a mid-plate positioned between a first plate and a second plate, the plates having a length, a width and a plate thickness, a first side of the mid-plate opposing the first plate and a second side of the mid-pate opposing the second plate. The first plate is spaced apart from the mid-plate defining a width of a first inter-plate space, and the second plate is spaced apart from the mid-plate defining a width of a second inter-plate space. An edge of the cassette has a cassette thickness defined by the thickness of each plate plus the width of the first and second inter-plate spaces, and a face of the cassette being defined by the length and width of the first or second plate. A plurality of diaphragm valves or pumps may comprise valve or pump actuation chambers connected to actuation channels running parallel to the face of the cassette within the first or second inter-plate space, and terminating in respective cassette valve or pump actuation ports at a first edge of the cassette between the first or second inter-plate space. A first fluid-handling pod may be positioned in an inter-cassette space between the middle cassette and the first or second cassette; the fluid-handling pod having a fluid connection to fluid channels in the middle, first or second cassette via a fluid conduit penetrating the face of the middle, first or second cassette. A second fluid-handling pod may comprise a diaphragm pump pod having an actuation and a fluid connection to actuation and fluid channels in the middle, first or second cassette via an actuation conduit and a fluid conduit, each penetrating the face of the middle, first or second cassette. The first edge of the middle, first and second cassettes may then located on a first side of the cassette assembly, so that the cassette valve or pump actuation ports are configured to plug into or unplug from an actuation port receptacle assembly opposite the first side of the cassette assembly. The actuation conduit of the diaphragm pump pod may connect to an actuation channel in a first or second inter-plate space of said middle, first or second cassette, and may have an uninterrupted connection to a cassette actuation port for the diaphragm pump pod on the first edge of said middle, first or second cassette. The fluid conduit of the diaphragm pump pod may connect to a fluid channel in a first or second inter-plate space of the middle, first or second cassette, and may connect with a diaphragm valve in the cassette, and an actuation channel of the diaphragm valve may then connect to a cassette actuation port for the diaphragm valve in the first edge of said middle, first or second cassette. The fluid conduit may be rigid. There may be a plurality of fluid-handling pods between the middle cassette and the first cassette, and between the middle cassette and the second cassette, and associated fluid conduits of this plurality of fluid-handling pods may be rigid, providing structural support for the cassette assembly. A cassette assembly frame may be configured to enhance the structural stiffness of the cassette assembly, the cassette assembly frame comprising a rigid support plate on a second side of the cassette assembly opposite the first side of the cassette assembly, the support plate configured to engage a cassette loading apparatus opposite the actuation port receptacle.

In another aspect of the invention, a manifold adaptor is configured to connect a pressure distribution manifold with a liquid-handling cassette assembly. A housing has a first side comprising a first set of transfer ports configured to connect to actuation output ports of the manifold, and has an opposing second side comprising a second set of transfer ports configured to connect to actuation input ports of the cassette assembly. The first set of transfer ports comprises a first spatial array configured to match a spatial array of the actuation output ports of the manifold. The second set of transfer ports comprises a second spatial array configured to match a spatial array of the actuation input ports of the cassette assembly, and the first spatial array of transfer ports is different from the second spatial array of transfer ports. The first spatial array may cover an area of the first side of the adaptor housing having a first length and a first width, and the second spatial array covers an area of the second side of the adaptor housing having a second length and a second width; and the second length may be greater than the first length, so that the housing of the manifold adaptor overhangs a side of the manifold. The second side of the housing may include an elastomeric wiper gasket comprising a plurality of wiper seals, each of the plurality of wiper seals being associated with a transfer port on the second side of the adaptor housing. The wiper gasket can be embedded under a top plate of the adaptor housing.

In another aspect, a seating apparatus is described for a cassette having a plug-in side and an opposing mounting side. The seating apparatus comprises: a stationary frame member connected to a movable cassette mount by a plurality of linkages on a first side of the cassette mount and on an opposing second side of the cassette mount. The linkages on the first side of the cassette mount are connected to a first stationary flange of the stationary frame member, and the linkages on the second side of the cassette mount connected to a second stationary flange of the stationary frame member. The linkages each may comprise a swing-arm having a first end pivotally coupled to the stationary flange and a second end coupled to an elongate slot in the cassette mount. The second end of the swing-arm can be configured to move in an arcuate path to move the cassette mount, so that the elongate slot restricts movement of the cassette mount by the swing arm to a linear motion toward or away from the stationary frame member. The cassette mount may comprise a first moveable flange and a first rail at the first side of the cassette mount, and a second moveable flange and a second rail at the second side of the cassette mount. Each of the moveable flanges may have a surface generally parallel to the direction of movement of the cassette mount, the elongate slot being formed in the moveable flange and oriented perpendicular to the direction of movement of the cassette mount, and the first and second rails may then be configured to hold the mounting side of the cassette. A handle assembly may be pivotally connected to the cassette mount, so that movement of a handle of the handle assembly in a direction away from the stationary frame member moves the cassette mount away from the stationary frame member; and movement of the handle in a direction toward the stationary frame member moves the cassette mount toward the stationary frame member. The pivotal connection of the handle assembly may comprise a first pivotal connection of a first handle arm to the first stationary flange, a second pivotal connection of a second handle arm to the second stationary flange, a third pivotal connection of the first handle arm to a handle swing arm connected to the first moveable flange of the cassette mount, and a fourth pivotal connection of the second handle arm to a handle swing arm connected to the second moveable flange of the cassette mount. The first and third pivotal connections and the second and fourth pivotal connections may be spaced apart from each other on the first and second handle arms. A third stationary flange of the stationary frame member may face the handle assembly and may be generally perpendicular to the first and second stationary flanges. The handle assembly may include a spring-loaded plunger configured to engage a hole or recess in the third stationary flange, so that the cassette mount may be locked into a retracted position when the handle of the handle assembly is moved toward the stationary frame member.

BRIEF DESCRIPTION OF THE DRAWINGS

Non-limiting embodiments of the present invention will be described by way of example with reference to the accompanying figures, some of which are schematic, and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 21 is an exploded view of the frame assembly shown in FIG. 20;

DETAILED DESCRIPTION

Cassettes with Liquid and Pneumatic Channels in Plane

In some pumping applications, it is advantageous to position the actuation ports of a fluidically or pneumatically actuated pump or valve cassette on the edge, thin or narrow side of the cassette, rather than on the broad side of the cassette. This allows the cassette to be plugged thin-side rather than broad-side into a receptacle comprising an array of actuation ports associated with a pressure delivery manifold. This may allow one to maximize the functions a pump/valve cassette can perform within a confined space. In some circumstances, overall space constraints may also make it advantageous to minimize the total thickness of the cassette. This can be achieved by making the cassette only minimally thicker than the excursion range of enclosed diaphragms. Ideally, each outer plate of the cassette functions primarily as the roof or end wall of any pump or valve actuation or liquid carrying chamber or channel, with a thickness insufficient to fully enclose any liquid or actuation channels to run generally parallel to the face or broad side of the cassette. The actuation channels are configured to run in a space between a midplate and an outer plate (e.g. first outer plate) of the cassette, within an inter-plate space that defines the maximum excursion range of one or more diaphragms of the cassette. The width of the inter-plate space (and consequently the maximum excursion range of a flexible membrane or diaphragm) can be pre-determined by the height of channel walls formed on the actuation and/or liquid-carrying side of the cassette midplate. The height of the channel walls on one side of a midplate may be different from the height of the channel walls on the opposing side of the midplate. For example, to accommodate a desired fluid flow rate, the channels walls on a liquid side of the midplate may be higher to provide for a greater cross-sectional area of the liquid-carrying channels, whereas the cross-sectional requirements (and thus the channel wall height) of the actuation channels on the actuation side of the midplate may be smaller.

Figure 1A:
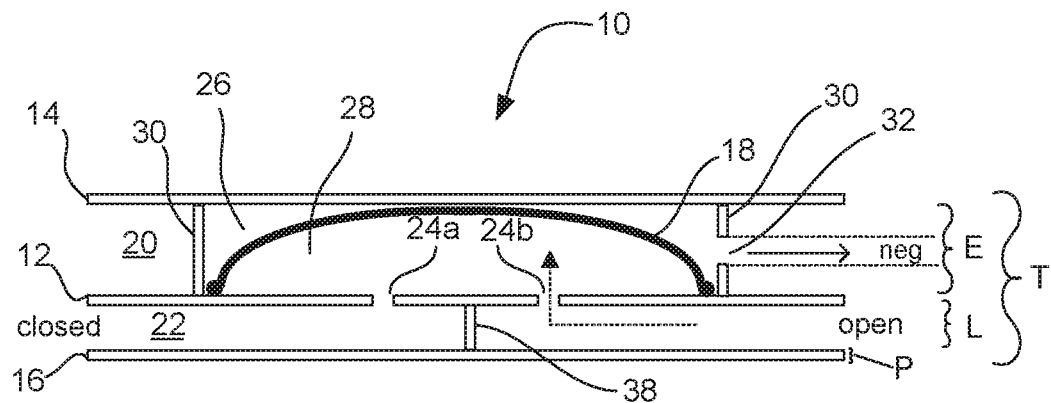
FIGS. 1A-1B are schematic cross section views of an embodiment of a pump cassette during a fill stroke and a deliver stroke.
Figure 1B:
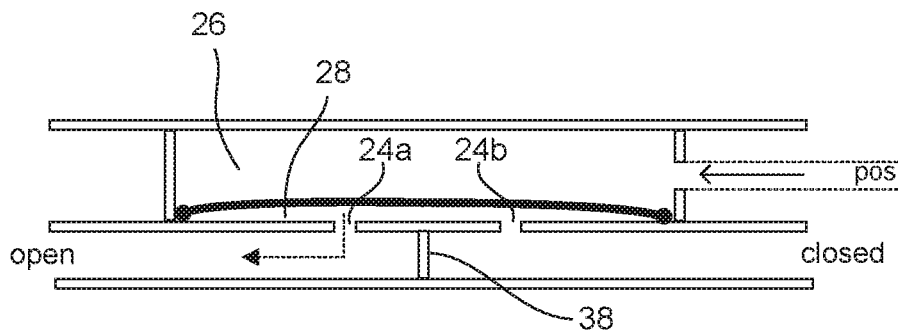
Figure 2A:
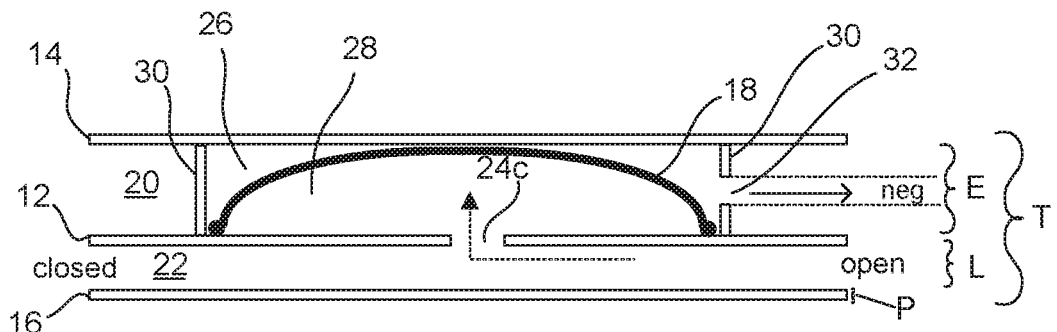
FIGS. 2A-2B are schematic cross-section views of another embodiment of a pump cassette during a fill stroke and a deliver stroke.
Figure 2B:
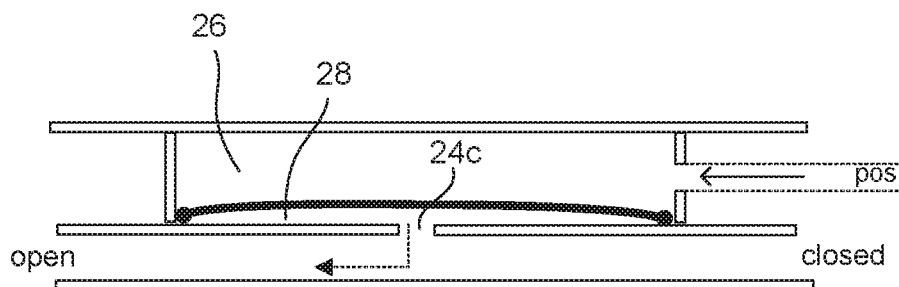

FIGS. 1A and 1B illustrate schematically a cassette 10 in cross-section near the end of a fill stroke, and near the end of a deliver stroke, respectively. A midplate 12 is positioned between a first outer plate 14 and a second outer plate 16. A flexible diaphragm 18 is positioned in the first inter-plate space 20, and liquid flow channels are present in the second inter-plate space 22. To reduce the thickness of a pump and/or valve cassette, any actuation channels preferably run in the first inter-plate space 20, a space defined by the excursion depth, depth of travel or linear range E that a diaphragm travels between the midplate 12 and the first outer plate 14. In the case of an onboard diaphragm pump, its stroke volume is a function of the depth of excursion E of its diaphragm 18 and the effective surface area the diaphragm occupies on the broad side of the cassette. The preferred depth of excursion E of a diaphragm may also depend on how efficiently the stroke volume of the diaphragm can be increased by increasing its effective surface area. In this embodiment, two pump chamber liquid ports 24a, 24b are shown, representing an inlet and an outlet, each connected to separate fluid channels within inter-plate space 22, the fluid channels schematically separated by wall 38. (The direction of liquid flow shown is arbitrary, and depends on which liquid line is open or closed by a downstream valve during a diaphragm fill stroke or delivery stroke). In another embodiment, as shown in FIGS. 2A and 2B, a single pump chamber liquid port 24c (or two or more such ports) may be used, which then alternates between being an inlet port and an outlet port depending on which downstream valves are open or closed in the single liquid line in inter-plate space 22. When the volume of actuation chamber 26 is at a minimum, the corresponding pump chamber 28 is at a maximum (fill stroke, see FIG. 1A, 2A). When the volume of actuation chamber 26 is at a maximum, the volume of corresponding pump chamber 28 is at a minimum (deliver stroke, see FIG. 1B, 2B). Once the excursion depth E of the diaphragms on the cassette have been chosen, the cassette thickness T can be reduced by avoiding locating actuation ports directly over the diaphragms being actuated (as in prior art designs). This is accomplished by placing the actuation ports on the thin or narrow side of the cassette and running actuation channels to their respective diaphragms in the first inter-plate space 20 in the cassette 10. This space is delimited by midplate 12 onto which the diaphragm 18 is seated and first outer plate 14 that provides a cover or roof for the actuation chamber 26 for each diaphragm 18. Surrounding the perimeter of each diaphragm is a wall 30 spanning the inter-plate space 20 that, together with the outer plate 14, completes each actuation chamber 26, except for an actuation port or window 32 connecting the actuation chamber 26 to its corresponding actuation channel (represented by the arrow in the first inter-plate space 20). The actuation channel then runs in the inter-plate space 20 to a peripheral edge or narrow side of the cassette, terminating there as a cassette actuation port (see, e.g. FIG. 9). Note that the actuation channel can be smaller than the depth provided by the inter-plate space 20, depending on what excursion depth E has been specified for the diaphragm 18. To minimize the overall thickness T of the cassette 10 for a given specified diaphragm excursion depth E, one can minimize the nominal thickness P of each plate 12, 14, 16 (within structural rigidity constraints, and any constraints placed on achieving a proper welding or cementing of the outer plate to the channel walls of the midplate). Depending on fluid flow rate requirements, one can also minimize the thickness of the cassette by reducing the depths of the liquid flow channels (i.e. the height of the channel walls) within the second inter-plate space 22.

The overall thickness T of the cassette can depend on the amount of depth required by the liquid flowpaths or channels on an opposing side of the midplate 12 of the cassette 10 within the second inter-plate space 22. In the pump shown in FIGS. 1A-1D and the valve shown in FIGS. 3A, 3B, the required depth of the liquid channel determines the depth of the second inter-plate space 22. Depending on the liquid flow rates specified for the cassette, the second inter-plate space 22 may have a depth L substantially smaller than the depth E of the first inter-plate space 20.

Figure 3A:
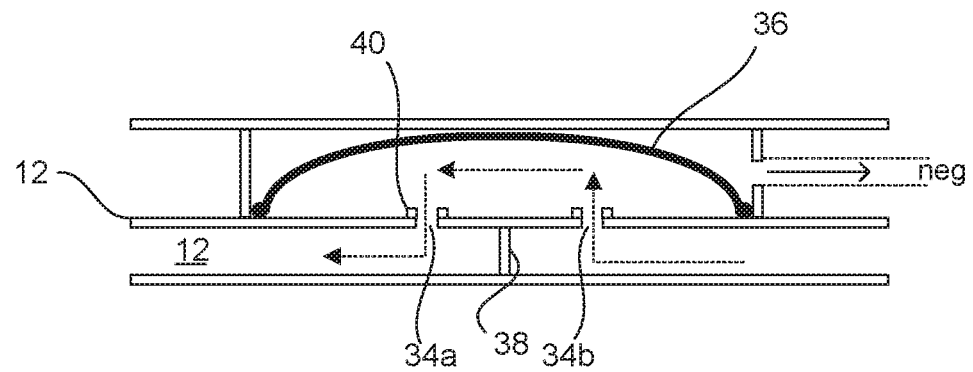
FIGS. 3A-3B are schematic cross-section views of an exemplary diaphragm valve during operation.
Figure 3B:
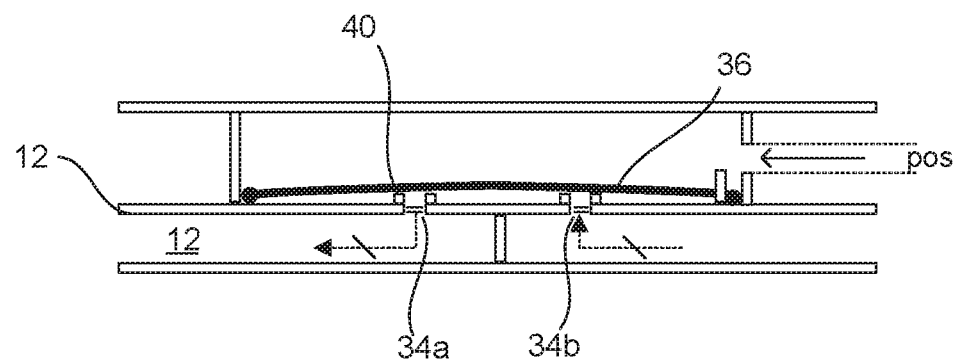

As shown in FIGS. 3A,B, for any given diaphragm valve station, there are at least two liquid channels: a first channel terminating into valve port 34a of midplate 12, and a second channel terminating into valve port 34b of midplate 12. (In some embodiments a plurality of liquid channels could terminate into separate valve ports in the midplate of a single valve station). As shown in FIGS. 3A and 3B, the excursion depth E is determined in the case of a diaphragm valve by the degree of relaxation required to allow the diaphragm 18 to lift away from the fluid ports 34a,b it is designed to occlude. The valve diaphragm 36 may then move away from the ports 34a, b under negative actuation pressure to allow liquid flow as shown in FIG. 3A, or may move to occlude the ports 34a, b under positive actuation pressure to interrupt liquid flow as shown in FIG. 2B. The separate liquid channels in the valve station of a cassette are represented schematically by the wall 38 shown in the second inter-plate space 12. In the illustration shown, the valve ports 34a, b may optionally comprise raised elements 40 (placed circumferentially around the valve port) to improve the sealing efficiency of the diaphragm. Such a raised element may only need be present around one of the valve ports to be effective. Thus as the valve diaphragm relaxes or is drawn away from the liquid ports of the valve, liquid is allowed to flow from one liquid channel, through its associated port into a liquid valve chamber, and then out through the liquid port of a second liquid channel connected to that valve station. The choice of cross-sectional area of the liquid channels may depend on a desired liquid flow resistance and a desired hold-up volume or dead space occupied by the liquid channels in the cassette. The desired cross-sectional area of the liquid channels will in turn determine the depth of the liquid channel (or channel wall height) occupying the second inter-plate space 22 between the cassette midplate 12 and the second outer plate 16. The liquid and actuation channels may be formed from the midplate or the respective outer plates, or may be formed independently of the outer plates or midplate. In a preferred arrangement, the midplate is formed in a mold, 3-D printed or otherwise cast with the desired channel walls on both sides of the midplate, so that the construction of the outer plates can be simplified. The outer plate 14 may comprise the roof or diaphragm-limiting wall of the actuation chamber 26, and the outer plate 16 may comprise the roof or the liquid channels in the cassette. In this way, the inter-plate space between the midplate and the outer plates can be further reduced.

As shown in FIG. 1A, in a preferred embodiment the thickness T of a pump or valve cassette 10 can thus be defined by the nominal thicknesses P of each of the midplate and the two outer plates, plus the excursion depth E of the diaphragm 18 and the depth L of the liquid channels defined by the second inter-plate space 22 provided on the cassette. To maximize the efficiency of positioning and distributing valve and pump stations on the midplate 12, it may be advantageous to place some actuation channels and actuation chambers on both opposing sides of a single midplate 12. In this case, the thickness T of a cassette will be determined by the excursion depth of the largest diaphragm on each side of the midplate. For example, if the excursion depths E of the pump diaphragms are the same on each side of the midplate 12, then the thickness T of the cassette will be equal to $(2 \times E)+(3 \times P)$.

Figure 4A:
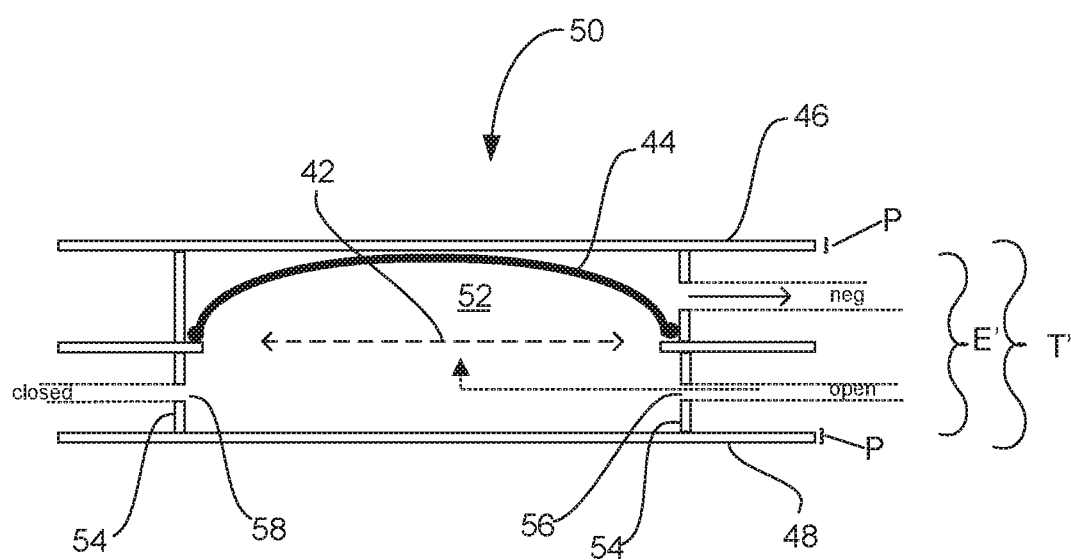
FIGS. 4A-4B are schematic cross-section views of another embodiment of a pump cassette during operation.
Figure 4B:
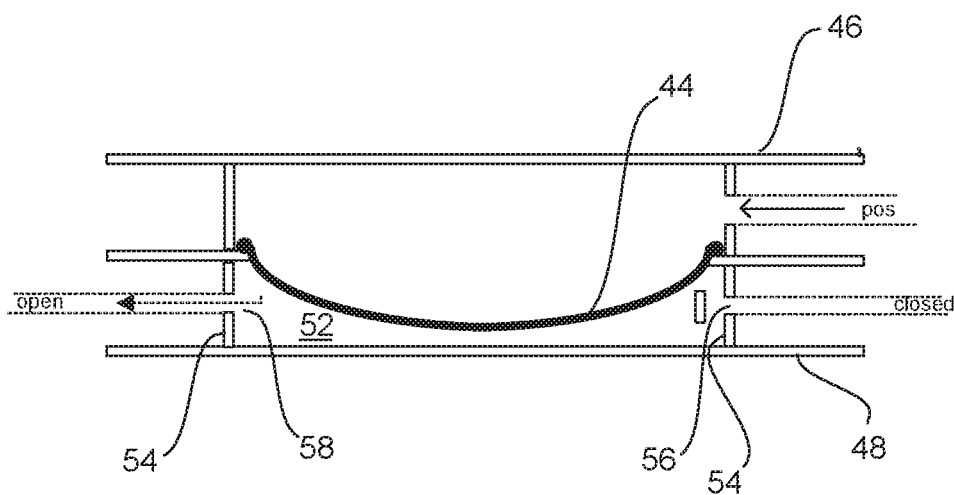

FIGS. 4A and 4B show an alternate embodiment of a diaphragm pump of a pump cassette 50. In this case, the pump chamber fluid ports have been replaced by a wide aperture 42 through which diaphragm 44 can pass as it moves from a fill position (FIG. 4A) to a deliver position (FIG. 4B). The overall thickness T' of this cassette is thus determined from the total excursion distance or length E' of the diaphragm 44, plus the thickness P of the two outer plates 46, 48. The pump diaphragm 44 exploits virtually the entire thickness of the cassette 50 to substantially increase the stroke volume of the pump. In this case, the pumping chamber 52 is defined by the liquid side of diaphragm 44 and a circumferential sealing wall 54 capped by the second outer plate 48. Liquid inlet/outlet pump ports 56, 58 are shown in this embodiment, although other embodiments may include only a single port acting as both inlet and outlet, or may include a plurality of ports whose inlet or outlet function is determined by downstream valves in liquid channels associated with each pump port. In this arrangement, the overall thickness of a cassette can be minimized, because the stroke volume generated by the diaphragm is essentially doubled in the absence of the midplate. For any desired pump stroke volume, the inter-plate distances can thereby be reduced substantially.

Figure 5A:
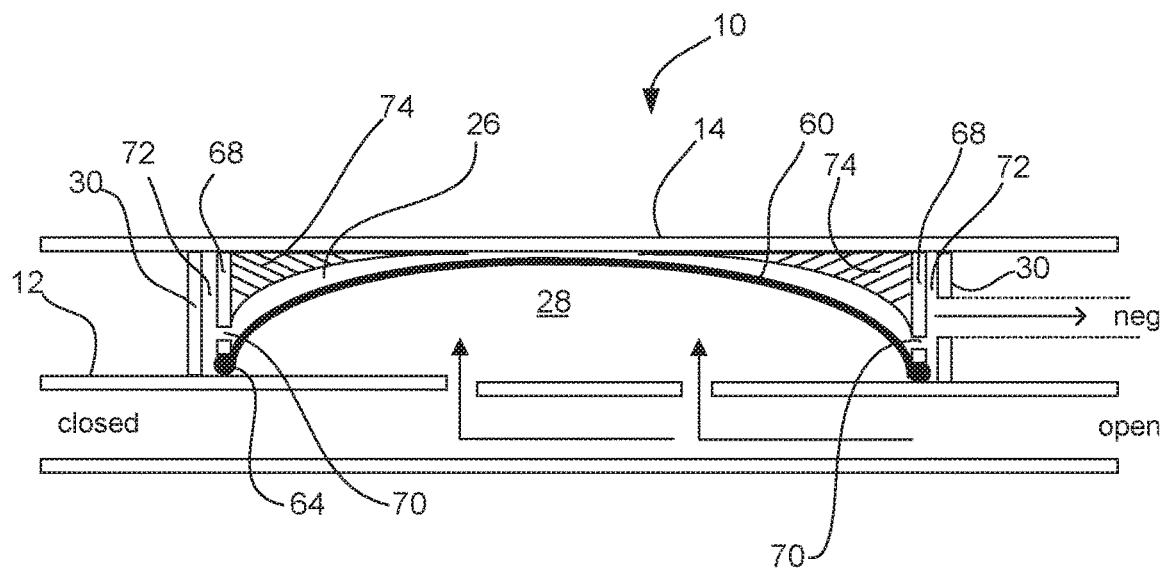
FIGS. 5A-5B are schematic cross-section views of optional additional features of exemplary pump cassettes during operation.
Figure 5B:
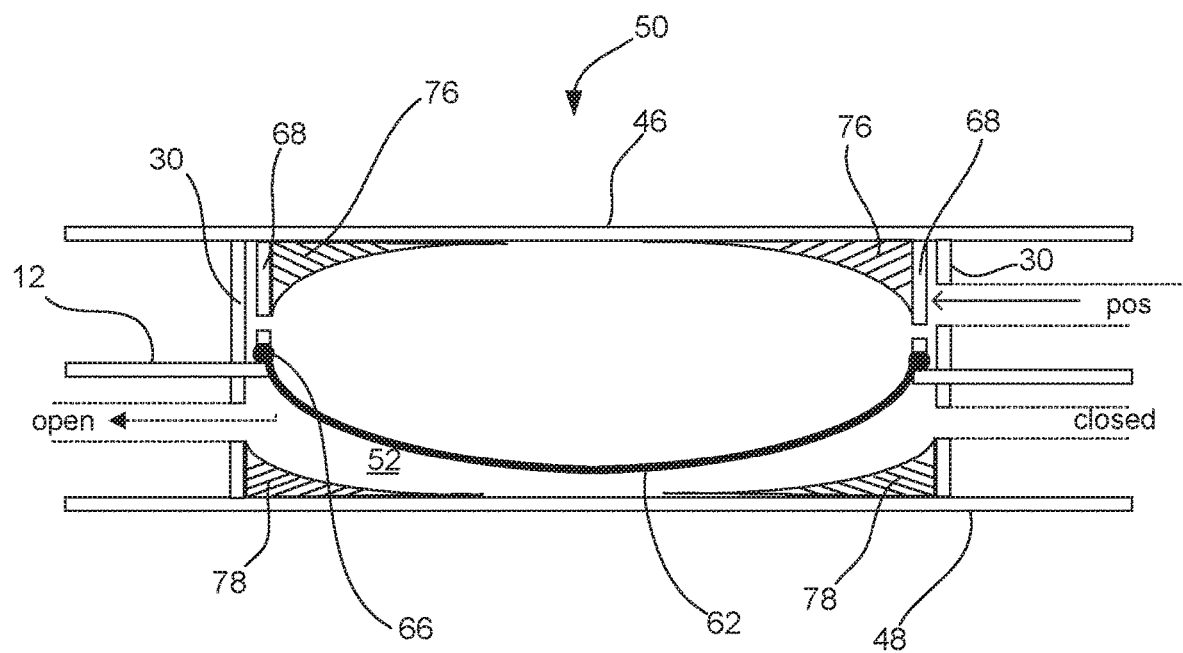

FIGS. 5A and 5B show additional features that optionally may be included in a pump or valve cassette. In this case diaphragms 60, 62 are shown to be secured against the midplate 12 by a diaphragm retainer or retaining wall 68 (also see retainer 100 in FIG. 8). In other embodiments, the perimeter bead 64, 66 respectively of diaphragms 60, 62 can be secured to the midplate 12 by an adhesive, by heat welding, by having a section of the midplate over-molded to surround and clamp the bead, by applying a solid continuous ring into position against the diaphragm bead, or by a number of other methods that ensure that the diaphragm is secured to the midplate and that a seal is formed between the diaphragm bead and midplate to segregate the liquid chamber 28 from the actuation chamber 26. In the example shown, a retainer or retaining wall 68, 100 is installed inside the perimeter wall 30 of the actuation chamber 26. Shown in cross-section, the illustrated portion of the retaining wall 68 displays two fenestrations, slots, windows or holes 70 that permit actuation pressure (e.g. pneumatic pressure) to be transmitted to the actuation side of the diaphragm 60. For most of its circumference, the retainer or retaining wall 68 extends uninterrupted from the inner side of the first outer plate 14 or 46 to a position adjacent the bead 64, 66 of diaphragm 60, 62. If the bead is made of elastomeric material, the retainer or retaining wall 68, 100 acts to partially compress the bead during assembly of the cassette as the first outer plate is installed against the opposing mid-plate. A tight fit helps to ensure that the diaphragm is securely installed and that an air/water-tight seal has been formed. In a preferred arrangement, two or even a plurality of retaining wall fenestrations 70 (or holes) can be distributed around the circumference of the retaining wall 68, so that positive or negative actuation pressure can be transmitted to a plurality of sections of the diaphragm 60, 62 relatively simultaneously.

In some cases, it may be advantageous to ensure that there is a continuous rigid clamping structure against the entire circumference of the diaphragm bead or rim. In that case, a plurality of holes in the retention wall 68, 100 may be preferable to a slot that extends to the diaphragm bead. Alternatively, a continuous rigid ring (e.g. metal or plastic washer) (not shown) applied against the diaphragm bead can be combined with a slotted retention wall 68, 100 to achieve the same result. Preferably, the outer edge of the ring or washer abuts the inner side of the perimeter wall of the valve or pump station and compresses only the bead portion of the diaphragm, and the inner edge of the ring or washer avoids contact with the diaphragm as it transitions from the diaphragm bead to the diaphragm body.

In the example shown, the diameter of the retainer or retaining wall 68, 100 is small enough to allow a gap 72 to exist between it and the perimeter wall 30 of the actuation chamber 26. The gap 72 permits fluidic or pneumatic actuation pressure to be distributed to the individual fenestrations 70 of the retaining wall 68. The retainer or retaining wall 68, 100 can be a separate element that is assembled with the other components of the cassette, or it may be formed or co-molded with either the midplate 12 or the first outer plate 14 of the cassette.

FIGS. 5A and 5B also illustrate that the inner wall of the actuation or first outer plate 14 or 46 optionally can comprise a curved buttress 74 or 76 that helps to conform the inner wall of the actuation chamber 26 to the curvature of the diaphragm 60, 62 as it extends fully toward the actuation-side first plate 14 or 46. This may help to reduce stress on the more peripheral portions of the diaphragm 60, 62 when fully retracted into the actuation chamber 26. Similarly, as shown in FIG. 5B, a curved buttress 78 can be positioned along the end wall (liquid or second outer plate 48) of the liquid pumping chamber 52 for a similar reason. In these examples, shaping the inner wall of the outer plates 14, 46 and 48 does not require the overall thickness of either cassette 10 or 50 to be increased. The buttresses 74, 76, 78 can either be separate inserts attached to the respective outer plates, or may be formed and co-molded with the outer plates such that any additional thickness of the outer plate is made to encroach the inter-plate space rather than extending beyond the outer surface of the outer plate. The outer plates may be molded to curve inward from the outside of the plate toward the actuation chamber or liquid chamber, while not increasing the overall thickness of the cassette.

Figure 6:
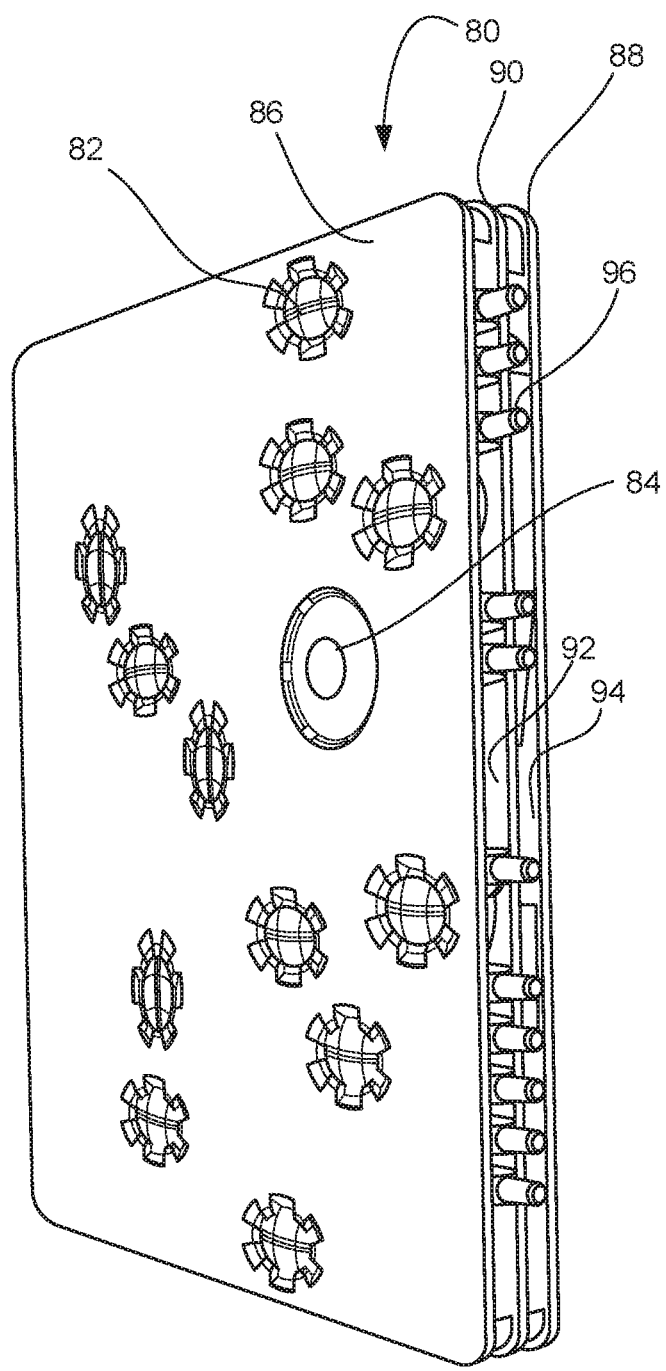
FIG. 6 is a perspective view of an exemplary pump or valve cassette.
Figure 7:
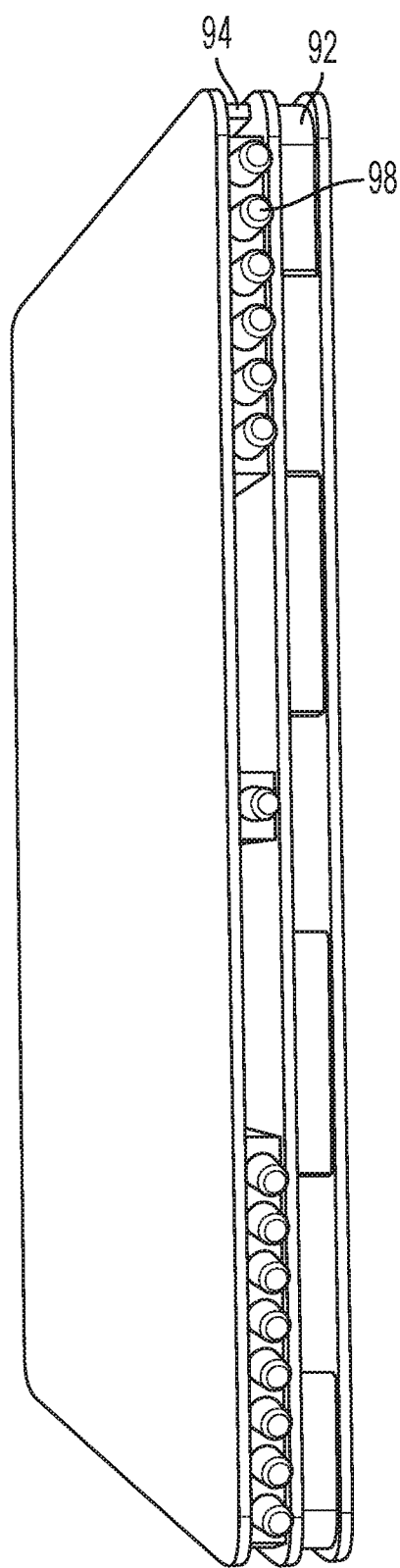
FIG. 7 is a front perspective view of the pump or valve cassette shown in FIG. 6.

FIG. 6 shows a rear perspective view of an exemplary cassette 80 that includes a plurality of valve stations 82 and an exemplary pump station 84. In one example, a cassette was constructed to have a length of about 16 cms, a width of about 19 cms and a thickness of about 1.5 cms. The first outer plate or actuation plate 86 has been molded with indentations on its external surface at the valve 82 and pump 84 stations to provide a curved inner surface to conform with the associated diaphragms in those regions. In this example, the nominal thickness of each of the first outer plate 86, the second outer plate or liquid-side plate 88 and the midplate 90 is approximately 2 mm, whereas the overall thickness of the cassette is approximately 15 mm. The first 92 and second 94 inter-plate spaces are each approximately 4.5 mm wide. In this example, the pump diaphragm has an excursion range approximately equal to the 4.5 mm wide first inter-plate space 92. The cassette actuation channel ports 96 are shown arrayed within the first inter-plate space 92 of the cassette 80. Thus a diaphragm excursion of about 4.5 mm can be achieved in a cassette whose width is about 10.5 mm plus the width desired for liquid channels in the second inter-plate space 94. In this case the second inter-plate space 94 has the same width as the first inter-plate space 92, but in other embodiments it could be less (depending on the flow characteristics desired for the liquid channels). In this example, the excursion range of a cassette diaphragm is about 30% of the total cassette width. FIG. 7 shows a front perspective view of the cassette of FIG. 6, revealing the cassette liquid channel ports 98 arrayed within the second inter-plate space 94 of the cassette 80.

Figure 8:
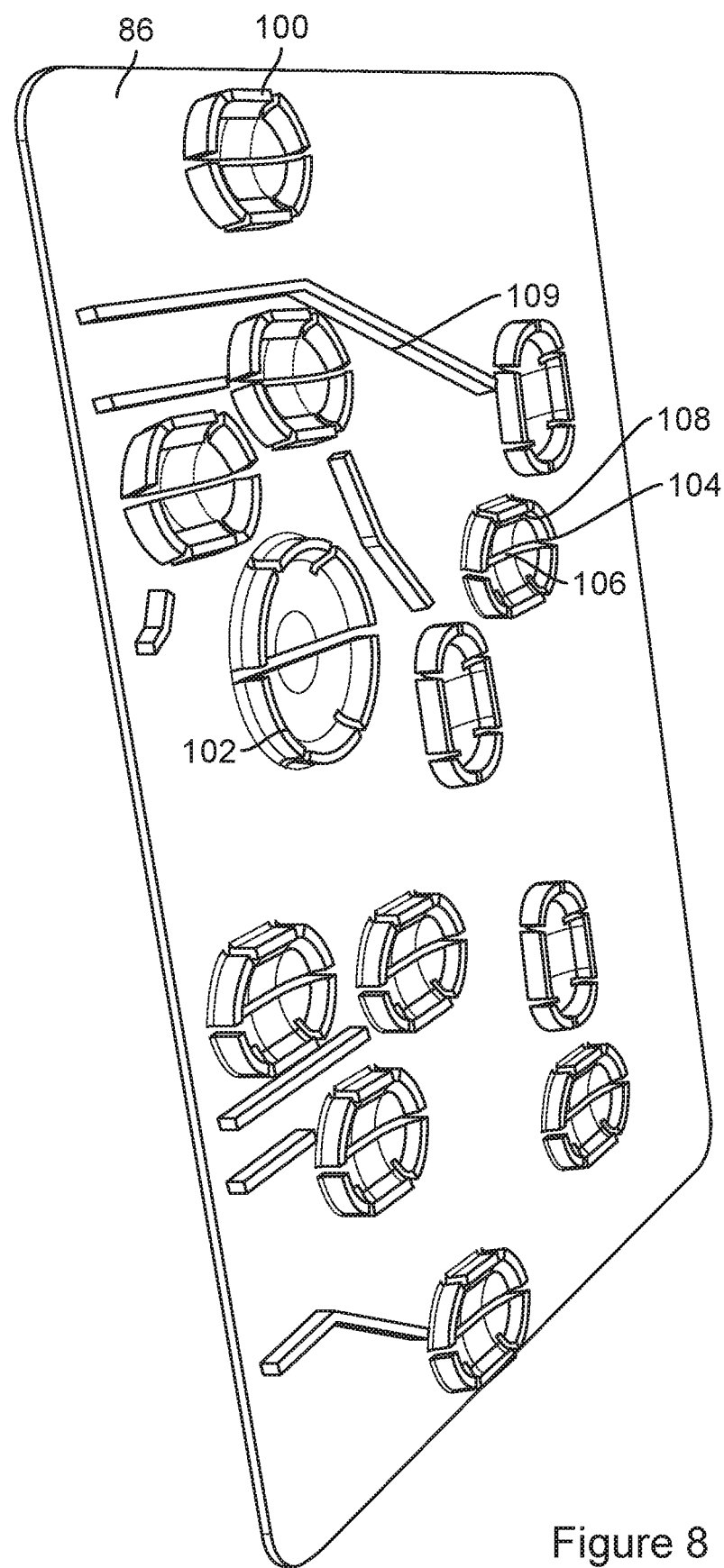
FIG. 8 is a perspective view of an inner side of an outer plate of the exemplary cassette shown in FIGS. 6 and 7.

FIG. 8 shows a perspective view of the inner side of the first outer plate 86 of cassette 80. In this example, the diaphragm retainer or retaining walls 100, 102 have been molded as an integral part of the internal side of the first outer plate 86. (In dual-duty cassettes, both sides of the mid-plate may be pump or valve actuation sides, so that both the first and second outer plates may include retainers or retaining walls 100, 102). In this example, each diaphragm retainer 100, 102 has a number of fenestrations or holes 104 and optionally a top-side groove 106 to distribute actuation pressure evenly over the diaphragm to be retained against the midplate 90. The curved inner walls 108 of the outer plate 86 in the valve and pump stations are arranged to conform with the associated diaphragm shape as it extends fully into the actuation chamber (within which the retainers 102 are placed). In some cases, optionally, ribs 109 may be included in the mold of the outer plate 86, which are configured to encroach mating actuation channels of the opposing midplate. Ribs 109 may be constructed to have a cross-sectional size and length to adjust the total volume of the associated actuation channel to a pre-determined volume. (This may help to minimize the amount of pneumatic gas volume to be delivered (or compressed), and may improve the responsiveness of the associated diaphragms to actuation by a pressure delivery manifold.

Actuation volume adjustment ribs may be particularly advantageous in an arrangement in which both sides of the midplate carry actuation and/or fluid channels, or in which the inter-plate space must accommodate a greater diaphragm excursion range. In that case, installing actuation volume adjustment ribs reduces the transmission volume of the actuation channels and may improve the performance of a cassette. In addition, when synchronous valve actuation is desired, it may be advantageous to match the actuation channel transmission volume between sets of valves having varying distances from the actuation ports of the cassette. Properly sized volume adjustment ribs can be used to fine-tune the cassette valve operations in this manner.

Figure 9:
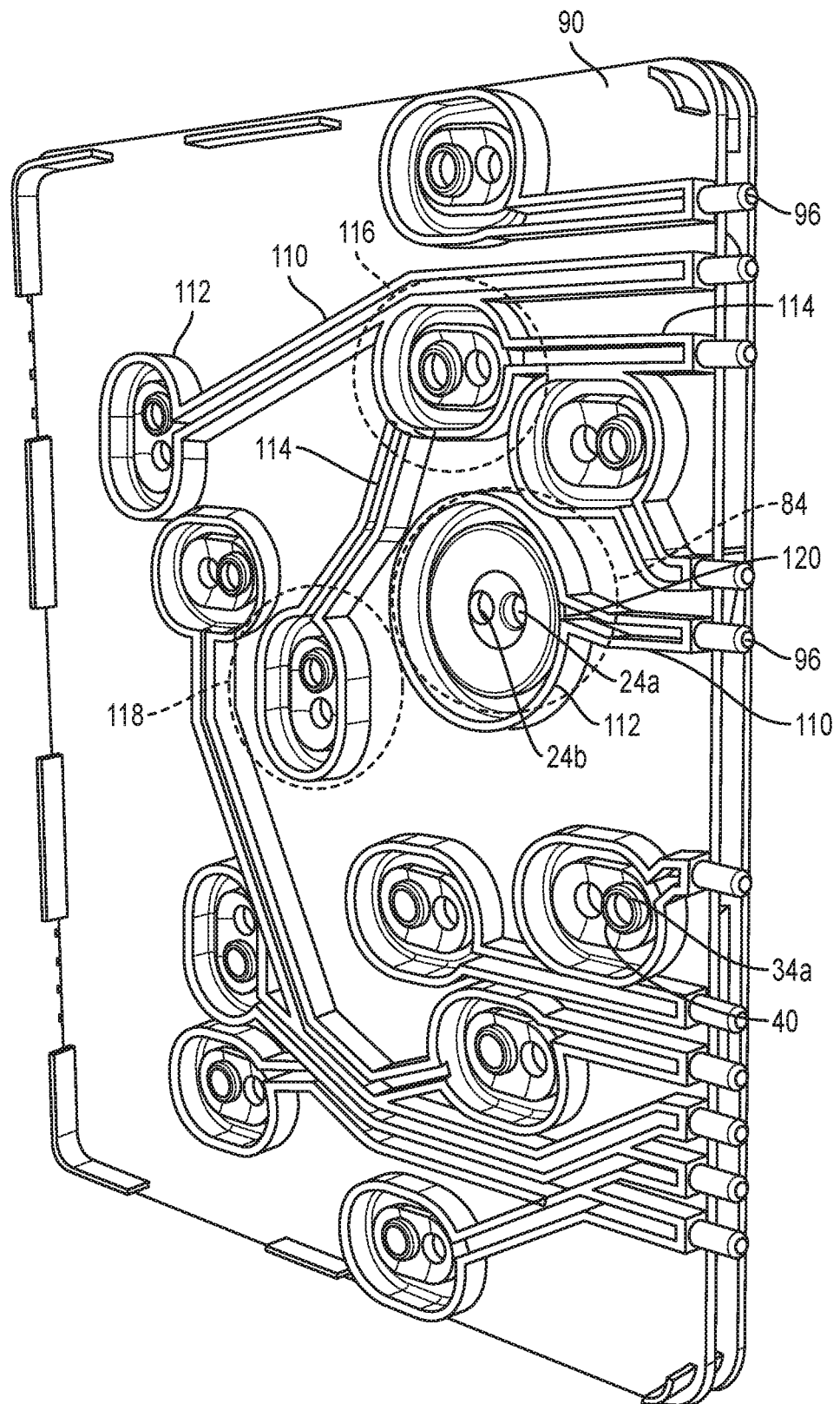
FIG. 9 is a perspective view of an actuation side of a midplate of the exemplary cassette shown in FIGS. 6, 7 and 8.

FIG. 9 shows a perspective view of the actuation side of the midplate 90 of cassette 80. In this example, the actuation channels 110, valve and pump station perimeter walls 112, and cassette actuation ports 96 have been formed or molded as part of the midplate 90. In this example, most of the diaphragm valve or pump stations are fed by a separate actuation channel 110 leading from a dedicated cassette actuation port 96. The cassette's fluidic or actuation channels can be a individually formed conduits, or each channel may comprise two walls spanning the inter-plate space, fused to and extending between the mid-plate and either the first outer plate or the second outer plate. In some cases, it may be desirable to actuate two or more valve stations at once, in which case a single actuation channel path 114 can supply the two or more valve stations, as shown with valve stations 116, 118. Each valve station is surrounded by a perimeter wall 112 that seals the station when the adjacent first outer plate 86 is welded to the midplate 90.

The cassette plates can be formed (e.g., injection molded) from moldable plastic material such as polysulfone that cures to a hard or rigid consistency. Other plastics or materials such as metal can also be used. Other methods of molding can be used, as well as newer techniques such as 3-D printing, to form the midplate and outer plates. The outer plates can be fused to the midplate using adhesives, or localized heating from ultrasonic or mechanical vibration. In a preferred method, the outer plates can be transparent, translucent, or can permit transmission of laser wavelengths to allow laser welding of the outer plates to an opaque midplate. The welding seals the valve and pump regions of the outer plate to the perimeter walls and channels of the respective valve and pump stations of the midplate.

Each perimeter wall 112 forms part of the actuation chamber of the respective valve or pump station, and each communicates with an actuation channel 110 via an actuation chamber port 120 in the perimeter wall 112. The pump station 84 in this example has two pump ports 24a, 24b connecting the liquid channel on the opposite (second) side of the midplate with the first side of the midplate shown in the drawing. One of these can function as a pump chamber inlet, while the other functions as a pump chamber outlet. In other embodiments, the pump region can have a single pump port or a plurality of pump ports. The valve stations in this example each have two ports connecting two separate liquid channels on the second side of the midplate with the valve station on the first side of the midplate shown. Also, in this example, one of the valve ports 34a has a raised perimeter lip 40 to improve sealing of the valve diaphragm against the valve port when positive pressure is applied to the diaphragm.

Figure 10:
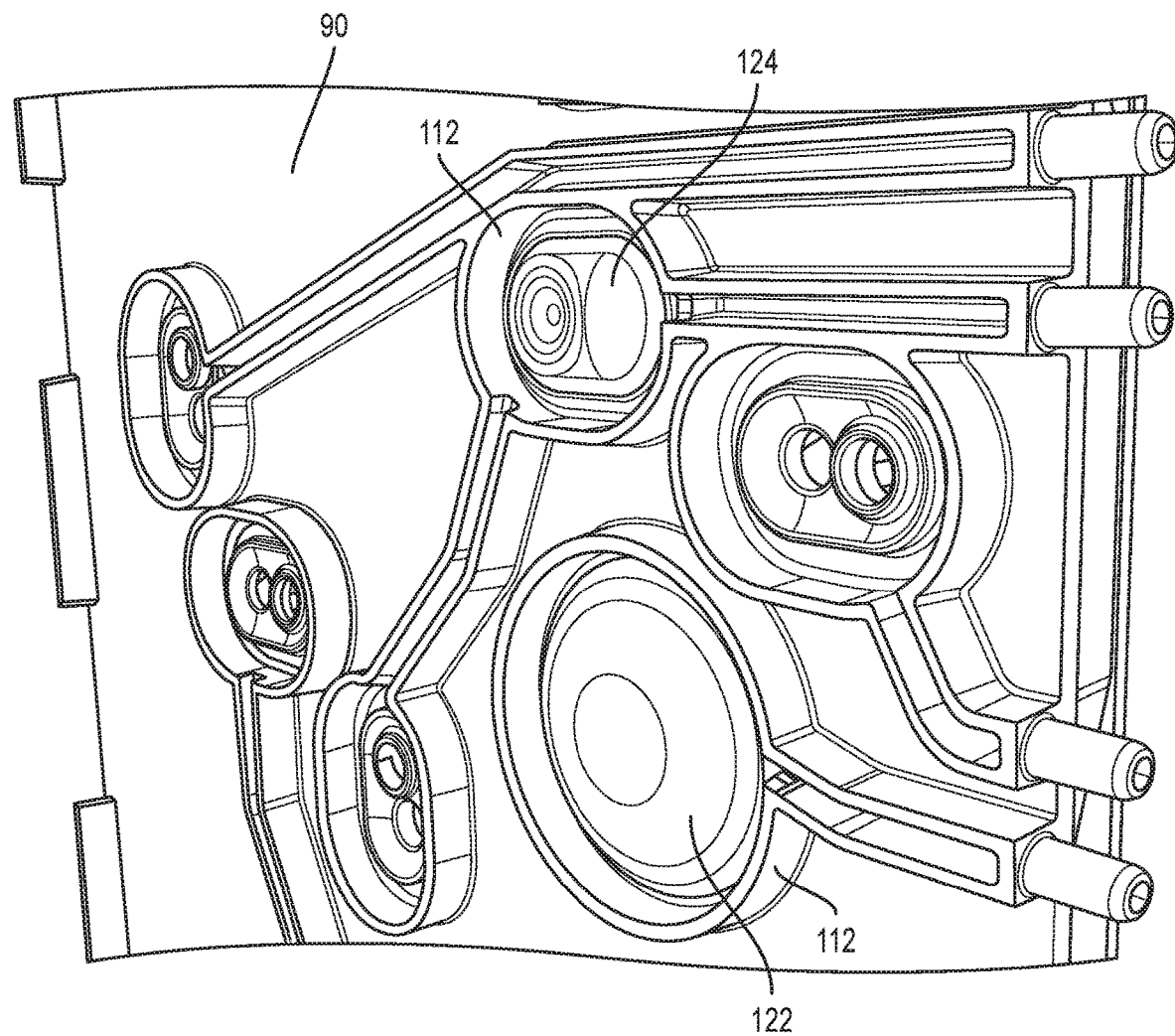
FIG. 10 is a close-up view of pump and valve stations of the actuation side of the midplate shown in FIG. 9.

FIG. 10 shows a close-up view of the midplate 90 of FIG. 9. In this case, a pump diaphragm 122 and valve diaphragm 124 are shown to be installed in their respective pump and valve stations. The diaphragms are held in place and sealed against the midplate 90 by corresponding retention walls or retainers 100, 102 shown in FIG. 8. Note that the retention walls or retainers 100, 102 fit (loosely) within the circumference of the perimeter or chamber walls 112 of the respective valve or pump stations. The difference in diameter of the perimeter wall and retention wall is sufficient to allow a gap 72 (see FIG. 5A) to exist between the two, so that actuation fluid or gas pressure can be distributed uniformly around the associated diaphragm.

Figure 11:
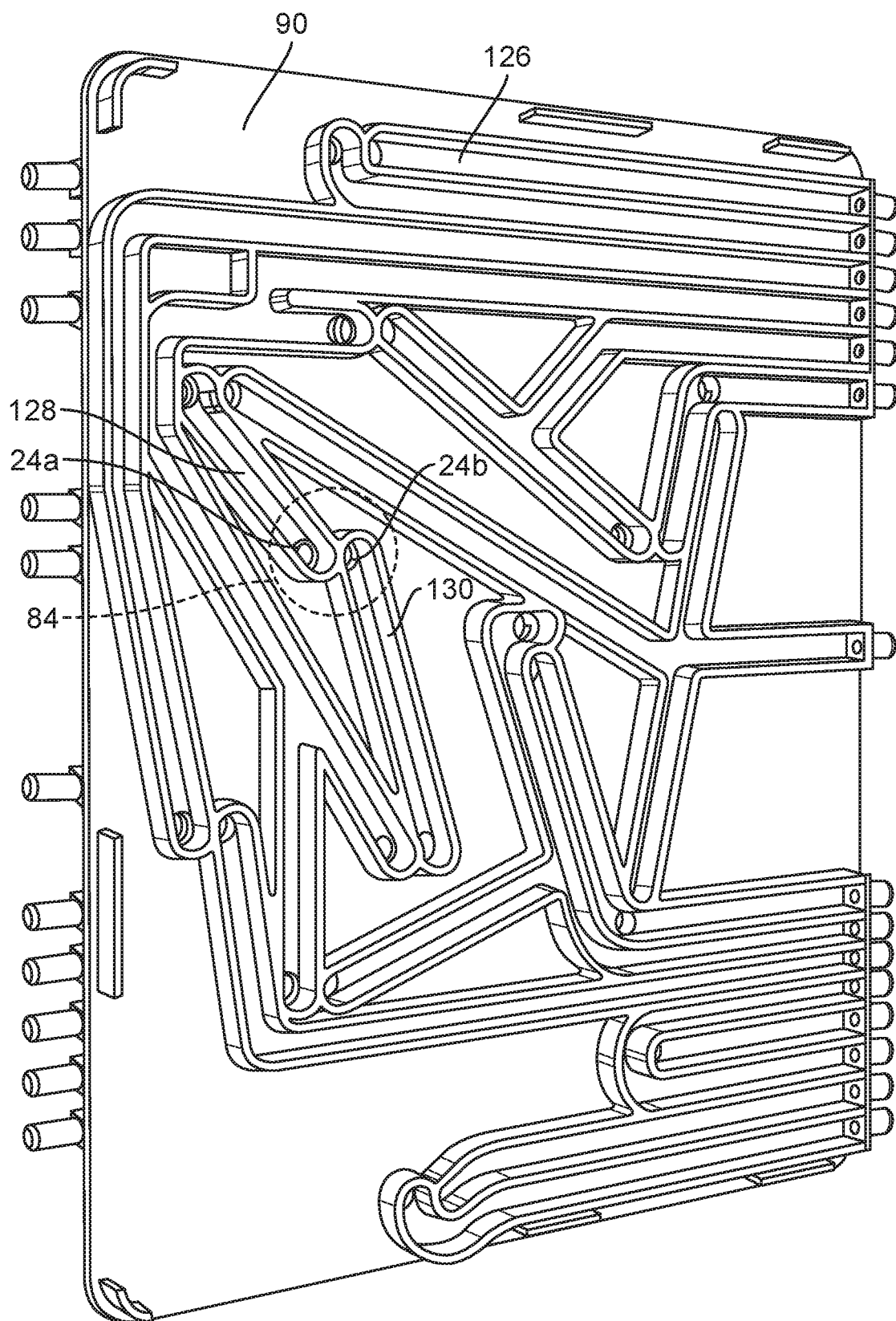
FIG. 11 is a perspective view of a fluid side of a midplate of an exemplary pump or valve cassette.

FIG. 11 shows the second side of midplate 90 of cassette 80. In this example, the liquid channels 126 have been molded in as part of the midplate 90. In the case of a pump station 84, each of the two ports 24a, 24b is associated with a separate liquid channel 128, 130, so that one port functions as an inlet port of the pump chamber, whereas the other port functions as an outlet port of the pump chamber. Whether a particular port functions as an inlet or outlet can be determined by which downstream valve is actuated or closed.

Figure 12:
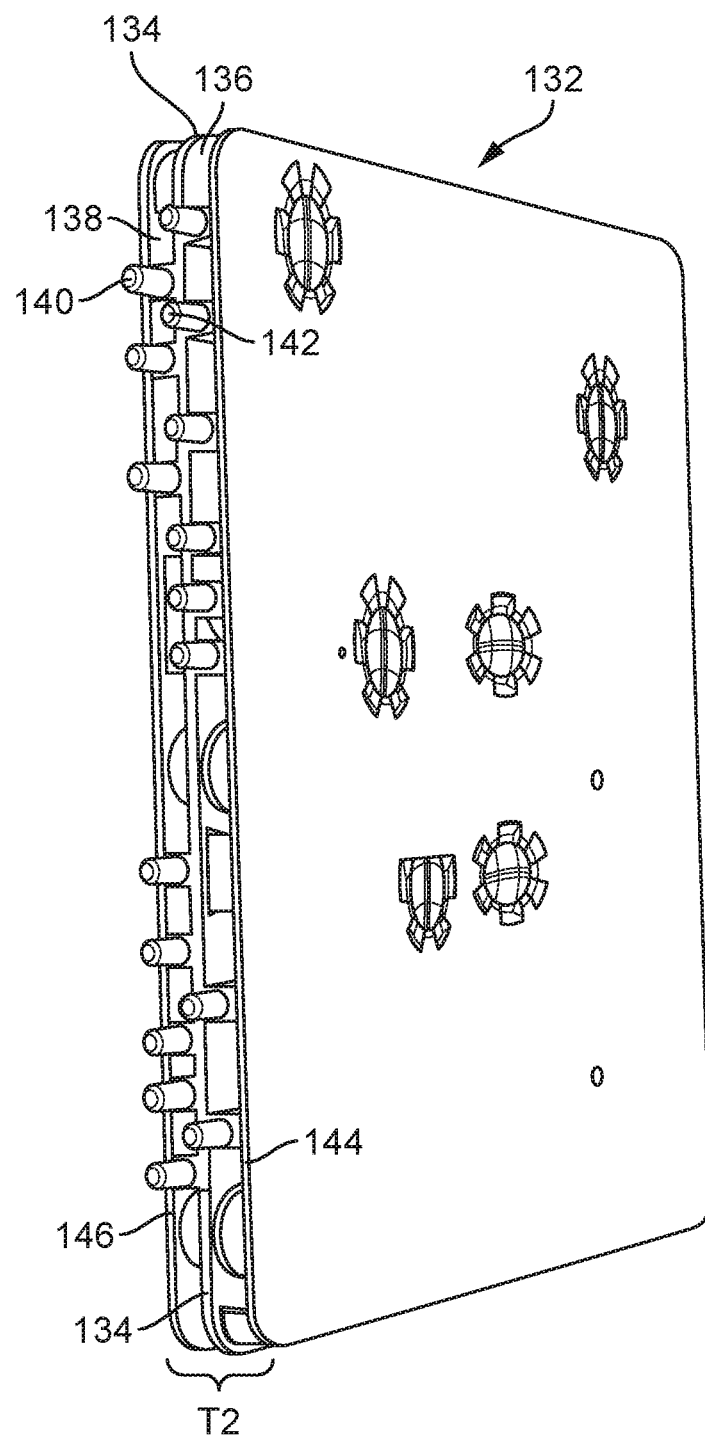
FIG. 12 is a perspective view of another embodiment of a pump or valve cassette.

FIG. 12 shows a variation of a cassette 132 that includes additional optional features (which may be individually included or excluded in any cassette design). In this case, the cassette incorporates actuation ports, actuation channels and actuation chambers on both sides of a midplate 134. Each of the first inter-plate space 136 and second inter-plate space 138 includes both actuation and liquid channels, as well as actuation and liquid cassette ports. In this view, two rows of actuation ports 140, 142 are visible on an edge or narrow side of the cassette, which allows that edge of the cassette to be plugged into a connector or interface communicating with a pressure distribution manifold. In this embodiment, the overall thickness T2 of the cassette, which includes the thickness of each of the midplate 134, first outer plate 144 and second outer plate 146, plus the width of the first 136 and second 138 inter-plate spaces, allows pump or valve diaphragms to be seated on either the first or second side of the midplate, or both. This potentially increases the number of valve or pump stations that can populate a cassette having a given broad-side dimension. In this embodiment, the overall thickness T2 of the cassette can be minimized while maximizing the density of pump or valve stations that can be included on the cassette 132, with the excursion ranges of the enclosed diaphragms comprising a substantial majority of the overall thickness of the cassette. For example, in a cassette with such a 'double-duty' midplate (allowing actuation channels and chambers on both sides of the midplate), nominal plate thicknesses of 2 mm, coupled with inter-plate spaces that are 5 mm each to accommodate diaphragm excursions of 5 mm, results in an overall cassette thickness of 16 mm, nearly ⅔ of which comprises desired diaphragm excursion ranges.

Figure 13:
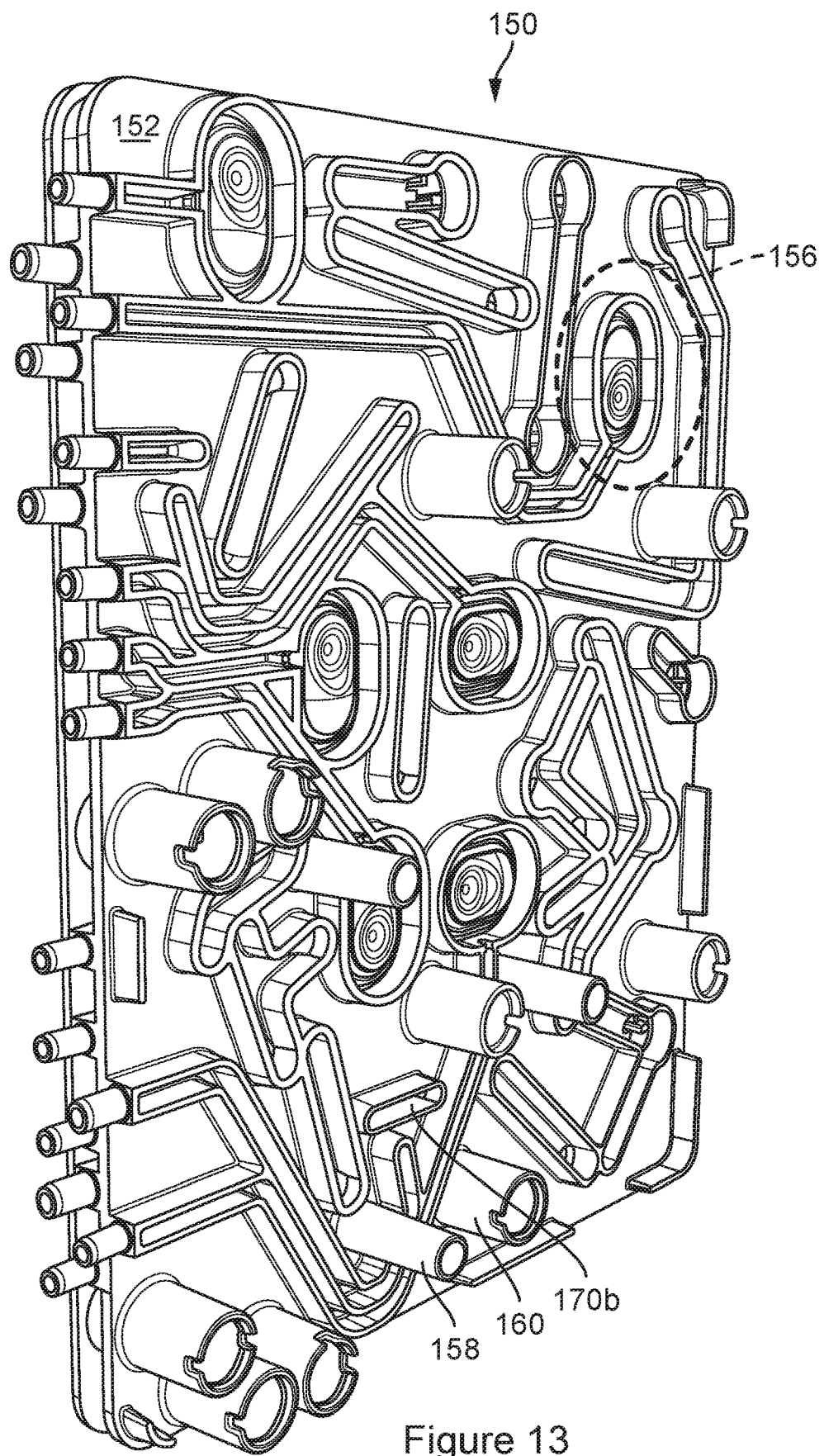
FIG. 13 is a perspective view of a first side of a midplate of the exemplary cassette shown in FIG. 12.

FIGS. 12 and 13 show a dual-duty cassette midplate 150 in which each of the first 152 and second 154 sides of the midplate include both actuation and liquid handling channels, incorporating actuation ports, actuation channels, actuation chambers, and liquid channels on each side of the midplate. A plurality of valve stations 156 are shown in this example, although on-board pump stations can also be included in other embodiments. In this respect, the cassette is similar to cassette 132 of FIG. 12.

Optionally, this midplate 150 is additionally designed to be used in a cassette assembly that incorporates outboard pump pods or liquid mixing pods whose volume requirements prevent including them as onboard pump or mixing chamber stations on an individual cassette. Where larger liquid stroke volumes are needed, two or more cassettes can be arranged so that liquid or actuation lines can be connected to extension conduits 158, 160 perpendicular to the face of the cassette that can connect to external pods situated between two cassettes. The conduits originate in the cassette mid-plate (e.g. formed or molded with the mid-plate), and penetrate either the first or second outer plate to provide for a direct connection to an external self-contained diaphragm pump, self-contained mixing chamber, or self-contained balancing chamber. If the conduits are rigid, they may also serve as structural members that help to hold the cassette assembly together. The perpendicular conduits may also be used as liquid ports for connection to a fluid source or destination external to the cassette. In this case, the conduit termination may be constructed to make a connection with a flexible or malleable tube. In this type of cassette, the cassette actuation ports and initial portions of the actuation channels can still all be located in the inter-plate space of the cassette, until they reach the point at which the fluid or actuation line must exit the cassette to connect to an associated pod pump, balancing chamber pod or mixing chamber. With this configuration, the cassette assembly is a substantial improvement over previously disclosed cassette assemblies because of the more efficient arrangement of the cassette actuation ports. Since the actuation ports are all located along an edge of the cassette, the cassette can be plugged directly into an associated pressure delivery manifold or a rigid receptacle array without the need for flexible tubing connections and separate connectors.

Figure 14:
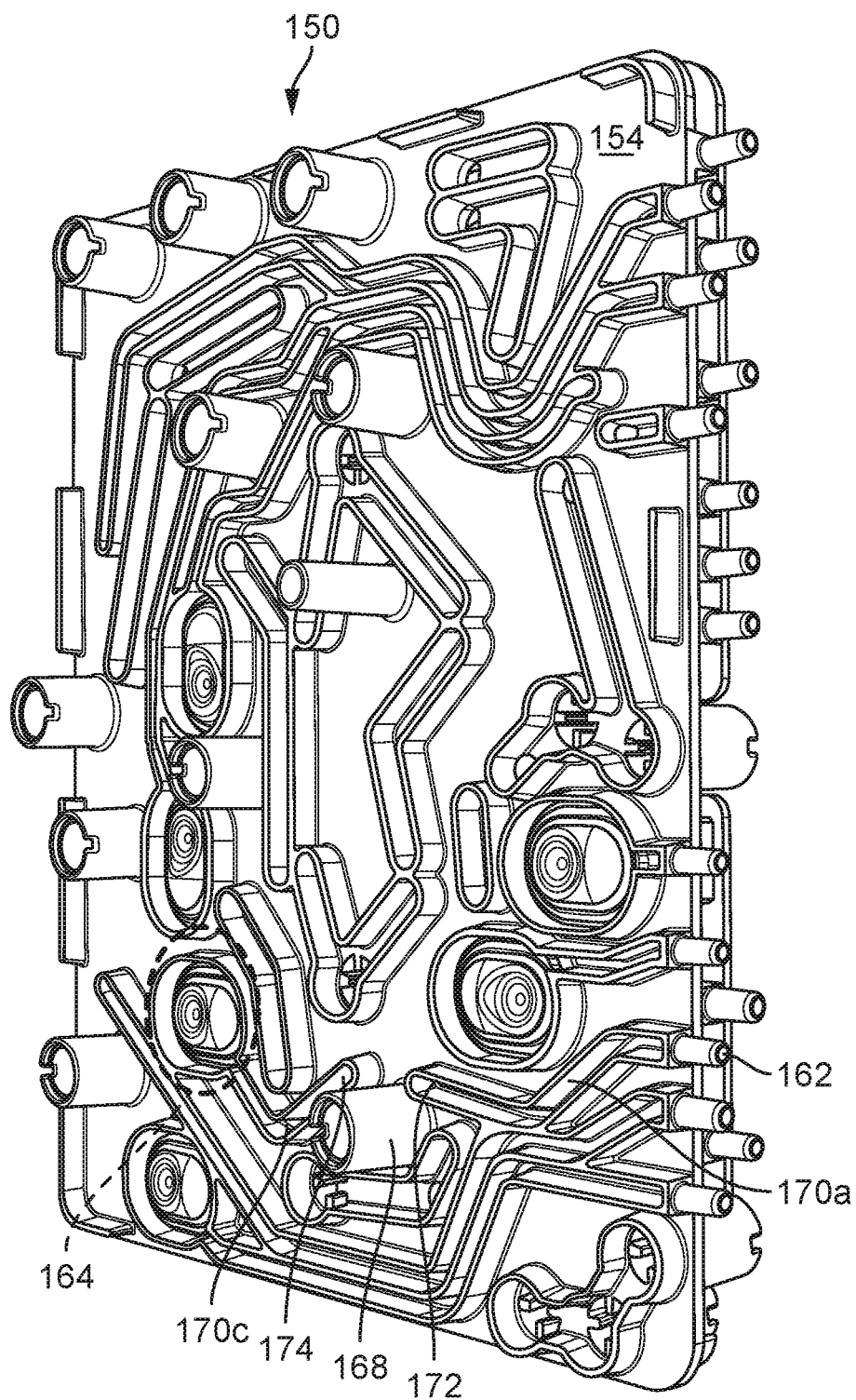
FIG. 14 is a perspective view of a second side of the midplate shown in FIG. 13.

The cassette midplate 150 in FIGS. 12 and 13 also shows that actuation channels and liquid channels can be routed from one side to the opposing second side of the midplate in order to increase the number of valve or pump stations that can be incorporated within a cassette of a particular size. The routing of an actuation or liquid channel may be impeded by the presence of other channels, pump stations or valve stations that prevent a direct route from a cassette port to the destination valve or pump station. In that case, re-directing the actuation or liquid channel to the first/second side of the midplate may allow the channel to bypass an obstructing structure on the second/first side of the midplate. The bypassing channel may simply make a single midplate penetration to the opposing side, or it may penetrate the midplate to bypass an obstructing structure, and then return to the starting side of the midplate to reach its pump or valve station destination. FIG. 14 shows the second side 154 of cassette midplate 150. An actuation port 162 arranged to supply valve station 164 lacks an uninterrupted path to the valve station because of the presence of an extension conduit 168. Actuation channel 170a connected to cassette actuation port 162 terminates in an actuation channel port 172 that penetrates the midplate 150. As shown in FIG. 13, actuation channel 170b on the first side 152 of midplate 150 can connect actuation channel 170a with actuation channel 170c via actuation channel port 174, to complete the actuation channel pathway from cassette actuation port 162 to valve station 164.

Figure 15:
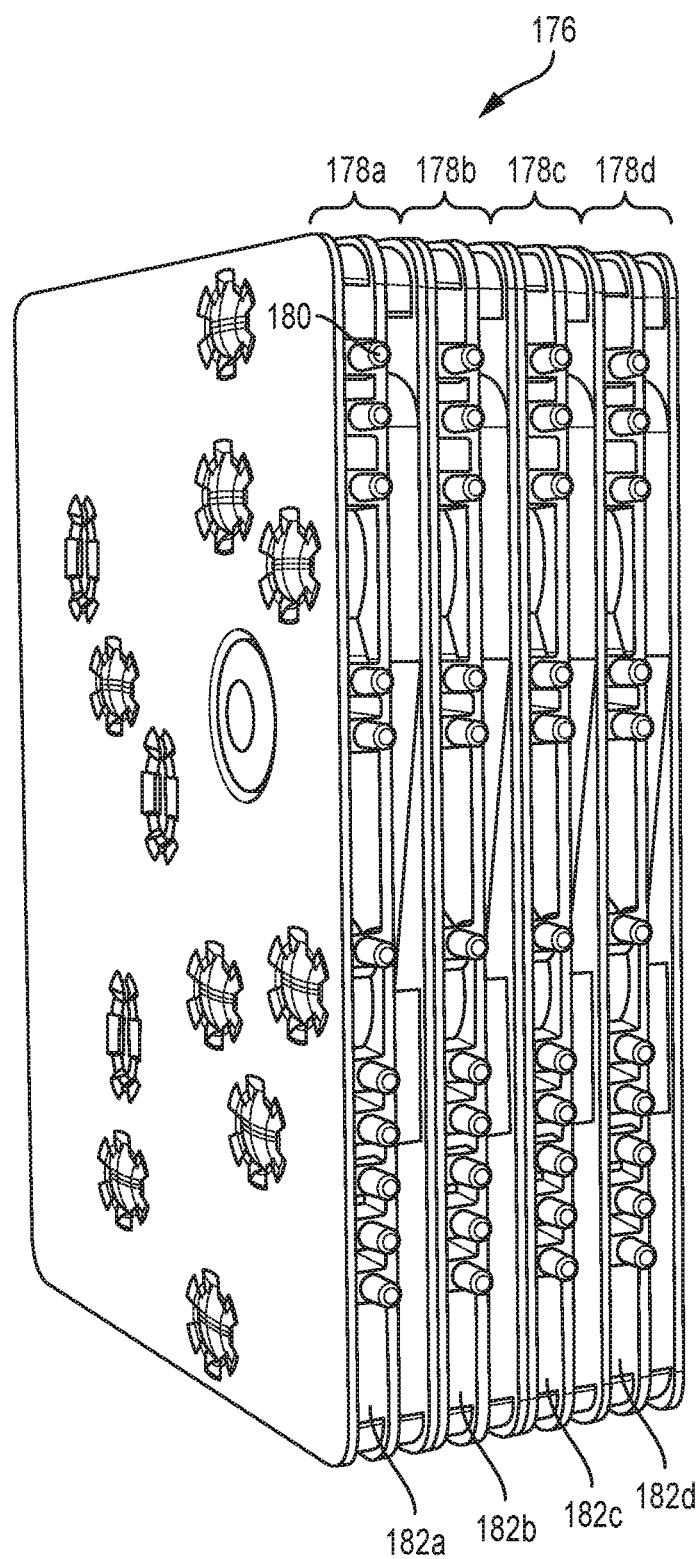
FIG. 15 is a rear perspective view of a cassette assembly.

Whether a cassette includes actuation channels and chambers, as well as liquid channels, on both sides of the midplate (i.e. a dual-duty midplate), a cassette can be arranged to have liquid cassette ports located on a narrow side or edge of the cassette, so that a plurality or bank of such cassettes can be stacked together to form a compact cassette group. FIG. 15 is a rear perspective view of a cassette group 176 comprising a plurality of individual cassettes 178a-d stacked broad-side to broad-side. Each cassette 178a-d has one or more cassette actuation ports 180 located on the narrow side of the cassette in the first inter-plate space 182a-d, with the actuation ports facing in the same direction so that the individual cassettes of the cassette group can be plugged into their respective corresponding connectors or receptacle ports of a receptacle assembly, the connectors or receptacle ports positioned next to each other and connected, mounted or attached to a pressure distribution manifold.

The cassettes of a cassette group can be arranged to be in contact with each other, whether or not they are fused or adhered to one another. Alternatively, they may be placed next to each other loosely or with some spacing, so that each cassette of a group can be individually inserted or removed from its corresponding receptacle assembly without disturbing the neighboring cassettes. This allows for individual cassettes to be placed on rails or tracks so that their actuation ports can be properly aligned with their respective connectors or receptacles, and so that they can more easily be inserted and removed. The cassette receptacle assemblies can be located next to each other to provide for a spatially compact cassette group. Optionally, the cassette receptacle assemblies may be located within a single housing, which can provide alignment and insertion/removal tracks for the individual cassettes. Or each cassette receptacle assembly may be included in a separate housing for the same purpose. In the setting of providing for individualized fluid circulation to an array of objects, the arrangement allows for a single cassette to be swapped out with a cassette having different features (with respect to number and distribution of pump and valve stations, and liquid flowpaths). Thus as the fluid circulation requirements for any individual object change, the cassette group configuration allows for convenient and rapid adaptation of a cassette with the needs of its associated object. Furthermore, neighboring cassettes of a cassette group can be interconnected via their respective liquid ports by means of, for example, jumper lines. In this way, complex liquid mixing procedures can be carried out when solutions with particular constituents at particular concentrations need to be provided to an object. Thus one or more cassettes of a cassette group can be dedicated to a single object if desired.

Figure 16:
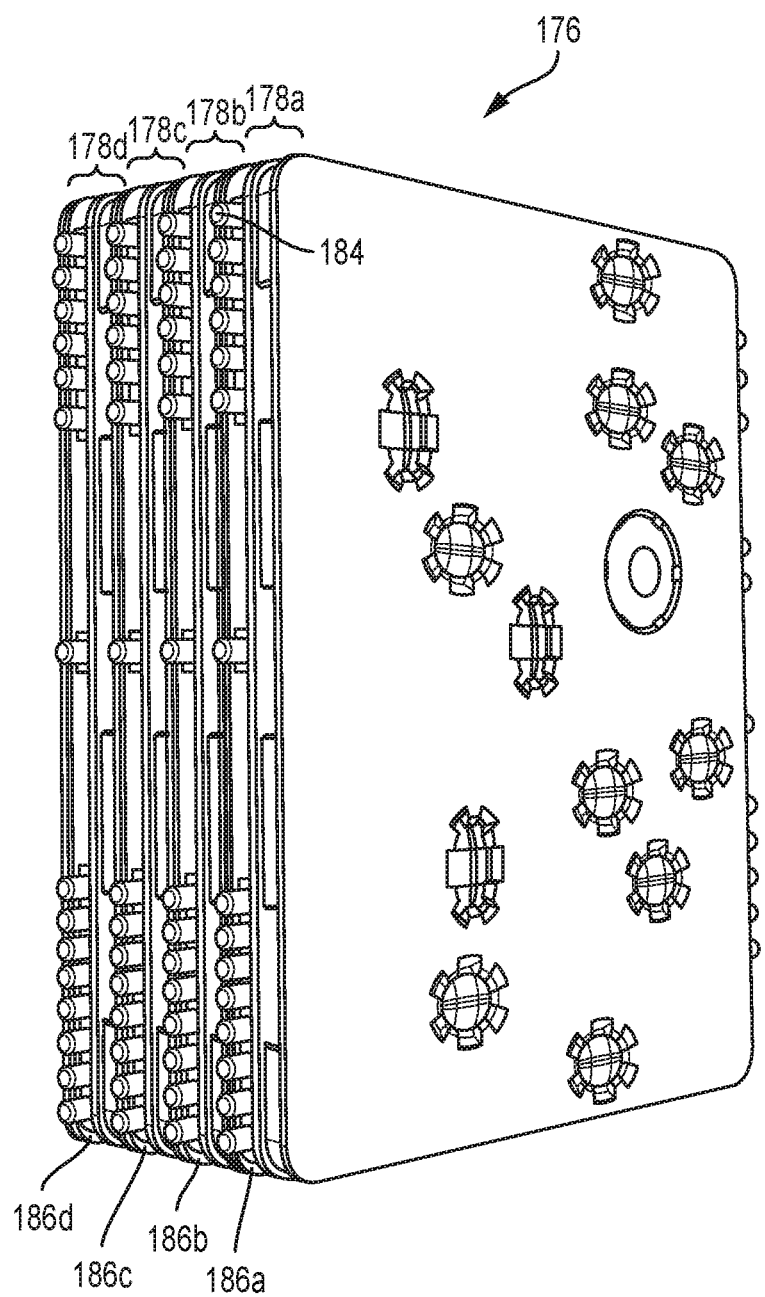
FIG. 16 is a front perspective view of the cassette assembly shown in FIG. 15.

FIG. 16 is a front perspective view of the cassette group 176 of FIG. 15. In this example, for convenience of illustration the cassette liquid ports 184 are located on a narrow side of each cassette 178a-d opposite that of the actuation ports 180. Although the actuation ports are preferably arrayed on the same corresponding edges of the cassettes (so that a pressure delivery manifold can be positioned behind the cassette group), the liquid ports of the individual cassettes need not all be positioned along the same edges of the cassettes. In this embodiment, the cassette liquid ports 184 are positioned within the second inter-plate spaces 186a-d of the respective cassettes 178a-d. The cassette group 176 can thus be oriented so that it is facing externally from one or more receptacle assemblies (not shown) connected, mounted or attached to a pressure distribution manifold. Each cassette 178a-d is capable of providing liquid circulation to a separate object, so that the number of individual cassettes in a group can be matched to an equal number of objects that require liquid circulation. For example, a plurality of biological cell stations, tissues or organs arrayed for growth, experimentation or testing can be supplied with circulating liquids, drugs, nutrients or other chemicals by a plurality of cassettes in a cassette group, each cassette potentially providing each cell station, tissue station or organ station with liquid solutions having similar or different compositions. A cassette group such as cassette group 176 can also be configured to serve as a solution mixing station, with the liquid output of one cassette of the group providing the liquid input of a neighboring cassette in the group, allowing for complex solution mixing protocols. As such, two or more cassettes can be re-configured to serve a single object.

FIG. 17A shows a rear perspective view, and FIG. 17B shows a front perspective view of a cassette group 186 that incorporates dual-duty midplate cassettes 188a-d. In other embodiments, a cassette group can incorporate one, two or more dual-duty midplate cassettes among one or more single-duty midplate cassettes. In this case, representative second inter-plate space 182a-d actuation ports 190 and representative first inter-plate space 186a-d liquid ports 192 are shown. Depending on the number and size of the individual pump and valve stations in the cassettes 188a-d, using dual-duty midplate cassettes may permit the placement of a greater density of multi-purpose valve and pump stations in a relatively confined space.

Figure 18:
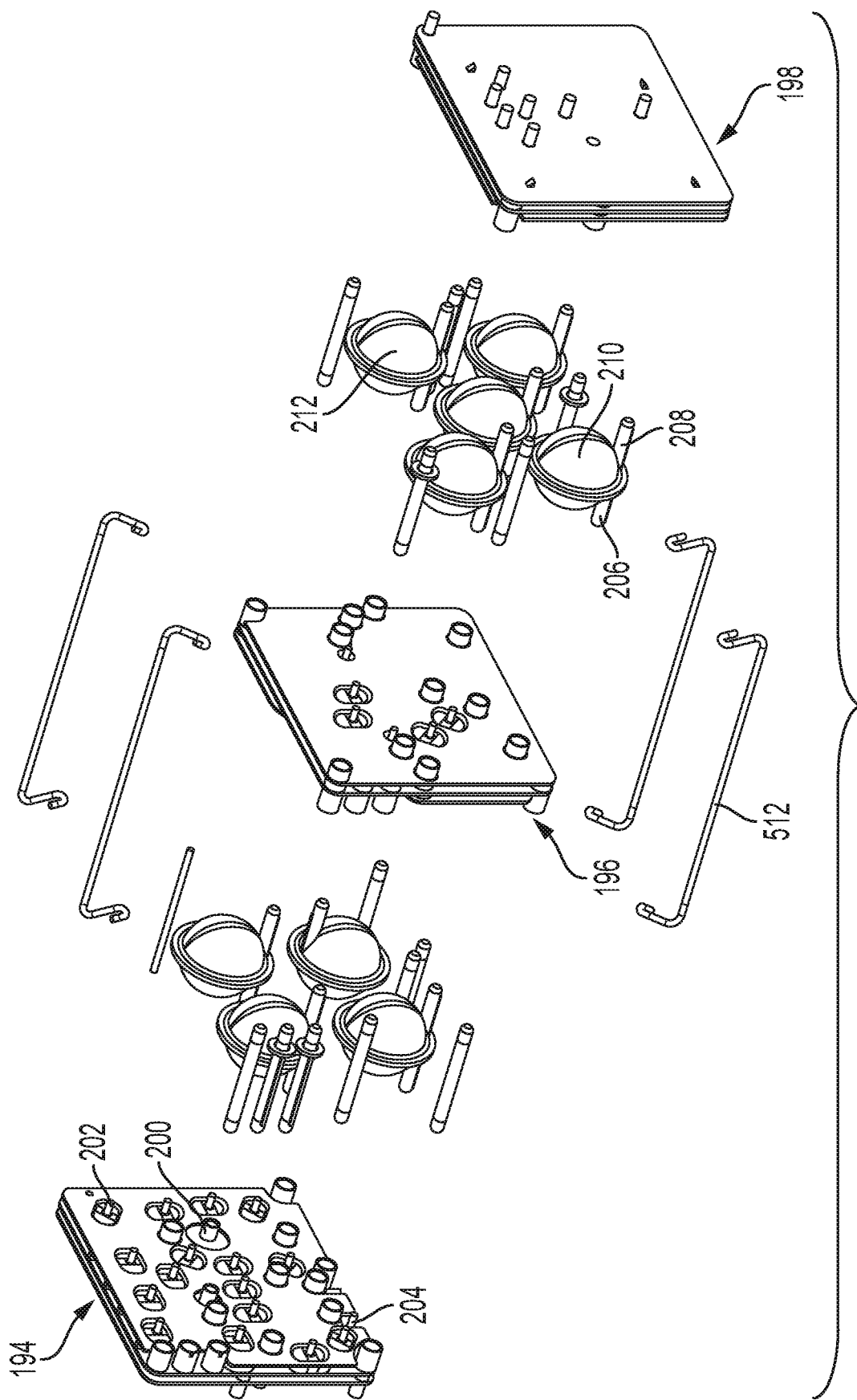
FIG. 18 is an exploded view of a prior exemplary cassette assembly.

In some applications, the stroke volume or liquid chamber volume of a pump or other type of chamber exceeds the volume that an on-board pump or chamber can accommodate. In this case, outboard pump or chamber pods have been used, and positioned between two cassettes. Liquid lines and/or actuation lines arise from opposing faces of the two cassettes to supply the outboard pumps or chambers, allowing liquid to flow, for example from a first cassette to the outboard pod and then to the second cassette, each cassette housing an upstream or downstream valve station to control the flow of liquid. Or an outboard pump actuation line may arise from the face of a first cassette, while the liquid inlet and outlet line may arise from the opposing second cassette. This type of cassette assembly also allowed for liquid lines to connect directly from the face of one cassette to the face of an opposing cassette. In prior implementations, as shown in FIG. 18, the faces of the opposing cassettes 194, 196, 198 also included actuation ports 200 for the on-board pump stations and actuation ports 202 for the valve stations, along with liquid ports 204 and liquid 206 and actuation 208 lines to the outboard pumps 210 or chambers 212. This arrangement led to a large number of flexible tube connections for both liquid and actuation lines plugged into the interior faces of the cassettes, which posed challenges for manufacturing, assembly and servicing.

Figure 19:
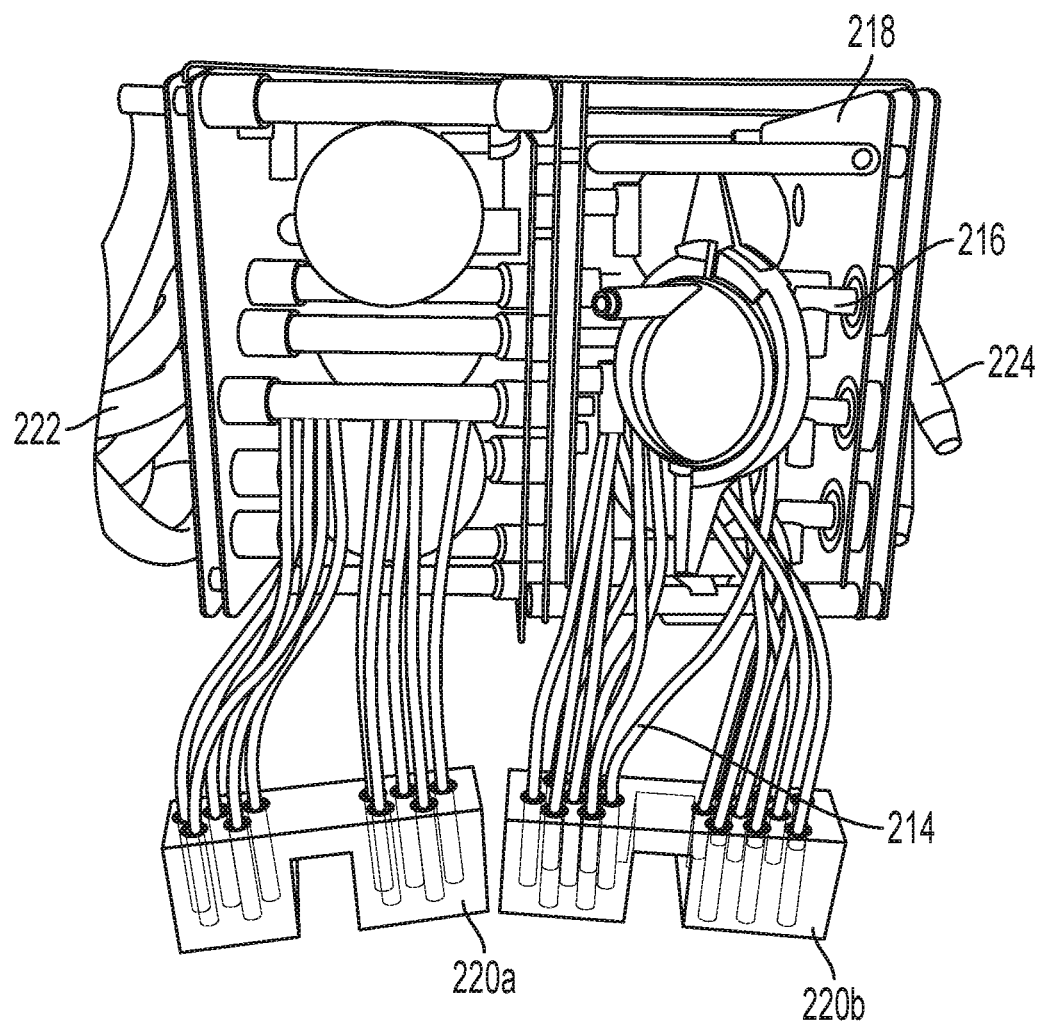
FIG. 19 is a side view of an assembled cassette assembly of FIG. 18, showing the pneumatic actuation lines of the assembly and associated connectors.

FIG. 19 shows a prior cassette assembly in which pneumatic actuation lines 214 ran from actuation ports 216 on the cassette faces 218 to block-style connectors 220a, b for subsequent connection to a pressure distribution manifold used to operate the cassette assembly. This was in addition to the liquid lines 222 that ran from liquid ports 224 on the individual cassettes. This type of cassette assembly has been substantially improved by incorporating the cassette designs of the present disclosure.

Dialysis Cassette Assembly

Figure 17:
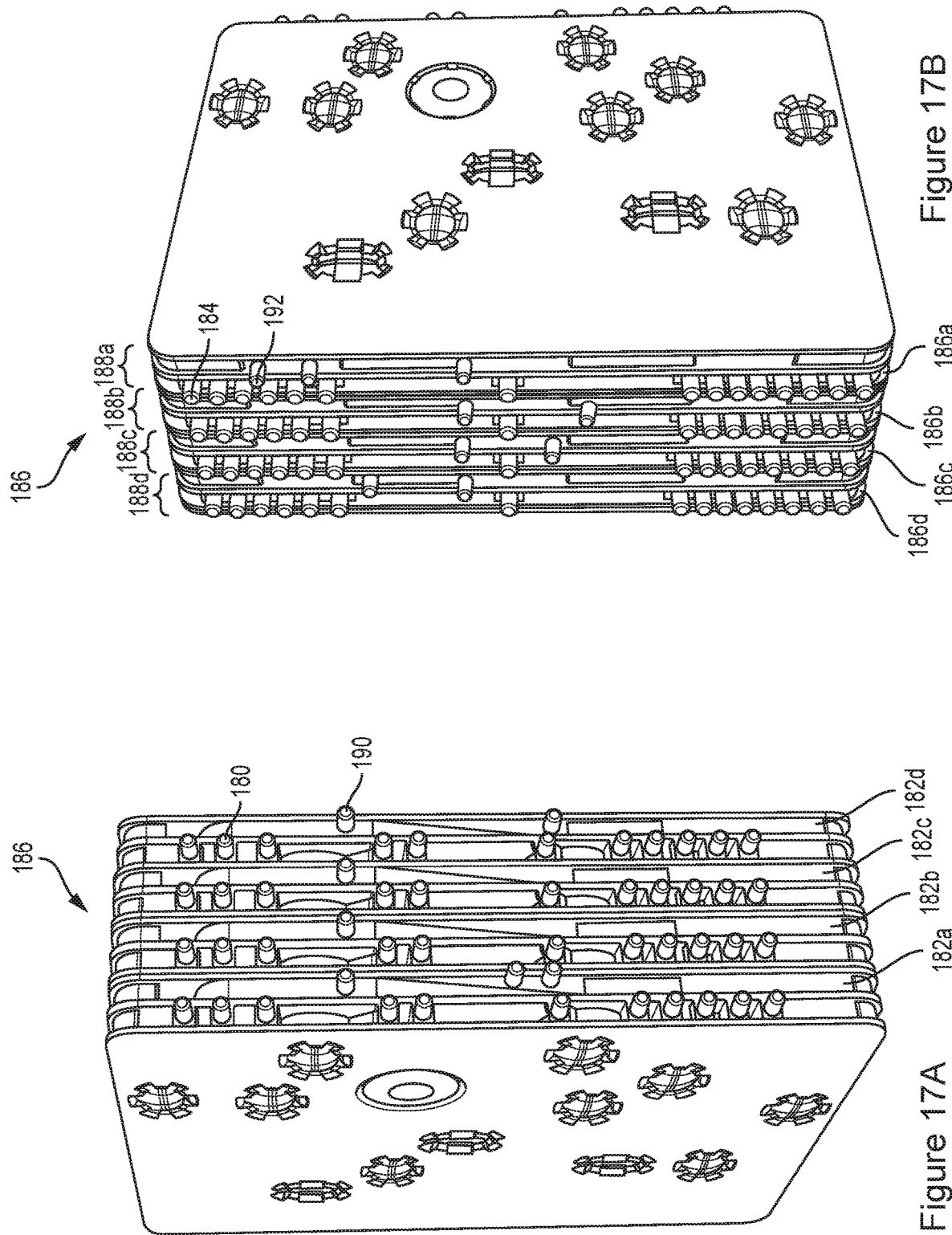
FIGS. 17A-17B depict front and rear perspective views of another embodiment of a cassette assembly.
Figure 20:
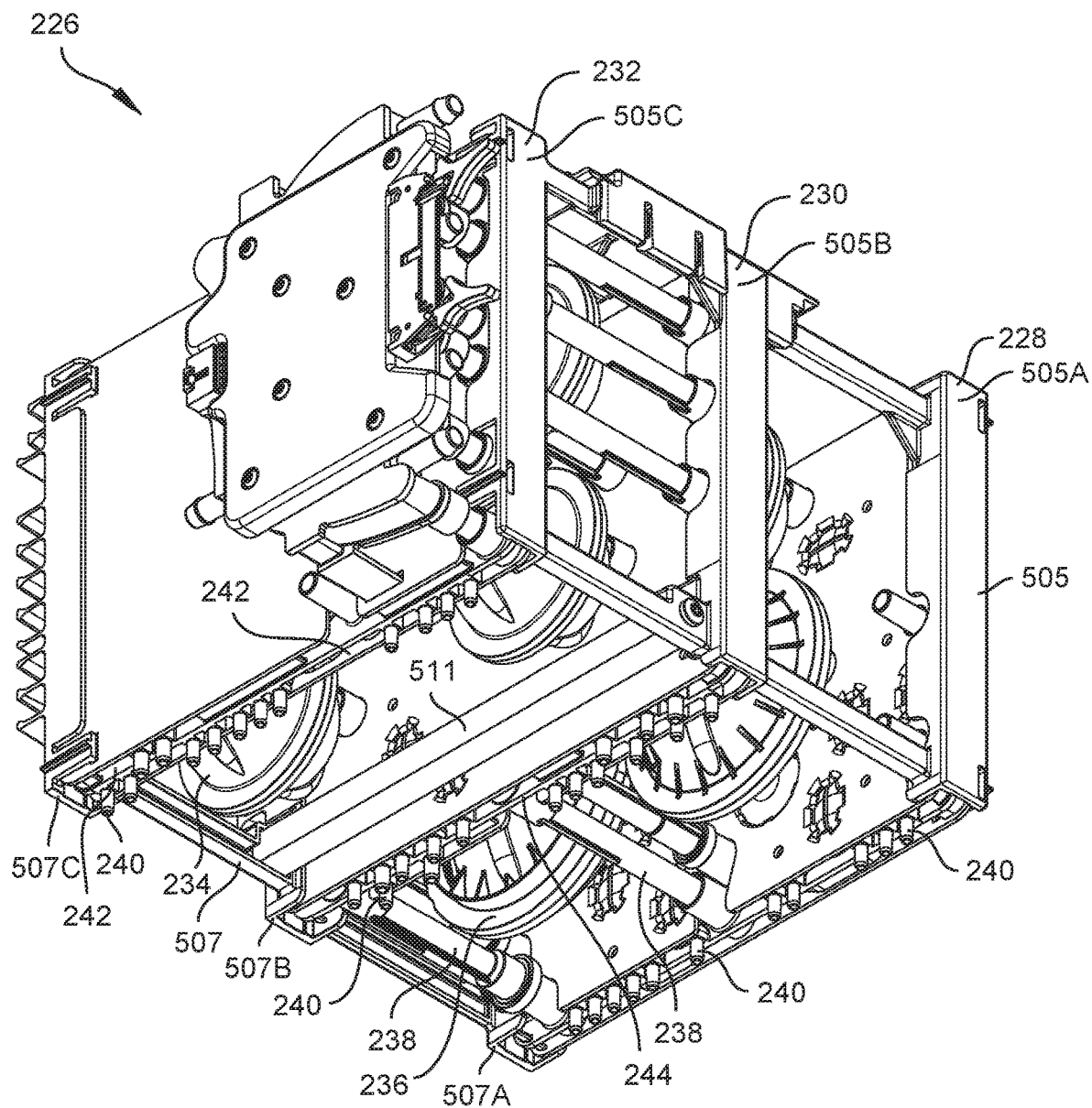
FIG. 20 is a perspective view of another embodiment of a cassette assembly secured in a frame assembly.

FIG. 20 shows an example of a cassette assembly 226 that performs substantially similar liquid-processing functions as the prior cassette assembly of FIGS. 17 and 18, and serves to illustrate how the cassettes of the present disclosure substantially improve the construction, assembly and servicing of such a cassette assembly. In this example, the cassette assembly 226 shown is used for mixing, processing and moving dialysate solution in a portable hemodialysis apparatus. But uses for this type of cassette or cassette assembly (i.e. cassettes having edge-mounted actuation ports with actuation channels running between plates and parallel to the cassette face) are by no means limited to hemodialysis systems. As shown in FIG. 20, three cassettes 228, 230, 232 are joined together by fluid-handling pods 234, 236. These inter-cassette pods may include self-contained diaphragm pumps having both actuation and fluid conduits, or other liquid-carrying chambers 236, having only fluid conduits. Examples of other types of liquid-carrying pods include fluid mixing chambers, or fluid balancing pods in which the flow through a first fluid line is balanced by the flow through a second fluid line through a pod having a first variable volume separated from a second variable volume by a flexible diaphragm. Each fluid-handling pod 234, 236 fluidly connects to either or both cassettes that flank it, either by flexible or rigid conduits. Rigid liquid conduits 238 may be preferred, because they can provide structural support for the cassette assembly. In the case of a diaphragm pump pod 234, both liquid-carrying and actuation conduits may extend to one or both cassettes flanking it. The conduits 238 penetrate the face of the flanking cassette to reach a fluid or actuation channel located in the first or second inter-plate space of that cassette. Generally, actuation channels driving the inter-cassette pump pods will course without interruption from a cassette actuation port to the actuation chamber of the pump pod. Fluid channels of either an inter-cassette pump pod or another type of fluid-handling pod will connect to a corresponding inter-plate fluid channel in one or both flanking cassettes via one or more diaphragm valves located in the cassette. The actuation channels of these diaphragm valves, the actuation channels for the pump pods, and any other actuation channel in the cassettes travel within the first or second inter-plate space of each cassette to a first edge of the respective cassette to terminate into a cassette actuation port 240. In the cassette assembly, each cassette 228, 230, 232 has actuation ports 240 located on a narrow side or edge of the respective cassettes, and are all configured to face in the same direction, so that the cassette assembly actuation ports occupy one side of the cassette assembly. This allows the cassette assembly 226 to be plugged into or unplugged from one or more receptacle assemblies in a single motion. With this arrangement, the need for flexible tubing to connect the cassette actuation ports to corresponding manifold output ports is eliminated. In the example shown in FIG. 20, cassette 228 is optionally configured as a single-duty mid-plate cassette (in which all actuation ports are located either in the first inter-plate space or the second inter-plate space). In the same example, cassettes 230 and 232 are optionally configured as dual-duty mid-plate cassettes, with some actuation ports located in both inter-plate spaces on either side of the cassette mid-plates 242, 244. Other arrangements are of course possible, depending on the fluid-handling tasks required of a similarly organized cassette assembly.

FIG. 21 depicts a partially exploded view of the example cassette assembly 226 shown in FIG. 20. The assembled cassettes 228, 230 and 232 along with the inter-positioned pumps 234 or other liquid carrying chambers 236 are held in a frame assembly, to assure proper alignment of the cassette ports during installation and operation. Previously disclosed cassette assemblies could rely on the rigid conduits (e.g. conduit 238), and some retaining bars or springs to keep the assembly together (see FIG. 18), but did not require precisely aligned actuation ports for directly plugging into a manifold assembly. In the presently disclosed cassette assembly, carrier frames 505 and/or 507 can eliminate this concern by compactly securing the cassette assembly 226 and retaining it in the required configuration or alignment. Exemplary embodiments in FIGS. 20 and 21 show a first carrier frame 505 and a second carrier frame 507 that can engage with the cassette assembly 226 from opposing directions. Some embodiments can provide similar carrier frames to secure the cassette assembly 226 from adjacent sides. Other embodiments can also provide a monolithic carrier frame to secure the cassette from more than one pair of opposing sides.

Carrier frames 505 and 507 can further include plate rails that can slide over the corresponding cassette plates of cassettes 228, 230 and 232 for engaging with the cassette assembly 226. Connecting the frame components together, and securing the enclosed cassette plates in rails may eliminate the need for puncturing or drilling holes into any of the three cassette plates in order to secure them to the frames. The rails configuration and absence of screws, nuts or clips through the cassette plates can reduce the possibility of damaging the cassette assembly and interfering with any of the pneumatic connections or pathways therein. For example, first carrier plate 505 can include a first set of plate rails 505A, 505B and 505C and the second carrier plate 507 can include a second set of the plate rails 507A, 507B and 507C. Plate rails 505A, 505B, 505C, 507A, 507B and 507C can comprise elongated slots capable of partially or completely receiving at least one edge or a portion of the edge of corresponding cassette plates of cassettes 228, 230 and 232. For example, with reference to first carrier frame 505, the plate rails 505A, 505B and 505C can receive edges of cassette plates of cassettes 228, 230 and 232, respectively. In an embodiment, the rails can include capping features. For example, rails 505A and 505C of the first frame 505 can include capping features 505F and 505G positioned on the ends of the respective rails. Plate rails 507A, 507B and 507C can engage with the cassette assembly 226 by receiving the edges of corresponding cassettes 228, 230 and 232. Moreover, walls of the plate rails 505A, 505B, 505C, 507A, 507B and 507C can also optionally include notches 506 configured to receive and cradle corresponding rigid liquid conduits 238 when the carrier frames 505, 507 engage with cassette assembly 226. Plate rails 505A, 505C, 507A and 507D can have a closed end and an open end. The open end of the rails may be included to avoid interfering with nearby cassette ports 240. It should be noted that the first and second carrier frames 505 and 507 can slide onto the respective cassette edges to engage with the cassette assembly 226 and may not require additional fastening devices to engage directly with the cassettes 228, 230 and 232. Additionally, securing features that supplement the rails i.e. features such as, but not limited to capping features 505F, 505G, and notches 506 and 508 can further strengthen the engagement between the cassette assembly and the frames, thus allowing any force application on the frame to be distributed more uniformly on the cassette assembly, and potentially avoiding straining or distorting the cassette assembly 226. This arrangement can aid in compactly installing and removing the cassette assembly 226 from an array of manifold receptacles of the hemodialysis apparatus 246 without causing the cassette assembly to rack, leading to misalignment of the cassette ports.

The plate rails 505A, 505B, 505C can be interconnected by an upper bar 505D and a lower bar 505E that extend perpendicular to the plate rails. The lower bar 505E interconnects the plate rails 505A to 505B and 505B to 505C at the open end of the rails and near the cassette ports 240. The upper bar 505D interconnects the plate rails 505A to 505B and 505B to 505C at the closed end of the rails. Similarly, rails 507A, 507B, 507C are interconnected by an upper bar 507D and a lower bar 507E that extend perpendicular to the plate rails. The lower bar 507E interconnects the plate rails 507A to 507B and 507B to 507C at the open end of the rails and near the cassette ports 240. The upper bar 507D interconnects the plate rails 507A to 507B and 507B to 507C at the closed end of the rails.

At least one cross bar 511 can be positioned to connect the first and the second carrier frames 505, 507 when the frames are positioned to engage with the cassette assembly 226. In this example, the cross bar 511 is disposed longitudinally through the cassette assembly 226 and connects the first and second carrier frames 505, 507 at opposing ends of the cross bar This arrangement helps to stabilize the side of the frames 505, 507 near the ports 240 of the cassettes 228, 230, 232. The cross bar 511 helps to prevent the frames 505, 507 from shifting position with respect to the cassette assembly 226. Connection between respective ends of the cross bar 511 and the corresponding carrier frames 505, 507 can be established by fastening features such as, but not limited to, screws, bolts, adhesive, laser or ultrasound welding, or other similar fastening mechanisms. Optionally, the cassette assembly 226 can provide alternative or additional connecting elements between the first carrier frame 505 and the second carrier frame 507 to secure them to each other and the cassette assembly 226, including, but not limited to, clips similar to clips 512 in FIG. 18, threaded rods, or zip-ties or other elements that limit the degree to which the frames 505, 507 can shift with respect to each other.

FIGS. 20 and 21 further depict a first support plate 513 and a second support plate 515. The first support plate 513 can be arranged to interconnect the first and the second carrier frames 505, 507 in their engagement with the cassette assembly 226. In the present example, the first support plate 513 is positioned on a side of the cassette assembly 226 that is perpendicular to the sides on which the first and second carrier frames 505, 507 are located. Furthermore the first support plate 513 is positioned on the carrier frame on a side opposite the cassette ports 240. First support plate 513 can additionally include flanges 513A and 513B on opposing edges. These flanges 513A, 513B can be structured to engage the upper bars 505D, 507D of the first carrier frame 505 and the second carrier frame 507. The first support plate 513 may be secured to the upper bars 505D, 507D mechanically with clips, screws or the support plate 513 may be bonded to the upper bars 505D, 507D. Alternatively, the upper plate 513 and at least one of the frames 505, 507 may be molded together. The first support plate 513 may engage the upper bars 505D, 507D when the carrier frames have engaged with the edges of the cassettes 228, 230, 232 of the cassette assembly 226. Thus, the first support plate 513 and the cross bar 511 may secure the first and the second carrier frames 505, 507 to each other during their engagement with the cassette assembly 226. The assembly comprising the carrier frames 505, 507, cross bar 511 and first support plate securely hold the cassette assembly 226, and help to more uniformly distribute external mechanical forces to the cassette assembly components to avoid distorting their relative positions.

First support plate 513 can further provide an inner surface 513D (see FIGS. 22A and 22B) facing the cassette assembly 226 and an opposing outer surface 513C, facing away from the cassette assembly 226. During installation of the cassette assembly 226, outer surface 513C of the first supporting plate 513 can interface with a cassette loading apparatus (not shown) which is described below. The inner surface 513D and outer surface 513C provide surfaces to which a cassette loading apparatus can apply forces to move the cassette assembly as a unit. First support plate 513 can also provide alignment features to appropriately load and station the cassette assembly 226 in the loading apparatus.

FIG. 21 also shows a second support plate 515 that can optionally be included to engage with one of the carrier frames 505, 507 to minimize twisting or flexing of the frames. In the present example, second support plate 515 is mounted to second carrier frame 507 and is attached to the frame through connecting elements 519. The connection may be achieved by receiving the connecting elements 519 into corresponding connecting junctions 520 provided on the second carrier frame 507. In another embodiment, the second carrier frame 507 can be integrated with a support plate such as, but not limited to, the second support plate 515 as a single component. Flexing or twisting of the first carrier frame 505 can also be reduced by including a diagonal crossmember 523. Crossmember 523 can be integral to structure of the second carrier frame 505 or can be attached on the frame separately. Additional support elements similar to support plates 513, 515 and support bracket 523 can be provided to supplement the carrier frames 505, 507 and retain the required arrangement of the cassette assembly 226.

Figure 22A:
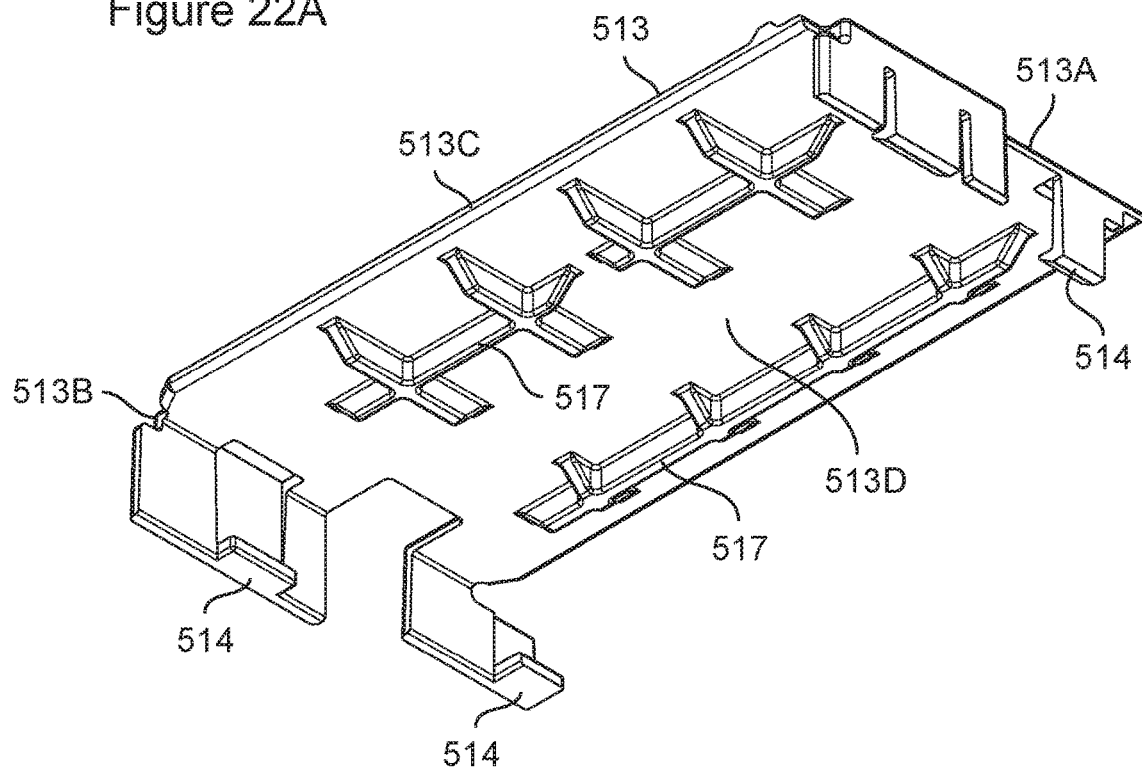
FIGS. 22A-22B are front and rear perspective views of a top plate of the exemplary frame assembly.
Figure 22B:
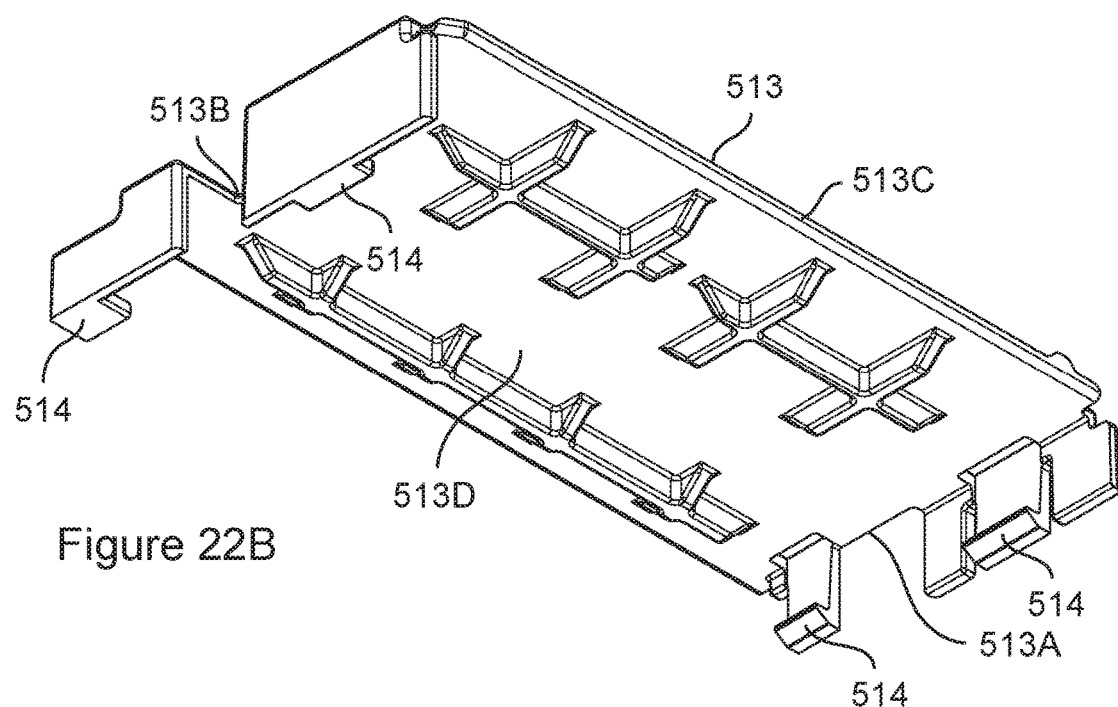

FIGS. 22A and 22B depict perspective views of an exemplary first support plate 513. Flanges 513A and 513B can further provide engagement features such as, but not limited to resilient clips or grippers 514. First support plate 513 can also include one or more clips 514 on non-flanged sides. Clips 514 can be constructed to engage edges of the carrier frames 505 and 507. For example, the clips 514 can be configured to engage the upper bars 505D, 507D. Alignment elements such as one or more nubs 516 (FIG. 21) may be included on edges of the carrier frames 505, 507. Nubs 516 can serve as alignment features for slots 514B on the first support plate 513 to ensure appropriate alignment and connection between the first support plate 513 and the carrier frames 505, 507. In the present example, the first support plate 513 may include longitudinal and/or transverse stiffeners 517 to reduce mechanically induced deformation of the first support plate 513.

Figure 23:
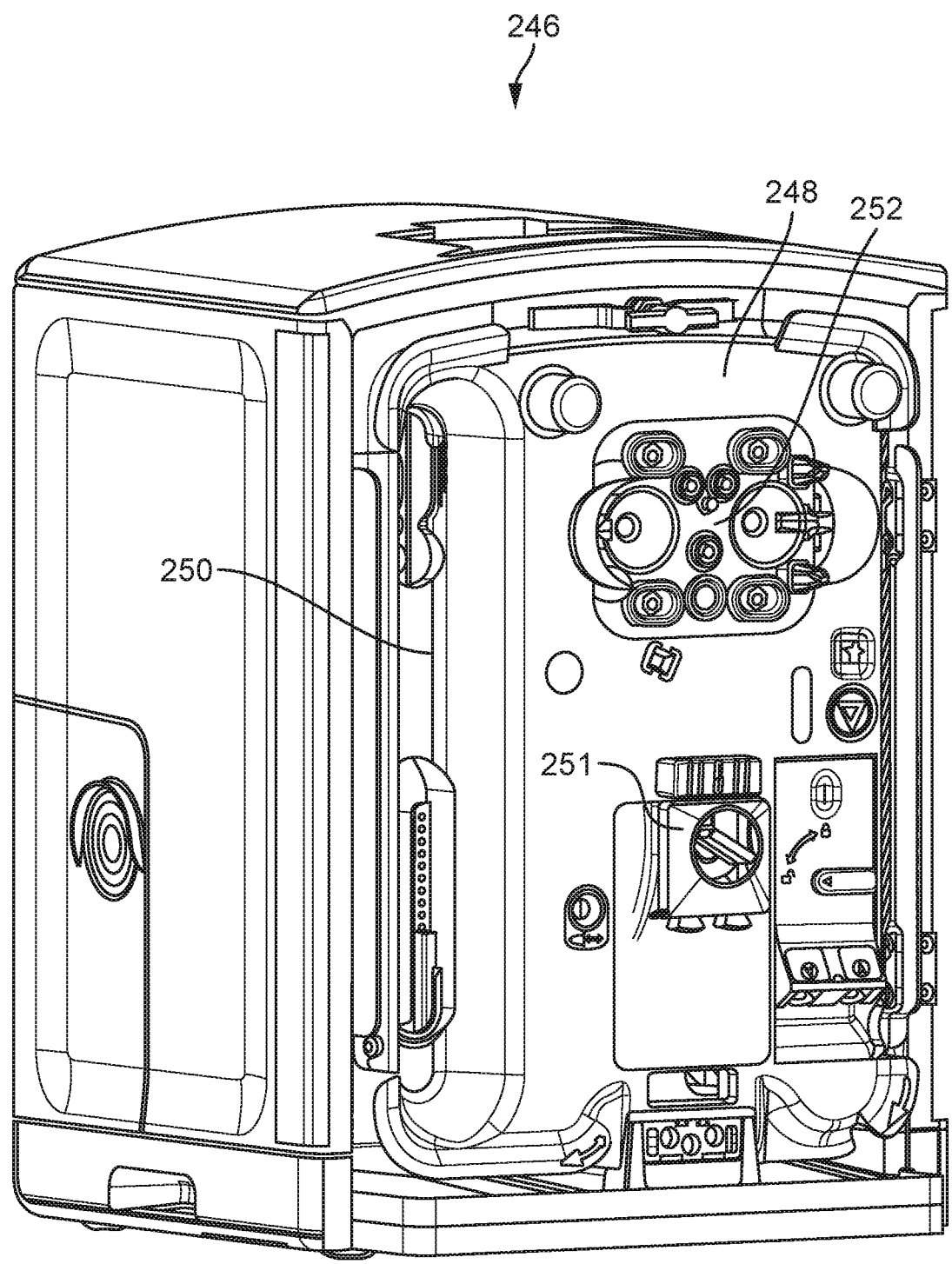
FIG. 23 is a front perspective view of a hemodialysis apparatus.

FIG. 23 shows a hemodialysis apparatus 246 configured to enclose the cassette assembly 226. A front panel 248 is configured to include a dialyzer recess and holder 250, a blood pump cassette receptacle assembly 252, and configured to hold a blood tubing set (not shown). The dialysate cassette assembly 226 is configured to be housed within the enclosure of apparatus 246 behind the front panel 248.

Figure 24:
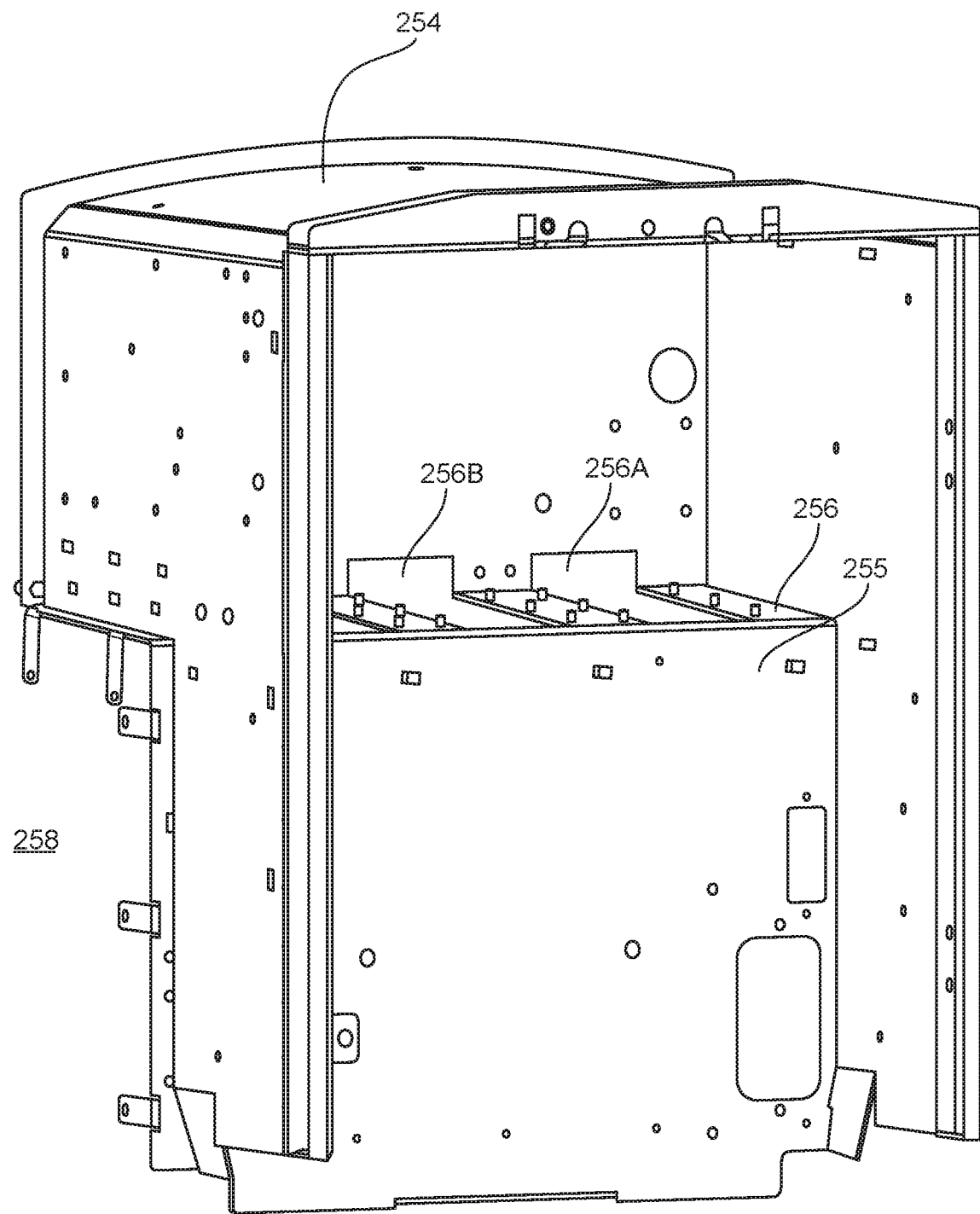
FIG. 24 is a front perspective view of a housing of the hemodialysis apparatus shown in FIG. 23.
Figure 25:
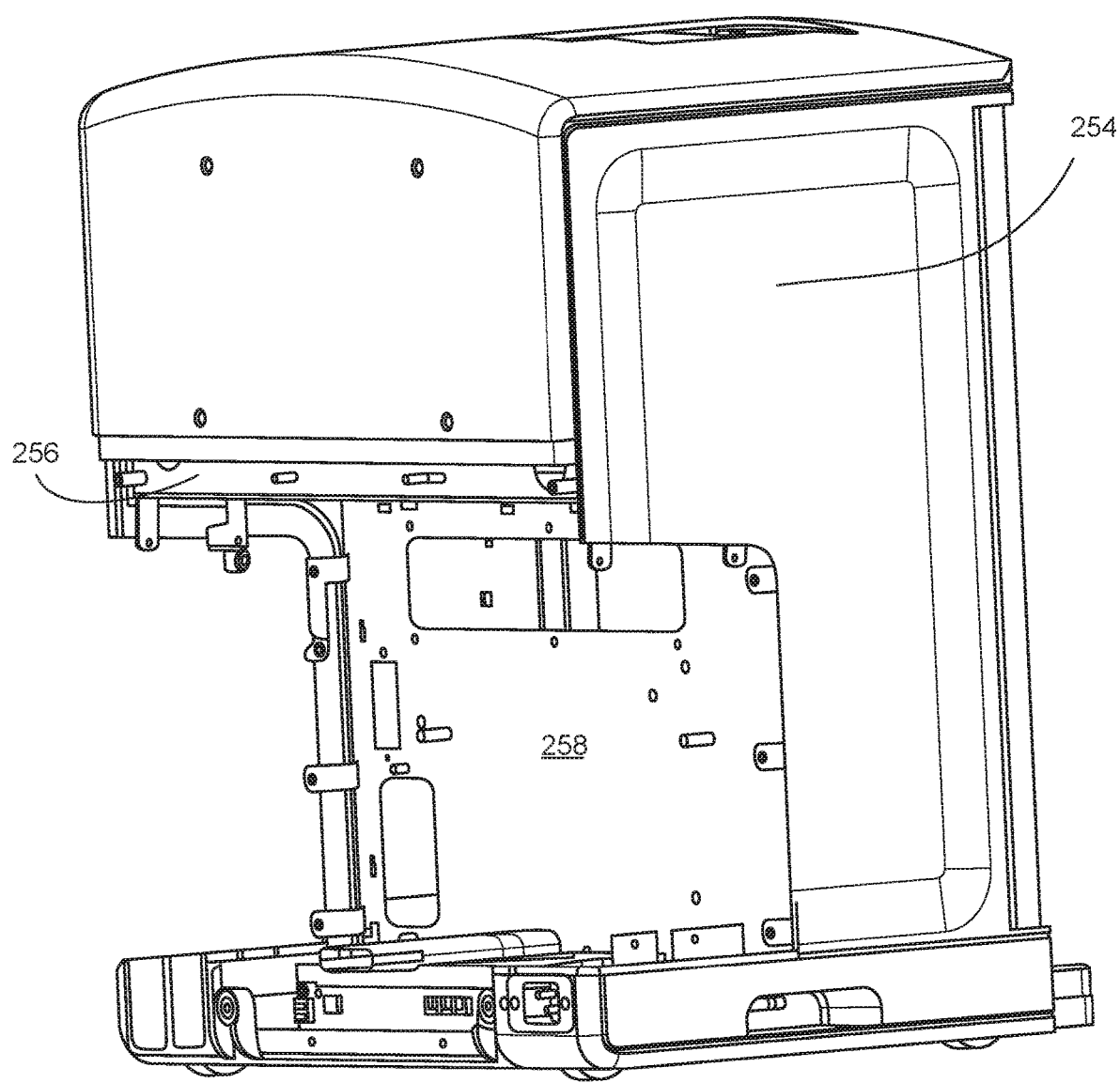
FIG. 25 is a rear perspective view of the housing shown in FIG. 24.

FIG. 24 shows an enclosure 254 for the apparatus 246 of FIG. 23, with the front panel 248 and other components removed. The internal configuration of the enclosure or housing 254 allows a cassette assembly 226 to be positioned above internal shelf 256 of the enclosure 254. The interior of enclosure 254 (e.g. below the shelf 256) is arranged to hold other components, such as a heater for dialysate solution, tubing for various liquid flowpaths, a dialysate reservoir or tank, and one or more devices to detect the conductivity and temperature of dialysate solution at various stages of mixing. Behind this enclosure 254 is a recess 258 arranged to hold a pressure distribution manifold (in this case a pneumatic actuation manifold) with electromechanical valves, and one or more electronic controllers, at least one of which is configured to control the electromechanical valves of the manifold. These components are positioned outside the enclosure 254 to help shield them from high temperatures that may be used when disinfecting the liquid-carrying components of the hemodialysis apparatus 246. FIG. 25 shows a rear perspective view of enclosure 254, highlighting the recess 258, which is located directly under shelf 256 of enclosure 254. Thus a pressure distribution manifold can be positioned directly below a cassette assembly 226, the cassette assembly being located within enclosure 254 and the pressure distribution manifold being located outside enclosure 254.

Loading and Locking the Cassette Assembly

Figure 30:
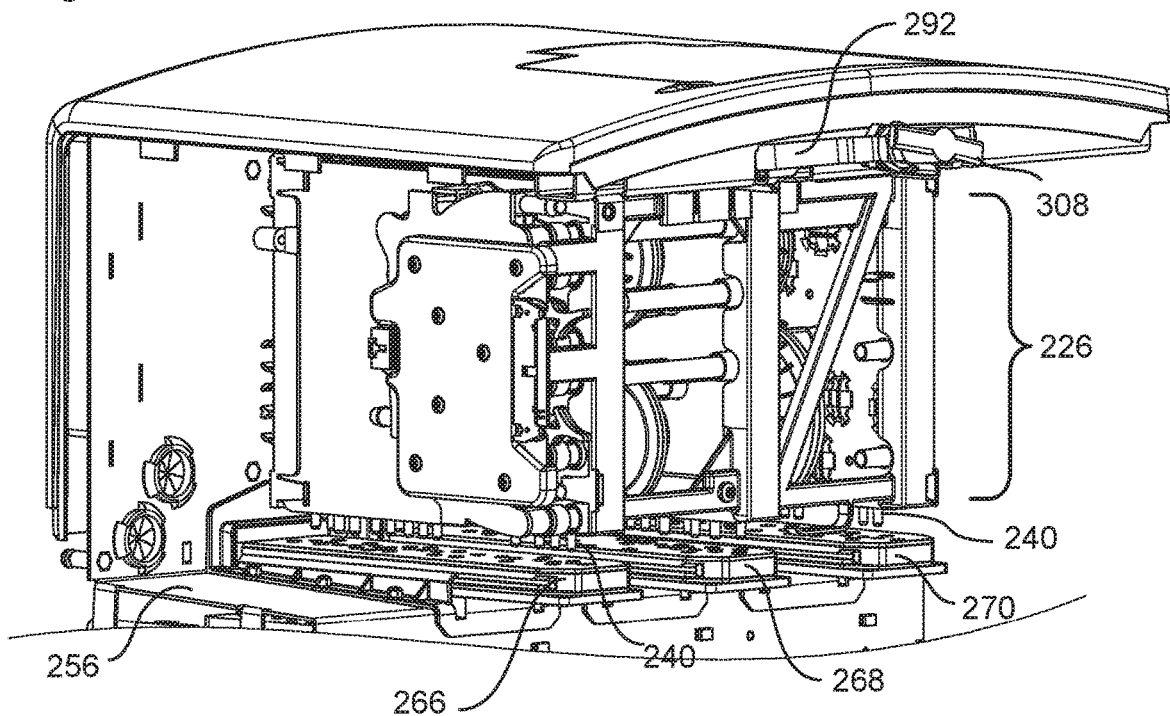
FIG. 30 is a perspective view of an upper portion of the housing of FIG. 24, enclosing a cassette assembly that is disconnected from a corresponding manifold assembly.
Figure 31:
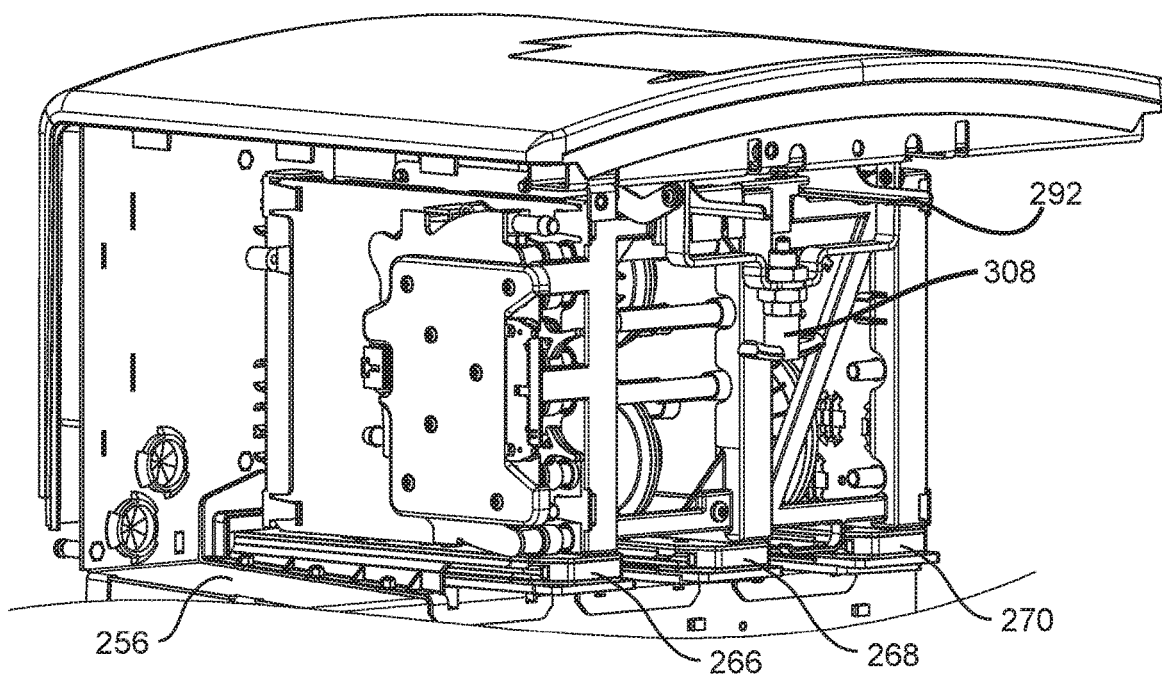
FIG. 31 is a perspective view of the upper portion of the housing as shown in FIG. 30, with the cassette assembly connected to the corresponding manifold assembly.

FIGS. 30 and 31 depict installation and retention of the cassette assembly 226 in the enclosure 254. In FIG. 30, the cassette assembly 226 is lifted just above three cassette receptacle assemblies, with three arrays of cassette actuation ports 240 aligned with their respective receptacle ports on adaptors 266, 268, 270. The receptacle assemblies are configured to adapt the actuation port arrays of the cassette assembly 226 with actuation outlets of a pressure distribution manifold located outside the enclosure and below shelf 256. Lowering the cassette assembly 226 allows the cassette actuation ports 240 to engage with their respective adaptors through a press-fit connection. Sealing of the individual actuation ports 240 can be accomplished through the use of O-rings, or gaskets with elastomeric wiper seals, or other means typically used in sealing press-fit connections. The adaptors in turn can provide a direct connection to output ports of the pressure distribution manifold (FIG. 32 to FIG. 37) located below shelf 256 and outside enclosure 254. FIG. 30 further depicts a cassette loading apparatus 292 that can receive the cassette assembly 226 during installation, and hold it in place. A handle 308 belonging to the loading apparatus 292, can operate to lock the cassette assembly inside the enclosure 254. A detailed description of the operation of apparatus 292 and handle 308 to lock and retain the cassette assembly is provided below with reference to FIG. 56 to FIG. 59. In one configuration, the loading assembly of FIG. 30 can be in an open position depicting the operation handle extending parallel and away from the cassette assembly. FIG. 31 depicts the cassette assembly 226 locked in the cassette receiving space by indicating the operation handle 308 to be angled downward, moving the loading apparatus toward the receptacle assemblies of the manifold, and thus pressing the cassette assembly 226 into the corresponding adaptor ports and securing it therein. In the present example, the loading apparatus 292 can comprise force application elements such as but not limited to, one or more bars that can interface with first support plate 513 (FIGS. 22A and 22B) and can be operated by the handle 308. Lowering the handle 308 can allow the force application elements to push on the first support plate 513. This force can be transmitted to the cassette assembly 226 through the cassette frames 505, 507, wherein the frames press the cassette assembly 226 towards the adaptors 266, 268 and 270. FIG. 31 depicts the cassette assembly 226 in the operative configuration, i.e. the cassette assembly 226 is pressed to align the array of cassette actuation ports 240 with their respective adaptors 266, 268 and 270. It should be noted that the handle 308 in FIG. 31 is shown in a closed configuration i.e. the cassette assembly 226 is locked inside the enclosure 254, with the handle positioned so that the front panel of the hemodialysis device can be installed without interference.

Figure 45:
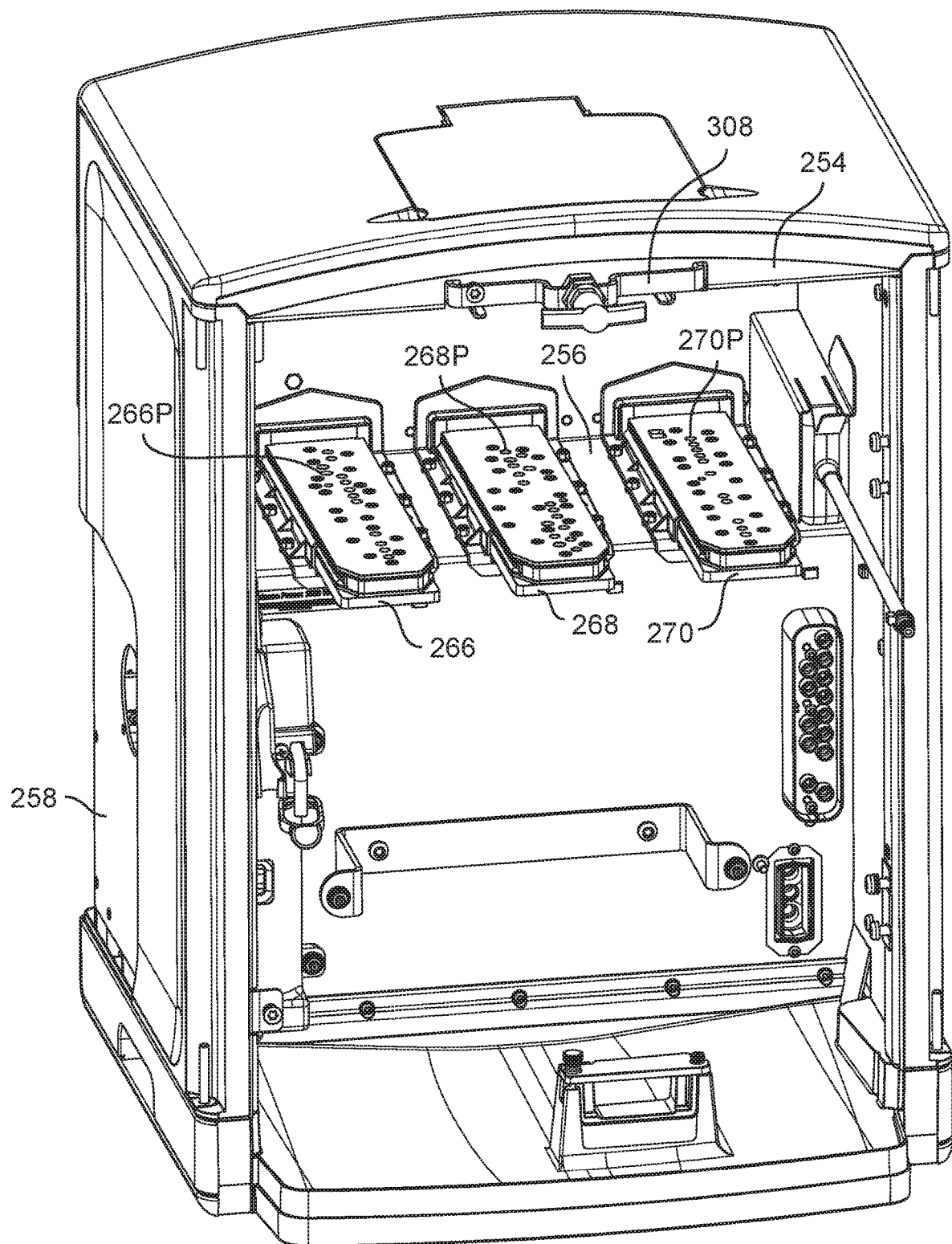
FIG. 45 is a front perspective view of the hemodialysis device housing, showing installation of the exemplary manifold adaptors.
Figure 46:
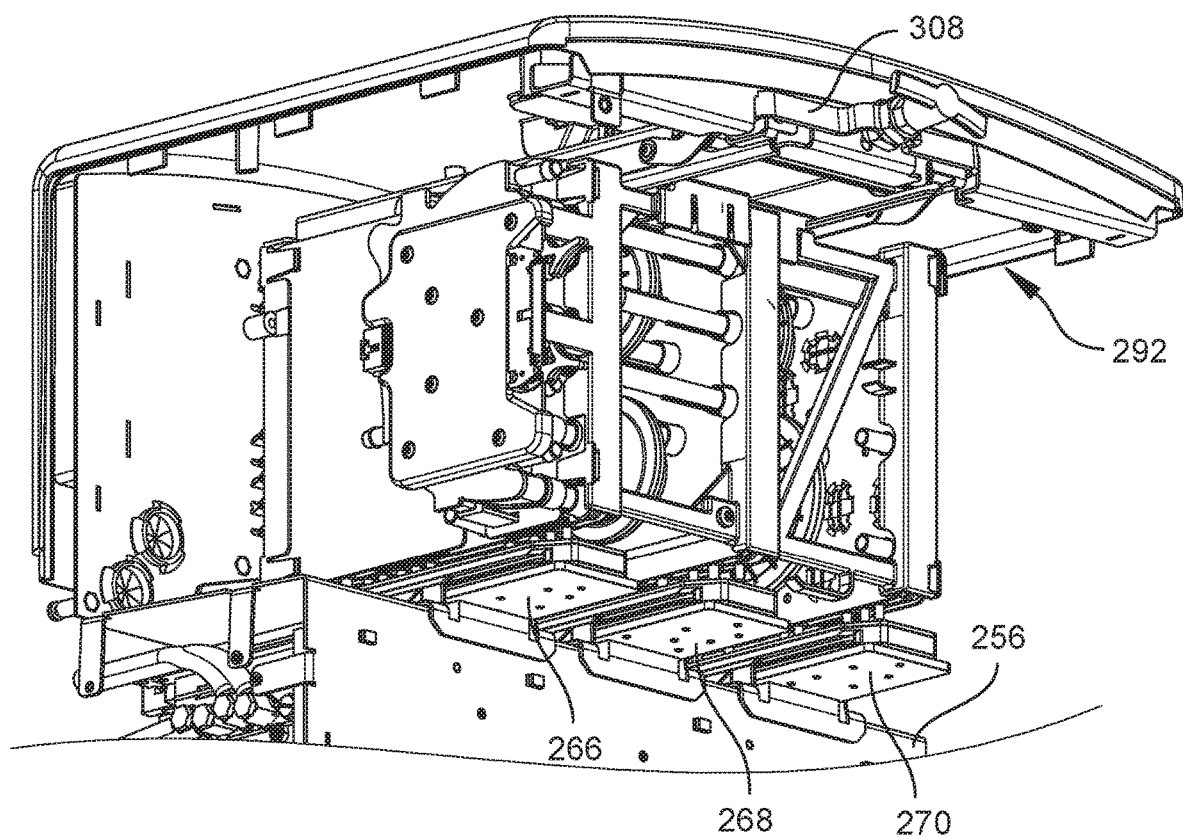
FIG. 46 is a front-left side perspective view of the exemplary cassette assembly positioned in an upper portion of the housing, and aligned with the manifold adaptors.

The embodiment of the hemodialysis apparatus 246 shown in FIGS. 45, 46 comprises an enclosure 254 in which the footprint of the cassette assembly 226 extends in a direction forward of—and overhangs—the shelf 256. For this reason, a group of manifold interfaces or adaptors 266, 268, 270 are configured to extend in a direction forward of the shelf 256 as shown in FIG. 45. The adaptors 266, 268 and 270 provide the requisite mating of cassette assembly 226 actuation ports 240 to their respective connectors or receptacle ports 272 located on the interfaces or adaptors 266, 268, 270. Adaptors 266, 268, 270 in this example serve as receptacle assemblies, providing an array of receptacle ports for mating with cassette ports 240 arrayed in each cassette 228, 230 and 232 respectively. FIG. 46 shows a bottom perspective view of enclosure 254 with installed interfaces/adaptors 266, 268, 270. The extent to which the adaptors overhang the enclosure shelf 256 (and therefore also the pressure delivery manifold 260) is apparent in this view. The adaptors 266, 268, 270 serve to map the cassette ports arrayed in an extended direction along the edges of the individual cassettes to a more spatially compact array of manifold ports located in risers or top blocks 276A-C between the adaptors 266, 268, 270 and an upper block 274 of the underlying pressure distribution manifold 272.

Pressure Distribution Manifold

Figure 26:
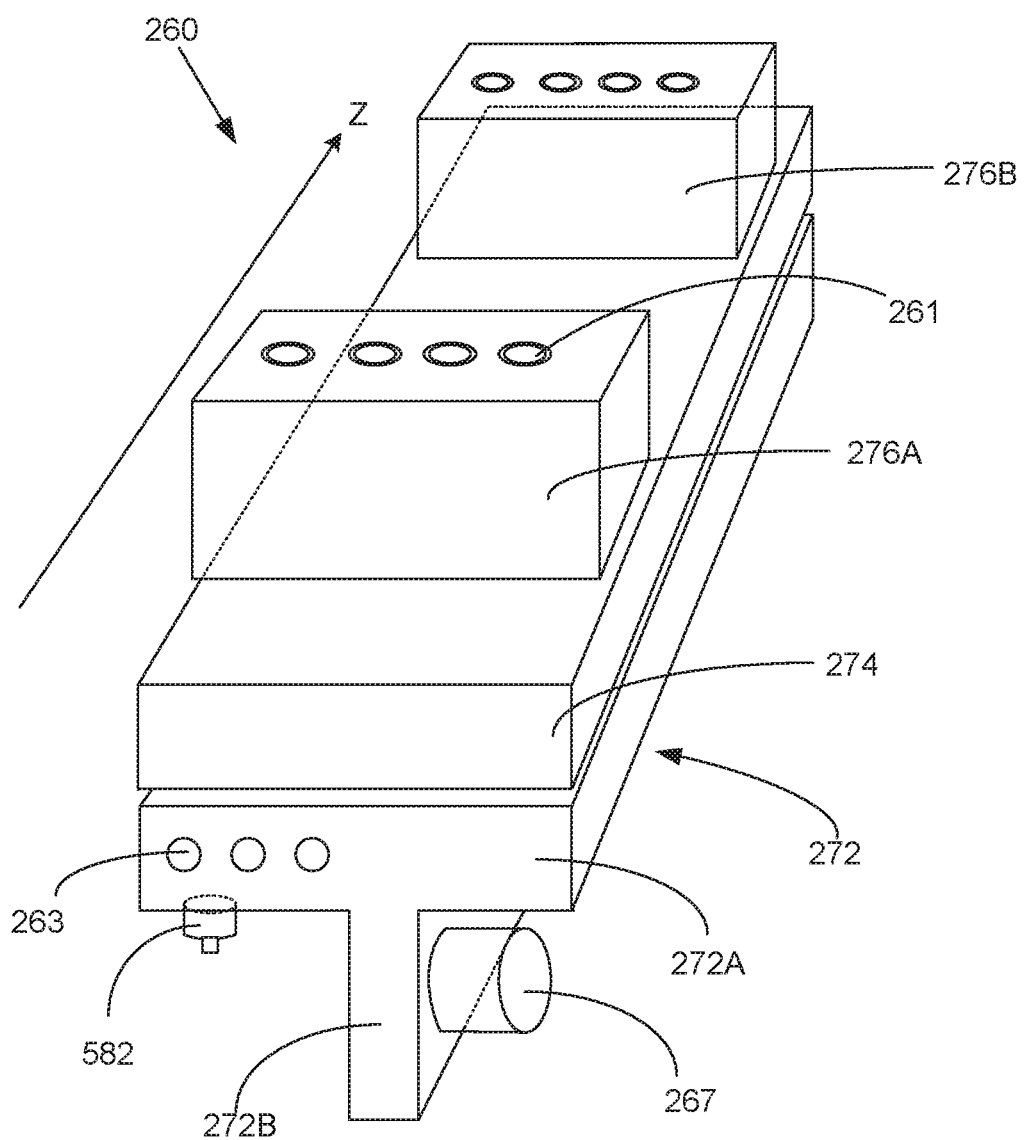
FIGS. 26-29 are schematic representations of an exemplary pressure distribution manifold.

FIG. 26 shows a schematic representation of an embodiment of a pressure distribution manifold (or manifold assembly). This manifold assembly is arranged to selectively provide pneumatic pressure (positive, negative or atmospheric) to control pneumatically-driven pumps and/or valves on two separate pump cassettes. In this improved embodiment, a first set of pneumatic outlets is configured for direct connection to a first pump cassette or cassette assembly (i.e. direct plug-in connection to the manifold assembly or to an adaptor directly connected to the manifold assembly). In an embodiment, the direct-connection interface is illustrated schematically as one or more risers or 'top blocks' 276A, 276B, which are positioned on a superior side of the manifold assembly 260. The top blocks include direct-connection ports 261 configured to connect directly with a first pump cassette (not shown), which can be positioned directly above the manifold assembly 260. The manifold or manifold assembly also includes a second set of pneumatic outlets configured for indirect connection to a second pump cassette via flexible or malleable tubing. Also shown in FIG. 26 is an exemplary fitting 582 for indirect connection to a second pump cassette (not shown), the connection configured for a flexible or malleable tube that travels some distance away from the manifold assembly 260 to a remotely located second pump cassette. In the context of the presently described hemodialysis device, the dialysate cassette assembly can be configured to plug directly into the manifold assembly via ports 261, and the blood pump cassette assembly (located more remotely on the front panel of the dialysis device) can be configured for pneumatic connection to the manifold assembly via flexible or malleable tubing to a plurality of fittings (here represented by the exemplary fitting 582).

FIG. 26 also shows another improvement in a manifold assembly 260, which helps to prevent or reduce the accumulation of particulate or liquid debris on internal sealing surfaces of electromechanical pneumatic control valves. An exemplary valve 267 is shown in a generally horizontal orientation. Any internal valve seats or sealing surfaces are oriented to avoid having horizontal surfaces on which debris can accumulate. In the schematic illustrations of FIGS. 26-29, a lower or bottom manifold block 272 mates with a middle manifold block 274. The lower manifold block 272 has a cross-sectional 'T'-shape (across the long axis 'Z' of the manifold assembly 260), comprising a horizontal portion 272A and a drop portion 272B onto which a plurality of valve mounting surfaces and openings are arranged. An exemplary valve 267 is shown mounted to one such surface and over one such opening. A valve face seal (not shown) is assumed to interface the valve body with the mounting surface of the drop portion of the manifold. The drop portion 272B is shown for convenience to have a vertical orientation with respect to the horizontal portion 272A. The drop portion 272B may also have a non-vertical orientation, such as one in which the valve mounting surfaces and openings are angled in an upward direction, which orients the valve body and face seal in a downward angled direction. This angled orientation will also help to prevent the accumulation of liquid (e.g. liquid condensate) or debris on valve components having sealing surfaces (e.g. valve seats). In many (but not all) valve embodiments, an associated internal valve plunger or piston will operate in a horizontal or near-horizontal direction, which is represented by the valve 267 illustrated schematically in FIGS. 26-29.

In the examples shown in FIGS. 26-29, pressure source lines 263 are shown to be embedded within the lower or bottom manifold block 272. Depending on how the internal pneumatic channels in the manifold assembly 260 are plumbed, these source lines can also be located in the middle block 274. In the schematic illustrations shown, each of the plurality of valves 267 receives an input line from one of the pressure source lines 263, and has an output line connected ultimately to an output port of the manifold assembly—either a direct-connect port 261 or an indirect-connect port 582.

Figure 27:
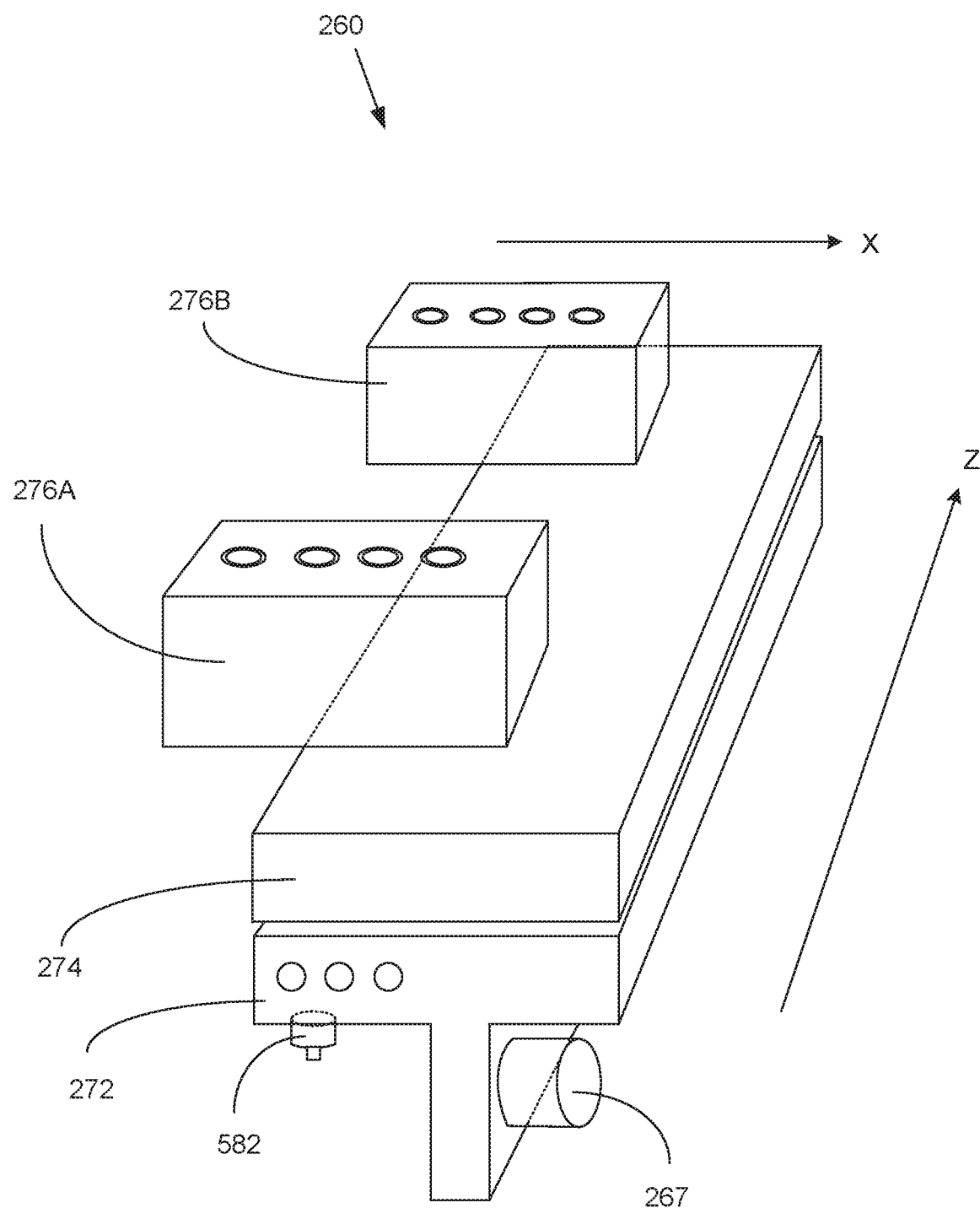

FIG. 27 shows a schematic illustration of an embodiment of a manifold assembly 260 in which the direct-connection blocks 276A, 276B overhang, are cantilevered or are offset with respect to the main body of the manifold assembly. In this illustration, the long axis ('Z') of the manifold assembly can be made to accommodate a pump cassette of any arbitrary length in the long-axis direction. But if the pump cassette is configured to also have an array of inlet ports that exceeds the main front-to-back ('X') dimension of the manifold assembly, the direct-connection blocks can be arranged to overhang the manifold assembly in that direction. Ports 261 can then be connected to channels within blocks 276A, B to be routed to a more compact array of one-to-one mapped ports on the top of middle block 274.

Figure 28:
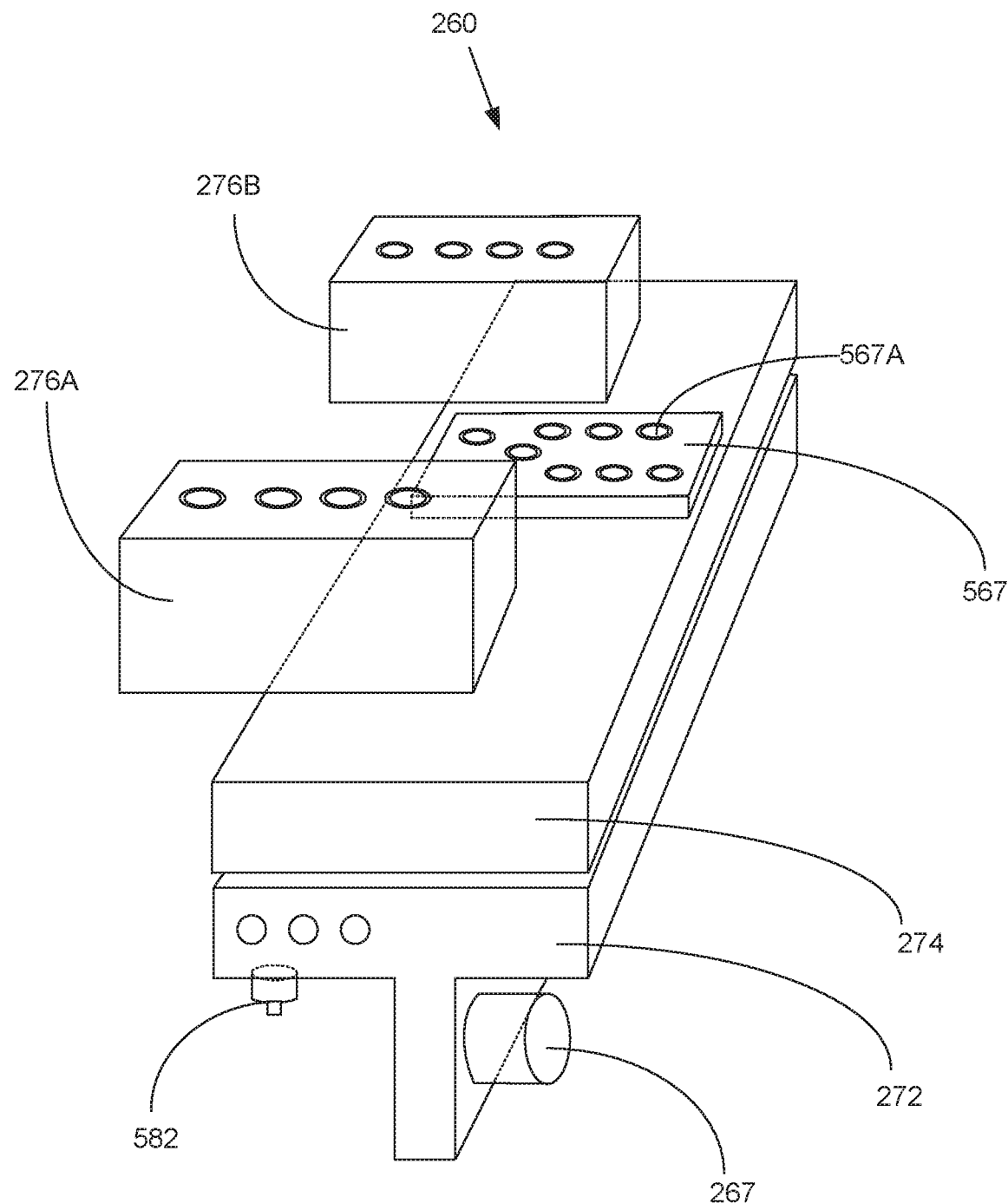

FIG. 28 shows a schematic illustration of an embodiment of a manifold assembly 260 in which an array of pressure sensor ports 567 has been positioned between the direct-connection blocks 276A and 276B. In this case, various pneumatic channels within the manifold assembly can have branch or in-line connections to sensor ports 567A of a pressure sensor array 567. In most (but not necessarily all) cases, these channels connect to the output line of a pneumatic control valve, and to an output port of the manifold assembly to which the valve output line is connected. In an example, an array of pressure sensing ports can be configured to mate with a printed circuit board (PCB) positioned above the array and including a corresponding array of pressure sensors. The pressure sensors of the PCB can be connected to a hemodialysis controller that uses pressure information to control the pneumatic control valves to deliver a pre-determined level and pattern of pressure to a pump or valve object in a connected pump cassette.

Figure 29:
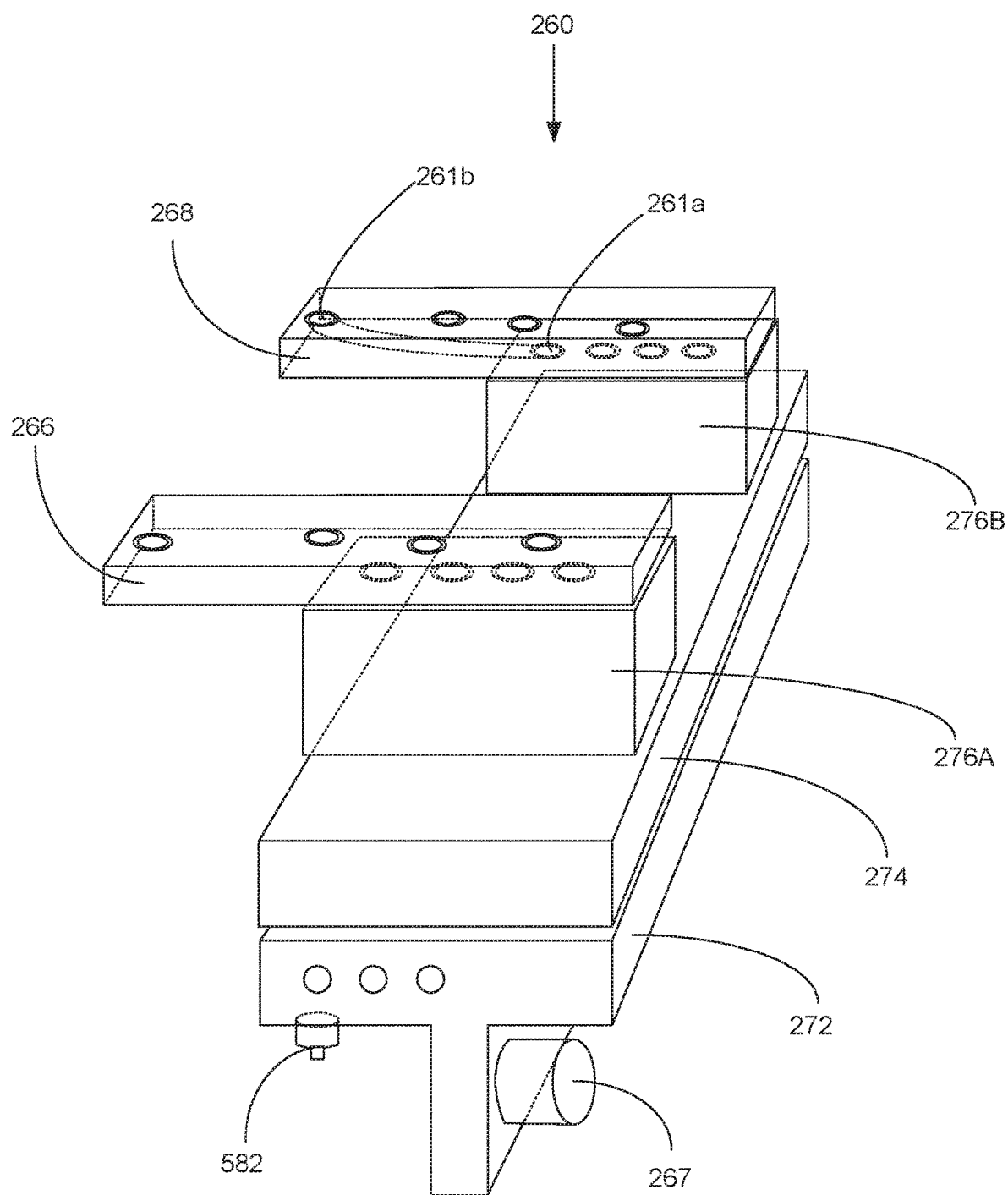

FIG. 29 shows a schematic illustration of an embodiment of a manifold assembly 260 that includes one or more manifold adaptors or interface blocks 266, 268. In this example, top blocks 276A, 276B function as risers to provide spacing between an installed direct-connection pump cassette and the main body of the manifold assembly 260. The risers may include pneumatic channels connecting a plurality of valves on the manifold (such as valve 267) to manifold adaptors or interface blocks 266, 268 to ultimately connect to an associated pump cassette. The manifold adaptors or interface blocks can be configured to spatially re-distribute output ports 261a—that are relatively closely spaced in a riser block or in the other blocks of the manifold—to a differently spaced array or distribution of output ports 261b. In this way, the direct-connection output ports of the manifold assembly can be arrayed or re-distributed spatially to match corresponding input ports of a mating direct-connection pump cassette. The manifold adaptor 266, 268 thus includes transfer ports on a first side facing and mating with the manifold 274 or its associated riser 276A,B, which map into corresponding transfer ports 261b on an opposing second side facing and mating with a pump cassette assembly. A first array of manifold output ports having a first spatial port configuration can therefore be directly mated to a second array of cassette input ports having a second spatial port configuration. The mapping between corresponding transfer ports is achieved through the routing of internal channels within the manifold adaptors 266, 268. In this case, the spatial array of the manifold or riser output ports has a length that is less than a length of the spatial array of the manifold adapter transfer ports on the second side of the adaptor. The result is that the manifold adapter overhangs the front side of the manifold in a cantilever fashion. These features help to disassociate the spatial and dimensional constraints of a pump cassette assembly from those of a manifold assembly configured to drive the cassette(s) of the pump cassette assembly. In the current embodiments, a manifold assembly can be made to be as compact as valve, channel and port constraints permit while retaining the ability to interface with a pump cassette that may have substantially different space constraints or spatial array requirements of its actuation ports.

Figure 32:
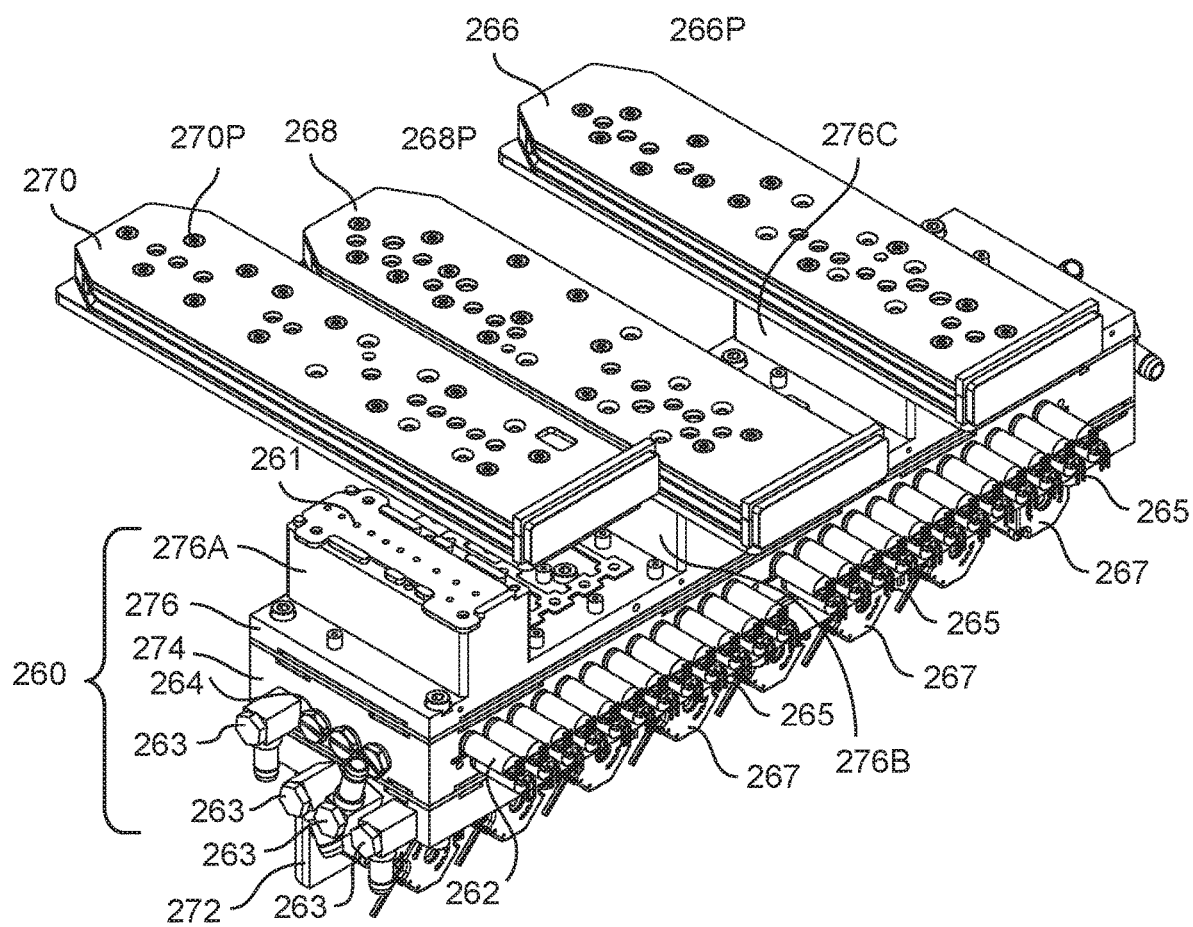
FIG. 32 is a rear perspective view of an exemplary pressure distribution manifold and associated interfacing adaptors.
Figure 33:
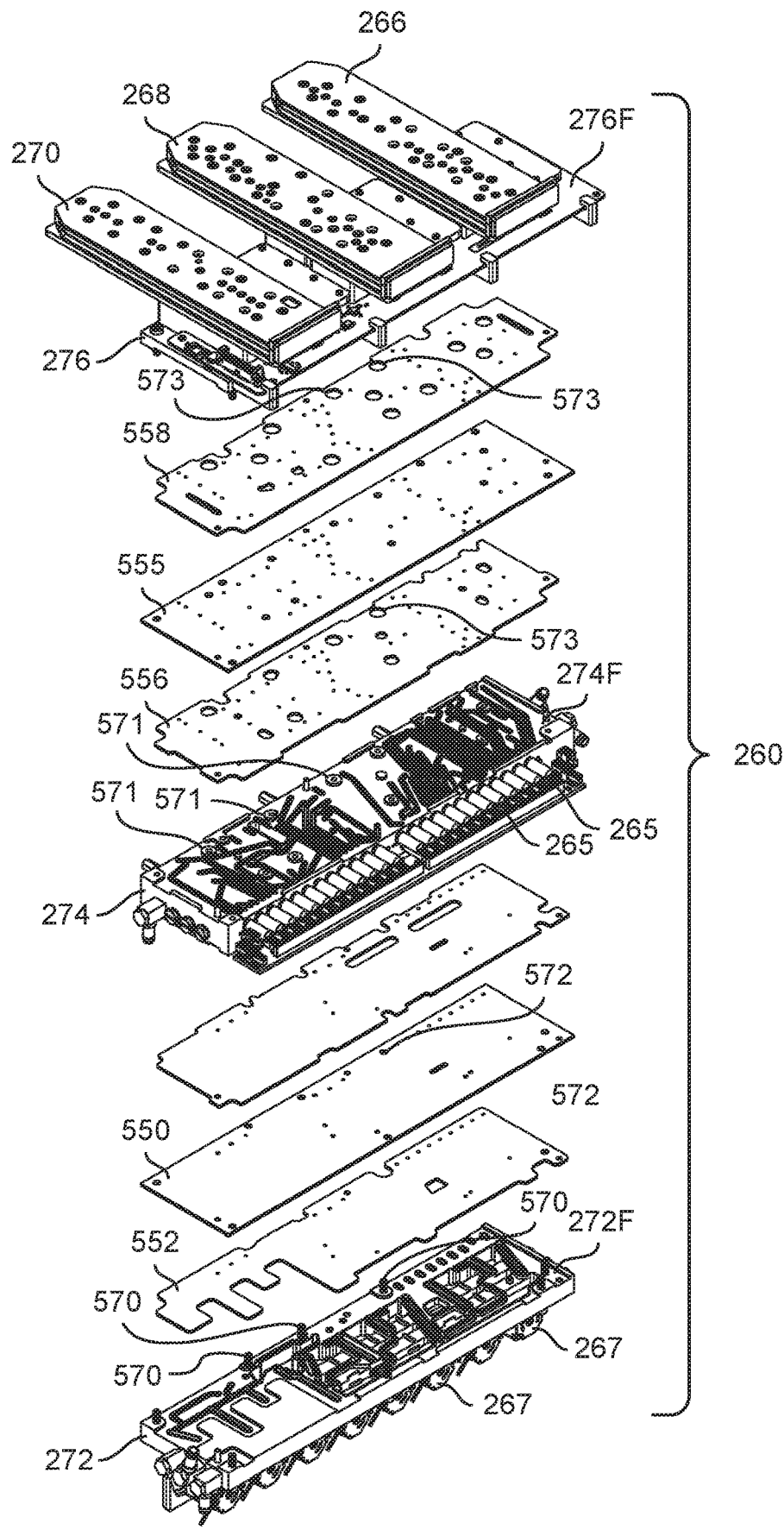
FIG. 33 is an exploded view of the pressure distribution manifold shown in FIG. 32.

FIGS. 32, 33 show the details of one embodiment of a pneumatic actuation manifold in the form of pressure distribution module 260. The pressure distribution module 260 provides selectable pneumatic connection from a plurality of pressure sources to the cassette assembly that plugs into the receiving ports on the platform of the manifold adaptors 266, 268, 270. The pressure distribution module 260 may further provide selectable pneumatic connection to a remote cassette via flexible or malleable pneumatic lines (not shown). The pneumatic connections are selectively controlled by digital or binary pneumatic valves 262, 265, 267 mounted in or on the manifold blocks. One or more controllers control the state of the valves based on received signals from pressure sensors mounted on the upper block 276 and in the case of a hemodialysis apparatus provide programed instructions to selectively activate valves and pump blood, dialysate and water in order to deliver a dialysis treatment to a patient.

The pressure distribution module 260 controls the action of pneumatically-driven diaphragm pumps and pneumatically-driven liquid valves by selective connection to one or more pressure reservoirs via digital or binary electromechanical valves. The electromechanical valves may comprise two-way or three-way digital valves. The digital valves can have two positions. A two-way digital valve is either open or closed. A three-way digital valve connects a common port to either a first or second port. One or more controllers control the state of the valves 262, 265, 267 based in part on signals received by the one or more controllers from pressure sensors 565 (see FIG. 34). The pressure reservoirs may include a high positive pressure reservoir, a low positive pressure reservoir, a negative pressure or vacuum reservoir, and a vent to atmosphere.

The pressure distribution module 260 may be assembled from a plurality of manifold blocks. The pressure distribution manifold 260 in FIGS. 32, 33 comprises a tee-shaped manifold block 272, a mid-manifold block 274 and an end-manifold block 276. The pressure distribution manifold 260 further comprises cartridge valves 265 mounted in the mid-manifold block 274 and surface mount valves 267 that mount on the vertical leg of the tee-shaped manifold block 272. Disposition of the pressure reservoir ports 263, first set of valves 265 and second set of valves 267 can be horizontal with respect to faces 272F, 274F and 276F (FIG. 33) belonging to manifold blocks 272, 274 and 276, respectively. This arrangement can help to avoid collection of debris or liquid in the valves that can potentially impair their function or shorten their maintenance-free life. Pressure sensors 565 (FIG. 34) are mounted to ports 567 on an upward facing surface of end-manifold block 276. The adaptors 266, 268 and 270 provide ports 266P, 268P, 270P to receive the ports 240 of the cassette assembly 226.

The mid-manifold block 274 and Tee-manifold block 272 may include internal supply lines for atmospheric pressure, low positive pressure, high positive pressure and negative pressure. One or more of these internal supply lines run through the length of the manifold blocks 272, 274. The ports for the internal supply lines are capped 264 or have a port 263 for a flexible tube connection to a pressure reservoir. Both end faces of the manifold blocks 272, 274 may include ports to connect the internal supply lines (not shown) to external pressure reservoirs.

A plurality of diaphragm pumps and diaphragm valves can be grouped in a single cassette as shown in FIGS. 6-13. A plurality of such cassettes may be joined together to form a cassette assembly 226 as shown in FIGS. 20, 21. In this case the assembly spaces the cassettes apart in order to accommodate outboard pumps, mixing chambers or fluid balancing chambers have volumes greater than can be accommodated within any one of the individual cassettes. The pressure distribution module 260 includes adaptors 266, 268, 270 that extend at a right angle to the long axis of the manifold blocks 272, 274 276. The adaptors extend the interface area of the pressure distribution module from the footprint of the manifold blocks and risers to any area required to accept the ports 240 of the cassette assembly 226. Pneumatic layout and port distribution on and within the adaptors 270, 268 and 266 and its sub-components (not shown) allow direct connection between the cassette assembly 226 and the manifold blocks 272, 274, 276, with one-to-one mapping of each port of the cassette assembly with corresponding actuation ports of the manifold assembly.

The external pressure reservoirs to which the pressure distribution module 260 may be connected may have volumes maintained at specified or pre-determined pressures by pumps controlled by a system controller. In an embodiment, a high-pressure reservoir can be maintained at a pressure of about 1050 mmHg, and a positive pressure reservoir can be maintained at a pressure of about 800 mmHg. The pressures actually delivered to various pneumatically actuated pumps and valves may vary based on the pressure reservoir ported by the two-way and three-way valves on pressure distribution module 260. Furthermore, intermediate pressures may also be delivered through a combination of rapid opening and closing of the on-off valves. Generally, a high pressure source may be useful for actuating diaphragm valves to ensure leak-free and reliable valve closure during operation of the cassette assembly.

FIG. 33 depicts an exploded view of the pressure distribution manifold 226. Manifold blocks 272, 274 and 276, can further comprise intermediary elements connecting features among each of the manifold blocks 272, 274 and 276. These intermediary elements and connection features can help in assembling the three manifold blocks and establishing pneumatic connection between the individual manifold blocks 272, 274 and 276. A first set of intermediary components may include, for example, a first plate 550, a first gasket 552 and a second gasket 554 that can be employed between the T-shaped manifold block 272 and the mid-manifold block 274 and a second set of intermediary components may include a second gasket plate 555, a third gasket 556 and a fourth gasket 558 positioned between the mid-manifold block 274 and the end manifold block 276. The two manifold blocks 272, 274 may be clamped together with a gasketed mid-plate 550 between them. The mid-plate 550 may also be referred to as a backing plate, as it provides a rigid surface that forces the gasket to seal against multiple channels that may be provided on the end-manifold block 276, Tee-manifold block 272 and the mid-manifold block 274. 2 Each manifold block 276, 274, 272 may comprise at least one face 276G, 274F, 272F (see FIG. 33, 35, 36) with channels and various ports mating with ported plates and gaskets, such as plates 550, 555 and gaskets 552, 554, 556, 558. The respective channels may be configured as grooves that include a solid bottom and two side walls with an open top. The channel may be cut into one face 276F, 274F, 272F of the manifold block or it may be formed with walls that extend above the surface of the manifold block face 276F, 274F, 274G and 272F. As shown in FIG. 33, the open top of the channels may be sealed by clamping a gasket 554,552, 556, 558 backed by a rigid flat mid-plate 550, 555 against the channels. In one example, the mid-plate 550 is a backing plate that forces the gasket 552 against all of the channels on face 272F and gasket 554 against the channels on face 274G. Note that face 274G is opposite face 274F in FIG. 33. The manifold block and gasket can include features to assure an essentially even distribution of pressure on the gasket. The mid-plate 550 provides a substantially smooth and rigid backing for the gaskets so that more than one manifold block may be assembled or sandwiched into the multi-part pneumatic manifold 260. The channels are linked to pressure sources, valves, sensors and outlet ports that reside on other faces of the blocks. The manifold blocks 276, 274, 272 may sandwich the gaskets 552, 554, 556, 558 and the mid-plate 550, 555 between them with mechanical fasteners 570 to seal the multiple channels on the channeled faces 272F, 274F, 274G, 276G of each of the manifold blocks 272, 274, 276. This sandwich construction allows the compact assembly of multiple manifold blocks with sets of channels on one face of each block 272, 274, 276.

Connection points of the T-shaped manifold block 272 can be configured to receive screws that extend through other components that assemble the pressure distribution manifold 260 as a unit. In this example, matching connection points 572 can be provided on the first gasket plate 550, connection points 573 on the mid-manifold block 274, connection points 573 on the third and fourth gaskets 556, 558. The first set of valves 265 can operate on pneumatic pathways within the manifold blocks 272, 274 and 276 and/or the pneumatic pathways that connect the manifold blocks 272, 274 and 276.

FIGS. 32 and 33 show an embodiment including a plurality of cartridge valves 265 and the connections to the pressure reservoirs 263. A cartridge valve is inserted in a manifold port. Corresponding cavities (not shown) are formed to accommodate seals on the outside of the cartridge valves 265. The machined cavity may have a set of dimensions defined by the manufacturer of the valve to assure sealing and proper functioning of the cartridge valve 265. Although in other embodiments the numbers may vary, in this particular embodiment, approximately forty-eight cartridge valves 265 mount on a side face of the mid-manifold block 274. This side of the mid-manifold block 274 is perpendicular to the channeled face 274F. In some embodiments, the cartridge valves are three-way valves, such as Lee LHDA Plug-In valves available from The Lee Company USA, Westbrook, Conn. The number of electromechanical valves is determined by the number of individual diaphragm pumps and valves to be operated in the direct-connect cassette assembly and a remote-connect cassette assembly (if desired), and the linear array of the electromechanical valves results in the extended length of the manifold assembly.

Figure 34:
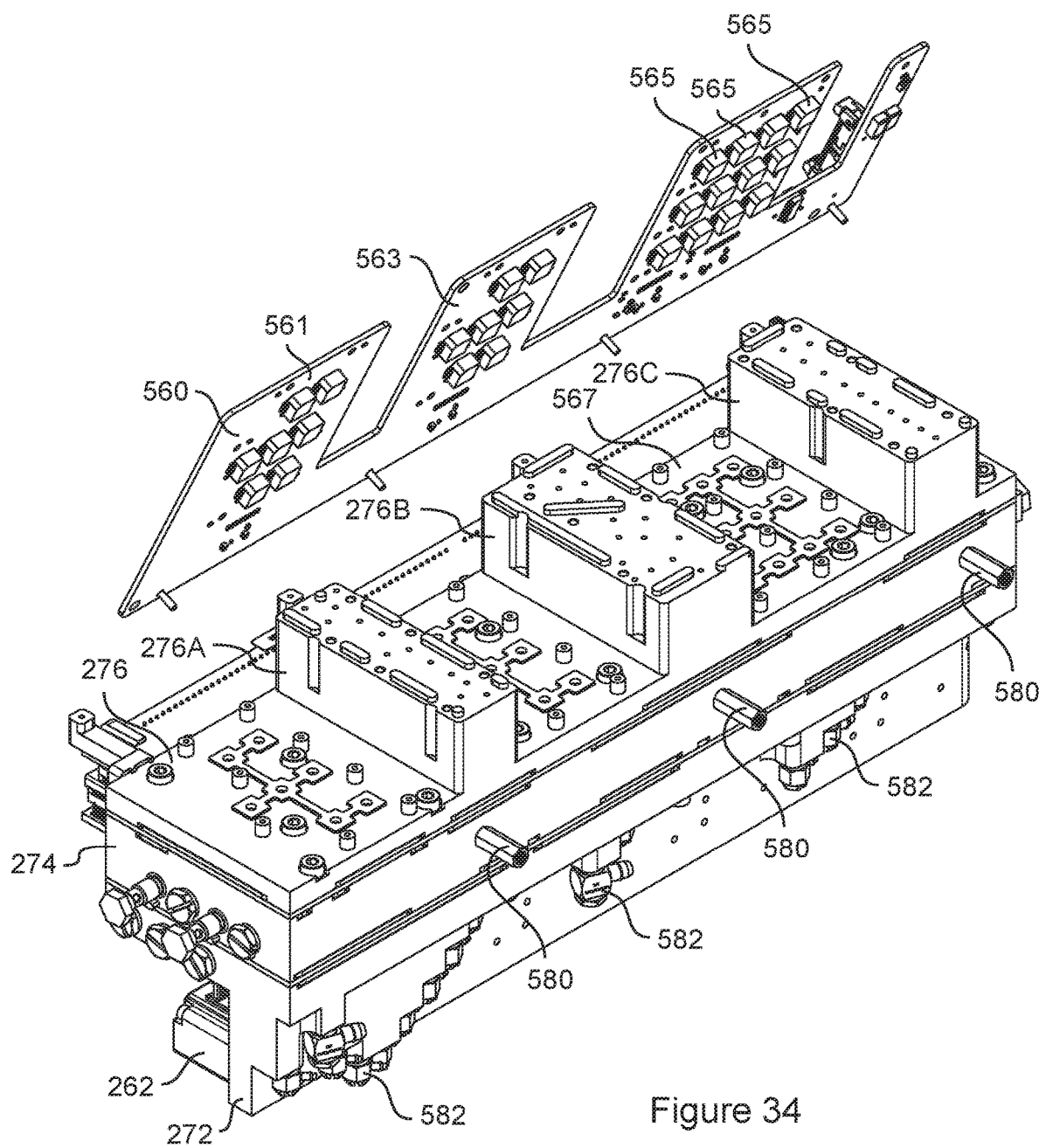
FIG. 34 is a perspective view of the exemplary pressure distribution manifold and an associated sensor board.
Figure 35:
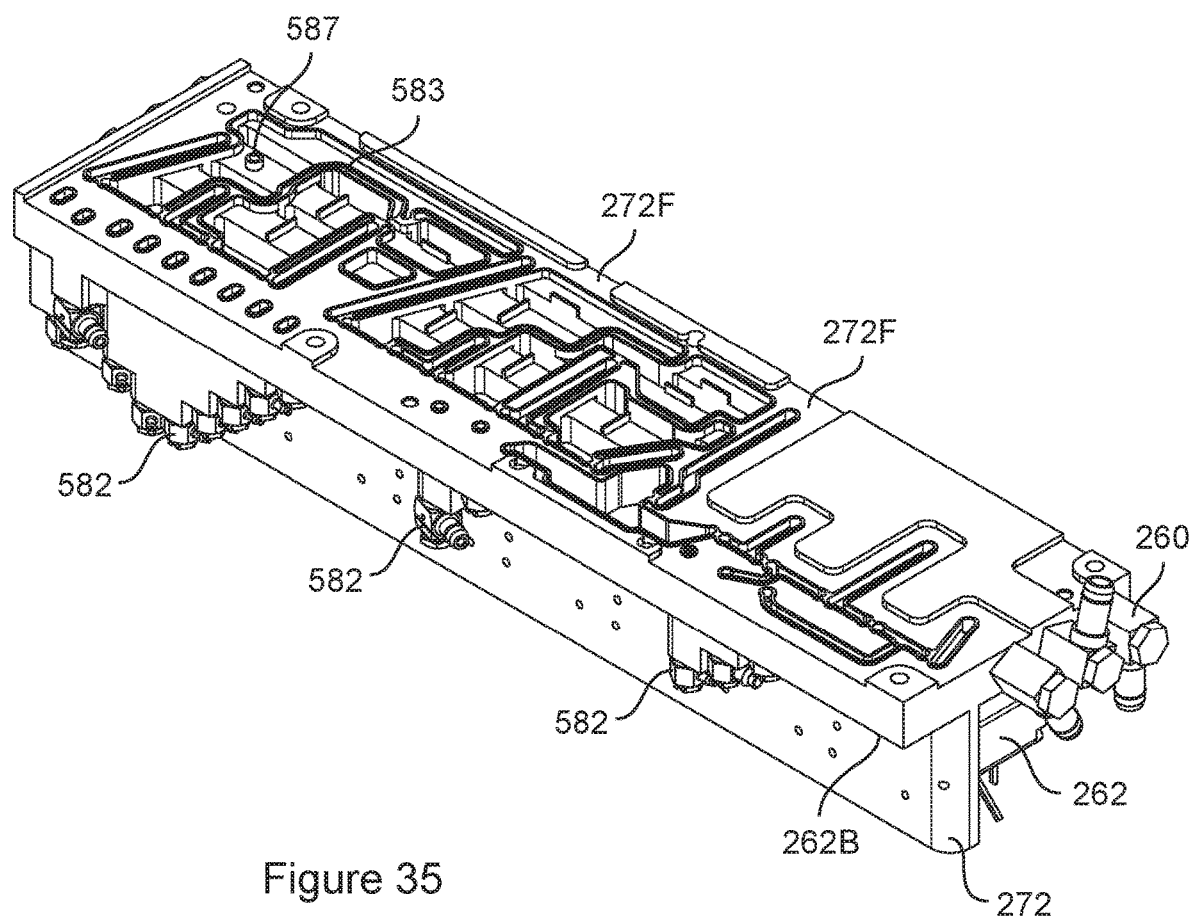
FIG. 35 is a perspective view of a lower block of the pressure distribution manifold shown in FIG. 34.

Referring now to FIG. 34, the pressure distribution manifold can serve as a pneumatic actuation device for components other than the cassette assembly 226. For example, pressure distribution manifold 260 can also be in pneumatic communication with other pneumatically driven valves, diaphragm pumps, pneumatic cylinders and remote cassettes that comprise diaphragm valves and diaphragm pumps. In one example, the pressure distribution module 260 controls the position of an occluder 251 in FIG. 23, the occluder comprising a pinch valve to block the blood lines, and driven by a pneumatic cylinder. In another example, the pressure distribution module 260 can be placed in pneumatic communication with a dialysate tank in order to make volume measurements of the tank using pressure information. Further, the pressure distribution module 260 may be arranged to control the pumping action of a blood pump cassette (not shown) that mounts on the blood pump cassette receptacle assembly 252 in FIG. 23. Referring now to FIG. 34, the ports 582 shown on the T-shaped manifold block 272 can be connected with one or more blood pump cassettes directly or through flexible or malleable tubing to establish the required pneumatic connection. The ports 582 include fittings that connect to a pneumatic tube and may be individually removable from the tee-shaped manifold 272. The pneumatic lines connected at one end to ports 582 may connect at a second end to a connector on the surface of the wall 255 (FIG. 24) of the dialysis machine. A second connector inside the housing may then make a connection using flexible tubes to, for example, a dialysate tank, a pneumatically actuated tubing occluder, and/or to a blood pump cassette receptacle assembly 252.

The cartridge valves 265 and the surface mount valves 267 in this example control the pneumatic pressure delivered to the occluder, blood pump cassette and other pneumatically driven items in the hemodialysis machine 246. Mounting features such as standoffs 580 can be provided to attach the pressure distribution module 260 to the back wall of the enclosure 254 and set the location of the adaptors 266, 268, 270 relative to enclosure 254.

Continuing to refer to FIG. 34, 35, valves 267 disposed on the T-shaped manifold block 272 are electromechanical valves that seal against a flat surface or a surface machined to accept the valve face. In some embodiments, the surface mount valves 267 can be proportional valves, or continuously variable valves (also referred to as 'vari-valves'). In other embodiments, the surface mount valves 267 are binary two-way or three-way valves. In some examples, surface 272F is generally horizontal, making the leg of the T-shaped cross-section of manifold 272 generally vertical. In a preferred arrangement, valve mounting surface of the leg is either vertical or tilted slightly upward, so that ports on the valve 267 are either horizontal or tilted downward to avoid collection of debris or liquid. Sealing features such as O-rings and/or other elements can be provided on the valves to prohibit leakage of fluid or air. The valves may be any digital two-way or three-way valve suitable for surface mounting, such as, for example, model 11-15-3-BV-12-P-0-0 from Parker Hannifin Corporation in Hollis, N.H.

Referring now to FIG. 34, the pneumatic flow on the pressure distribution manifold 226 can be monitored through one or more pressure sensors, these sensors can be mounted on a sensor board (e.g. PCB). In the present example, the sensor board 560 can be positioned over a surface 567 of an upper manifold block 276, in spaces between the risers 276A-C. The pressure sensors 565 may be directly mounted to the face 276F of the first end-manifold block 276. The pressure sensors 565 may be integrated circuits soldered to a printed circuit board (PCB) 560. As shown in FIG. 34, a printed circuit board 560 including one or more pressure sensors 565 may be mounted on the top face 276F that is parallel to the channeled face of the second end-manifold block 276 with a gasket to pneumatically isolate each sensor, and with a plate (not shown) to hold the PCB 560 in place and compress the gasket sufficiently to seal each pressure sensor from the atmosphere. The sensor board 560 can be coupled with the surface 567 of the end manifold block though fastening components such as screws, nut-bolt pairs, rivets, adhesive or a combination of such fastening mechanisms. An example pressure sensor 565 may be obtained from Freescale Semiconductor, Inc. in Tempe, Ariz. (part no. MPXH6250A). The PCB including a plurality of pressure sensors 565 may be mounted as a unit to the end-manifold block 276. The pressure sensing face of each pressure sensor 565 may be fluidly connected to the desired pressure sources such as reference volumes or more remotely to the actuation chambers of diaphragm pumps, or to a dialysate reservoir tank. In some cases the sensors are arranged to monitor liquid pressures in various diaphragm pumps of the liquid handling cassettes. The end-manifold block 276 provides risers 276A, 276B and 276C that can interface with the respective adaptors 270, 268 and 266. The manifold assembly is constructed so that the sensor board 560 avoids interfering with the engagement between the risers and the corresponding adaptors. The risers also provide separation between the liquid handling cassette assembly above and the temperature sensitive sensor board 560, allowing for placement of insulation 269A between the two. (see, e.g., FIG. 48).

Figure 36:
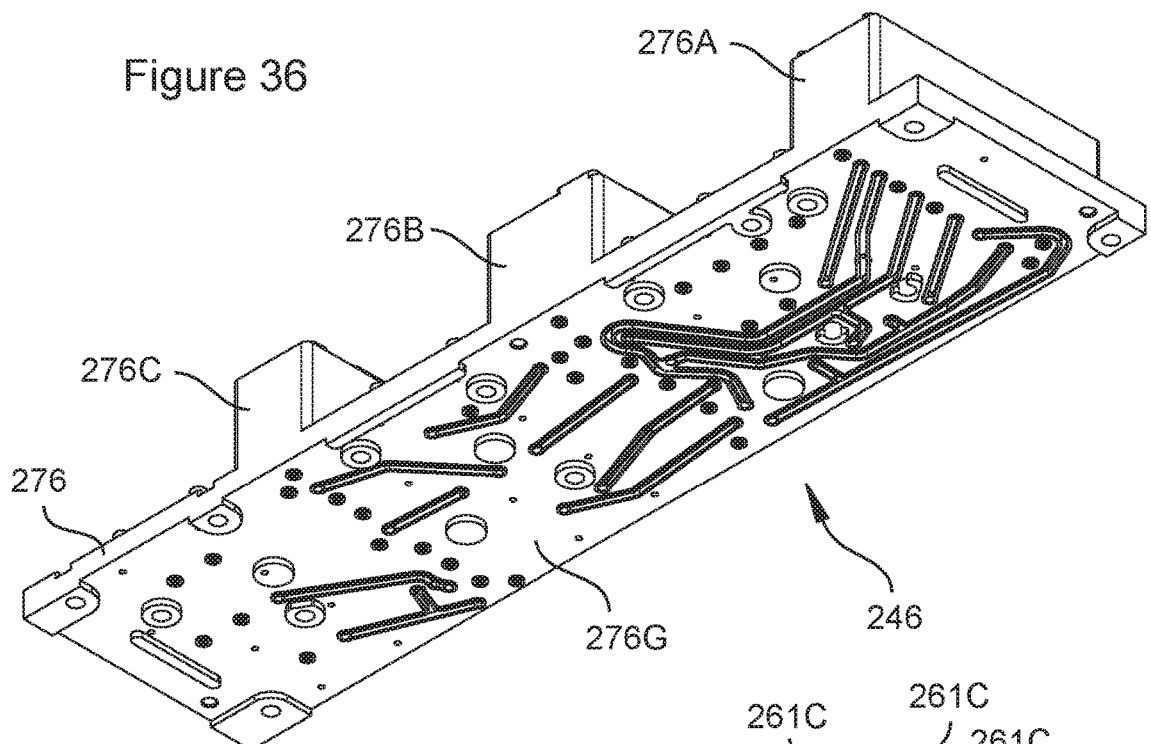
FIGS. 36-37 are inferior and superior perspective views of an upper block of the pressure distribution manifold shown in FIG. 34.
Figure 37:
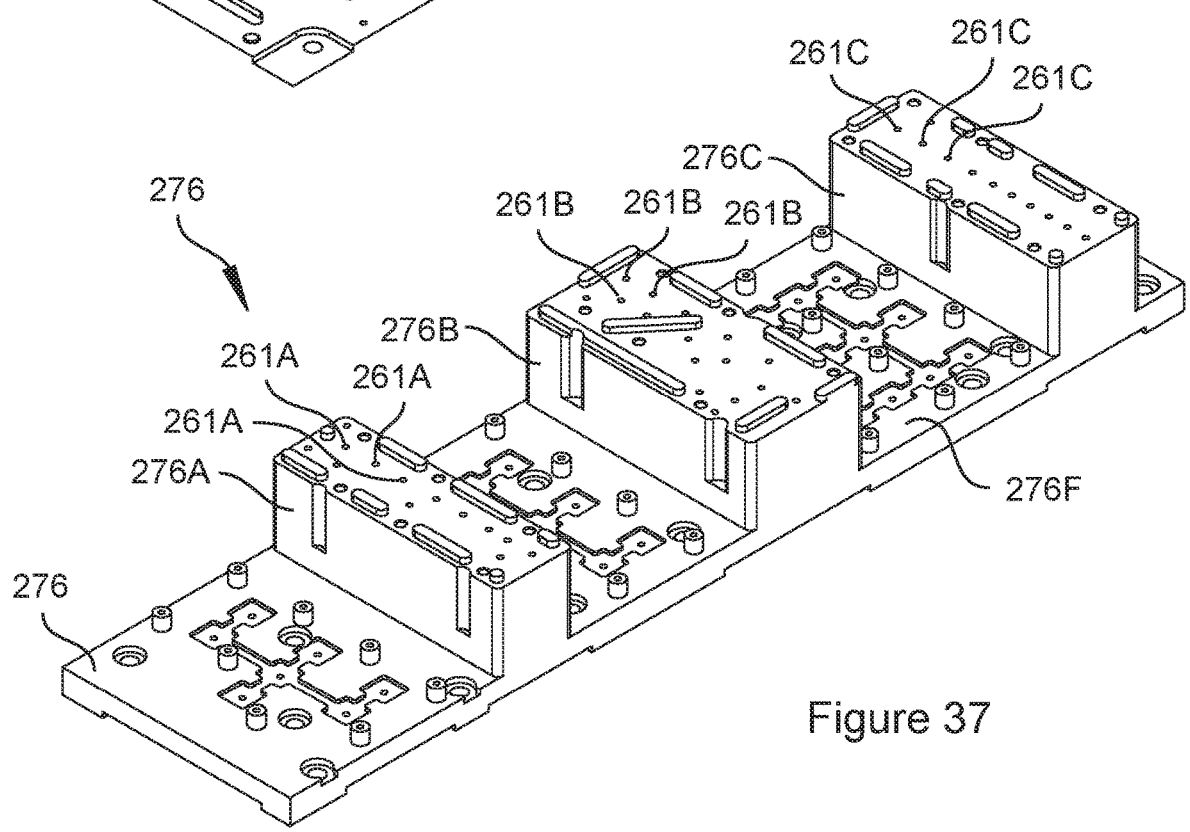

FIGS. 36 and 37 illustrate the second manifold block 276 with a face 276F and a base surface 276G. Base surface 276G can be configured to mate with one or more intermediary components such as gaskets, gasket plates and/or other manifold blocks. As shown, the base surface 276 can comprise a plurality of pneumatic channels 574 that are sealed by gasket 558 (FIG. 33). In some examples, the channels 574 may connect pressure ports 567 on face 276F to holes 261A, 261B, 261C in the risers. In other examples, the channels 574 may connect pneumatic pathways or holes through the gasket 558 to either the pressure ports 567 or holes 261A, 261B, 261C. Face 276F can comprise the risers 276A, 276B and 276C that can serve as mounting surfaces for corresponding adaptors 270, 268 and 266, respectively. Pneumatic ports 261A, 261B and 261C, on the risers 276A, 276B and 276C, can interface with the respective adaptors 270, 268 and 266 for transmitting pneumatic pressure to the cassette assembly 226. Secure connection between the riser ports 261 and the adaptors can be established via mechanical fittings such as nut-bolt pairs, threaded or push-screws or similar mechanisms. The mechanical assembly can also include mating of the blocks with intermediary components such as one or more gaskets 568 (FIG. 32), gasket plates and/or similar components.

Pneumatic Connections in Manifold

The structure and function of the manifold 260 in FIG. 32 can be further understood by examining the pneumatic pressure sources, conduits, valves, sensors and exit ports of manifold 260. In an example presented in FIG. 32, the manifold 260 has tens of valves, sensors and ports. The following section describes 3 exemplary pathways that comprise sources, valves, conduits, ports and in one example a pressure sensor. The example pathways serve to illustrate how elements of the manifold in FIGS. 32 and 33 come together to provide selectable fluid connections between pressure sources and actuation chambers of pneumatically driven valves and pumps, and provides fluidic connections to pressure sensors. The pressure sensors provide information to a controller that controls the valves in order to safely pump blood, dialysate and water to provide therapy to a patient.

Figure 38:
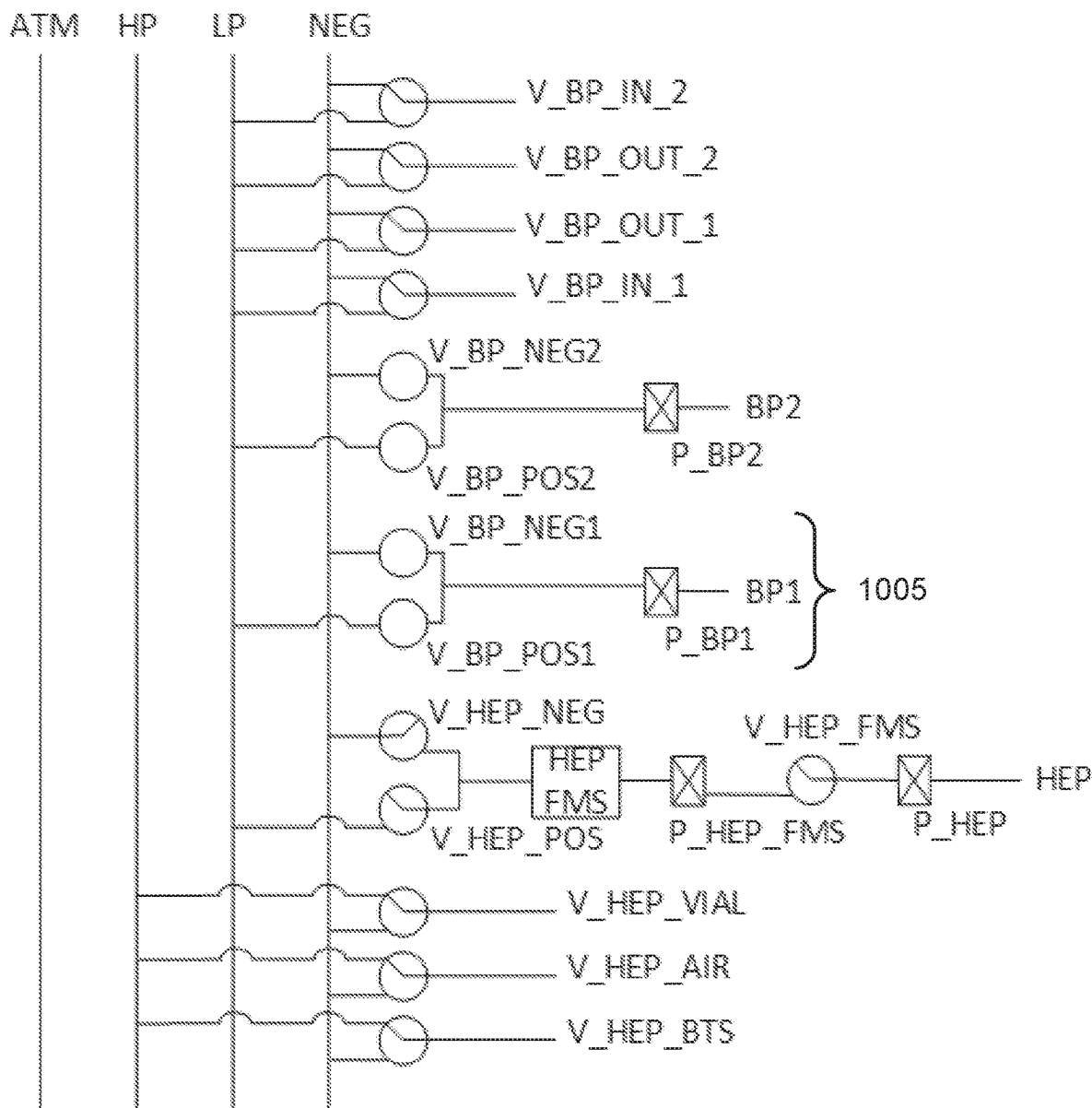
FIG. 38 is a flowpath schematic of an arrangement of pneumatic channels in the exemplary pressure distribution manifold.

The pneumatic manifold schematic in FIG. 38 describes the pneumatic connections to a blood pump cassette. (The blood pump cassette in this case is located on a front panel of the dialysis unit, so it connects to the manifold using flexible tubes rather than a direction connection). The pneumatic circuits in FIG. 38 selectively connect the actuation chambers of the blood, and heparin pumps and associated valves to the high positive pressure source HP, low positive pressure source LP or negative pressure source NEG. The circuit 1005 connects a blood pump BP1 to a pressure sensor P_BP1, the low pressure source LP via valve V_BP_POS1 and the negative pressure source NEG via valve V_BP_NEG1.

Figure 39:
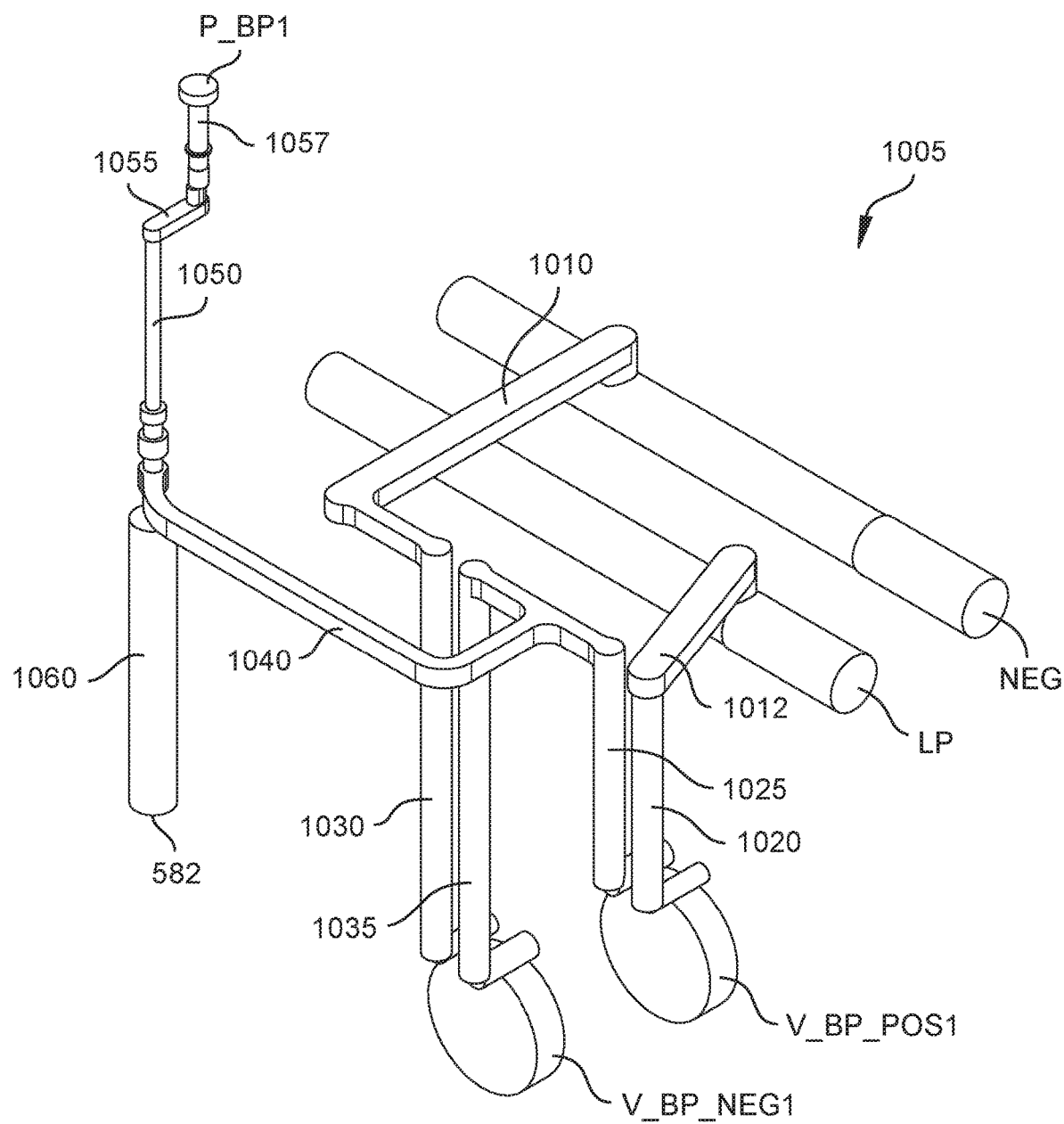
FIG. 39 is a perspective view of an exemplary pneumatic channel in the pressure distribution manifold.
Figure 40:
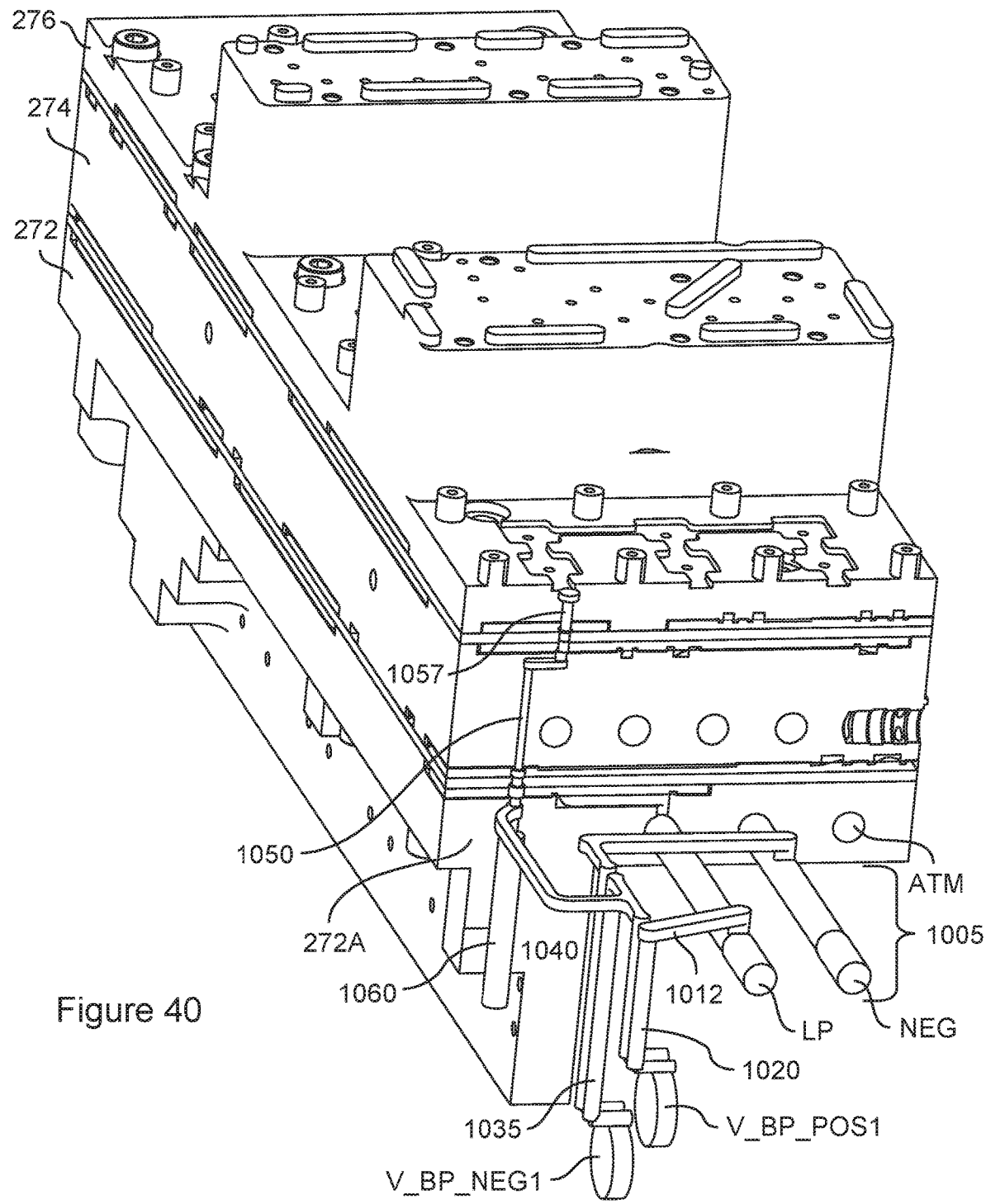
FIG. 40 is a perspective view of the disposition of the exemplary pneumatic channel shown in FIG. 39 in the pressure distribution manifold.

The blood pump actuation circuit 1005 in the manifold 260 is presented in FIGS. 39, 40. The flowpaths are the holes and channels of the various blocks of manifold 260. The low pressure source LP is a conduit in horizontal portion 272A of Tee manifold that runs the length of the Tee manifold block 272. The negative pressure source NEG is a conduit that parallel to LP through the long axis of the Tee manifold block 272. Positive pressure flows from the LP conduit through flow channel 1012 that is located on top of the Tee manifold 272, then through a hole 1020 through the vertical leg 272B of the Tee manifold to the electromechanical valve V_BP_POS1. When the valve V_BP_POS1 opens, the positive pressure flows up through hole 1025, which is in the vertical leg 272B to channel 1040 located on top of the Tee manifold 272. The low pressure then flows through hol 1060 to port 582, where a fitting allows for a flexible or malleable line to connect the port to the (remote) blood pump cassette. The pressure in the blood pump connected to port 582 is monitored by a pressure sensor mounted to port P_BP1. Port BP1 is located on the lower of the two upward facing surfaces of the top manifold block 276. The port P_BP1 is fluidically connected to channel 1040 via hole 1057 in the top manifold block 276, a channel 1055 on the top of mid manifold block 274 and a hole 1050 through the mid manifold block 274.

Shown embedded in the manifold assembly 260 in FIG. 40, in circuit 1005, the Tee manifold block 272 selectively connects an actuation chamber in a blood pump cassette (plugged into cassette receptacle 252 in FIG. 23) to either the low pressure source LP or the negative pressure source NEG via two valves. A pressure sensor mounted to the top manifold block 276 is fluidically connected through holes and channels in the top and mid manifold blocks. Other pneumatic circuits may connect actuation chambers for the diaphragm pumps in the cassette assembly 226 to two of the low pressure LP, atmospheric ATM and negative pressure NEG sources via valves on the vertical leg 272B of the Tee manifold block 272.

Figure 41:
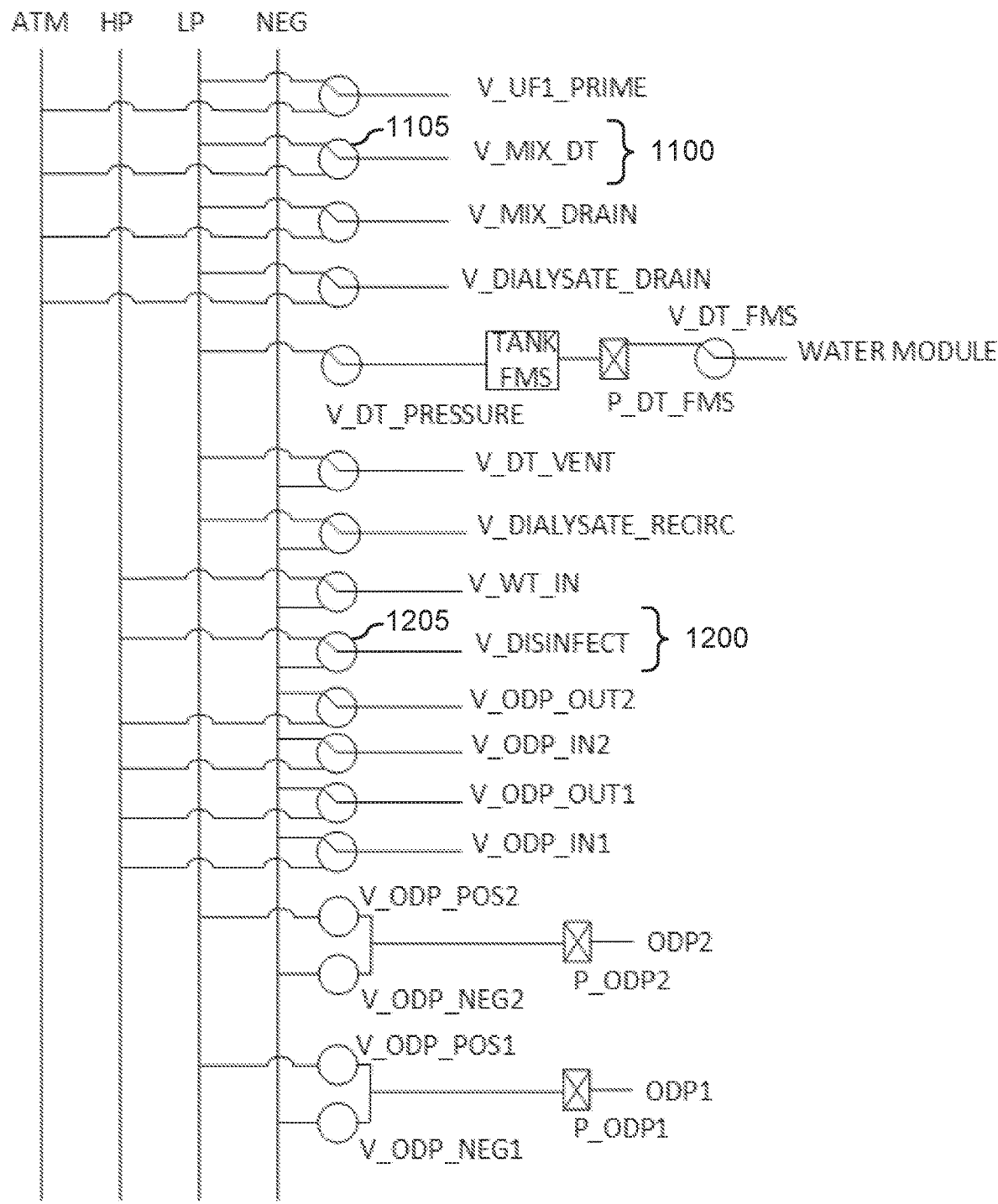
FIG. 41 is a flowpath schematic of an arrangement of pneumatic channels in the exemplary pressure distribution manifold.

The pneumatic schematic in FIG. 41 describes the pneumatic connections to the various actuation ports of the cassette assembly 226. The pneumatic circuits in FIG. 41 selectively connect the actuation chambers of the various valves (and the two diaphragm pumps that happen to be illustrated here) on an outer dialysate cassette (ODC) to at least one of the atmospheric pressure ATM, high positive pressure source HP, low positive pressure source LP, and negative pressure source NEG. Circuit 1100 is an example pneumatic circuit that connects the diaphragm valve V_MIX_DT in the ODC cassette to either the ATM or LP pressure sources via a 3 way valve 1105. Circuit 1200 is an example pneumatic circuit that connect the liquid valve V_DISINECT in the ODC cassette to either the HP or NEG pressure sources via a 3 way valve 1205.

Figure 42:
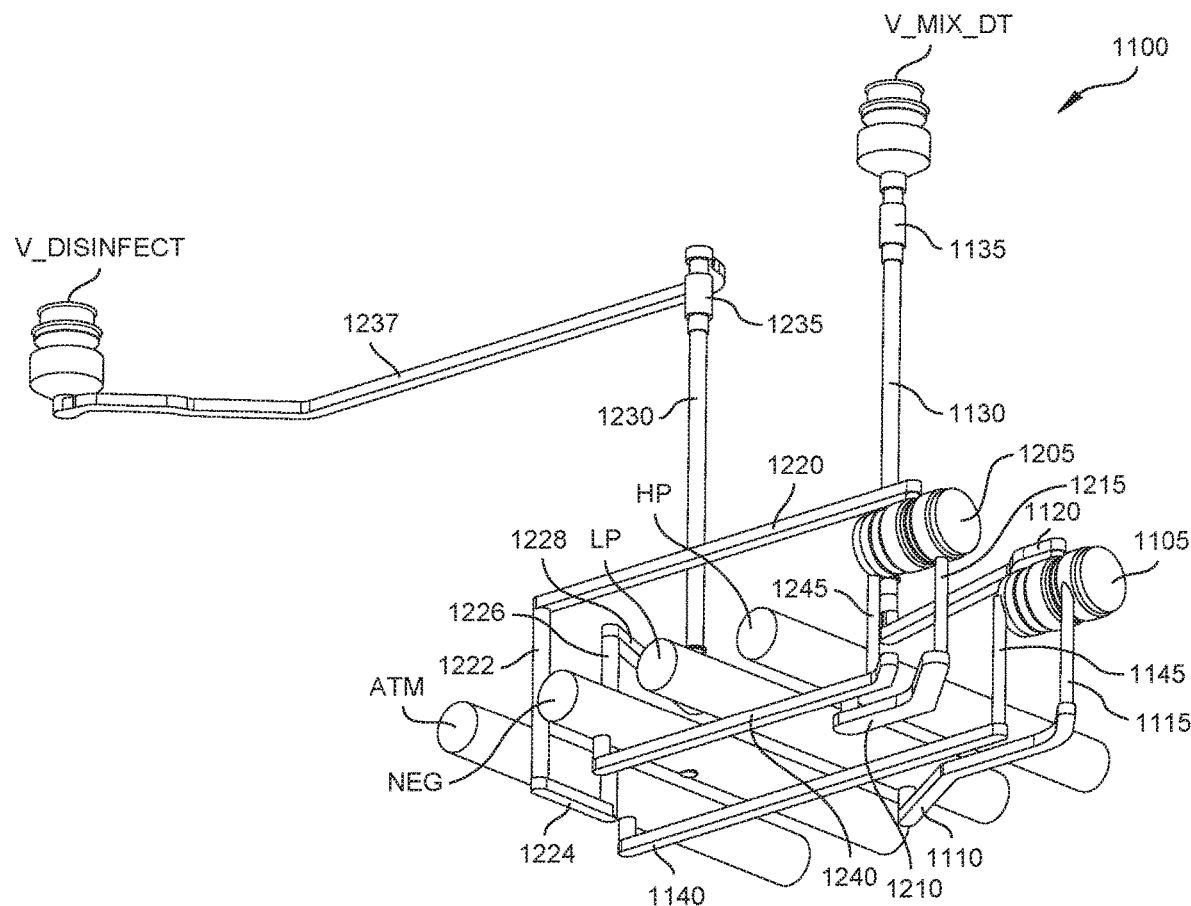
FIG. 42 is a perspective view of another exemplary pneumatic channel in the pressure distribution manifold.
Figure 43:
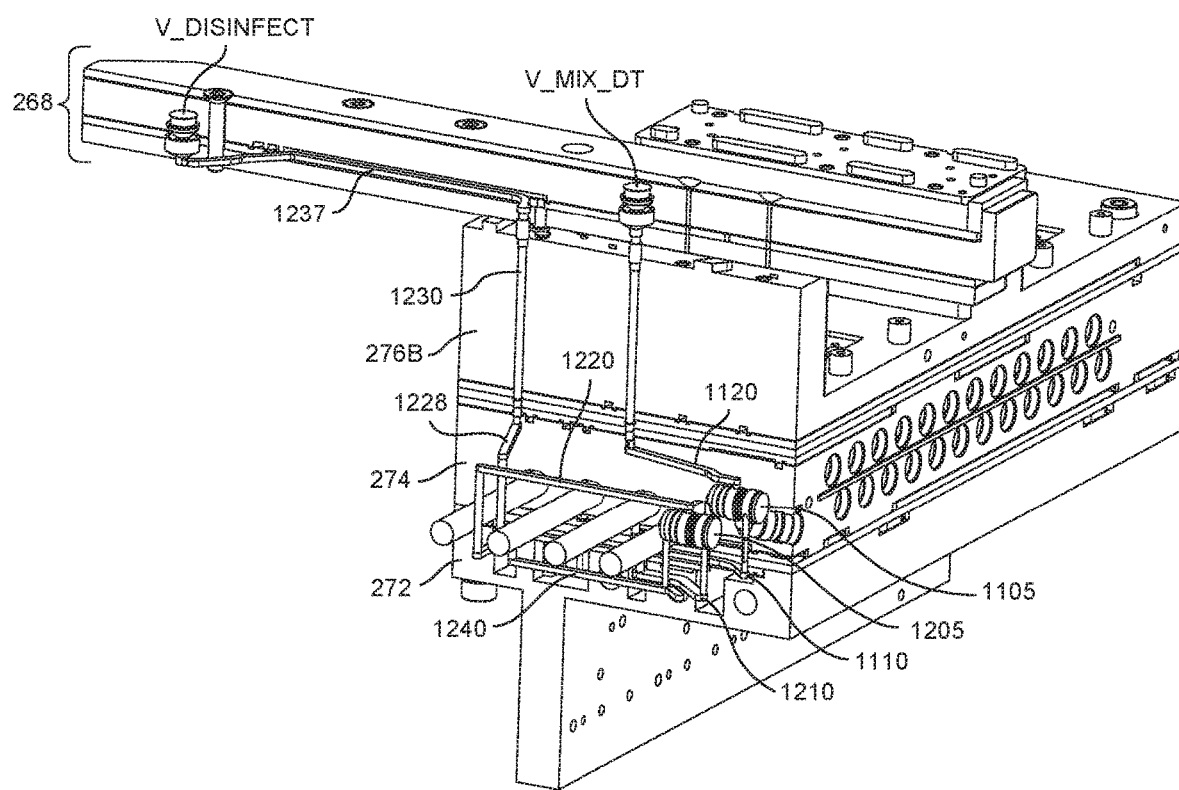
FIG. 43 is a perspective view of the disposition of the exemplary pneumatic channel shown in FIG. 42 in the pressure distribution manifold.

The Mix_DT valve circuit 1100 and the DISINFECT valve circuit 1200 in the manifold 260 are presented in FIGS. 42, 43. The flowpaths comprise the holes and channels of the various blocks of manifold 260. The pressure sources, ATM, NEG, LP, HP, are conduits arranged along the long axis of the mid-block 274. The MIX_DT circuit 1100 connects either the low pressure source LP or the atmospheric source ATM to the outlet port V_MIX_DT for the MIX_DT liquid valve in the cassette assembly 226. The low pressure source LP is connected to the valve 1105 via a channel 1110 on the bottom face of the mid manifold block 274 and hole 1115. The atmospheric source ATM is connected to the valve 1105 via a channel 1140 on the bottom face of the mid manifold block 274 and hole 1145. The valve 1105 is connected to the outlet port V_Mix_DT via channel 1120 on the top of the mid manifold block 274, hole 1130 through the top manifold, and hole 1135 through the adaptor 268.

The DISINFECT circuit 1200 connects either the high pressure source HP or the negative source NEG to the outlet port V_DISINFECT for the DISINFECT liquid valve in the cassette assembly 226. The high pressure source HP is connected to valve 1205 via a channel 1210 on the bottom face of the mid manifold block 274 and hole 1215. The negative source NEG is connected to the valve 1205 via a channel 1240 on the bottom face of the mid manifold block 274 and hole 1245. The valve 1205 is connected to the outlet port V_DISINFECT via channel 1220 on the top of the mid manifold block 274, hole 1222 through the mid manifold 274, channel 1224 on the bottom of the mid manifold, hole 1226 back through the mid manifold, channel 1228 on top of the mid manifold, hole 1230 through the top manifold 276 and through the adaptor rail 268 via hold 1235 and channel 1237.

FIG. 43 shows how the circuits above are physically embedded within manifold assembly 260. Also shown is the mapping of these actuation ports from an array on the riser 276B to a spatially different array of actuation ports of manifold adaptor 268, providing an actuation port array that matches the actuation port array of the cassette assembly 226.

Figure 44:
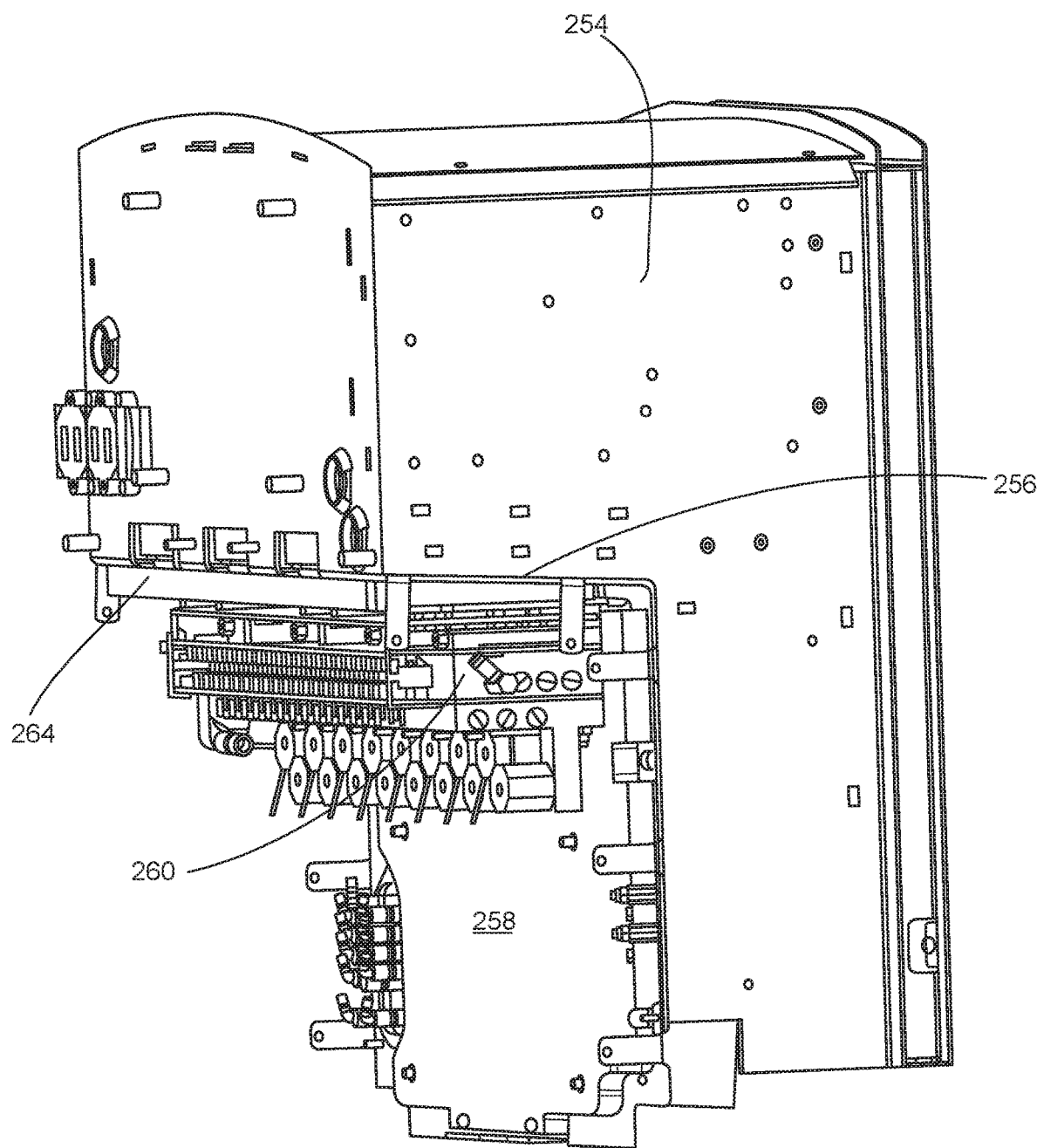
FIG. 44 is a rear perspective view of a hemodialysis device housing, showing the placement of the pressure distribution manifold.

FIG. 44 illustrates the pressure distribution manifold 260 installed in the recess 258 of enclosure or housing 254. This arrangement can allow appropriate alignment between the ports 261 on the risers of the pressure distribution manifold 260 and the respective ports on the mating surface of the adaptors 266, 268 and 270. In the present embodiments, the manifold 260 is positioned below some thermal insulation 264. Insulation 264 can be provided between the body of the manifold 260 and the shelf 256. This arrangement isolates the temperature sensitive electronics from heated fluids circulating in components inside the enclosure or housing 254.

As shown in FIG. 45, in this embodiment of the hemodialysis apparatus 246 and enclosure 254, the footprint of the cassette assembly 226 extends forward from a front face of the apparatus 246. With reference to a user or operator facing the hemodialysis apparatus 246, the the cassette footprint extends over the front edge of the shelf 256. For this reason, one or more adaptors 266, 268, 270 are configured to provide the requisite mating of cassette assembly 226 actuation ports 240 to their respective connectors or receptacle ports 266P, 268P and 270P located on the interfaces or adaptors 266, 268, 270. Adaptors 266, 268, 270 in this example serve as receptacle assemblies, providing a first spatial array of receptacle ports for mating with identically arrayed cassette ports 240 of each cassette 194, 196 and 198 respectively of the cassette assembly 226. FIG. 46 shows a bottom perspective view of enclosure 254 with installed interfaces/adaptors 266, 268, 270. The extent to which the adaptors overhang the enclosure shelf 256 (and therefore also the underlying pressure delivery manifold 246) is apparent in this view.

Figure 52:
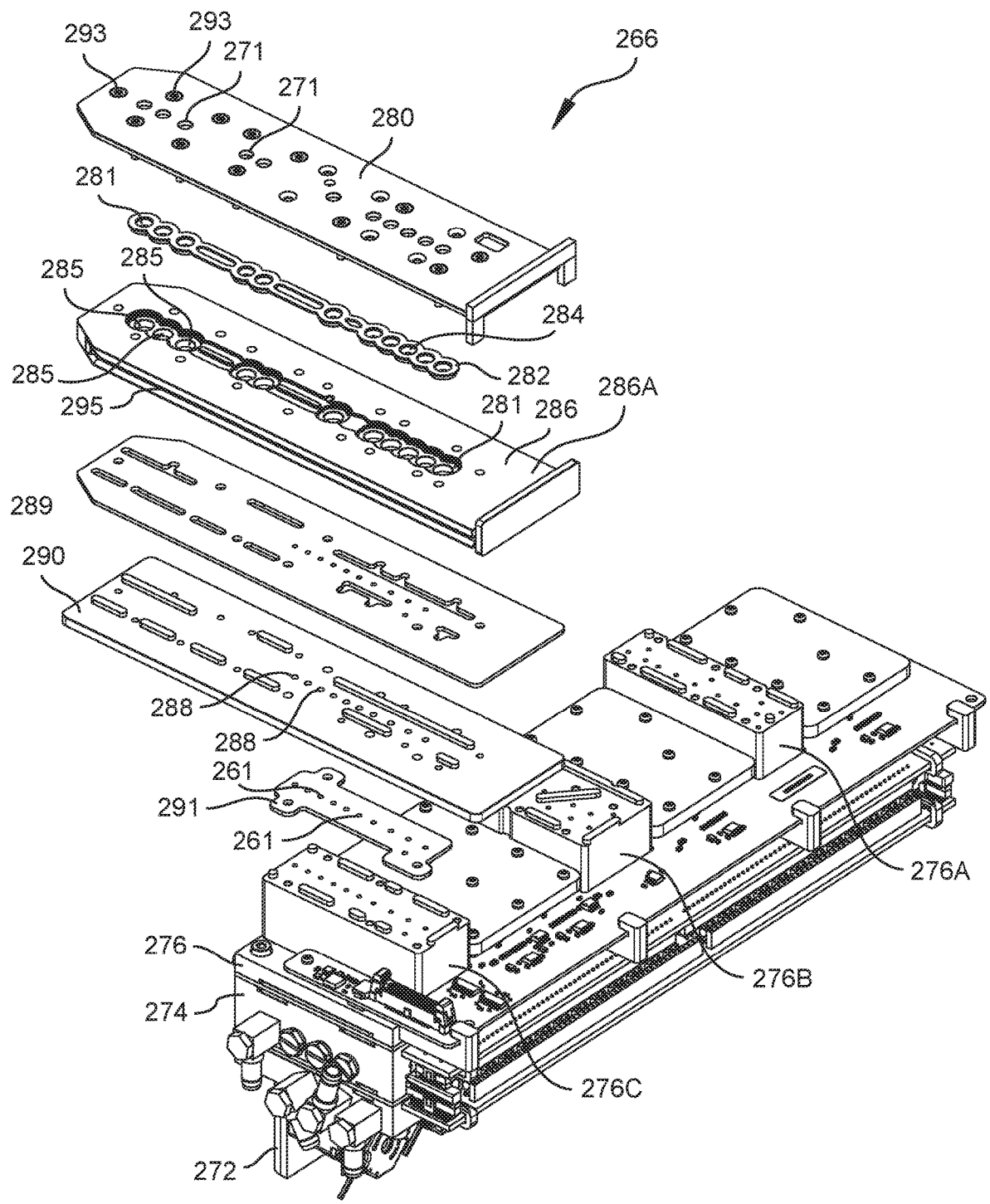
FIG. 52 is a partially exploded superior perspective view of an exemplary manifold adaptor positioned over the pressure distribution manifold.

FIG. 32 shows how adaptors 266, 268, 270 are mounted to the top side of manifold risers 276A-C, and how they overhang the front side of manifold 260. The first spatial array of receptacle ports 266P, 268P and 270P connect with a second (in this case more compact) spatial array of output ports 261 of the top block or riser 276A-C of the manifold 260. Internal channels within the adaptors 266, 268, 270 are routed to the respective risers 276A, 276B and 276C mounted above a corresponding array of manifold output ports. FIG. 52 shows the manifold/adaptor assembly with adaptor 266 removed and exploded to fully reveal the construction of the adaptors, as well as risers 276C, 276A and 276B.

Figure 47:
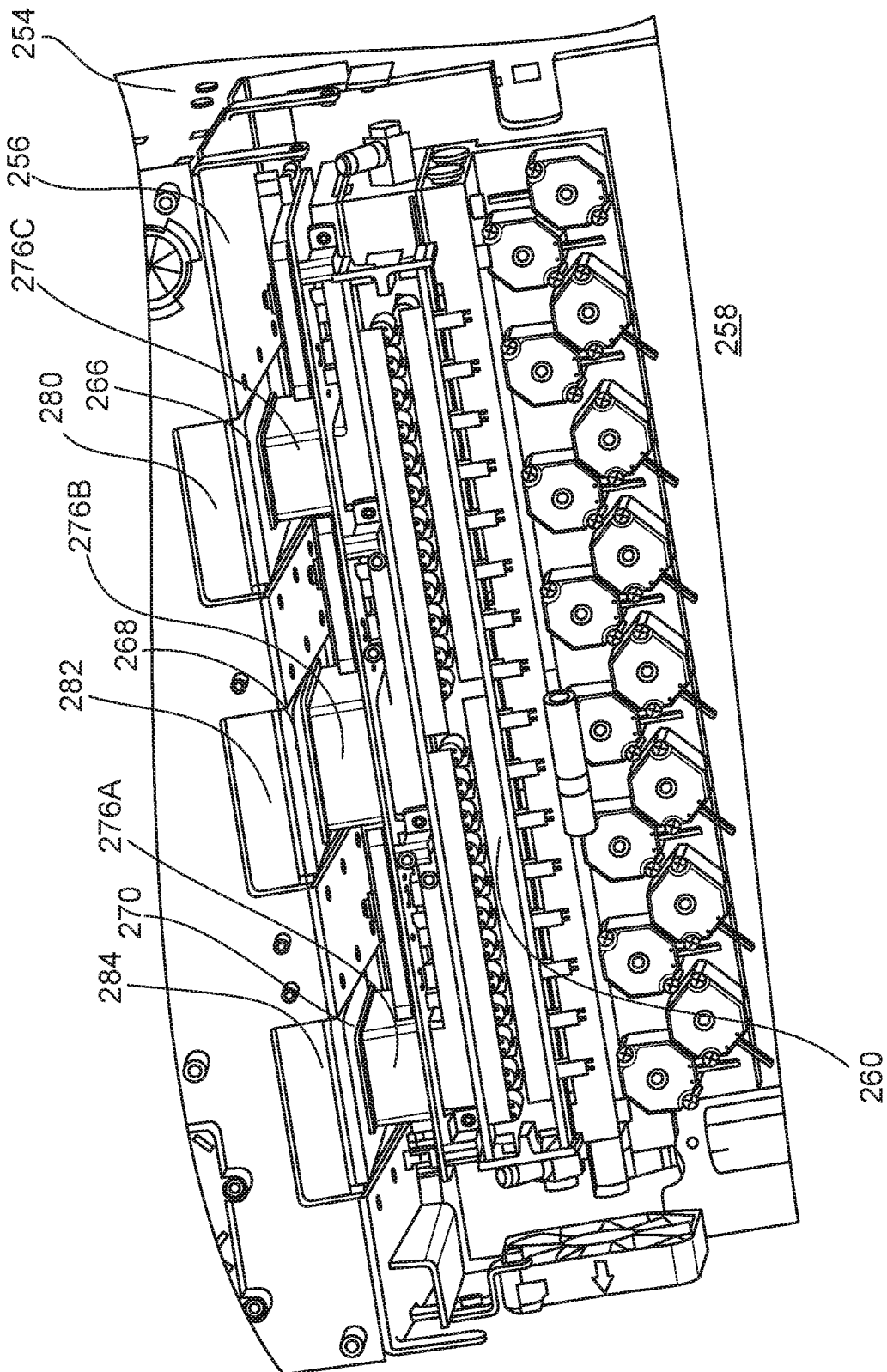
FIG. 47 is a perspective view of the exemplary pneumatic distribution manifold, positioned below the housing cutouts for the manifold adaptors.
Figure 48:
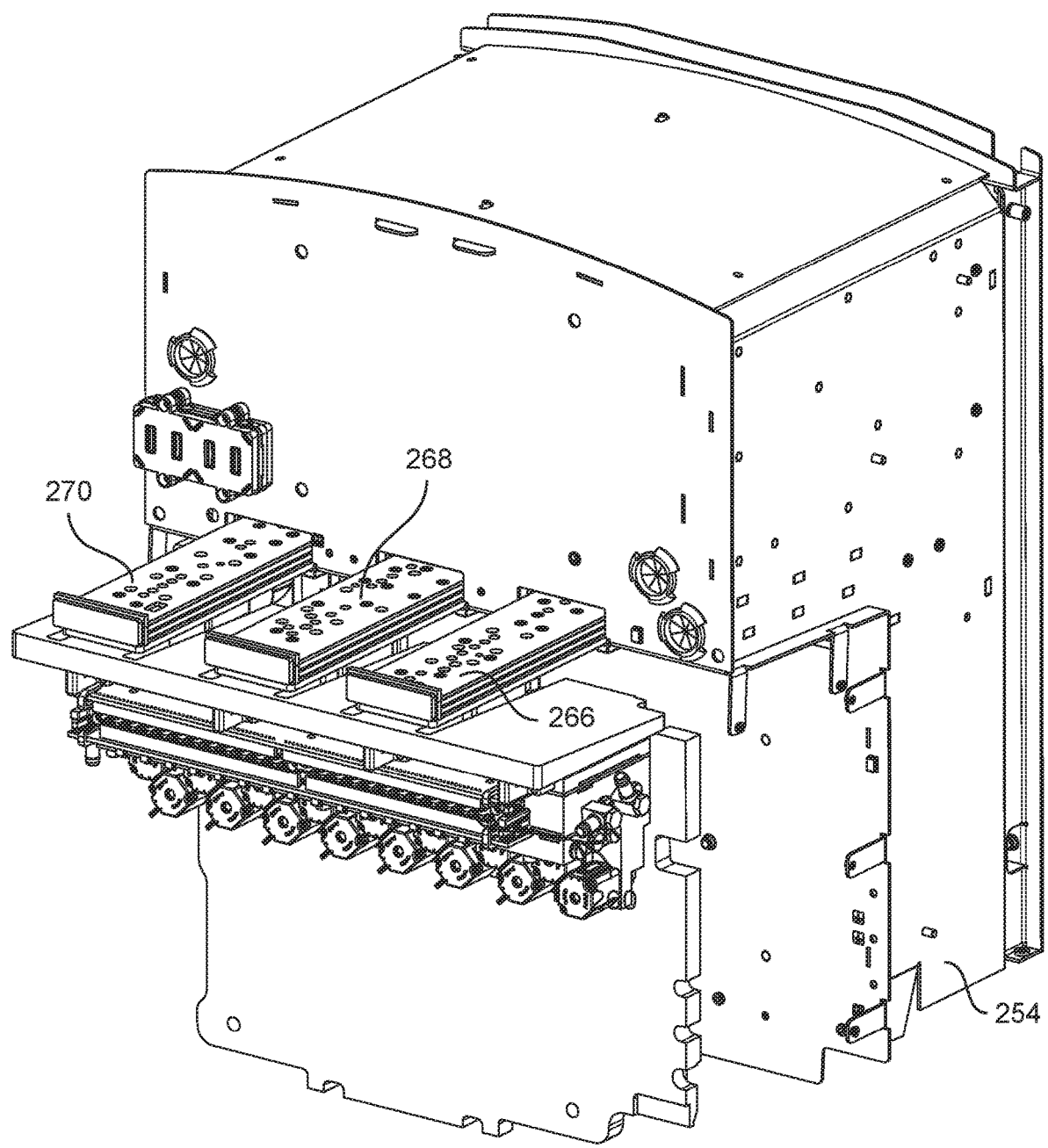
FIG. 48 is a rear perspective view of the hemodialysis device housing, showing installation of the exemplary pressure distribution device and the interfacing adaptors.

FIGS. 47, 48 are rear views of manifold 260, and illustrate that risers 276A, 276B and 276C allow adaptors 266, 268, 270 to be slid into their respective positions in enclosure 254 from the rear of the enclosure via slots or cutouts 280, 282, 284 of the shelf 256 of enclosure 254. The risers 276A, 276B and 276C are made sufficiently tall to allow for the placement of insulation—either rigid foam insulation or other types of insulation—to provide a thermal barrier between the shelf 256 and the body of the manifold 260, as well as the electronic components (control boards, sensors, etc.) located in recess 258. (See, e.g., insulation 269A wrapped around the risers in FIG. 48). FIG. 48 shows how an assembly comprising manifold 260, its attached risers and adaptors 266, 268 and 270, along with other related components, can be slid into position as a group into the recess 258 of enclosure 254.

Figure 49:
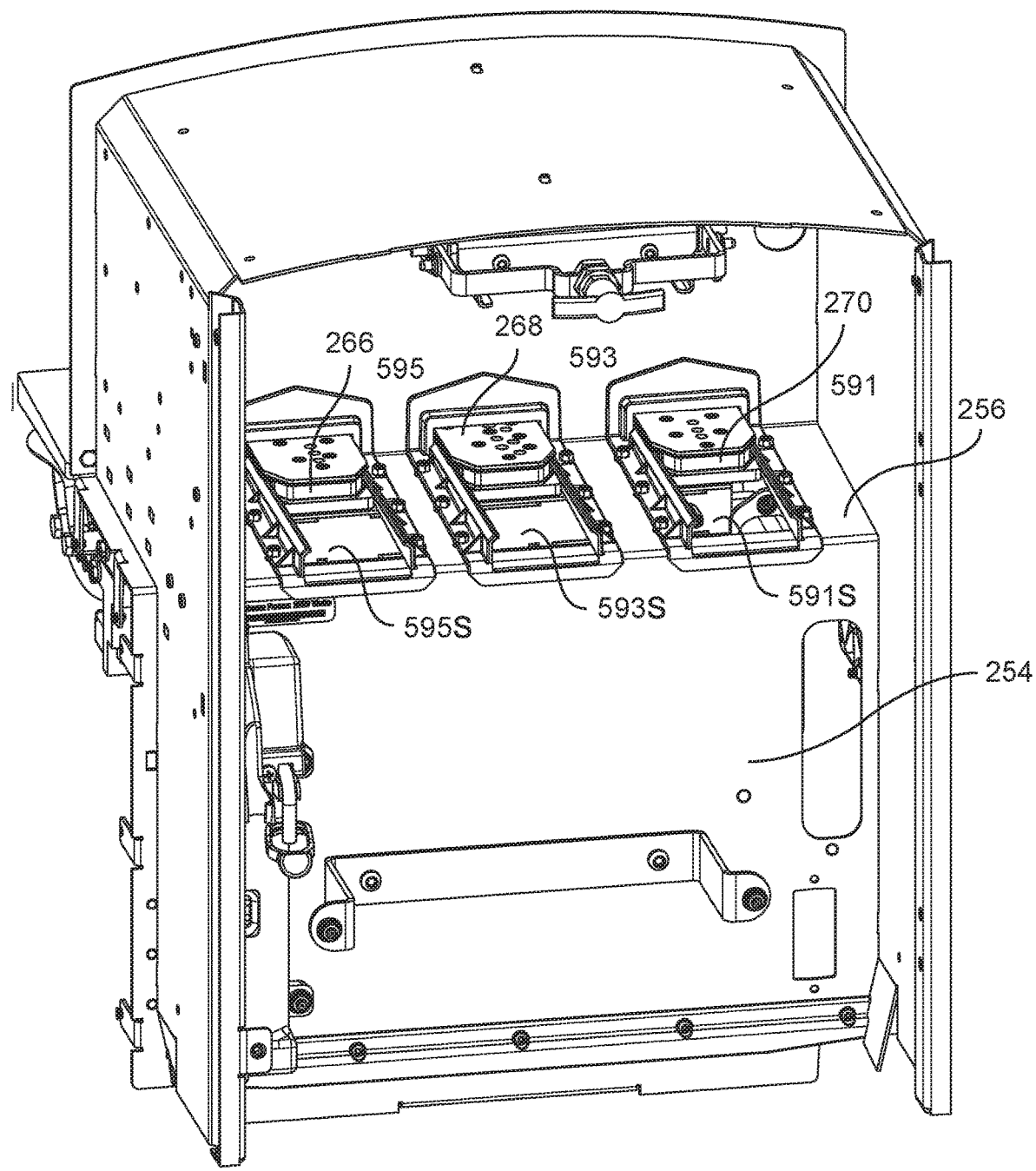
FIG. 49 is a front perspective view of the hemodialysis device housing, showing installation of the exemplary interfacing adaptors.
Figure 50:
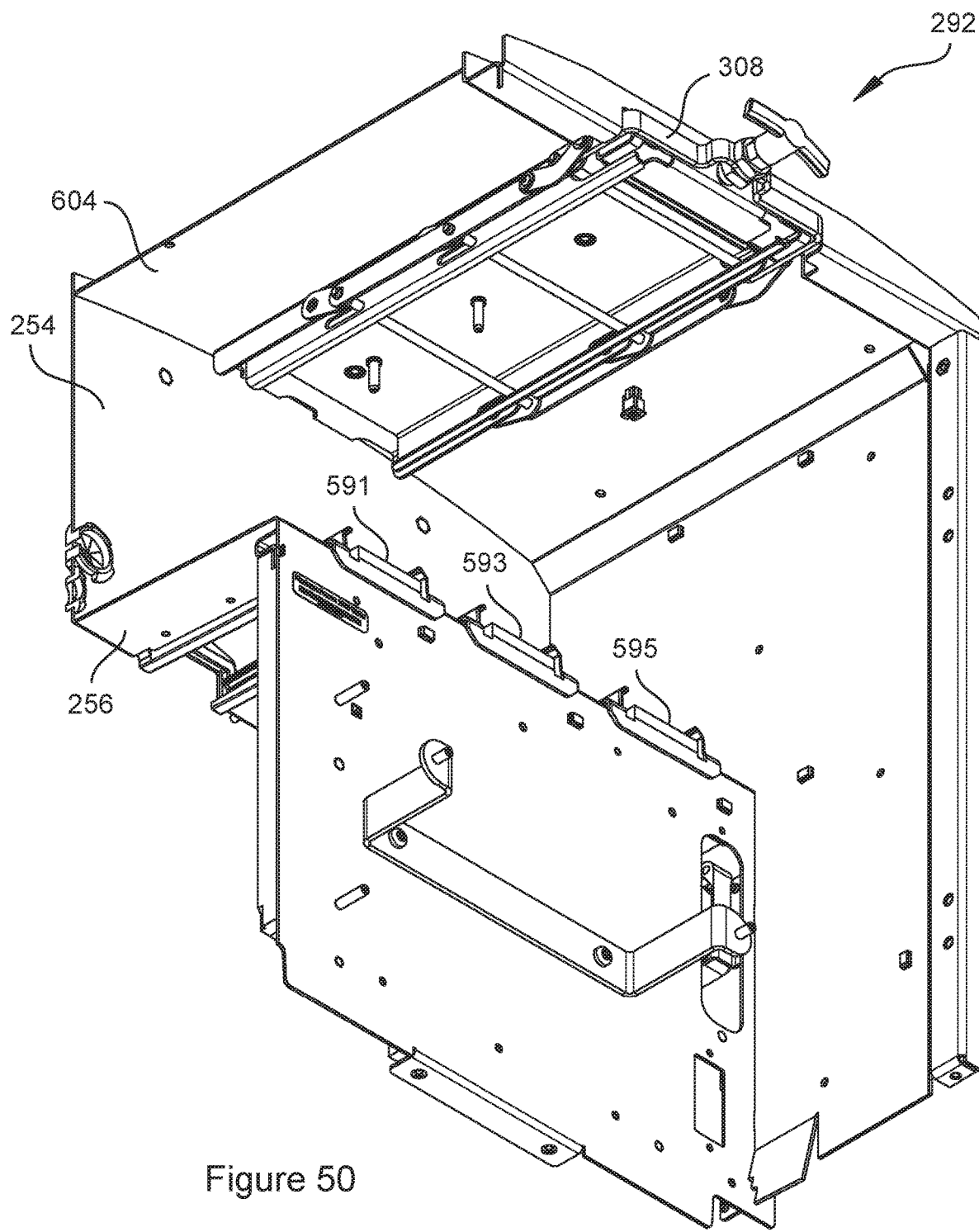
FIG. 50 is a partial cutaway view of the hemodialysis device housing, showing an exemplary cassette loading assembly mounted on the ceiling of the housing.
Figure 51:
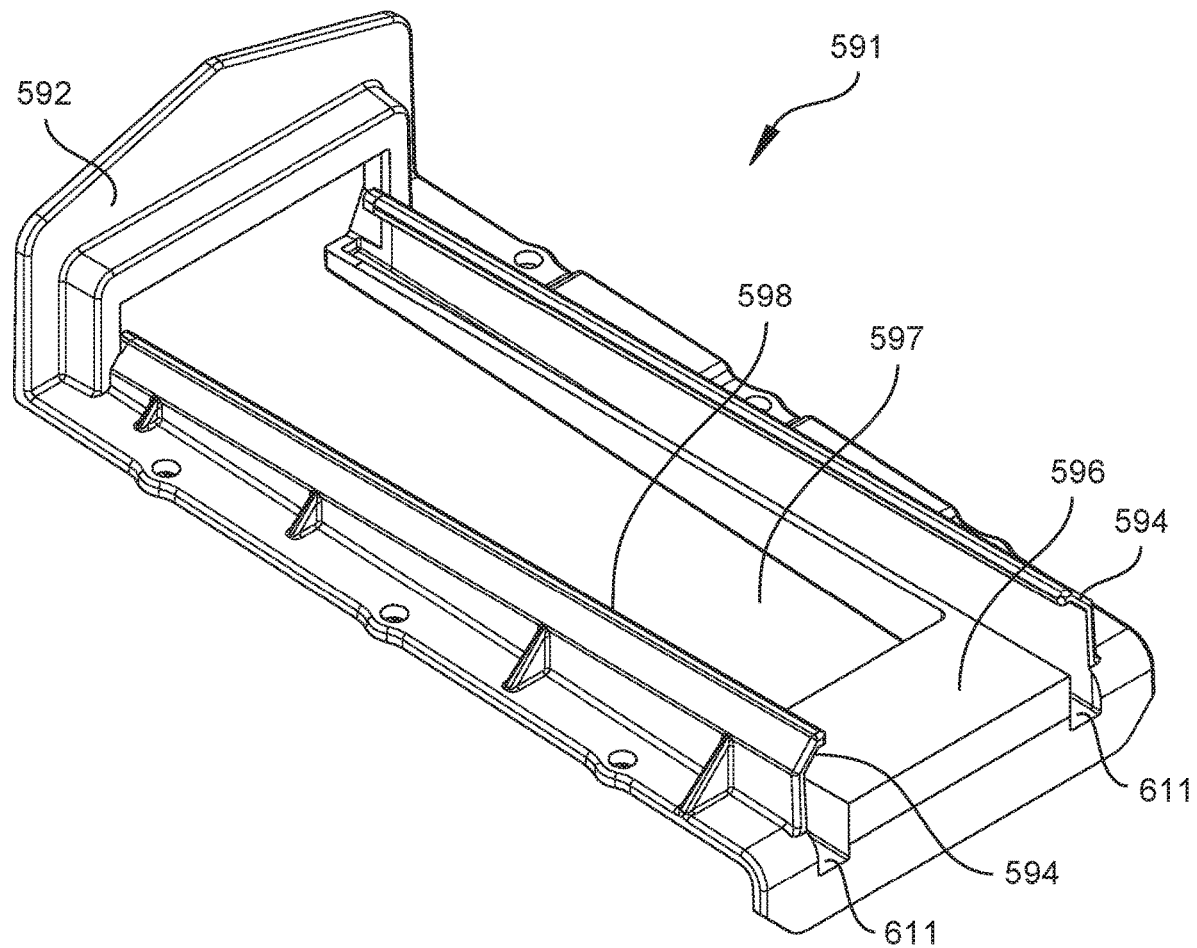
FIG. 51 is a perspective view of an exemplary manifold adaptor rail.

FIGS. 49 to 51 illustrate engagement between the adaptors and their respective rails wherein the adaptors are located within the enclosure to receive the cassette assembly from the cassette loading apparatus within housing 254. Adaptor receptacles or adaptor rails 591, 593 and 595 may be integrated with shelf 256 of the enclosure 254 or can be separate component/s that can mechanically attach to the enclosure 254. In one embodiment, shelf 256 includes spaces to receive or attach the adaptor rails 591, 593 595. FIG. 48 specifically depicts a rear (outside) view of the enclosure 254 with adaptors 266, 268, 270 partially inserted into respective adaptor rails 595, 593 and 591 (shown in FIG. 49). The manifold 260 is attached to the adaptors 266, 3268, 270 before the manifold/adaptor assembly is slid into its final location in the enclosure 254 as defined by the adaptors and adaptor rails. As shown in FIG. 49, the rails 591, 593 and 595 are located in the spaces 591S, 593S and 595S respectively. FIG. 49 depicts a front (inside) view of the adaptors 266, 268 and 270 partially received into their respective adaptor rails in the enclosure 254.

Proper alignment of the adaptors 266, 268, 270 and the pneumatic manifold 260 can be important to ensure that the plurality of pneumatic ports 240 of the cassette assembly 226 align with the matching receptacle ports 266P, 268P, 270P to provide the necessary pneumatic connection to cassette assembly 226. The final positioning of the adaptor is defined by adaptor rails that are positively mounted on the same enclosure that mounts the cassette loader 292 on the roof of the enclosure 254. As a result, the retaining mechanisms for the above mentioned components should be appropriately positioned to achieve the alignment of pneumatic ports between the three assemblies i.e. the cassette assembly 226; the adaptors 266, 268, 270 and the pneumatic manifold 260. FIG. 50 depicts a cassette loader 292 with an operating handle 308. The cassette loader 292 can be mounted on an inner surface of a roof 604 of the housing or enclosure 254. As illustrated, the cassette loader 292 and the adaptor rails 591, 593 and 595 are positioned on opposing surfaces of the enclosure 254 and maintain a fixed spatial relationship with each other.

FIG. 51 depicts an example adaptor rail 591 that can comprise a head-rest or flange 592 and a tray portion 597 with a raised platform 596 that can partially of completely occupy the tray portion 587. Head rest 592 with the tray portion 597 forms a frame of the rail 591. The tray portion 597 can receive the corresponding adaptor, and the corresponding adaptor can rest on the raised platform 596. The tray portion 597 can also comprise fencing contours 594 that can be curved according to the edges of the corresponding adaptor received in the rail 591, such that the adaptor can slide down into the receiving rail. In this embodiment, the tray portion 597 can further provide a cut-out region 597 where the received adaptor can interface with a corresponding riser on the pneumatic manifold 260. Elongated slots or grooves 611 may optionally be provided between the sides of the raised platform 596 and the fencing contours 594. Elongated grooves 611 can collect any leaking liquid and help to divert any leaking liquid or condensation away from the top surface of an installed adaptor, which might risk reaching the electronics disposed below the shelf 256 or in the recess area 258.

Figure 53:
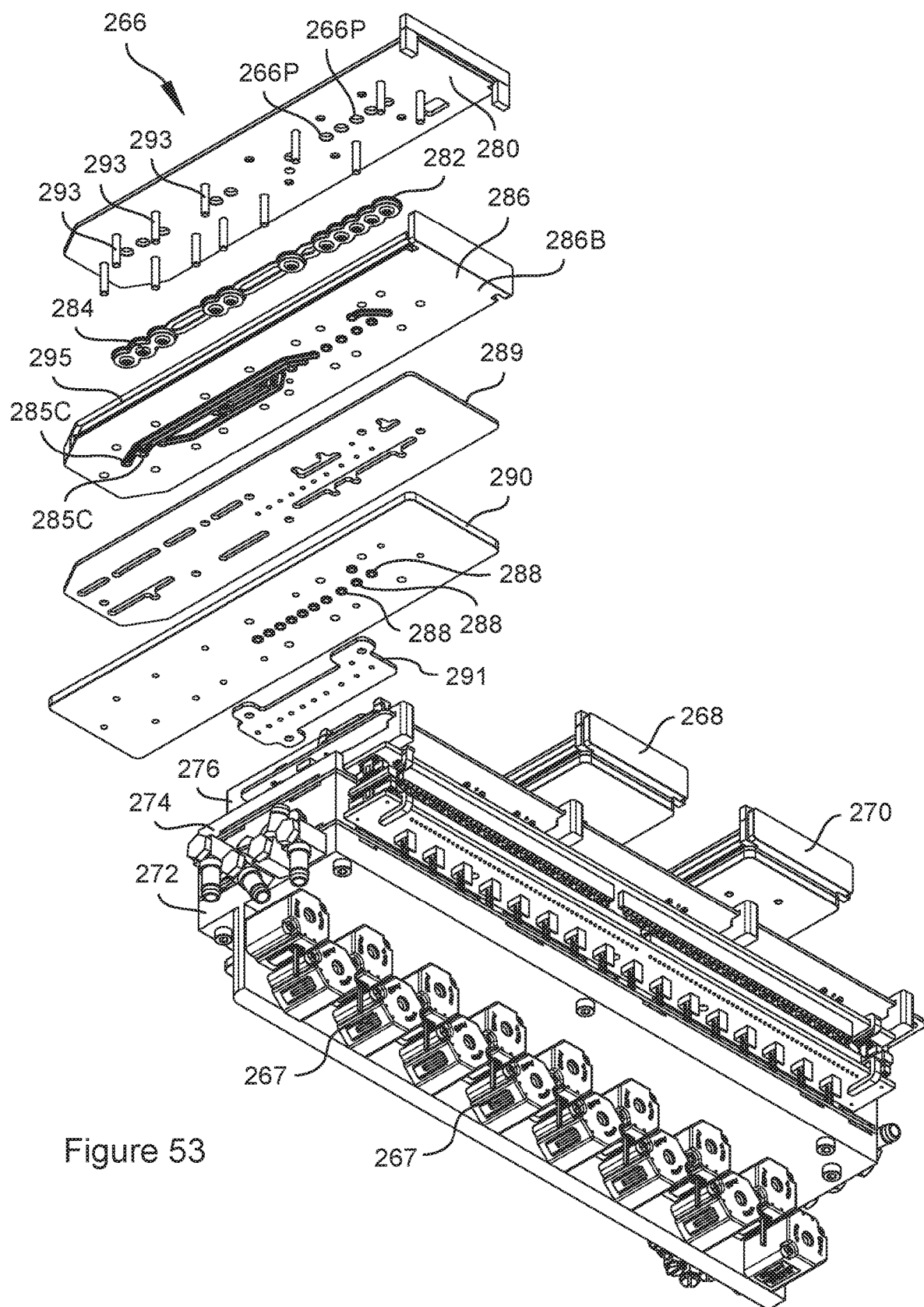
FIG. 53 shows the partially exploded view of the manifold adaptor of FIG. 52, viewed from an inferior perspective.

FIGS. 52 and 53 depict an exploded view of an example adaptor 266 and its interaction with the corresponding riser 276C. More specifically, FIG. 52 depicts a top down view of the plurality of plates and gasket/s that can collectively form the adaptor 266. And FIG. 53 depicts a bottom up view of the same exploded view of adaptor 266. An adaptor is arranged to provide individual pneumatic pathways between the first port array of cassette assembly 226 and the second port array of pneumatic manifold 260. In this example, the pneumatic ports 240 on the cassette assembly are distributed over an extended surface area away from the narrow dimension of the manifold assembly 260. The adaptor acts to converge this first larger spatial array into a smaller spatial array of the pneumatic ports 261 on the risers of the manifold 260. As illustrated in FIGS. 52 and 53, exemplary adaptor 266 can comprise a plurality of layers or plates comprising pneumatic openings and channels that converge to a smaller surface area as the layers progress towards the respective riser. Top plate 280 of the adaptor 266 includes pneumatic ports 271 and connecting features to engage with the subsequent plates of the adaptor. Pneumatic ports 271 and connecting features 293 can be seen through the top view of the top plate 280 in FIG. 52, and through the bottom view of the top plate 280 as shown in FIG. 53. Top plate 280 rests on an intermediate block 286 that includes corresponding pneumatic ports 285 on its first surface 286A. These pneumatic ports 285 coincide with the pneumatic ports 271 on the top plate 280. A wiper gasket 282 can be received into a gasket receptacle 281 recessed into a first surface of the intermediate block 286. The continuous elastomeric gasket 282 can be formed from a mold, with appropriately located wiper seals 284. The wiper seals 284 provide a sufficient sealing engagement between cassette ports 240 and corresponding adaptor receptacle ports 271, while providing lower frictional resistance to the installation and removal of cassette assembly 226 than, for example, individual O-ring seals.

FIG. 53 depicts a second opposing surface 286B of the intermediate block 286. This surface includes pneumatic channels 286C in fluid communication with the ports 281 on the first surface 286A. Channels 285C can be laid out to converge and connect the pneumatic ports 281 on the first surface 286A to the pneumatic ports distributed on the second surface 286B. As depicted, the pneumatic ports on the second surface 286B occupy a smaller area and different spatial array compared to the pneumatic ports on the first surface 286A. The channels 285C ensure that the pneumatic ports 281 converge or shift toward the port array of the riser side of the adaptor 266. A second intermediate block 290 can include pneumatic ports 288 to coincide with the array of pneumatic ports provided on the second surface 286B of the intermediate block 286. A second gasket 289 can be positioned between the first intermediary block 285 and the second intermediary block 290. Gasket 289 can allow appropriate sealing between the first intermediary plate 286 and the second intermediary plate 290, and allow the gasket to be compressed to an extent required to create a seal. In one embodiment, a set of alignment features can be provided on the gasket 289 as well as on one or both of the adjoining plates. In this case the plates can be the first intermediary block 286 and the second intermediary block 290. Moreover, a transitional gasket 289 can include pneumatic ports corresponding to the pneumatic ports 285 on first intermediary block 286 and the pneumatic ports 288 on the second intermediary block 290. A riser gasket 291 can be positioned between the second intermediary block 290 and the corresponding riser, which in this example is riser 276C. This gasket is arranged to seal the interaction between the second intermediary block 290 and the riser 276C. A plurality of gasket alignment features can be provided on mating surfaces of the second intermediary bock 286 and the riser 276C. The preceding discussion is meant to also apply to the adaptors 268, 270 and the interacting risers 276B and 276A. Number and spatial distribution of pneumatic ports on the other adaptor-riser interaction embodiments can differ, and in this embodiment do differ.

Figure 54:
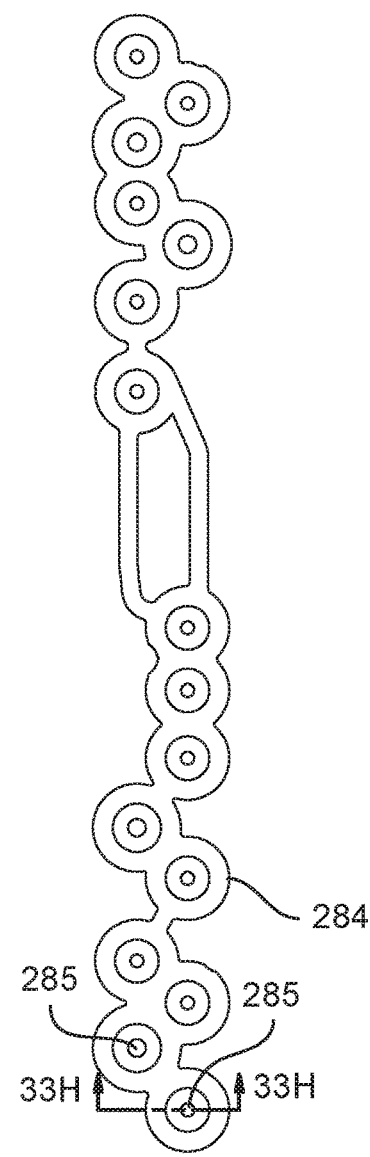
FIG. 54 is a plan view of an exemplary wiper gasket of a manifold adaptor.
Figure 55:
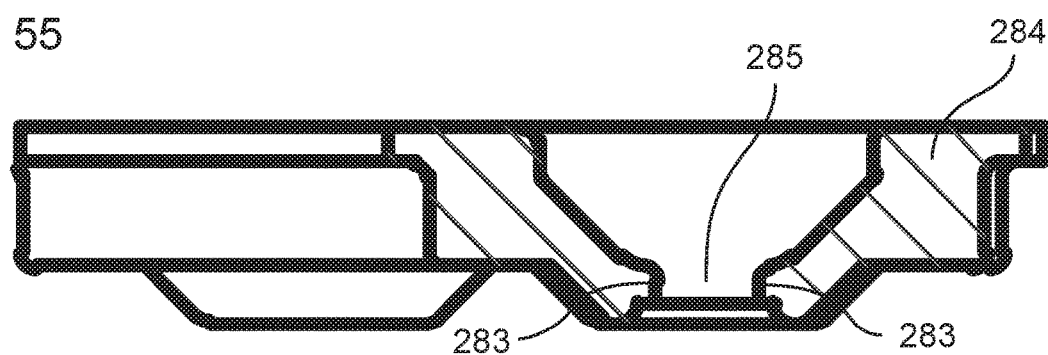
FIG. 55 is a cross-sectional view of a section of the wiper gasket of FIG. 54.

Sealing components between ports typically include O-rings when there is pneumatic interaction between the ports. In case of the adaptors, a plurality of O-rings can be used to ensure a sealing engagement between the mating ports. However a plurality of spatially arrayed O-rings can exhibit relatively poor alignment tolerances when a plurality of pneumatic ports 240 are inserted into the corresponding adaptor ports. In addition to tolerance issues, a plurality of O-ring connections may create a greater than desirable engagement/disengagement force between the cassette assembly 226 and its associated adaptors. In an alternative arrangement, a web of wiper gaskets can be employed to make the required seal, and can be installed between two interacting plates or blocks of an adaptor. FIG. 53 illustrates an exemplary wiper gasket 284 that can be molded as a single unit, thereby substantially simplifying assembly and installation procedures. FIG. 54 depicts an exemplary wiper gasket used in one of the manifold adaptors. FIG. 55 shows a cross-sectional view 33H of the wiper gasket of FIG. 54. As illustrated, gasket 284 can be formed to annularly encircle port 285 and form a conical periphery recess toward the pneumatic port 285. Gasket 284 can optionally include an annular nodule or ridge 283 constructed into the wiper gasket 284 to cover a portion of the port 285. This arrangement and construction of the wiper gasket 284 may allow insertion of the cassette ports 240 with an acceptable amount of force, and can also ensure sealing between the adaptor and cassette during operation (i.e. during application of positive and negative pressure through the ports of the adaptor).

Figure 56:
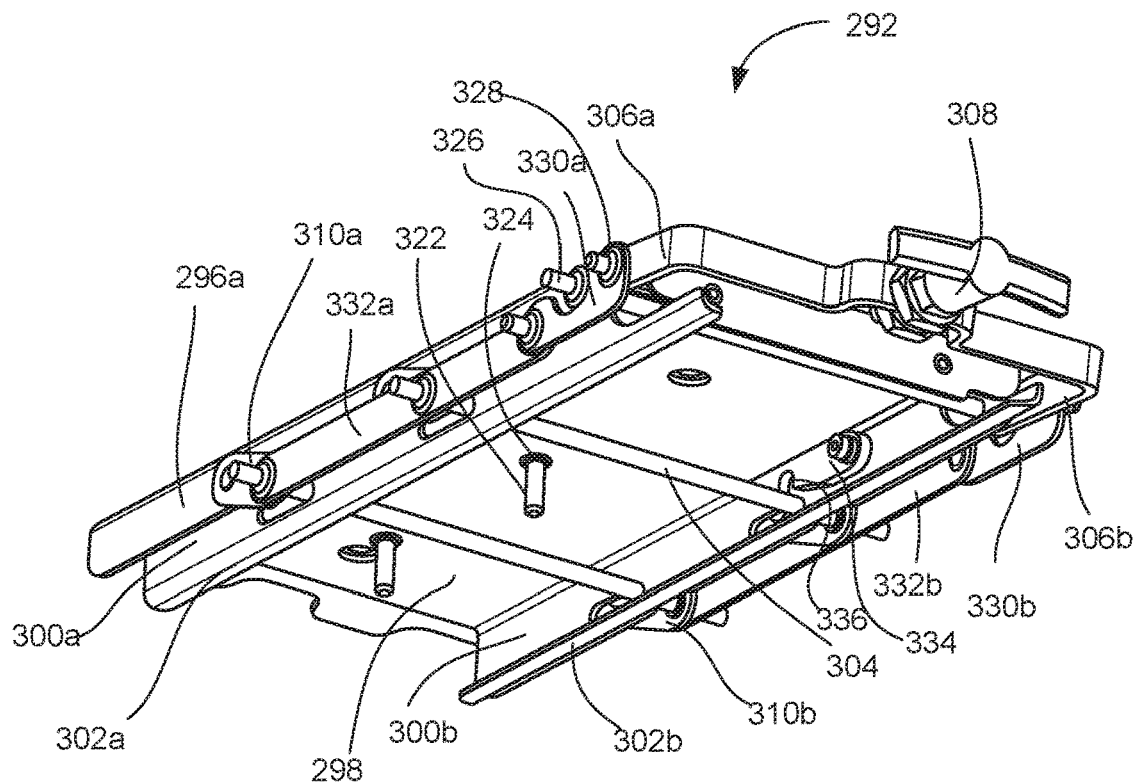
FIG. 56 is an inferior perspective view of the exemplary cassette loading assembly when the operating handle is in a raised (disengaged) configuration.
Figure 57:
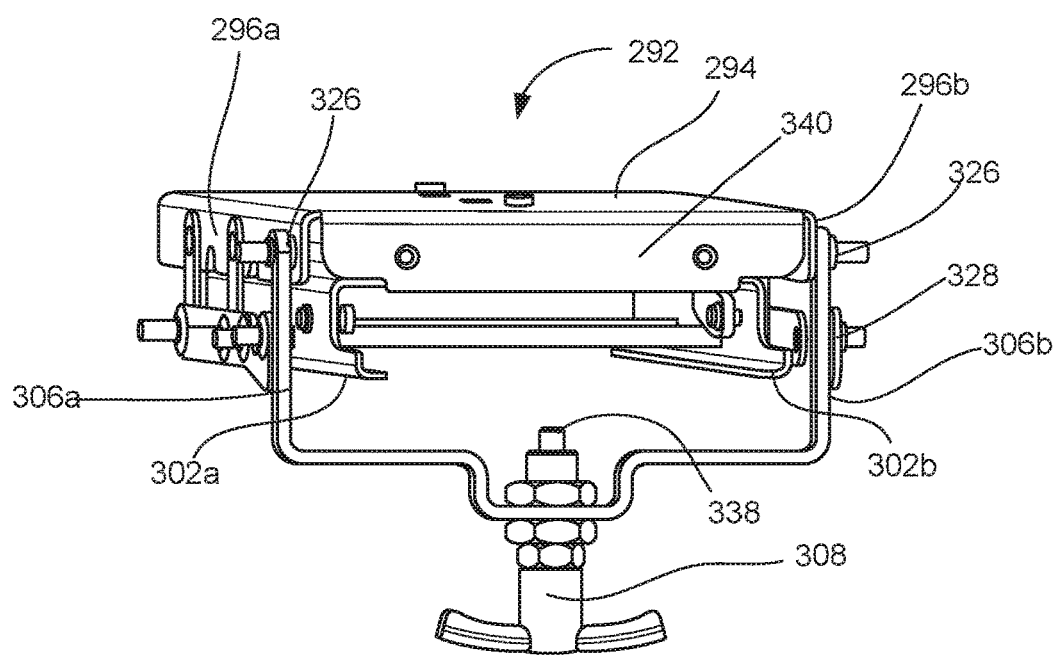
FIG. 57 is a front perspective view of the exemplary cassette loading assembly when the operating handle is in a lowered (engaged) configuration.

FIG. 56 and FIG. 57 show a cassette seating apparatus or cassette loader 292 used to secure a first side of cassette assembly 226 in order to move the cassette assembly linearly toward or away from one or more arrays of receptacle assemblies arranged to mate with a corresponding array of cassette ports 240 on one or more of cassettes 228, 230 and 232 on an opposing second side of cassette assembly 226. In the example described below, the receptacle assemblies comprise manifold adaptors 266, 268, 270, but the cassette loader can be used in any other system in which a ported cassette is to be plugged in and out of any type of receptacle array, including, for example, a fixed multi-port receptacle or a moveable connector equipped with an array of ports, among other possibilities. The receptacle ports to which cassette actuation ports connect can also be arranged on a frame, housing or even directly on a manifold output port array, rather than the exemplary adaptors 266, 268, 270 shown, if the two sets of mating ports can be arranged to be properly aligned. The cassette seating apparatus 292 has a generic utility in assisting a cassette with external ports to engage with or disengage from mating connectors or receptacle ports on any device.

FIG. 56 shows cassette loader 292 in a retracted position, which moves the cassette assembly linearly away from receptacle ports 261b of FIG. 29, or ports 266P, 268P and 270P of FIGS. 30, 32, 45, or more generally ports 271 of FIG. 52, which in this example are arrayed on adaptors 266, 268, 270. Note that cassette seating apparatus or cassette loader 292 can be used to seat or unseat a cassette or cassette assembly onto or from a receptacle assembly, as long as a single cassette or group of cassettes has either liquid or actuation ports on a side opposite that of a side secured by the cassette seating apparatus 292.

In this example, the cassette seating apparatus 292 comprises a stationary frame 294 that includes stationary members 296a,b. Stationary members 296a,b are coupled to a linkage that in turn interacts with a movable cassette mount 298. Movable cassette mount 298 is configured to hold a cassette or cassette assembly, and in this example comprises a flange 300a,b leading to a cassette mount rail 302a,b. In this example, cassette mount rails 300a,b allow a cassette or cassette assembly to be slid into position on the seating apparatus 292, and held. Other examples can include a clamping apparatus that can grasp the cassette or cassette assembly. In this example, independent movement of an installed cassette or cassette assembly is limited by the presence of one or more crossmembers 304 limiting top-side movement of the installed cassette or cassette assembly, and by actuator arms 306a,b of an operating handle 308, the actuator arms 306a,b moving into a position to interfere with lateral movement of an installed cassette or cassette assembly.

Figure 58:
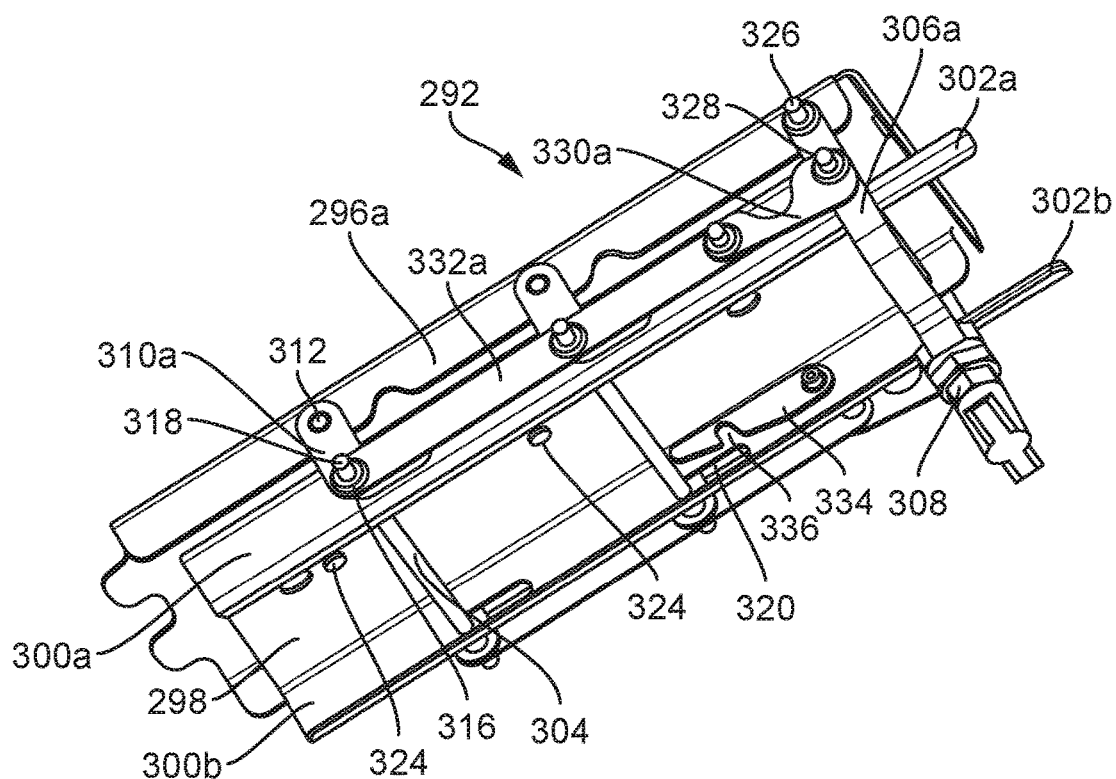
FIG. 58 is an inferior perspective view of the exemplary cassette loading assembly of FIG. 57 with the operating handle in a lowered configuration.

As shown in FIGS. 56-58, the linkage may comprise two or more swing arms 310a,b, each said swing arm pivotably connected 312 on a first end to stationary members 296a,b. Each of the swing arms 310a,b is arranged to move in a plane generally parallel to the direction of motion of cassette mount 298 with respect to stationary member 296a,b. A second end of each swing arm 308a,b comprises a hub 316 coupled to an axle or pinion 318, the axle/pinion configured to interact with flange 300a or 300b that is generally parallel to a plane of motion of the swing arm 310a,b. The axle or pinion 318 is positioned within an elongate slot 320 in the flange 300a or 300b that translates an arcuate motion of the second end of the swing arm 310a,b toward or away from stationary member 296a,b into a linear motion of the cassette mount rail 302a, 302b toward or away from the stationary member 296a, 296b. In this example, axle or pinion 318 optionally extends from flange 300a to flange 300b to also serve as a crossmember 304. Axle or pinion 318 can interact slidably with slot 320, or by other means (such as, for example through a circular bearing or wheel positioned in slot 320).

To help ensure linear motion of cassette mount 298, one or more guide elements (such as, e.g. post 322) can optionally be included to limit lateral movement of cassette mount 298 and its attached mount rails 302a,b. A guide element 322 can be rigidly attached or mounted to stationary frame 294 (or alternatively stationary members 296a,b), and extend in the desired direction of movement of cassette mount rails 302a,b. The guide element 322 can interact with cassette mount 298 (or alternatively flange 300a or 300b, or mount rail 302a or 302b), through a guide hole 324 (or a guide rail, track or other element) that confines the relative movement of cassette mount 298 to a fore and aft direction with respect to the frame 294 or stationary members 296a,b.

Figure 59:
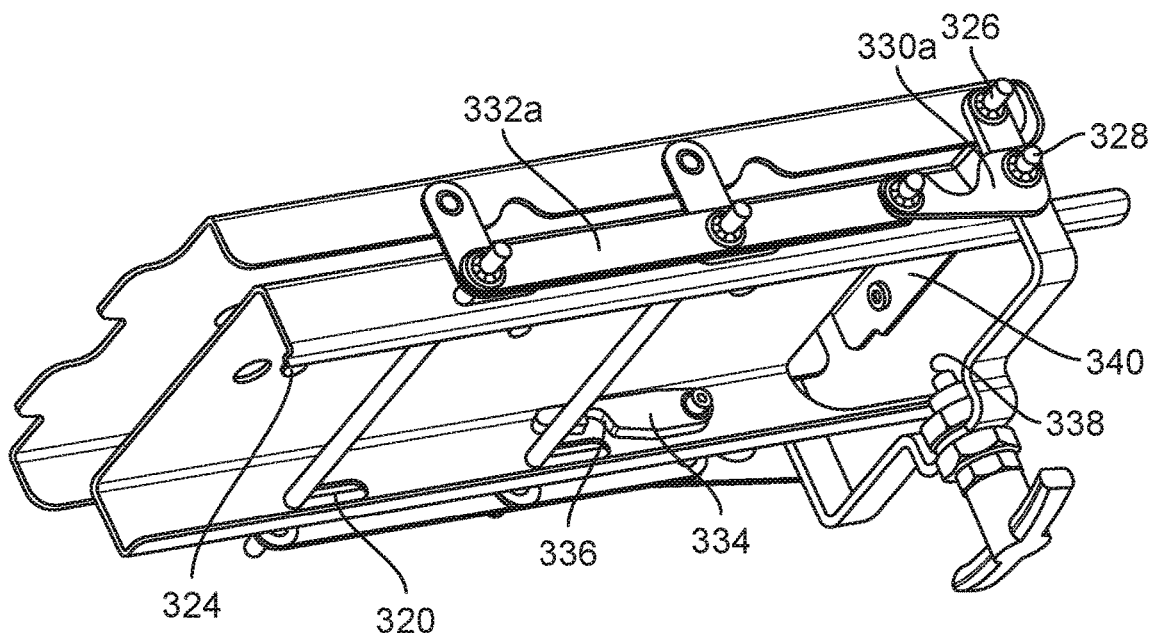
FIG. 59 is a rear perspective view of the exemplary cassette loading assembly of FIGS. 57 and 58 with the operating handle in a lowered configuration.

FIG. 56 shows the cassette seating apparatus 292 in a nearly fully retracted position, with cassette mount 298 retracted away from an associated receptacle assembly sufficiently to disengage cassette actuation (or liquid) ports of an installed cassette from their respective receptacle ports. (See, e.g., FIGS. 30, 31). FIG. 57-59 shows the cassette seating apparatus 292 in an engagement position, with the cassette mount extended linearly away from stationary frame 294 or stationary members 296a, 296b sufficiently to engage cassette actuation (or liquid) ports of an installed cassette with their corresponding receptacle ports. Actuator arms 306a,b of handle 308 are pivotally connected on a distal end 326 to stationary members 296a, 296b. Each actuator arm 306a,b is also pivotally connected on a more proximal portion 328 of the arm 306a,b to a first end of a connecting member 330a,b. A second end of connecting member 330a,b is then pivotally connected to an actuator bar 332 having a pivotal connection to the second end of each swing arm 310a,b comprising the linkage of cassette seating apparatus 292. Connecting member 330a or 330b moves eccentrically with respect to the axis of rotation of actuator arm 306a or 306b, which allows for the displacement of actuator bar 332a,b and swing arm 310a,b away from stationary member 296a, 296b.

Optionally, a cassette mount retaining member 334 can be used to hold cassette mount 298 in a retracted position. In one example, cassette mount retaining member 298 may comprise a pawl, which is pushed aside by crossmember 304 (or alternatively another element attached to cassette mount 298, flange 300, rail 302 or shaft/pinion 318) when handle 308 is pulled fully into a retracted position (see FIG. 56). When crossmember 304 reaches a pawl recess 336, it drops down to engage crossmember 304, and holds cassette mount 298 in its retracted position. In an additional or alternative embodiment, handle 308 may include a movable plunger element (substituting for handle post 338—See FIG. 57, 59) that can engage or penetrate a hole or recess (not shown) in a forward flange 340 of stationary frame 294. Optionally, the plunger can be spring-loaded to automatically engage the forward flange when handle 308 is released by a user.

As applied to hemodialysis enclosure 254 (see FIG. 23), cassette seating apparatus 292 can be mounted to a ceiling of the interior of enclosure 254, as shown in FIGS. 45 and 46. This is in a position opposite the receptacle assemblies 266, 268, 270 (in this case manifold adaptors). Cassette assembly 226 can be seen installed in a cassette seating apparatus 292 by means of a cassette assembly frame plate 513, for example, as shown in FIGS. 21 and 46. In FIGS. 30 and 31, cassette assembly ports 240 are shown to be directly adjacent corresponding receptacle ports on receptacle assemblies, and disengage completely from them as the handle 308 is placed in a retracted position (FIG. 30).

Pneumatic Pump System Using Binary Valves

Figure 60:
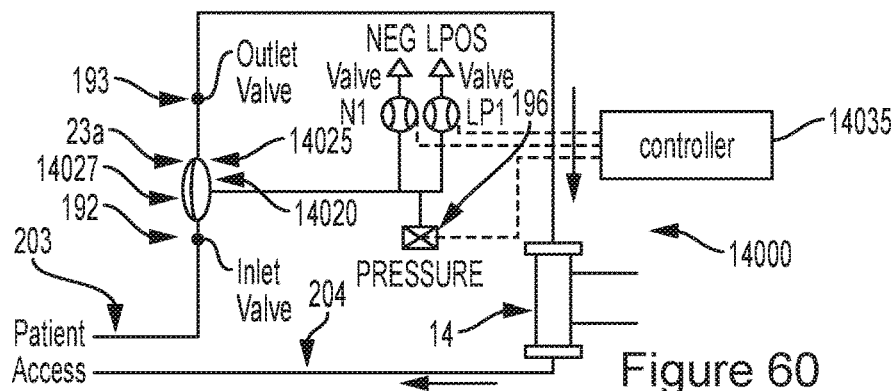
FIG. 60 is a schematic representation of a fluid flowpath in the hemodialysis device.

FIG. 60 is a schematic view showing an embodiment of a pressure actuation system 14000 for a positive displacement diaphragm pump ('pod pump') 234, such as that shown in FIG. 20. In this example, air pressure is used as a control fluid (e.g., such that the pump is pneumatically driven). Other fluids (e.g., water or water-based solutions) may also be used as control fluids in other embodiments.

In FIG. 60, the pressure actuation system 14000 alternately provides positive and negative gas pressure in the actuation chamber 14020 of the pod pump 23a. The pneumatic actuation system 14000 includes an actuation-chamber pressure transducer 14020, a positive-supply valve LP1, a negative-supply valve N1, a positive-pressure gas source LPOS, a negative-pressure gas source NEG, a positive-pressure source pressure transducer (not shown), a negative-pressure source pressure transducer (not shown), as well as an electronic controller 14035. The electronic controller receives pressure data from pressure sensor 14020 and controls valves N1, LP1 to control operation of pump 23a. These two valves are controlled by an electronic controller 14035. (Alternatively, a single three-way valve may be used in lieu of the two separate valves LP1, N1.) In some cases, the positive-supply valve LP1 and the negative-supply valve N1 are binary on-off valves that are either fully open or fully closed.

The positive-pressure source LPOS provides to the actuation chamber 14020 positively pressurized control gas to urge the diaphragm 14025 towards a position to minimize the pumping chamber 14027 volume (i.e., the position where the diaphragm is against the rigid pumping-chamber wall). The negative-pressure source NEG provides to the actuation chamber 14020 negatively pressurized control gas to urge the diaphragm 14025 in the opposite direction, towards a position to maximize the pumping chamber 14027 volume (i.e., the position where the diaphragm is against the rigid actuation-chamber wall).

The controller 14035 may also receive pressure information from three other pressure transducers: an actuation-chamber pressure transducer 14020, a transducer on LPOS and a transducer on NEG. As their names suggest, these transducers respectively measure the pressure in the actuation chamber 14020, the positive-pressure source LPOS, and the negative-pressure source NEG. The controller 14035 monitors the pressure in the two sources LPOS, NEG to ensure they are properly pressurized (either positively or negatively). A compressor-type pump or pumps may be used to maintain the desired pressures in reservoirs that comprise sources for LPOS, NEG.

In one embodiment, the pressure provided by the positive-pressure reservoir LPOS is under normal conditions of sufficient magnitude to urge the diaphragm 14025 all the way against the rigid pumping chamber wall. Similarly, the negative pressure (i.e., the vacuum) provided by the negative-pressure source NEG is preferably of sufficient magnitude, under normal conditions, to urge the diaphragm all the way against the rigid actuation chamber wall. In preferred embodiments, however, the positive and negative pressures provided by the sources LPOS, NEG are kept within safe enough limits to avoid excessively high liquid pressures that could harm a patient to which the pumping system may be connected.

The controller 14035 monitors the pressure information from the actuation-chamber-pressure transducer 196 and, based on this information and possibly a timer, controls the valving mechanism (valves LP1, N1) to urge the diaphragm 14025 all the way to its minimum-pumping-chamber-volume position, followed by a switch of pressure to pull the diaphragm 14025 all the way back to its maximum-pumping-chamber-volume position.

The pressure actuation system comprises a pressure distribution manifold, which may contain the actuation-chamber pressure transducer 14020, the transducer for LPOS source, the transducer for NEG source, the positive-supply valve LP1, the negative-supply valve N1. The controller 14035 may be mounted on the manifold, and the positive-pressure gas source LPOS, and the negative-pressure gas source NEG may include conduits running through the manifold. The manifold may be constructed to fit entirely or mostly in the hemodialysis housing recess 258 (see, e.g. FIGS. 44, 48). In this arrangement, the components that come into contact with blood or dialysate (namely, pod pump 23*a*, the inlet valve 192 and the outlet valve 193) may be located in an insulated enclosure 254 or a front panel 248 (see FIG. 23) so that the pump, valves and interconnecting liquid paths can be more easily accessed and/or disinfected.

Pumping Process with Binary Valves

Figure 61:
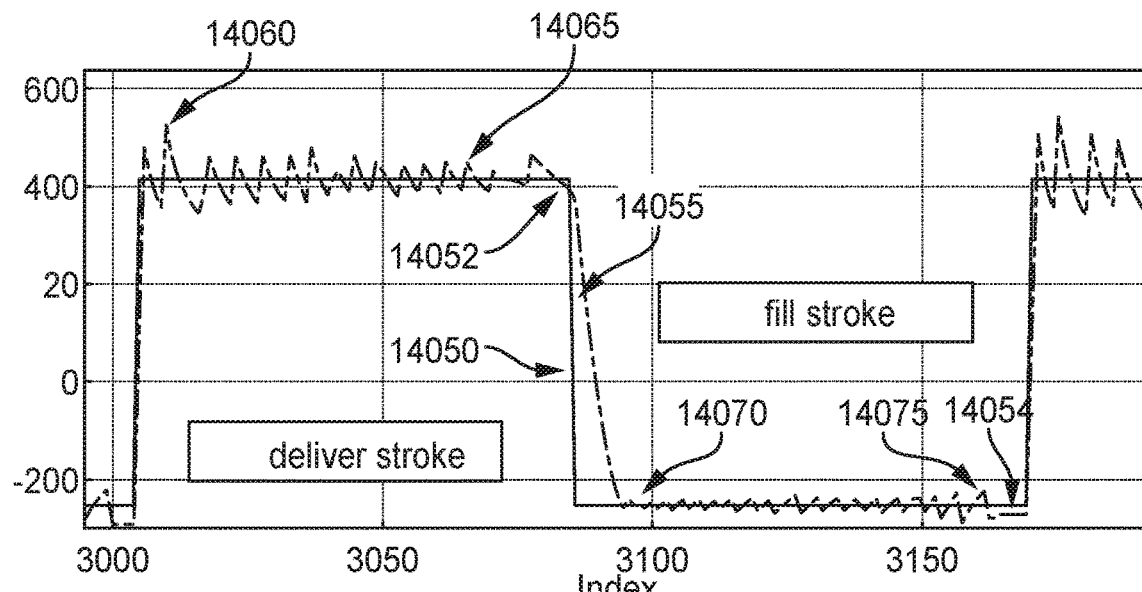
FIGS. 61 and 62 are graphical representations of pressure variation in an actuation chamber of a pump in the hemodialysis device.
Figure 62:
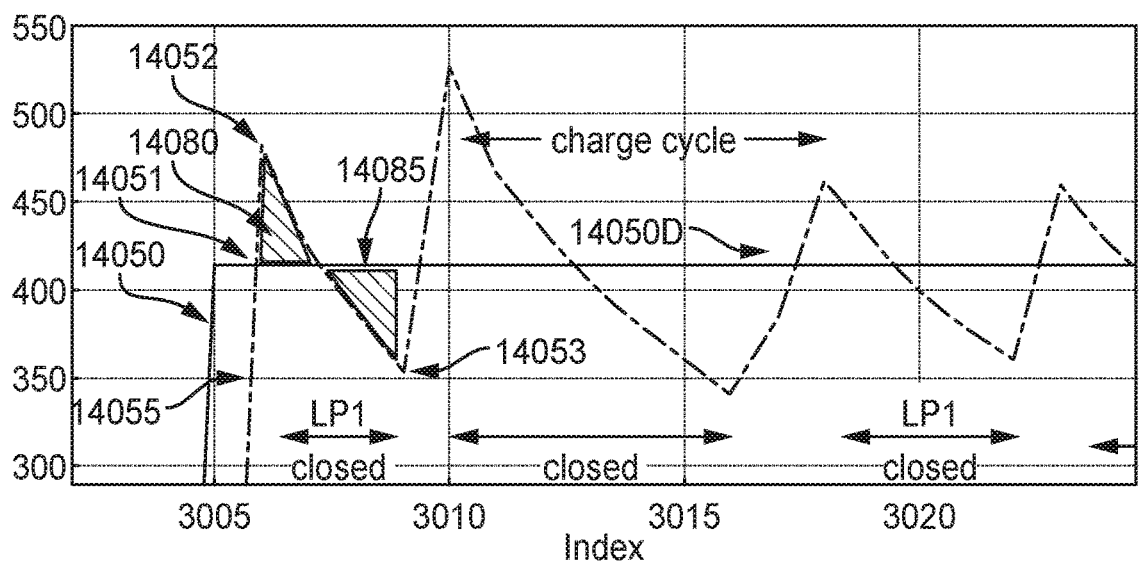

The process of pumping liquid through the pod pump 23*a* can be better understood by referring to FIGS. 61 and 62. Referring now to FIG. 61, the target pressure 14050 and the actual pressure 14055 measured by a pressure sensor 196 (FIG. 60) are plotted against time for one deliver stroke and one fill stroke. A deliver stroke comprises using positive pressure from the LPOS source to drive the diaphragm 14025 from one side of the pump pod 23*a* to the other and expelling the liquid in the pumping chamber 14027. A fill stroke by contrast, uses sub-atmospheric pressure from the NEG source to pull the diaphragm 14025 back across the pod pump 23*a* and fill the pod pump with liquid. In some examples, the fill stroke is completed by connecting the actuation chamber 14020 to atmosphere, allowing liquid pressure in the system to drive the diaphragm across the pod pump chamber.

In a binary valve-driven pump 14000, the deliver and fill pump strokes comprise multiple charge cycles which produce the jagged pressure trace 14050 of FIGS. 61 and 62. A detail of the start of a deliver stroke is shown in FIG. 62, in which during liquid movement, the actual pressure 14055 rises when the valve LP1 is open and falls when the valve LP1 is closed. In the deliver stroke, the movement of liquid from the pumping chamber 14027 decreases the volume of the pumping chamber; and because the total volume of the pod pump is fixed, this increases the volume of the actuation chamber 14020. The increased volume of the actuation chamber results in a reduction of the pressure in the actuation chamber if the pneumatic valve LP1 is closed. A charge cycle comprises the pressure rise resulting from an open valve and the pressure decay when the valve is closed. The length of the charge cycle may vary as shown in FIG. 62, where 3 complete charge cycles are shown and each has a different duration. FIG. 62 plots the details of a delivery stroke, in which positive pressure is applied. Referring now the fill stroke to FIG. 61, the pressure trace 14055 has a similar jagged pattern. However, during the fill stroke, the pressure drops quickly when the N1 valve is open, exposing the actuation chamber to the NEG source, and recovers more slowly toward atmospheric pressure when the N1 valve is closed. Once again the charge cycle comprises a rapid increase in the magnitude of the actuation chamber pressure and a slower pressure decay toward atmospheric pressure when the N1 valve is closed.

Where in previous applications and disclosures, continuously variable valves were used to control diaphragm pumps, binary valves are herein described that are either fully open or fully closed and not designed to be partially open. Binary valves and the associated control electronics are generally less expensive than variable-opening valves. In addition, binary valves may require less functional checks/monitoring, and may be less sensitive to the presence of debris in the pneumatic passages leading to or away from them. The inherent digital or on/off functionality of the binary valves require unique control algorithms for pressure control and detection of end-of-stroke, and flowpath occlusions.

The controller 14035 controls the valves N1 and LP1 based on received signals from the pressure sensor or transducer 196 according to a number of algorithms that may run sequentially or simultaneously. These control algorithms are unique to binary valves due to their inherent digital or on/off functionality. The control algorithms include algorithms to control the fluid flow rate through the pump, to control the pressure inside the actuation chamber 14020, to detect an end-of-stroke (EOS) condition, to detect a full occlusion of the inlet line, to detect a full occlusion of the outlet line, to detect partial occlusions, and to measure an access metric (an indication of the quality of the blood flow obtained from a patient's venous or fistula access).

The controller 14035 computes information about liquid flow through the pump based on the pressure signal from sensor 196 when the valves N1, LP1 are closed. The controller 14035 uses the received pressure data to control the actuation chamber pressure, detect EOS, occlusions, partial occlusions and determine the access metric.

Pressure Control Description

The flow rate through a pneumatically actuated diaphragm pump such as pod pump 23*a* is controlled by setting a target pressure for the actuation chamber 14020. The pod controller 14035 then controls pressure in the actuation chamber 14020 as measured by a pressure sensor 196 fluidically connected to the actuation chamber 14020 by controlling a valve N1, LP1, that fluidically connects a pressure source to the actuation chamber of the pump. In an exemplary control algorithm, the controller averages the pressure data from pressure sensor 196, while the binary valve N1, LP1 is closed, and opens the valve N1, LP1 when the accumulated averaged pressure approaches or equals the target pressure. In one example the controller 14035 closes the valve N1, LP1 when the magnitude of the pressure data equals or exceeds the target pressure. In one example, the controller 14035 closes the valve N1, LP1 when the magnitude of the pressure data equals or exceeds the target pressure minus a predetermined constant value. In another example, the predetermined value, rather than being constant, varies with the stroke direction and the duration or stage of the stroke. In another example, the controller 14035 integrates the difference between the magnitude of the measured pressure and target pressure and opens the valve N1 LP1 when an integrated difference approaches or equals zero.

Fluid flow through the pump is controlled by the magnitude of negative pressure applied to the actuation chamber to fill the pumping chamber with liquid and the magnitude of the positive pressure applied to the actuation chamber to deliver liquid from the pumping chamber. In some examples, the pod pump controller 14035 is programmed to receive or compute a desired flow rate and/or the maximum displaced volume of the pod pump 23a. The controller 14035 may set initial target pressures for fill and deliver strokes. The controller controls the pressure in the actuation chamber to reach or approach a target pressure. The controller monitors the time to complete a stroke and determine the actual flow rate by dividing the displaced volume by the stroke completion time. The controller 14035 may change the target pressure based on a difference between the most recent actual flow rate and the desired flow rate. For example, the controller 14035 may increase the target pressure if the measured actual flow rate was below the desired flow rate. In another example, the controller may decrease the target pressure if the measured actual flow rate is above the desired flow rate. The controller 14035 may modify the deliver stroke independently of the fill stroke. In one example controller 14035 may use a feedback loop that modifies the deliver target pressure based on the measured flow rate during deliver strokes in order to achieve a desired flow rate. In another example the feedback loop modifies the negative fill target pressure to be based on the measured flow rate during fill strokes in order to achieve a desired fill rate.

In previous disclosures, a chamber connected by a binary valve to a pressure source has been controlled based on limits about the target pressure. The controller would connect the pressure source to the chamber by opening a valve between them when the magnitude of the measured pressure in the chamber was some predetermined amount below the target pressure magnitude. The controller would then close the valve when the magnitude of the measured pressure in the chamber was a second predetermined value above the target pressure magnitude. In some cases, applying this limit approach to pneumatic diaphragm pumps produces an average chamber pressure magnitude that is less than the target pressure magnitude. In some cases, opening the valve produces a very rapid increase in the magnitude of the pressure in the chamber, while the drop in the pressure magnitude due to liquid flowing in or out of the pumping chamber was much slower. This mismatch in rate of pressure changes biases the magnitude of the time-averaged pressure below the target pressure magnitude. In cases in which the liquid flow into or out of the pump varies with time, the offset between the average pressure and the target pressure can also change with time, making it difficult to continuously correct for the mismatch in rate of pressure changes.

The pressure in the actuation chamber may be controlled by comparing the measured pressure to a target pressure. The controller opens and closes a pneumatic valve that connects the actuation chamber to a pressure source or reservoir. The controller may open and close valve LP1 during the delivery stroke to maintain the pressure in the actuation chamber 14030 near the delivery target pressure 14052. The controller 14035 opens and closes valve N1 during the fill stroke to maintain the pressure in the actuation chamber 14030 near the fill target pressure 14054. In one example, the controller closes pneumatic valve when the magnitude of the measured pressure exceeds the target pressure, and reopens the pneumatic valve when the averaged measured pressure in the actuation chamber approaches or equals the target pressure.

In the algorithm shown in FIGS. 63 and 64, referencing FIG. 62 and described below, the controller 14035 controls the valves N1, LP1 to hold the average pressure in the actuation chamber 14020 at the target pressure by maintaining the average pressure in the actuation chamber at the target pressure while the valves N1, LP1 are closed. Referring now to pressure control algorithm 14100 in FIG. 63 and referencing FIG. 60, a pump controller (that may be separate or distinct from controller 14035 in FIG. 60) selects the stroke direction 14105 and target pressure, Fill and PTF (Pressure-Target-Fill) or Deliver and PTD (Pressure-Target-Deliver). If a Fill stroke is selected, then in 14110 the controller 14035 opens the valve fluidically connecting the NEG source or reservoir to the actuation chamber 14020, and monitors the pressure sensor 196 in 14120. At each time step in Block 14130, the controller evaluates whether the pressure magnitude is greater than the magnitude of the target pressure, and if not leaves the valve open. In block 14140, once the magnitude of the measured pressure is equal to or greater than the target pressure, the N1 valve is closed. In block 14150, the difference between the measured pressure P and the target pressure TTF is summed at each time step. In block 14160, the end-of-stroke function or algorithm checks for an end-of-stroke and directs the controller logic to end-of-stroke 14200 if the EOS criteria are met. Note that the logic in block 14160 may be positioned anywhere in the flow chart between 14140 and 14180, or may be a separate function from the pressure control algorithm 14100. In block 14170 the summed pressure difference is compared to zero. If the summed pressure difference is greater than zero, controller logic returns to 14150 for an additional time step. In the case in which the sum of pressure differences is equal to or less than zero the controller logic zeros the pressure difference sum in block 14180 and returns the logic to block 14110 where the N1 valve is opened.

A single controller can coordinate the timing of pump strokes, the setting of target pressures, and the operation of the pneumatic control valves. Alternatively, the tasks can be divided between two or more controllers, for example with a main controller determining the timing of pump strokes and the target pressures, and a sub-controller controlling the pneumatic control valves. Referring to FIGS. 63 and 60, if a main controller selects a deliver stroke, it also defines a target pressure and the sub-controller moves the logic to block 14210 (FIG. 63) in which the LP1 valve is opened. In a series of steps similar to the Fill process, the pressure in the actuation chamber 14020 is monitored by pressure sensor 196 in block 14220. Block 14230 evaluates the pressure against the target pressure and if the measured pressure is equal to or greater than the target pressure, directs the logic to block 14240 where the LP1 valve is closed. Referring now to FIG. 60, the chamber pressure 14055 continues to increase after the LP1 valve is commanded to close at 14051, where the chamber pressure exceeds the target pressure. The chamber pressure 14055 may increase to 14052 due to the delay in the valve closing and due to fluid/thermal dynamics that may affect the chamber pressure.

Figure 63:
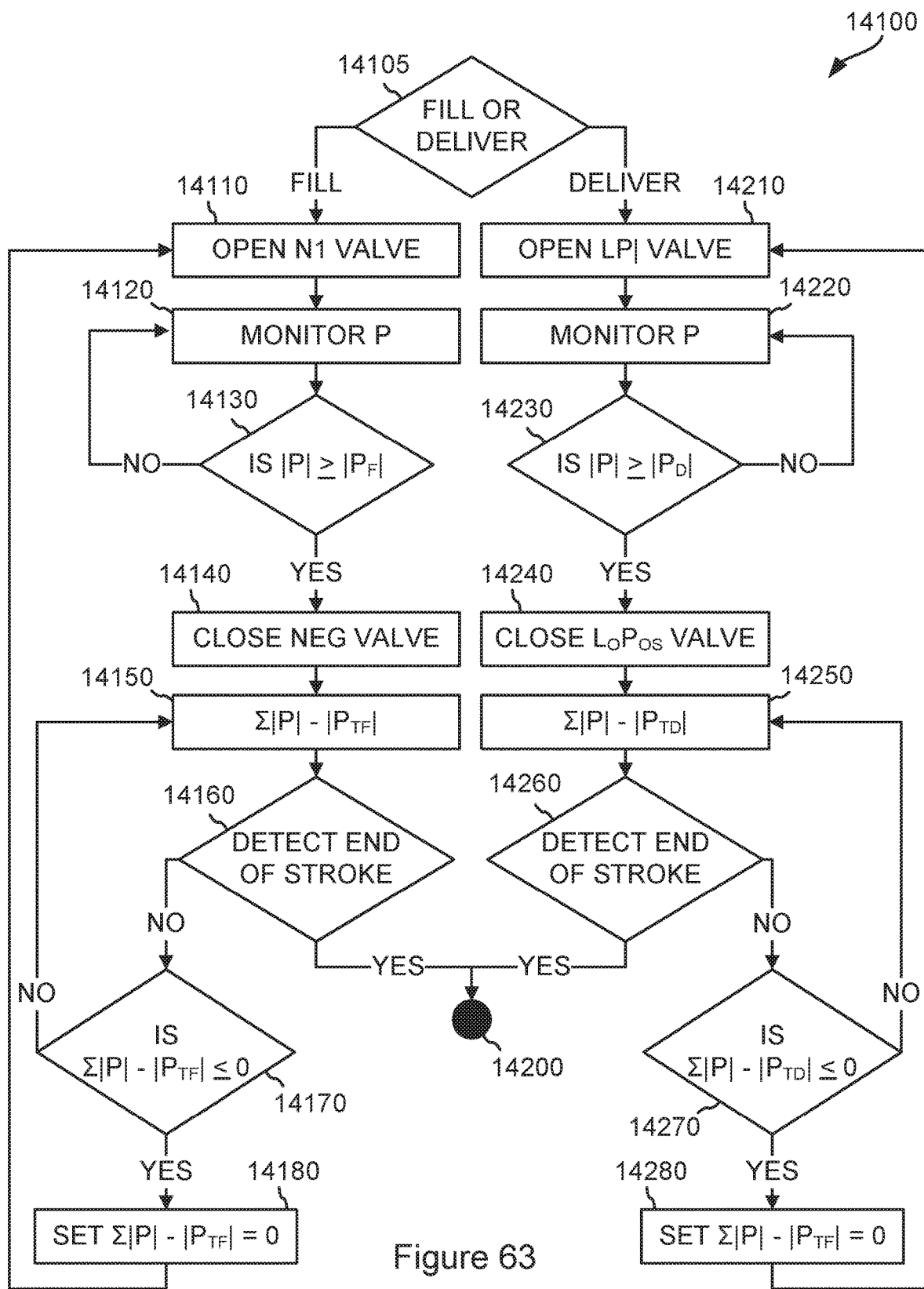
FIG. 63 is an exemplary flowchart for an algorithm to control pressure of an actuation chamber of a pneumatically actuated pump.

Referring to FIG. 63, in block 14250, the difference between the chamber pressure P and the target pressure PTD is summed for each time step. The sum of this difference between the chamber pressure P and the target pressure PTD from point 14052 until the chamber pressure 14055 equals the target pressure 14050 is the area 14080 in FIG. 62. The area 14085 is the sum of difference between the chamber pressure and the target pressure when the magnitude of the chamber pressure 14055 is less than the magnitude of the target pressure 14050. Referring again to FIG. 63, in block 14260 the EOS algorithm is run and the stroke ended at 14200 if an EOS is detected.

In block 14270, the sum of pressure difference from block 14250 is evaluated. Block 14270 directs the logic to 14210 where the LP1 valve is reopened, if the sum of the pressure differences is less than or equal to zero. The pressure difference sum is set to zero in block 14280 before the logic reaches block 14210, at which point LP1 is opened. Alternatively, the pressure difference sum may be zeroed any time in the logic after block 14270 and before block 14240

Referring now to FIG. 62, the criteria of block 14270 can be graphically represented as the instance in which the area of 14080 is equal to the area of 14085. The criteria of block 14270 is met when the sum of the actual pressure 14055 less the target pressure 14050 (for actual pressures greater than the target pressure) is equal to the sum of the target pressure 14050 less the chamber pressure 14055 (for chamber pressures less than the target pressure). Alternatively, the criteria of 14270 is met when the sum of [the average pressure magnitude less the target pressure magnitude] is equal to or less than zero.

In one example, blocks 14130 & 14230, the chamber pressure P is compared to predetermined pressures PD, PF that are different by a pressure offset from the target pressures PTD, PTF. In some examples, in order to limit the overshoot of the pressure, the magnitudes of PD, PF are a predetermined value less than the magnitude of the target pressures PTD, PTF. Referring now to FIG. 62, if PD is less than the Target pressure (14050D), then the signal to the valve LP1 in FIG. 60 will be sent sooner and the peak pressure at 14052 will be lower. In one example, the magnitude of the pressure offset is different for the fill stroke and the deliver stroke because the mean pressures for fill stroke and deliver stroke are different.

As the delay in the valve actuation is a fixed value and the pressure overshoot is inversely proportional the volume of the actuation chamber (which changes during the stroke), the overshoot can also vary, as can be seen in FIG. 61. In general, the overshoot is largest at the start of the deliver stroke 14060 and end of the fill stroke 14075 when the actuation chamber 14020 volume has the smallest volume. The offset for the fill and deliver strokes may vary during the stroke. In one example, the offset magnitude is largest at the beginning of the deliver stroke and is reduced with each charge cycle until the offset reaches a minimum value. In the same or another example, the offset magnitude is smallest at the beginning of the fill stroke and increases with each charge cycle until the offset reaches a maximum value. The offset values may vary with time, number of charge cycles, valve openings or the summed differential pressures when the valves are closed during the stroke.

Figure 64:
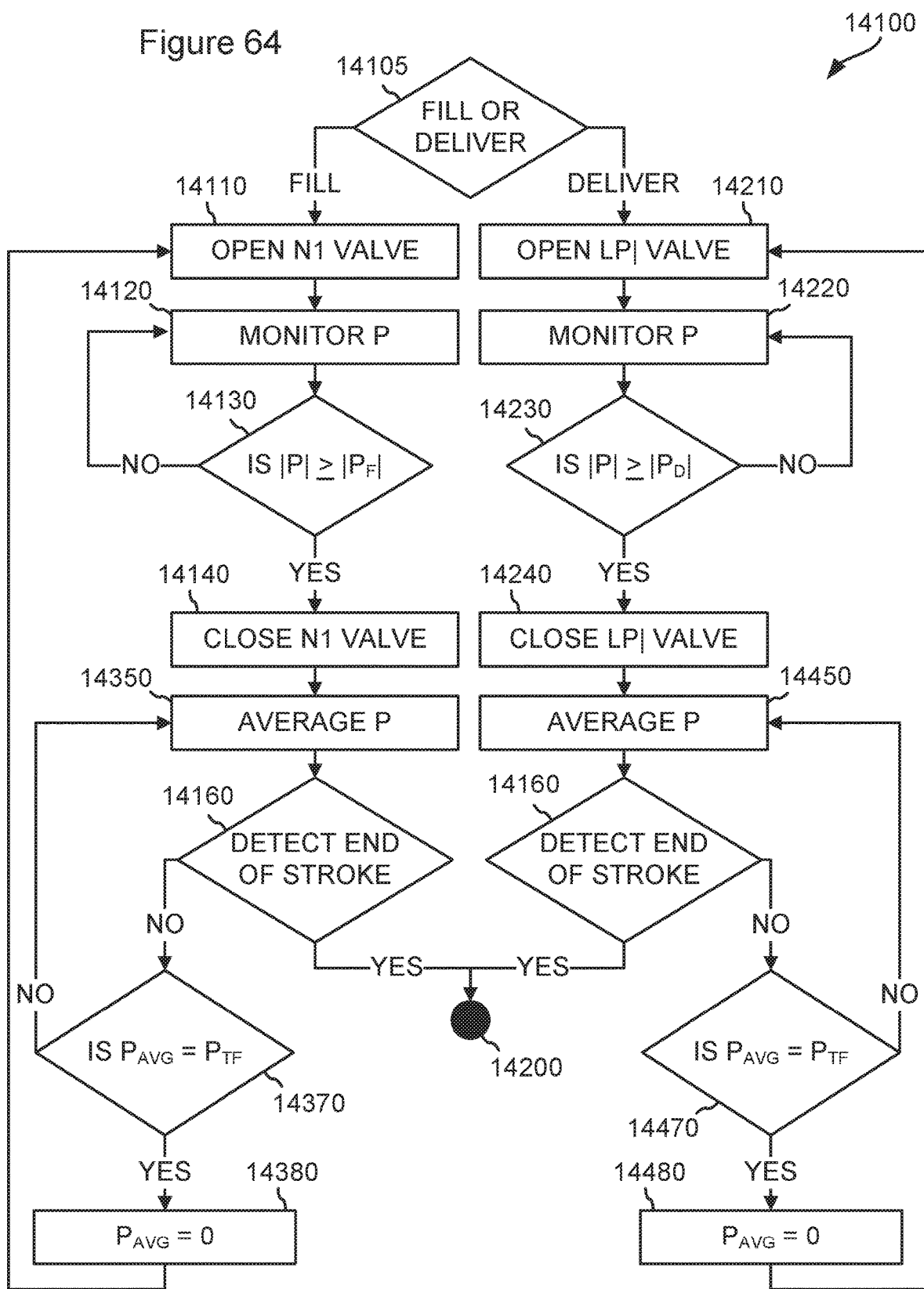
FIG. 64 is an exemplary flowchart for an alternative pressure control algorithm for a pneumatically actuated pump.

Another example of the pressure control algorithm 14300 is presented FIG. 64. The algorithm 14300 is similar to algorithm 14100 except for elements 14350, 14370, 14380, 14450, 14470 and 14480, in which the averaged pressure replaces the difference between the measured pressure and the target pressure. In blocks 14350 and 14450, the pressure sensor 196 measurements are averaged while the valves N1, LP1 are closed. In Block 14370 and 14470, if the averaged pressure, PAVG is equal to the target pressure within some predetermined margin, the logic proceeds to blocks 1410, 14210 respectively to open the valve N1, LP1 after zeroing out the average pressure.

Detecting End-of-Stroke

The accurate or reliable determination of flowrates and flow volumes through a pump 23a as pictured in FIG. 60 depends on an accurate or reliable algorithm to determine end-of-stroke (EOS). The end-of-stroke occurs when the diaphragm 14025 has moved across the cavity of the pump body and reached one of the walls of the pump body. The controller 14035 detects the condition of the chamber against the wall by observing that the chamber pressure magnitude, as measured by the pressure sensor 196, does not drop when the valve N1, LP1 is closed. The chamber pressure does not drop because the diaphragm 14025 is against the wall of the chamber and cannot move, and therefore cannot change the volume of the actuation chamber 14020.

The EOS detection algorithm detects an end-of-stroke condition based on valve conditions, chamber pressure and rate of change of the chamber pressure. The algorithm detects an EOS condition for a pneumatically driven diaphragm pump, where the pneumatic pressure is controlled by a pneumatic valve connecting the pump to a pressure reservoir, a pressure sensor measuring the pneumatic pressure applied to the pump and a controller in communication with the pump and pneumatic valve. In one example, the EOS detection is based on the number of charge cycles executed by the pneumatic valve and the rate of pressure change while the pneumatic valve is closed. In another example, the EOS is declared when a predetermined number of charge cycles have occurred and the rate of pressure magnitude change is less than a predetermined rate. In another example, the EOS detection is declared when a predetermined number of charge cycles have occurred, the pressure is within a predetermined range and the rate of pressure magnitude change is less than a predetermined rate.

Referring now to FIG. 60, the controller 14035 changes stroke direction from deliver to fill or fill to deliver after detecting an end-of-stroke (EOS). The end of stroke algorithm is described schematically in FIG. 65 and can be understood with reference to FIG. 61. The EOS algorithm 14300 runs as part of the pressure control algorithm 14100, in blocks 14160 and 14260, or the EOS algorithm may run in parallel. Block 14310 monitors the pressure in the actuation chamber as sensed by pressure sensor 196 (FIG. 60). In block, 14320, the number of charge cycles that have occurred during the current stroke are compared to a predetermined number. If more than the predetermined number of charge cycles have occurred, then in block 14330 the minimum rate of pressure magnitude change (dP/dt) is compared to a predetermined rate (dPEOS). If the minimum rate of change is less than the predetermined rate, then in block 14340 the difference between the current pressure P and the target pressure PT is evaluated. If the difference is smaller than a predetermined difference DP, an EOS is declared and the controller changes pump strokes, target pressure, and switches the state of the hydraulic valves 192, 193 (valves which in the presently described dialysis system may be diaphragm valves that can also be actuated by pressures delivered by the manifold and controlled by the controller). If the difference between the chamber pressure and the target pressure is greater than the predetermined difference, then the controller 14035 declares an occlusion.

Figure 65:
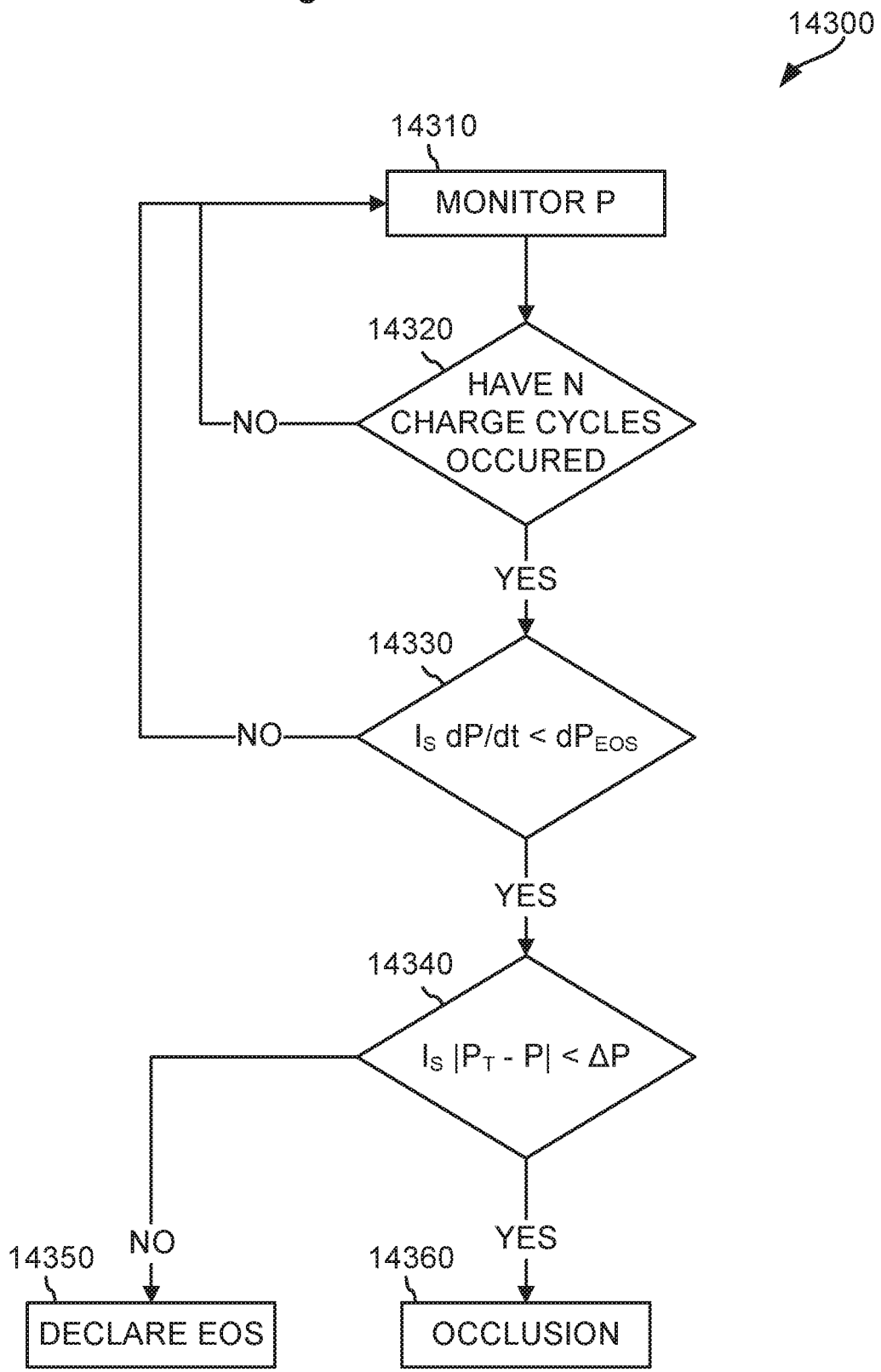
FIG. 65 is an exemplary flowchart for an end-of-stroke detection algorithm for an exemplary pneumatically actuated pump.

Still referring to FIG. 65, in block 14330, dP/dt is the minimum rate of change of the magnitude of the pressure in the actuation chamber. In some examples, the minimum rate of change is only determined while the pneumatic valves, N1, LP1 are closed. In some examples, the minimum rate of change of pressure magnitude is derived from a low pass filtering of the pressure values. In another example, the rate of change of pressure magnitude is itself is low-pass-filtered before being compared to the predetermined rate of pressure change (dPEOS).

Occlusion Detection

Referring now to FIG. 60, the controller 14035 can be configured to detect occlusions in the flow to and from pump 23*a*. The user interface may signal an alert or an alarm that an intake or outlet line is occluded. In one example, a user can be instructed to inspect the blood lines 203 and 204 for kinks, compressions or other obstructing elements. An occlusion detection algorithm can be considered a safety feature that prevents thrombosis in the blood circuit, or can identify a problem with fluid flow in the water or dialysate circuits.

Occlusions in the pump inlet and outlet lines are detected by the controller 14035 based on information received from the pressure sensor 196, while actuation chamber 14020 is isolated from pressure reservoirs NEG, LPOS. The pressure sensor 196 measures the pressure in the actuation chamber. The controller 14035 detects occlusions in the inlet line during fill strokes and occlusions in the outlet line during deliver strokes. The controller 14035 sums the change in pressure that occurs in the actuation chamber while the valve N1, LP1 is closed. The controller 14035 determines the presence of an occlusion by comparing the sum of the pressure changes over all the charge-cycles during a single pump stroke to sums of pressure difference during previous strokes and to an predetermined value. The controller 14035 may also base the detection of an occlusion on the number of charge cycles completed before an end-of-stroke is detected and/or the difference between the actuation chamber pressure and the target pressure.

Figure 66:
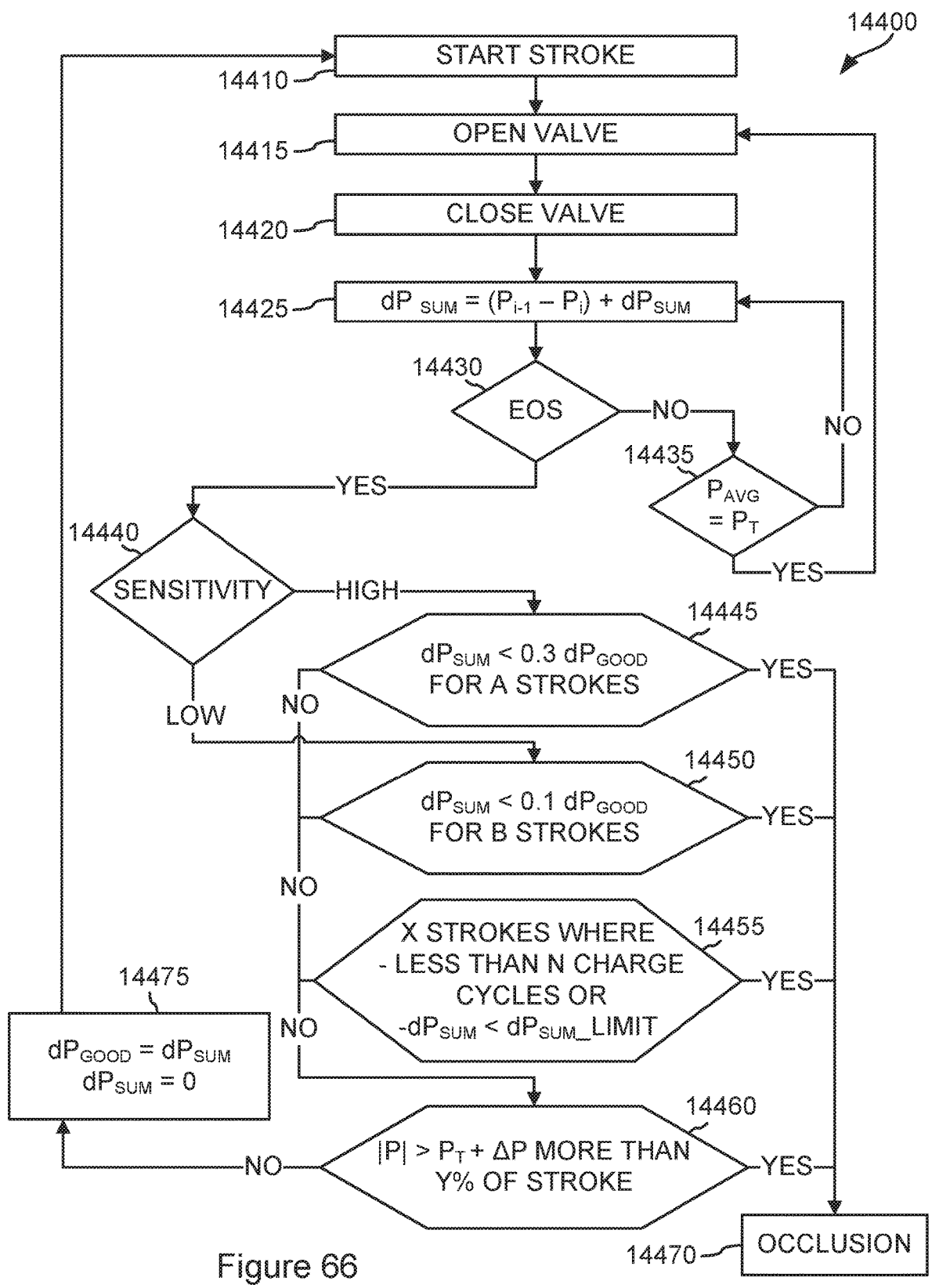
FIG. 66 is an exemplary flowchart for an occlusion detection algorithm for fluid pathways in a diaphragm-based pumping system.

Referring now to FIG. 66, where the occlusion algorithm 14400 is presented as a flow chart starting at step 14410 in which either a fill stroke or deliver stroke is initiated by setting a target pressure and then opening a valve N1, LP1 (FIG. 60) in step 14415. The valve N1, LP1 is closed in step 14420. In step 14425 the controller sums the pressure change (dPSUM) while the pneumatic valves N1, LP1 are closed. The sum of pressure changes (dPSUM) is summed over the entire stroke including multiple charge cycles 14427. In one example, the controller 14035 determines the pressure change from the previous time step to the current time step: Pi−1-Pi and adds this pressure change to the current sum of pressure changes for each time step that the pneumatic valve N1, LP1 is closed. In one example, the controller determines the pressure change between the time the valve N1, LP1 closes and then reopens and then adds this pressure change to the sum of pressure changes (dPSUM) that includes all the pressure changes since the stroke started at step 14410.

Continuing to refer to FIG. 66, the occlusion algorithm 14400 checks for an End-of-Stroke condition in step 14430 after updating the sum of pressure change (dPSUM) in step 14425. If an EOS is not detected, then the controller 14035 in step 14435 checks to see if the charge cycle is complete and it is time to reopen the valve. The end of charge cycle step 14435 can be done based on one or more parameters, including (but not limited to) the current pressure, the average pressure during the current charge cycle, or the integrand of the pressure difference between the target pressure and chamber pressure during the current charge cycle. If step 14435 determines the charge cycle is not complete, then sum of pressure changes is updated for the next time step in step 14435. If the charge cycle is complete, then the pneumatic valve N1, LP1 is reopened in step 14415.

When an end-of-stroke is determined in step 14430, the occlusion algorithm 14400 proceeds to multiple independent occlusion tests in steps 14440, 14450, 14455, 14460. Step 14440 directs the logic for low sensitivity to step 14450 and high sensitivity to step 14445. In one example, step 14440 selects low sensitivity for short or partial strokes of the blood pump due to the variability of short stroke in the blood pump. In short strokes, the diaphragm is not driven against the inside wall of the pod pump. Instead, the delivery stroke is shortened. In some medical applications, the short deliver stroke may be beneficial in reducing damage to blood cells between the diaphragm 14025 and the walls of the pod pump 23*a*. The short strokes have greater variability; and to avoid false occlusion detections, the low sensitivity occlusion test in step 14450 may be preferred. In one example, step 14440 directs the logic to step 14445 for all non-short stroke operations.

Continuing to refer to FIG. 66 where the occlusion algorithm 14400, in step 14445, compares the sum of pressure differences during just completed stroke (dPSUM) to the sum of pressure difference for the last good stroke in the same direction (dPGOOD). In one example, an occlusion is detected when two consecutive strokes in the same direction have a dPSUM that is less than 30% of the last good stroke (dPsum). In more general terms, an occlusion is detected when one stroke has a dPSUM that is less than a predetermined fraction of the last good stroke (dPsum). In one example, an occlusion is detected when more than two strokes have a dPSUM that is less than a predetermined faction of the last good stroke (dPsum). If an occlusion is detected, the logic moves to step 14470 where an occlusion alert or alarm is sent to the user interface (UI), and in one example the pump may be stopped. In some embodiments, the UI indicates which pump and where the inlet or the outlet line is occluded. If an occlusion is not detected in 14445, the logic moves to step 14455.

FIG. 66 outlines the occlusion algorithm 14400 includes, in low sensitivity step 14450, a comparison of the sum of pressure differences during just-completed stroke (dPSUM) to the sum of pressure difference for the last good stroke in the same direction (dPGOOD). In one example, an occlusion is detected when three consecutive strokes in the same direction have a dPSUM that is less than 10% of the last good stroke (dPsum). In one example, an occlusion is detected when one stroke has a dPSUM that is less than a second predetermined fraction of the last good stroke (dPsum). Alternatively, an occlusion is detected when more than three strokes have a dPSUM that is less than a predetermined faction of the last good stroke (dPsum). If an occlusion is detected the logic moves to step 14470 where an occlusion alert or alarm is sent to the user interface (UI) and in one example the pump is stopped. In an embodiment, the UI indicates which pump and where the inlet or the outlet line is occluded. If an occlusion is not detected in 14450, the logic moves to step 14455.

In step 14455, the controller 14035 detects an occlusion if in one or more consecutive strokes in the same direction either of the following conditions occur: less than a predetermined number of charge cycles occur, or the sum of the pressure changes (dPsum) is less than a predetermined limit (dPsum_limit). In one example, an occlusion is detected if either condition occurs in 3 consecutive strokes in the same direction. In another example an occlusion occurs if either conditions occurs in 2 consecutive cycles. In another example, the predetermined number of charge cycles is 5. In another example, predetermined number of charge cycles is half of the number of charge cycles in a typical stroke. If an occlusion is detected the logic moves to step 14470 in which an occlusion alert or alarm is sent to the user interface (UI). In one exemplary response, the pump is stopped. The controller may send data to the UI to indicate which pump is affected and whether the occlusion occurred in the inlet or the outlet line. If an occlusion is not detected in 14455, the logic moves to step 14460.

In step 14460, the controller 14035 detects an occlusion if the magnitude of the pressure in the actuation chamber 14020 is significantly greater than the target pressure for a predetermined period of time. In one example, step 14460 detects an occlusion if the magnitude of the pressure in the actuation chamber 14040 is larger than the target pressure magnitude by more than 60 mmHg for a predetermined period of time. In another example, the predetermined period of time in step 14460 is 25% of the stroke duration, the stroke duration being the time from the start of the stroke to EOS detection.

Partial Occlusion Detection

A partial occlusions may limit the flow rate, but not block the flow in liquid lines. The functions of the hemodialysis machine may be modified and/or the messages to the user may be changed depending on whether a partial occlusion or a full occlusion is detected. The controller detects a partial occlusion based on the flow rate of a recent stroke and stroke target pressure of that recent stroke. The pump controller varies the target pressure to achieve a desired flow rate and increases the target pressure for the next stroke, if the last stroke flow rate was below the desired flow rate. There are maximum target pressures for a given pump, in which the maximum pressure may be a function of the pressure reservoir pressure and/or the use of the given pump. In an example, a partial occlusion can be declared if the recent flowrate through the pump does not achieve the desired flow rate despite setting the target pressure for that recent stroke to the maximum value. In another example, a partial occlusion can be declared when the flowrate of a recent stroke is less than 75% of the desired flowrate despite the target pressure for the recent stroke having been set to the maximum value. In a hemodialysis system, the partial occlusion detection feature can be applied to the blood pumps to determine if there is a problem with an individual's vascular access or with the positioning of a set of blood lines.

Blood Flow Metrics

In an embodiment, the controller may be programmed to provide a user of an extracorporeal or hemodialysis system an indication of blood flow metrics (the quality or rate of flow of blood from a venous access or arterio-venous fistula) during the course of each pump fill-stroke. For example, a flow metric value may be transmitted to a graphical user interface, providing the user with an ongoing indication of the quality or adequacy of blood flow in the blood line during therapy. A user interface (such as, e.g. an electronic tablet) may provide the user with raw flow metric data. In another embodiment, the flow metric may be proportionally scaled to a range of 1 to 5, with the value '5' representing, for example, excellent flow, a value '3' representing marginal flow, and a value '1' occluded flow. Thus a specified range of flow metric values may be mapped into each of a set value of '1' to '5,' simplifying a user's interpretation of the adequacy of blood flow in the blood line. In other embodiments, the flow metric may be displayed to the user graphically, such as a moving or expanding bar graph, a dial gauge, or a set of colored lights, for example.

In a preferred embodiment, a marginal or sub-optimal flow metric may cause the controller to alert the user, so that the user may attempt to improve blood flow in the blood line (e.g., reposition the line, straighten out the line, adjust the vascular access cannula, etc.). The controller may be programmed initiate a procedure to pause or stop the dialysate pump that includes signaling the user and providing sufficient passage of time before the pausing or stopping of a dialysate pump to allow the user to correct the condition. The user may be alerted to the low-flow condition during a fill-stroke, so that a timely adjustment by the user allows the flow metric to be restored to an acceptable value before the end of the fill-stroke. Alternatively, the controller may be programmed to allow sub-optimal flow metric values for two or three (or more) consecutive fill-strokes before commanding the dialysate pump to stop. Thus a timely correction of the low-flow condition by the user may forestall the interruption of dialysate pumping operations, and possibly interruption of therapy. In an example, the controller may be programmed to pause or stop the dialysate pump if the flow metric remains below 150 (e.g., as dP/dt in mm Hg/sec.) for three consecutive fill-strokes, and may be programmed not to re-start the dialysate pump until the flow metric exceeds 200 for five consecutive blood pump strokes. In some of these embodiments, the controller allows the blood pump to continue to operate while the dialysate pump has been suspended, so that the user has an opportunity to restore a blood flow condition that allows the dialysate pump to be re-started, thus avoiding early termination of therapy.

Referring now to FIGS. 60 and 62, the controller 14035 may determine the flow metric during a fill stroke based on the actuation chamber pressure while the pneumatic valve N1 is closed. The actuation chamber pressure is measured by the pressure sensor 196 which is in communication with the controller 14035. In one example, the controller 14035 may determine the flow metric based on the rate of change of the signal from the pressure sensor 196 while the valve N1 is closed. In another example the controller 14035 may determine the flow metric based on the minimum rate of change of the actuation pressure during the stroke while the valve N1 is closed (i.e., the lowest or near-lowest rate of pressure change detected by the controller). In another example, the controller 14035 may determine the flow metric based on the minimum rate of change of the actuation pressure during the stroke, excluding the charge cycle that produced an end-of-stroke signal. In one example, the rate of change in the actuation pressure is determined during each charge cycle using a low-pass-filter and the minimum values of the rate of change for each charge cycle are low-pass-filtered over a stroke to determine the flow metric.

Figure 67:
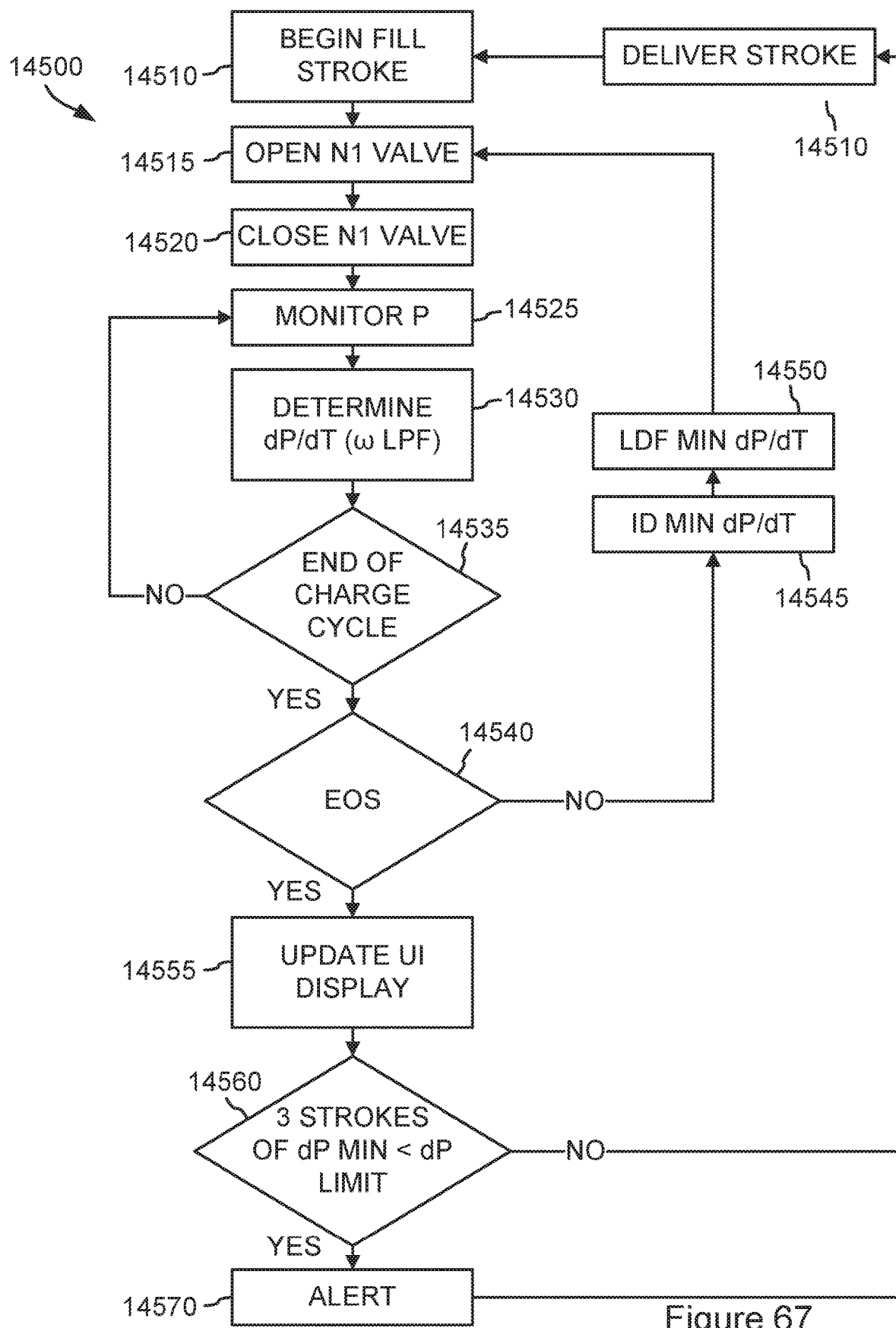
FIG. 67 is an exemplary flowchart for an algorithm to determine resistance to flow during a pumping fill stroke.

FIG. 67, illustrates the flow metric algorithm 14500 as a flow chart starting with "begin a fill stroke" with a blood pump (23a in FIG. 60). The upstream valve 192 is opened and the downstream valve 193 is closed. The fill stroke continues by opening pneumatic valve N1 in step 14515 and closing valve N1 in step 14520 to create a desired negative or below ambient pressure in the actuation chamber 14020 of the blood pump 23a. The negative pressure in the actuation chamber 14020 draws blood from the access site through the tubing 203 into the pumping chamber of blood pump 23a. The magnitude of the negative pressure in the actuation chamber 14020 decreases as the filling pump chamber expands and compresses the gas in the actuation chamber 14020. This reduction in the magnitude of the negative pressure is sensed by pressure sensor 196 and communicated to controller 14035 in step 14525 (FIG. 67). The controller analyzes the data, and (optionally) using a low-pass filter (LPF) function determines the rate of change of pressure (dP/dt) in the actuation chamber in step 14530. If the end of the charge cycle has occurred, step 14535 directs the logic to step 14540 at which end-of-stroke (EOS) is determined. If the end of the charge cycle has not occurred, then the logic is directed to 14525 in which the pressure signal continues to be monitored. If an EOS is not detected in step 14540, then the controller determines, in step 14545, the smallest magnitude of dP/dt while the valve N1 was closed. The minimum or lowest dP/dt of the current charge cycle detected by the controller is then used in the LPF to update the minimum dP/dt for the fill stroke in step 14550 and then the valve N1 is reopened to start the next charge cycle in step 14515.

If an EOS is detected in step 14540, then the logic flows to step 14555, at which the pod controller 14035 reports out the minimum dP/dt to a controller that converts the minimum dP/dt value to a more easily understood indicator that in turn is displayed on the user interface (UI). The UI may be a graphical display unit such as a tablet computer. The indicator is the flow metric of the intake blood line and access. In an example, the minimum dP/dt values are displayed as a value from 1 to 5, where 1 is an occluded access, 3 is a marginal access and 5 is freely flowing access. Here access means the system of needle or cannula, placement of needle or cannula and flow restrictions at inlet to needle or cannula. In an example, the flow metric is 1 or occluded for minimum dP/dt less than 25 mmHg/s, the flow metric is 2 or poor for a minimum dP/dt between 25 and 50 mmHg/s, the flow metric is 3 or marginal for a minimum dP/dt between 50 and 75 mmHg/s, the flow metric is 4 or good for a minimum dP/dt between 75 and 100 mmHg/s and the flow metric is 5 or excellent for a minimum dP/dt between 100 and 125 mmHg/s. In addition to displaying the flow metric on the UI in step 14555, the flow metric algorithm 14500 in step 14560 evaluates the flow metric and issues an alert to the user 14570 if the flow metric remains below a predetermined value for more than a predetermined number of strokes or period of time. In an example, step 14560 indicates an alert in step 14570 if three consecutive fill strokes have a dP/dt below a value of 50 mmHg/s. In this case the logic moves to a deliver stroke of the blood pump in step 14580 regardless the flow metric or minimum dP/dt and then returns to begin a fill stroke in step 14510.

Interface with Water Purification Device

The hemodialysis device or apparatus (HDD) can be configured to interact and communicate with a water purification device (WPD) that provides water to the HDD system for mixing dialysate solution and for disinfecting the HDD before or after a dialysis treatment. In previous disclosures, (see, e.g., US Patent Application Publication No. US/2016/0058933), a series of messages and data could be exchanged between HDD controller(s) and a WPD controller. In a more streamlined approach, the types of interactions between the two devices can be limited, instead relying on pre-programmed or autonomous functions of the WPD. In one example, the WPD can be a water vapor compression/distillation apparatus. Alternatively or additionally, other water purification devices and methods can be used, such as semi-permeable membrane filtration, reverse-osmosis, ultraviolet irradiation, charcoal adsorption, or any combination of these.

An HDD controller can be configured to send a Start signal to the WPD, representing a command to start normal-temperature water production, with the WPD proceeding according its independently programmed processor. This is the mode typically used when purified water is to be delivered to the HDD for dialysate mixing and therapy. The HDD controller can also send a Start Hot Water command to the WPD, representing a command to start hot water production according to the WPD's pre-programmed processes. This is the mode typically used to perform a disinfection procedure for the WPD. The line connecting the WPD with the HDD (the water inlet line of the HDD) and the HDD itself can be disinfected using operations programmed into one or more HDD controllers.

The HDD controller can also command the WPD to enter either a Standby mode or state, or an Idle mode or state. In a water vapor compression/distillation apparatus, an Idle state may involve pausing pumps or compressors, turning off heaters, closing valves and deactivating control loops and water level controllers. A Standby mode or state allows the WPD to produce purified water relatively quickly; and optionally in a vapor/distillation system this may include filling the purification system with water and heating it to a point at which purified water production can begin, control a vent valve to maintain a low pressure vapor temperature target, as well as optionally producing enough water to fill a reservoir, or alternatively sending excess water it produces to drain. If the WPD is starting from an inactive (Off) state or an Idle state, the HDD controller optionally can be programmed to send the command early enough to allow the WPD to be producing water by the time the HDD expects to receive water delivery. (In some cases, this may amount to about 2 hours from a cold start or a start from Idle mode, or as little as about 10 minutes from a Standby mode). In most cases, the HDD controller will command an idling WPD into a Standby mode when the two systems establish communications, or when one or both systems reboot after being powered off. This may not occur if an error condition has been flagged.

During water delivery, the HDD controller can send a Stop signal to the WPD, which commands the WPD to enter a Standby state. In this case, the Standby state is an autonomous function of the WPD that keeps water production or purification sufficiently active to be able to deliver water on command by the HDD within a relatively short time period (e.g., within about 10 minutes of a Start or Resume command being sent by the HDD to the WPD). Among other operations, this may include filling the purification system with water and heating it to a point at which purified water production can begin quickly.

The HDD controller can also send a Start Disinfect command to the WPD, which is generally scheduled to occur after a dialysis therapy has been concluded, or during a time between therapy sessions with the HDD. In this case, the WPD enters an automated hot water production mode. In a typical sequence, the HDD first commands the WPD into a water production mode, followed by a command to a disinfect mode once the WPD signals that it has entered the water production mode. Once the water produced by the WPD reaches a specified temperature (e.g. 90 deg. C.), the HDD controller is signaled, and the HDD initiates an Inlet Line disinfection procedure. The Inlet Line includes a flowpath within the HDD before a branch point connects it to a flowpath to either drain or to the mixing circuit of the HDD. (Beyond this branch point, the HDD internal flowpaths can be disinfected through programmed circulation of hot water or chemical disinfectant without any 'blind ends'). This state also disinfects any tubing that connects an output port or line of the WPD to an input port or line of the HDD.

A controller of the HDD can be programmed to disinfect the WPD-HDD connecting line and flowpath at a pre-determined minimum temperature for a pre-determined minimum amount of time. For example, the disinfect temperature can be set at 85 deg. C. for a minimum time of 35 minutes. The temperature can be measured by a temperature sensor located at the water inlet line of the HDD. To reduce the number of temperature sensors in the HDD system, the inlet water temperature sensor preferably can also be located in a position in the HDD flowpaths that can monitor the temperature of disinfection fluid circulating through the HDD flowpaths during HDD system disinfection. Depending on the distance the incoming water travels before reaching the temperature sensor, the minimum disinfection temperature may optionally be adjusted to account for heat loss before the water reaches the sensor.

Figure 68:
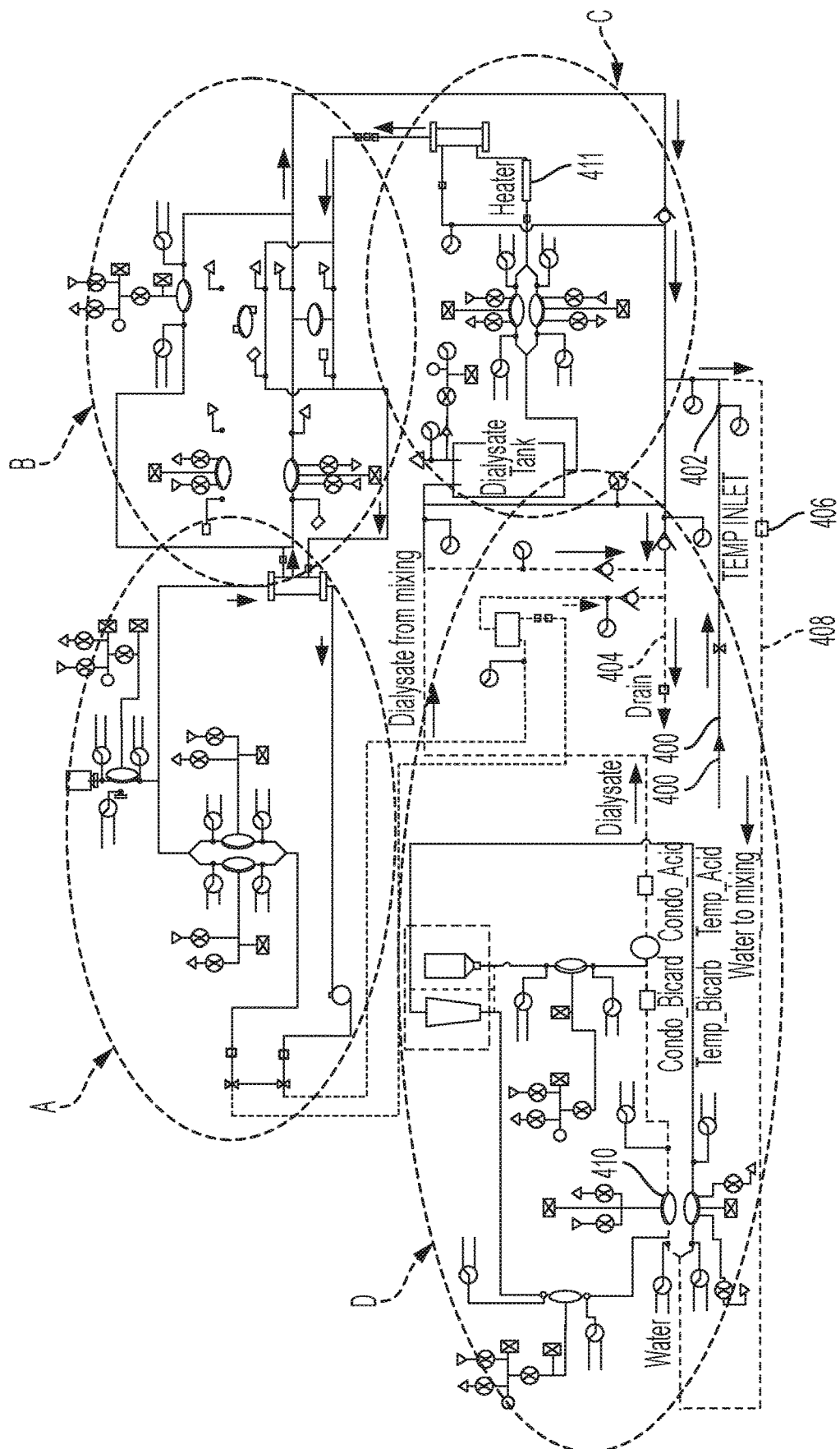
FIG. 68 is a schematic representation of the fluid flowpaths in an exemplary hemodialysis system.

FIG. 68 shows a schematic illustration of a fluid flowpath for a hemodialysis system described in previous applications. Section A represents a blood flow path of the system, section B represents a dialysate fluid balancing and dialyzer delivery section, section C represents a dialysate storage, heating and ultrafiltration section, and section D represents a water inlet and dialysate mixing section. The water inlet line 400 is configured to connect externally to a water source. In the current embodiment, the water source comprises a water purification device (WPD), such as a water vapor compression/distillation apparatus. For ease of reference, inlet water line 400 is meant herein to represent the entire water line connection between the purified water outlet of a WPD and the point 402 at which the HDD inlet water line has a valved connection to the internal flowpaths of the HDD. In reality, this inter-device water line may comprise one or more connectors or valves. But for disinfection purposes, the inlet water line 400 can be considered to include the entire inter-device water line.

Although the internal fluid flowpaths of the WPD and of the illustrated HDD can be configured to achieve a thorough and complete disinfection process, disinfection of the inlet water line and/or the inter-device line connecting the WPD to the HDD may require special attention. Note that the inlet water line 400 has a valved connection 402 to the internal HDD flowpaths, and that this inter-device fluid connection (WPD outlet line and HDD inlet line) becomes a blind end for purposes of thorough disinfection—either chemical or thermal. This condition is reflected in the outlet line of the WPD as well. Although the HDD dialysate heater can be used to heat water that can then be pumped by one or more dialysate pumps in a reverse direction through the HDD inlet line, through the WPD outlet line, and thence to a drain connection of the WPD, it may be more efficient for purified hot water (or water containing an appropriate chemical disinfectant) to be produced by the WPD and sent to the HDD in the normal forward direction, with the disinfecting liquid then being discharged to a drain line 404 of the HDD.

Figure 69:
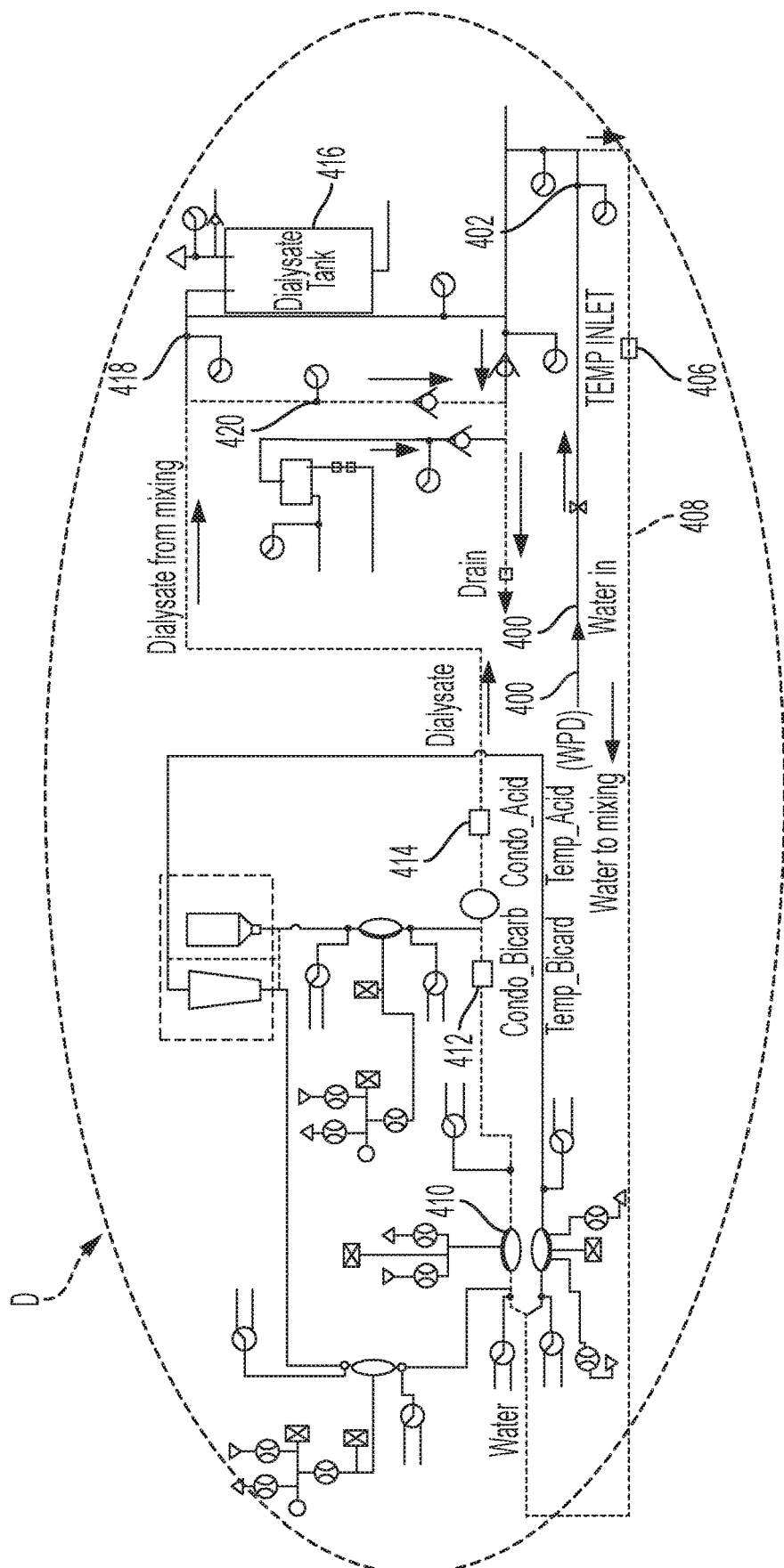
FIG. 69 is a schematic representation of an isolated view of a section of the fluid flowpaths of the hemodialysis system shown in FIG. 68.

FIG. 69 shows an isolated view of the section D portion of the HDD system flowpath. Although a temperature sensor can be located in line 400, it would only serve to monitor incoming water temperature. For purposes of disinfection, incoming heated water could be directed directly to drain 404, but this flowpath would depend on the action of a water pump located in the WPD. On the other hand, a temperature sensor 406 can be located in an internal line 408 connected to water pump 410, which can then provide the pumping action needed to move the water through the line 400 and 408. This sensor can also be used to monitor liquid temperature during disinfection of various internal flowpaths in the HDD system. Heated liquid from section C in FIG. 68 can be directed to flowpaths in section D via water line 408. The inlet line disinfecting flowpath incorporating water pump 410 in the illustrated system of FIG. 69 (see also FIG. 68) can be directed through conductivity/temperature sensors 412, 414 in the dialysate mixing path, and thence made to bypass the dialysate tank 416 by closing valve 418 and opening valve 420, which leads to the drain line 404. Note that in an alternative embodiment, the monitoring of the temperature of disinfecting liquid can also be done using existing temperature sensors already installed for the purpose of mixing dialysate (i.e. sensors 412 or sensors 414), without adding a temperature sensor in the water inlet line 400 or 408. In all of these cases, either actively managed valves or passive check valves ensure that the disinfecting liquid is being directed to the drain line 404.

Figure 70:
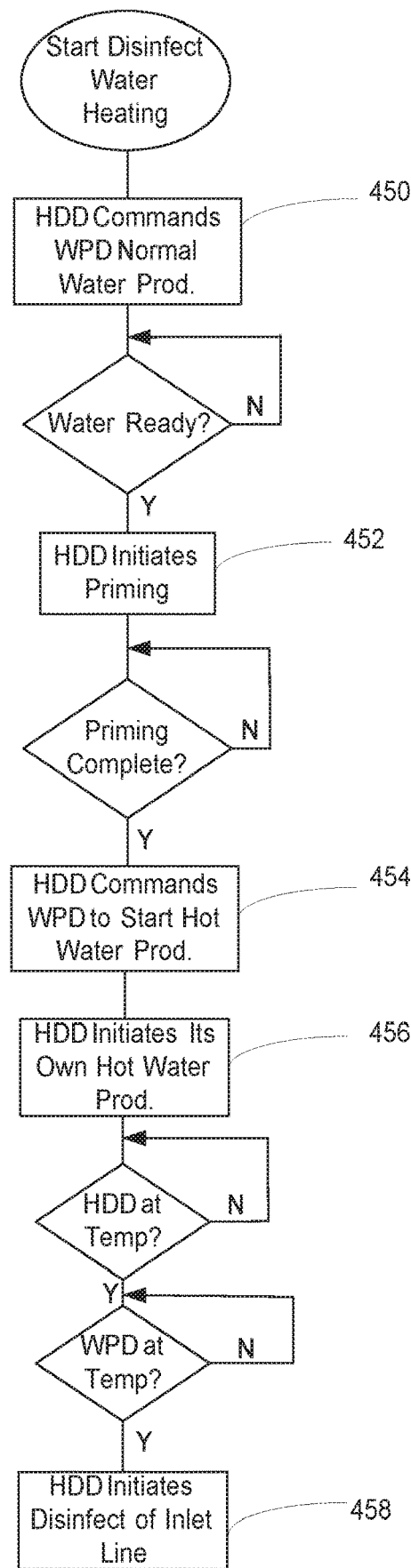
FIG. 70 is a state diagram representing a disinfect procedure for the hemodialysis system.

In an embodiment, and as shown in FIG. 70, initiation of a disinfection procedure may first involve having the HDD command 450 the WPD to begin normal water production. Following this, the HDD initiates 452 the priming of its flowpaths with water from the WPD. The HDD then commands 454 the WPD to produce water heated to the required disinfection temperature. Optionally, the temperature at which the WPD produces heated water is higher than the minimum disinfection temperature specified for the line interconnecting the WPD and HDD. This is to account for heat losses of the water as it travels though the interconnecting line. For example, if the minimum disinfect temperature is 85 degrees C., then the WPD may be programmed to produce water at 90 degrees C. at its outlet. Optionally, the HDD may be programmed to initiate 456 its own hot water production using its internal heater (e.g. heater 411 shown in FIG. 68). This prepares the HDD to perform its own disinfection after the inter-device line 400 has been disinfected, and helps to maintain a high ambient temperature in the HDD housing to limit heat losses during disinfection of the inter-device line 400. Once both the HDD and WPD have heated their respective fluid flowpaths to the specified temperatures, the HDD controller may then command the WPD to begin delivering 458 heated water from its product outlet line to the inter-device line (inlet line 400) connecting the WPD to the HDD.

The water disinfect temperature may vary during the disinfection period. Optionally, a controller of the HDD can be programmed to track the amount of time during which the measured temperature meets or exceeds the minimum disinfect temperature programmed into the controller.

Figure 71:
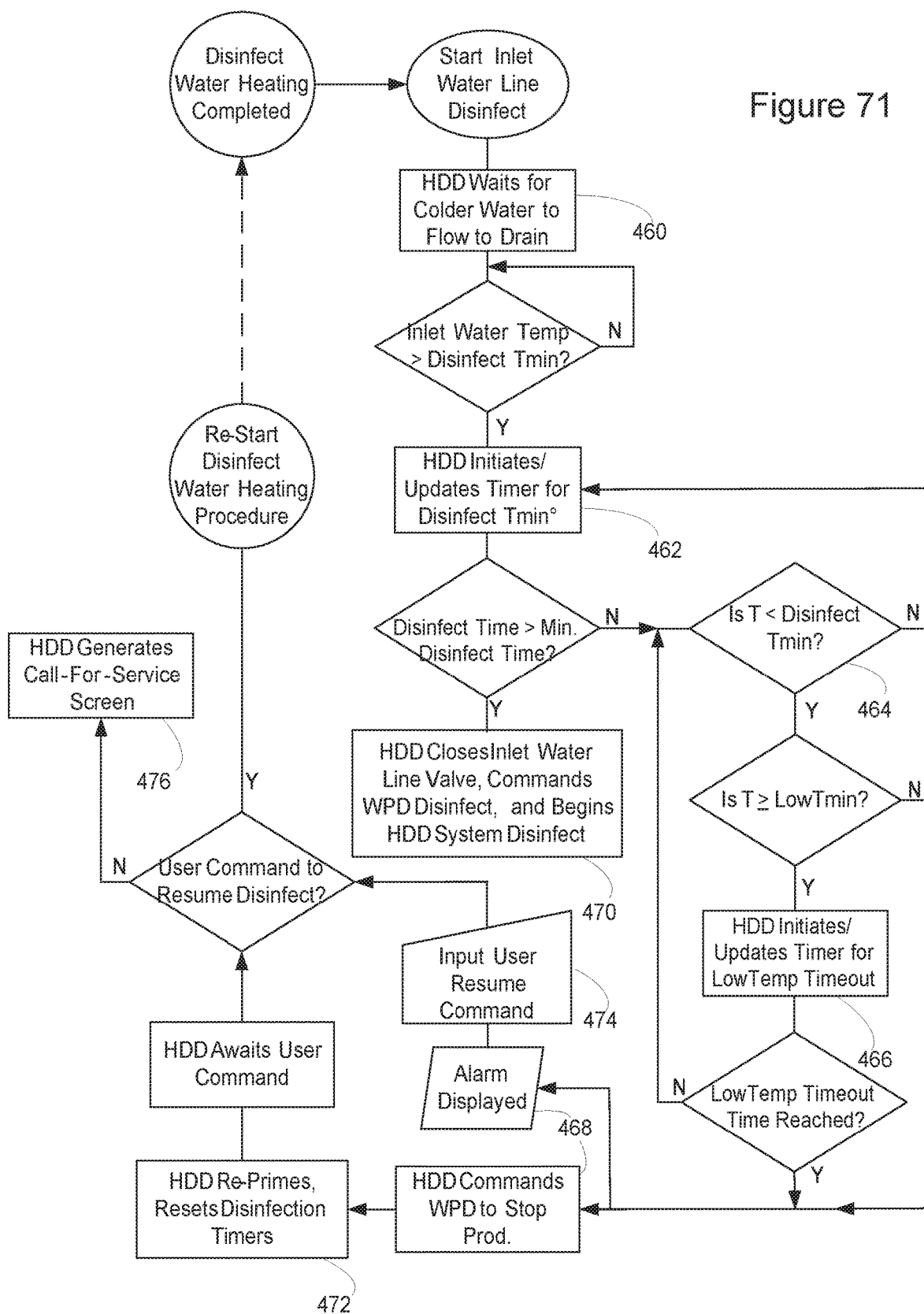
FIG. 71 is a state diagram representing temperature control prior to and during a disinfect procedure.

As shown in FIG. 71, optionally before initiating a disinfection counter for the inter-device line 400, the HDD controller begins controlling an internal HDD pump and associated valves to circulate 460 incoming heated water from the WPD for a pre-determined period of time to fill the disinfecting flowpath fully with heated water. In addition to the inter-device line, in one example this flowpath may include the flowpath within the HDD that directs the disinfecting water through the water pump 410 in the mixing circuit, through a line that leads to the dialysate tank 416 but is diverted to drain 404 by one or more valves 418, 420. (See, e.g., FIG. 69). In one example, the HDD controller directs heated water from the WPD to the HDD drain for approximately 2 minutes before the inter-device line disinfection counter is started.

The HDD controller may be programmed to include a pre-determined minimum disinfection temperature (e.g., 78 deg. C.). Once this temperature is detected by a temperature sensor (e.g., sensor 406, or sensor 412 or 414), the controller initiates a disinfection timer 462. If this minimum disinfect temperature is maintained 464 for a pre-determined minimum disinfect time (e.g., 35 minutes), then the controller may declare disinfection of the inter-device line 400 to be complete. The disinfect timer is updated 464 as long as the temperature detected is at or above the minimum disinfect temperature.

Optionally, the controller may be programmed to include a timer 466 that accumulates an amount of time at which the temperature detected is less than the minimum disinfect temperature but greater than or equal to a pre-determined low-temperature threshold value (e.g., 70 deg. C.). If a pre-determined low temperature timeout value is reached (e.g., 10 minutes to timeout the disinfection cycle), then the controller may signal an alarm to the user interface and command the WPD to suspend water production 468. Optionally, the controller may also be programmed to signal an alarm and command the WPD to suspend water production 468 if the detected temperature is less than a pre-determined low-temperature threshold value (e.g., 70 deg. C.).

If the inter-device line 400 disinfection is successful 470, then the HDD controller can close the inlet water line valve 402, command the WPD to begin its disinfection procedure, and initiate the HDD disinfection procedure. If the inter-device line 400 disinfection fails, the user is notified and the WPD is commanded to suspend water production 468. The HDD controller under these circumstances optionally initiates a re-priming procedure of its flowpaths, and resets the disinfection timers at 472. The HDD controller then can await a user input 474 to either re-attempt the disinfection procedure, or not. If not, the HDD optionally can initiate a call for service 476. The controller may provide the appropriate instructions to a user on the user interface, or it may be configured to automatically send the appropriate messages to a remote server and service center via an internet communication link.

The HDD controller may command the WPD to a Flush mode, in which source water flows into the system and through any filters therein. This is commonly performed after a filter replacement. If a filter replacement is indicated (e.g., a carbon filter), the HDD controller may first command the WPD into an Idle state, followed by an alert to a user on a graphical user interface that the WPD is ready to have its filter replaced. Once the user indicates completion of this task, the HDD may then command the WPD to a Standby state, followed by a Flush mode. The HDD commands a return to the Standby state at the completion of this task, so that a water production state can be quickly initiated at the start of therapy. The Flush mode may also be commanded prior to fluid sampling in order to ensure a more reliable indication of the quality of the filters. It may also be commanded if the WPD system has been in an Idle or Standby state for more than a pre-determined period of time.

Status messages may be sent between a Water Layer of the HDD system controller architecture and a Therapy Layer of the HDD system controller architecture. Example messages that the Water Layer can receive from the WPD may include:
 The current operational state of the WPD
 The identification code or identifier of the current WPD
 The date that the WPD filter was installed
 Whether the filter needs to be replaced
 Whether communication with the WPD has been lost
 Whether the WPD indicates an operational error
 Whether the WPD indicates a failsafe error
 The time since the WPD was last disinfected
 Whether the WPD needs to be disinfected
 The software version installed on the WPD system controller Status messages regarding the operational state of the WPD may include one or more of the following:
 WPD active (independent of HDD); initiation of communications link between HDD and WPD causes the HDD to command the WPD to Standby state.
 WPD at Idle; product valve is closed.
 WPD at Standby; product valve is open.
 WPD producing normal temperature water; product valve is open.
 WPD awaiting filter replacement; product valve is closed.
 WPD flushing lines and filter after filter replacement.
 WPD producing hot water; product valve opens when at temperature.
 WPD disinfecting; product valve is closed.
 WPD producing water sample for testing (eg. Chloramine testing); product valve is closed.
 WPD awaiting user entry in GUI to deliver water sample for testing.
 WPD is in a failsafe state; product valve is closed.

Preferably, the HDD controller commands the WPD to remain in Standby mode whenever it is not performing another operation. If it is in another operation (for example, disinfecting) the HDD controller waits for this operation to be completed. Once the WPD is in Standby mode, the HDD controller may check to see if the WPD is due for a filter flushing operation. If so, the WPD initiates a filter flush operation. The HDD may also command a filter flush operation if, for example, there is a power interruption before a filter flush has been completed after filter replacement.

Optionally, prior to the initiation of water production for a therapy, the HDD may be programmed to require the user to sample product water from the WPD for various contaminants, such as chloramine. The HDD may command the WPD to initiate a water sampling state. When the WPD indicates a ready condition for sampling. The HDD then alerts the user to collect and test a water sample. If the user indicates that the sample has passed the test, the HDD may then command the WPD to begin water production for a therapy. The HDD may optionally command the WPD into a Standby state if the user indicates that the sample has failed the test.

Errors originating from the WPD during water production can be signaled to the HHD, which may then send a command to acknowledge the error condition and issue an alert via an interface (e.g. the HDD interface) to the user. The WPD controller then waits for a command originating from the user to either attempt to resume water production or to transition to a Standby state. A failsafe error condition would generally cease WPD operations and signal the HDD to initiate a therapy termination procedure.

What is claimed is:

1. A fluid-handling cassette assembly comprising:
 a middle cassette interposed between a first outer cassette and a second outer cassette;
 each said cassette comprising:
  a mid-plate positioned between a first plate and a second plate, said plates having a length, a width and a plate thickness, a first side of the mid-plate opposing the first plate and a second side of the mid-pate opposing the second plate;
 the first plate spaced apart from the mid-plate defining a width of a first inter plate space, and the second plate spaced apart from the mid-plate defining a width of a second inter-plate space;
 an edge of the cassette having a cassette thickness defined by the thickness of each plate plus the width of the first and second inter-plate spaces, and a face of the cassette being defined by the length and width of the first or second plate;
 a plurality of diaphragm valves or pumps comprising valve or pump actuation chambers connected to actuation channels running parallel to the face of the cassette within the first or second inter-plate space, and terminating in respective cassette valve or pump actuation ports at a first edge of the cassette between the first or second inter-plate space; and a fluid-handling pod positioned in an inter-cassette space between the middle cassette and the first or second cassette; said pod having a fluid connection to fluid channels in the middle, first or second cassette via a fluid conduit penetrating the face of the middle, first or second cassette;

wherein the first edge of the middle, first and second cassettes are located on a first side of the cassette assembly, so that the cassette valve or pump actuation ports are configured to plug into or unplug from an actuation port receptacle assembly opposite the first side of the cassette assembly.

2. The cassette assembly of claim 1, wherein the fluid-handling pod comprises a diaphragm pump pod having an actuation and a fluid connection to actuation and fluid channels in the middle, first or second cassette via an actuation conduit and a fluid conduit, each penetrating the face of the middle, first or second cassette.

3. The cassette assembly of claim 2, wherein the actuation conduit of the diaphragm pump pod connects to an actuation channel in a first or second inter-plate space of said middle, first or second cassette, and has an uninterrupted connection to a cassette actuation port for the diaphragm pump pod on the first edge of said middle, first or second cassette.

4. The cassette assembly of claim 2, wherein the fluid conduit of the diaphragm pump pod connects to a fluid channel in a first or second inter-plate space of said middle, first or second cassette, and connects with a diaphragm valve in said cassette, and wherein an actuation channel of said diaphragm valve connects to a cassette actuation port for said diaphragm valve in the first edge of said middle, first or second cassette.

5. The cassette assembly of claim 1, wherein the fluid conduit is rigid.

6. The cassette assembly of claim 5, comprising a plurality of fluid-handling pods between the middle cassette and the first cassette, and between the middle cassette and the second cassette, and wherein associated fluid conduits of this plurality of fluid-handling pods are rigid and provide structural support for the cassette assembly.

7. The cassette assembly of claim 1, comprising a cassette assembly frame configured to enhance the structural stiffness of the cassette assembly, the cassette assembly frame comprising a rigid support plate on a second side of the cassette assembly opposite the first side of the cassette assembly, said support plate configured to engage a cassette loading apparatus opposite the actuation port receptacle.

8. A fluid-handling cassette assembly comprising:
a middle cassette interposed between a first outer cassette and a second outer cassette;
each said cassette comprising:
a mid-plate positioned between a first plate and a second plate, said plates having a length, a width and a plate thickness, a first side of the mid-plate opposing the first plate and a second side of the mid-pate opposing the second plate;
the first plate spaced apart from the mid-plate defining a width of a first inter plate space, and the second plate spaced apart from the mid-plate defining a width of a second inter-plate space;
an edge of the cassette having a cassette thickness defined by the thickness of each plate plus the width of the first and second inter-plate spaces, and a face of the cassette being defined by the length and width of the first or second plate;
a plurality of diaphragm valves or pumps comprising valve or pump actuation chambers connected to actuation channels running parallel to the face of the cassette within the first or second inter-plate space, and terminating in respective cassette valve or pump actuation ports at a first edge of the cassette between the first or second inter-plate space;
a first fluid-handling pod positioned in an inter-cassette space between the middle cassette and the first or second cassette; said pod having a fluid connection to fluid channels in the middle, first or second cassette via a fluid conduit penetrating the face of the middle, first or second cassette; and
a second fluid-handling pod comprising a diaphragm pump pod having an actuation and a fluid connection to actuation and fluid channels in the middle, first or second cassette via an actuation conduit and a fluid conduit, each penetrating the face of the middle, first or second cassette;
wherein the first edge of the middle, first and second cassettes are located on a first side of the cassette assembly, so that the cassette valve or pump actuation ports are configured to plug into or unplug from an actuation port receptacle assembly opposite the first side of the cassette assembly.

9. The cassette assembly of claim 8, wherein the actuation conduit of the diaphragm pump pod connects to an actuation channel in a first or second inter-plate space of said middle, first or second cassette, and has an uninterrupted connection to a cassette actuation port for the diaphragm pump pod on the first edge of said middle, first or second cassette.

10. The cassette assembly of claim 8, wherein the fluid conduit of the diaphragm pump pod connects to a fluid channel in a first or second inter-plate space of said middle, first or second cassette, and connects with a diaphragm valve in said cassette, and wherein an actuation channel of said diaphragm valve connects to a cassette actuation port for said diaphragm valve in the first edge of said middle, first or second cassette.

11. The cassette assembly of claim 8, wherein the fluid conduit is rigid.

12. The cassette assembly of claim 11, comprising a plurality of fluid-handling pods between the middle cassette and the first cassette, and between the middle cassette and the second cassette, and wherein associated fluid conduits of this plurality of fluid-handling pods are rigid, providing structural support for the cassette assembly.

13. The cassette assembly of claim 8, comprising a cassette assembly frame configured to enhance the structural stiffness of the cassette assembly, the cassette assembly frame comprising a rigid support plate on a second side of the cassette assembly opposite the first side of the cassette assembly, said support plate configured to engage a cassette loading apparatus opposite the actuation port receptacle.

* * * * *